US011329233B2

(12) United States Patent
Stoessel et al.

(10) Patent No.: US 11,329,233 B2
(45) Date of Patent: May 10, 2022

(54) HETEROCYCLIC COMPOUNDS FOR USE IN ELECTRONIC DEVICES

(71) Applicant: Merck Patent GmbH, Darmstadt (DE)

(72) Inventors: Philipp Stoessel, Frankfurt am Main (DE); Nils Koenen, Griesheim (DE); Philipp Harbach, Muehltal (DE); Dominik Joosten, Frankfurt am Main (DE); Amir Parham, Frankfurt am Main (DE); Anja Jatsch, Frankfurt am Main (DE)

(73) Assignee: MERCK PATENT GMBH, Darmstadt (DE)

( * ) Notice: Subject to any disclaimer, the term of this patent is extended or adjusted under 35 U.S.C. 154(b) by 316 days.

(21) Appl. No.: 16/463,908

(22) PCT Filed: Nov. 30, 2017

(86) PCT No.: PCT/EP2017/080913
§ 371 (c)(1),
(2) Date: May 24, 2019

(87) PCT Pub. No.: WO2018/100029
PCT Pub. Date: Jun. 7, 2018

(65) Prior Publication Data
US 2019/0296250 A1 Sep. 26, 2019

(30) Foreign Application Priority Data

Dec. 2, 2016 (EP) ..................................... 16201964

(51) Int. Cl.

| | | |
|---|---|---|
| *H01L 51/00* | (2006.01) | |
| *C07D 225/04* | (2006.01) | |
| *C09K 11/06* | (2006.01) | |
| *C07D 405/10* | (2006.01) | |
| *C07D 409/10* | (2006.01) | |
| *C07D 403/04* | (2006.01) | |
| *C07D 403/10* | (2006.01) | |
| *C07D 405/12* | (2006.01) | |
| *C07D 401/04* | (2006.01) | |
| *C07D 405/04* | (2006.01) | |
| *C07D 409/04* | (2006.01) | |
| *C07D 493/04* | (2006.01) | |
| *C07D 403/14* | (2006.01) | |
| *C07D 405/14* | (2006.01) | |
| *C07D 471/04* | (2006.01) | |
| *C07D 491/048* | (2006.01) | |
| *H01L 51/50* | (2006.01) | |
| *C07D 495/04* | (2006.01) | |
| *C07D 409/14* | (2006.01) | |

(52) U.S. Cl.
CPC ........ *H01L 51/0072* (2013.01); *C07D 225/04* (2013.01); *C07D 401/04* (2013.01); *C07D 403/04* (2013.01); *C07D 403/10* (2013.01); *C07D 403/14* (2013.01); *C07D 405/04* (2013.01); *C07D 405/10* (2013.01); *C07D 405/12* (2013.01); *C07D 405/14* (2013.01); *C07D 409/04* (2013.01); *C07D 409/10* (2013.01); *C07D 409/14* (2013.01); *C07D 471/04* (2013.01); *C07D 491/048* (2013.01); *C07D 493/04* (2013.01); *C07D 495/04* (2013.01); *C09K 11/06* (2013.01); *H01L 51/006* (2013.01); *H01L 51/0052* (2013.01); *H01L 51/0054* (2013.01); *H01L 51/0056* (2013.01); *H01L 51/0058* (2013.01); *H01L 51/0059* (2013.01); *H01L 51/0061* (2013.01); *H01L 51/0067* (2013.01); *H01L 51/0071* (2013.01); *H01L 51/0073* (2013.01); *H01L 51/0074* (2013.01); *H01L 51/50* (2013.01); *C09K 2211/1018* (2013.01); *H01L 51/0085* (2013.01); *H01L 51/5016* (2013.01); *H01L 51/5056* (2013.01); *H01L 51/5096* (2013.01); *H01L 2251/5384* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 9,133,119 B2 | 9/2015 | Parham et al. | |
| 2015/0322198 A1* | 11/2015 | Hayer | .............. C08L 65/02 252/500 |
| 2017/0018721 A1 | 1/2017 | Tsang et al. | |
| 2017/0324038 A1 | 11/2017 | Jatsch et al. | |

FOREIGN PATENT DOCUMENTS

| | | |
|---|---|---|
| KR | 20160079546 A | 7/2016 |
| WO | WO-2011088877 A1 | 7/2011 |
| WO | WO-2016078747 A1 | 5/2016 |

OTHER PUBLICATIONS

International Search Report for PCT/EP2017/080913 dated Mar. 23, 2018.
Written Opinion of the International Searching Authority for PCT/EP2017/080913 dated Mar. 23, 2018.

* cited by examiner

*Primary Examiner* — Jay Yang
(74) *Attorney, Agent, or Firm* — Faegre Drinker Biddle & Reath LLP

(57) ABSTRACT

The invention relates to heterocyclic compounds, particularly for use in electronic devices. The invention further relates to a method for producing the compounds according to the invention, and to electronic devices comprising same.

16 Claims, No Drawings

HETEROCYCLIC COMPOUNDS FOR USE IN ELECTRONIC DEVICES

CROSS-REFERENCE TO RELATED APPLICATIONS

This application is a national stage application (under 35 U.S.C. § 371) of PCT/EP2017/080913, filed Nov. 30, 2017, which claims benefit of European Application No. 16201964.0, filed Dec. 2, 2016, both of which are incorporated herein by reference in their entirety.

The present invention relates to heterocyclic compounds, especially for use in electronic devices. The invention further relates to a process for preparing the compounds of the invention and to electronic devices comprising these compounds.

The construction of organic electroluminescent devices (OLEDs) in which organic semiconductors are used as functional materials is common knowledge in the art. Emitting materials used are frequently organometallic complexes which exhibit phosphorescence. For quantum-mechanical reasons, up to four times the energy efficiency and power efficiency is possible using organometallic compounds as phosphorescent emitters. In general terms, there is still a need for improvement in OLEDs, especially also in OLEDs which exhibit phosphorescence, for example with regard to efficiency, operating voltage and lifetime.

The properties of organic electroluminescent devices are not only determined by the emitters used. Also of particular significance here are especially the other materials used, such as host and matrix materials, hole blacker materials, electron transport materials, hole transport materials and electron or exciton blocker materials. Improvements to these materials can lead to distinct improvements to electroluminescent devices.

Frequently used according to the prior art as matrix materials for phosphorescent compounds and as electron transport materials are aromatic or heteroaromatic compounds, for example triarylamine derivatives or carbazole derivatives. In addition, triazine derivatives or pyrimidine derivatives are also used as matrix materials, and there are also known compounds having both carbazole structures and structures derived from triazines or pyrimidines.

In general terms, in the case of these materials, for example for use as matrix materials, there is still a need for improvement, particularly in relation to the lifetime, but also in relation to the efficiency and operating voltage of the device.

The problem addressed by the present invention is therefore that of providing compounds which are suitable for use in an organic electronic device, especially in an organic electroluminescent device, and which lead to good device properties when used in this device, and that of providing the corresponding electronic device.

More particularly, the problem addressed by the present invention is that of providing compounds which lead to a high lifetime, good efficiency and low operating voltage. Particularly the properties of the matrix materials too have an essential influence on the lifetime and efficiency of the organic electroluminescent device.

A further problem addressed by the present invention can be considered that of providing compounds suitable for use in a phosphorescent or fluorescent OLED, especially as a matrix material. A particular problem addressed by the present invention is that of providing matrix materials suitable for red-, yellow- and green-phosphorescing OLEDs and possibly also for blue-phosphorescing OLEDs. In addition, fluorescent emitters having excellent properties should be provided.

Moreover, the compounds should be processable in a very simple manner, and especially exhibit good solubility and film formation. For example, the compounds should exhibit elevated oxidation stability and an improved glass transition temperature.

A further object can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, these problems are solved by particular compounds described in detail hereinafter. The use of the compounds leads to very good properties of organic electronic devices, especially of organic electroluminescent devices, especially with regard to lifetime, efficiency and operating voltage. The present invention therefore provides electronic devices, especially organic electroluminescent devices, containing such compounds, and the corresponding preferred embodiments.

The present invention therefore provides a compound comprising at least one structure of formula (I) and/or (II):

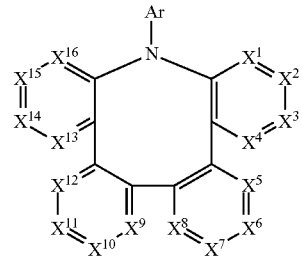

Formula (I)

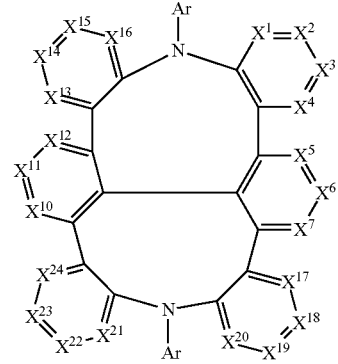

Formula (II)

where the symbols used are as follows:

$X^1, X^2, X^3, X^4, X^5, X^6, X^7, X^8, X^9, X^{10}, X^{11}, X^{12}, X^{13}, X^{14}, X^{15}, X^{16}, X^{17}, X^{18}, X^{19}, X^{20}, X^{21}, X^{22}, X^{23}, X^{24}$ is N or $CR^1$, preferably $CR^1$;

Ar is the same or different at each instance and is an aromatic or heteroaromatic ring system which has 5 to 60 aromatic ring atoms and may be substituted by one or more $R^1$ radicals;

$R^1$ is the same or different at each instance and is H, D, F, Cl, Br, I. $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $NR^2$, $P(=O)$ $(R^2)$, $-C(=O)O-$, $-C(=O)NR^2-$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^2$ radicals, or an aryloxy or heteroaryloxy group which has to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; or a combination of these systems; at the same time, two or more $R^1$ radicals together may form a ring system;

$R^2$ is the same or different at each instance and is H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $-R^3C=CR^3-$, $Si(R^3)_2$, $Si(R^3)_2$, $Ge(R^3)_2$, $Sn(R^3)_2$, $C=O$, $C=S$, $C=Se$, $C=NR^3$, $NR^3$, $P(=O)$ $(R^3)$, $-C(=O)O-$, $-C(=O)NR^3-$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^3$ radicals, or an aryloxy or heteroaryloxy group which has 5 to 40 aromatic ring atoms and may be substituted by one or more $R^3$ radicals, or an aralkyl or heteroaralkyl group which has 5 to 40 aromatic ring atoms and may be substituted by one or more $R^3$ radicals, or a diarylamino group, diheteroarylamino group or arylheteroarylamino group which has 10 to 40 aromatic ring atoms and may be substituted by one or more $R^3$ radicals, or a combination of these systems; at the same time, two or more $R^2$ substituents together may also form a ring system;

$R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more $R^3$ substituents together may also form a ring system.

Adjacent carbon atoms in the context of the present invention are carbon atoms bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

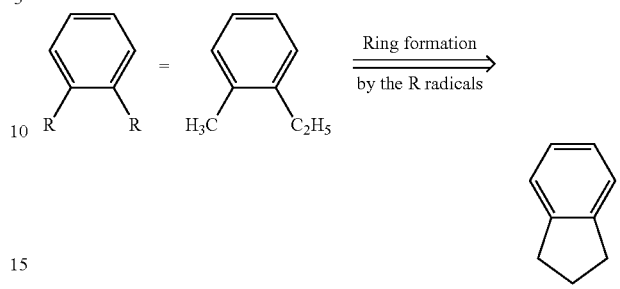

In addition, however, the abovementioned wording shall also be understood to mean that, if one of the two radicals is hydrogen, the second radical binds to the position to which the hydrogen atom was bonded, forming a ring. This shall be illustrated by the following scheme:

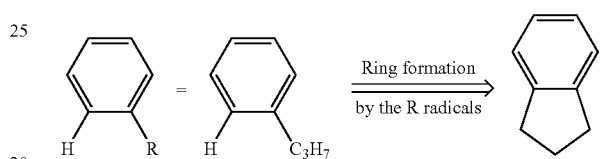

A fused aryl group, a fused aromatic ring system or a fused heteroaromatic ring system in the context of the present invention is a group in which two or more aromatic groups are fused, i.e. annelated, to one another along a common edge, such that, for example, two carbon atoms belong to the at least two aromatic or heteroaromatic rings, as, for example, in naphthalene. By contrast, for example, fluorene is not a fused aryl group in the context of the present invention, since the two aromatic groups in fluorene do not have a common edge. Corresponding definitions apply to heteroaryl groups and to fused ring systems which may but need not also contain heteroatoms.

An aryl group in the context of this invention contains 6 to 60 carbon atoms, preferably 6 to 40 carbon atoms; a heteroaryl group in the context of this invention contains 2 to 60 carbon atoms, preferably 2 to 40 carbon atoms, and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 60 carbon atoms, preferably 6 to 40 carbon atoms, in the ring system. A heteroaromatic ring system in the context of this invention contains 1 to 60 carbon atoms, preferably 1 to 40 carbon atoms, and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for a plurality of aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be replaced by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcycloheptyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl, A $C_1$- to $C_{40}$-alkoxy group is understood to mean, for example, methoxy, trifluoromethoxy, ethoxy, n-propoxy, i-propoxy, n-butoxy, butoxy, s-butoxy, t-butoxy or 2-methylbutoxy.

An aromatic or heteroaromatic ring system which has 5-60 aromatic ring atoms, preferably 5-40 aromatic ring atoms, and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

It may preferably be the case that, in the structure of formula (I), not more than 4, preferably not more than 2, of the symbols $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$ are not CH or CD or, in the structures of the formula (II), not more than 8, preferably not more than 4, of the symbols $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ are not CH or CD.

In a preferred configuration, the compounds of the invention may contain at least one structure of the formula (I-1) and/or (II-1)

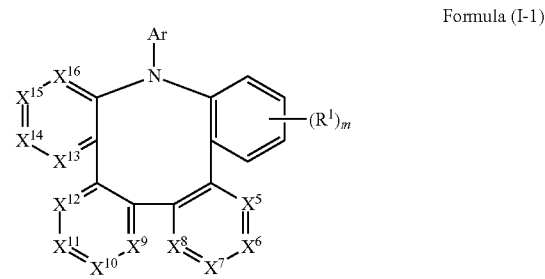

Formula (I-1)

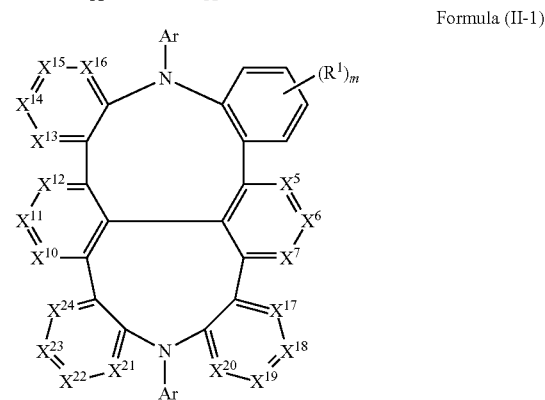

Formula (II-1)

where m is 0, 1, 2, 3 or 4, preferably 0, 1 or 2, and the symbols $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $R^1$ and Ar used have the definition given above, especially for formula (I) and/or (II), where preferably not more than two $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ groups per ring are N.

Preferably, the compounds of the invention may comprise structures of the formulae (I-2) and/or (II-2)

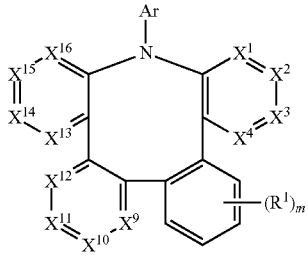

Formula (I-2)

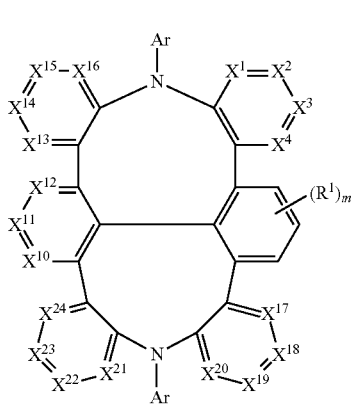

Formula (II-2)

where m is 0, 1, 2, 3 or 4, preferably 0, 1 or 2, and the symbols $X^1$, $X^2$, $X^3$, $X^4$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $R^1$ and Ar used have the definition given above, especially for formula (I) and/or (II), where preferably not more than two $X^1$, $X^2$, $X^3$, $X^4$, $X^9$, $X^{10}$, $X^{11}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ groups per ring are N.

Preferably, the compounds of the invention may comprise structures of the formulae (I-3) and/or (II-3)

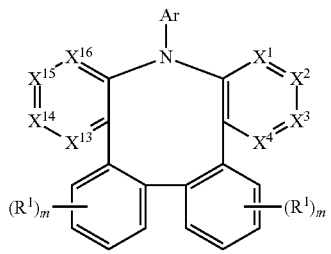

Formula (I-3)

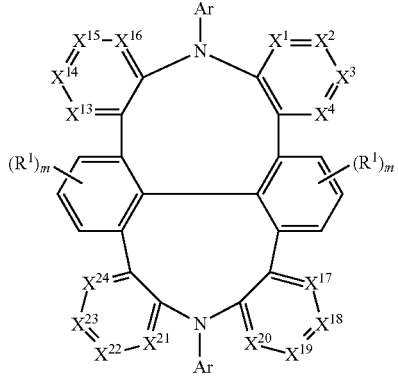

Formula (II-3)

where the symbols $X^1$, $X^2$, $X^3$, $X^4$, $X^{33}$, $X^{14}$, $X^{35}$, $X^{16}$, $X^{17}$, $X^{18}$, $X^{19}$, $X^{20}$, $X^{21}$, $X^{22}$, $X^{23}$, $X^{24}$, $R^1$ and Ar used have the definition set out above, especially for formula (I) and/or (II), and m is in each case independently 0, 1, 2, 3 or 4, preferably 0, 1 or 2, where preferably not more than two $X^1$, $X^2$, $X^3$, $X^4$, $X^5$, $X^6$, $X^7$, $X^8$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ groups per ring are N.

Preferably, the compounds of the invention may comprise structures of the formulae (I-4) and/or (II-4)

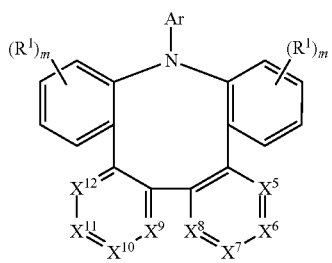

Formula (I-4)

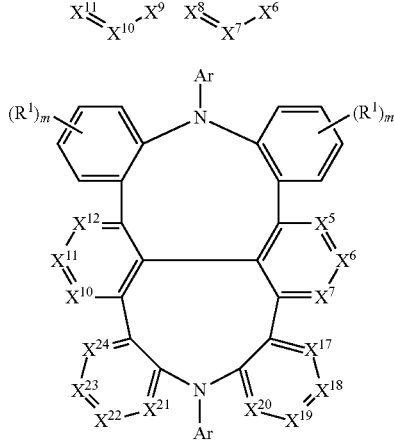

Formula (II-4)

where the symbols $X^5$, $X^6$, $X^7$, $X^8$, $X^9$, $X^{10}$, $X^{11}$, $X^{12}$, $X^{17}$, $X^{18}$, $X^{19}$, $X^{20}$, $X^{21}$, $X^{22}$, $X^{23}$, $X^{24}$, $R^1$ and Ar used have the definition set out above, especially for formula (I) and/or (II), and m is in each case independently 0, 1, 2, 3 or 4, preferably 0, 1 or 2, where preferably not more than two $X^1$, $X^2$, $X^3$, $X^4$, $X^5$, $X^6$, $X^7$, $X^8$, $X^9$, $X^{10}$, $X^{11}$, $X^{12}$, $X^{17}$, $X^{18}$, $X^{19}$, $X^{20}$, $X^{21}$, $X^{22}$, $X^{23}$, $X^{24}$ groups per ring are N.

In a further-preferred embodiment, the compounds of the invention may have structures of the formulae (III) and/or (IV)

Formula (III)

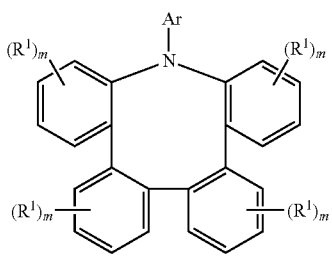

Formula (IV)

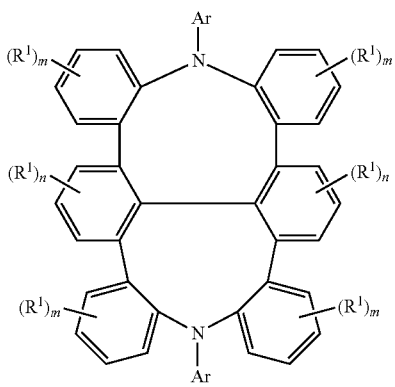

where the symbols $R^1$ and Ar used have the definition given above, especially for formula (I) and/or (II), and m at each instance is in each case independently 0, 1, 2, 3 or 4, preferably 0, 1 or 2, and n at each instance is in each case independently 0, 1, 2 or 3, preferably 0 or 1.

It may preferably be the case that the sum total of the indices m in the structure of the formula (III) is not more than 4, preferably not more than 2 and especially preferably 0, or the sum total of the indices m and n in the structure of the formula (IV) is not more than 6, preferably not more than 2 and especially preferably 0.

It may also be the case that the compounds of the invention comprise structures of the formulae (V) and/or (VI)

Formula (V)

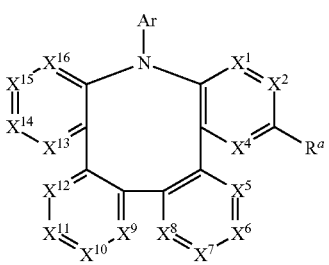

Formula (VI)

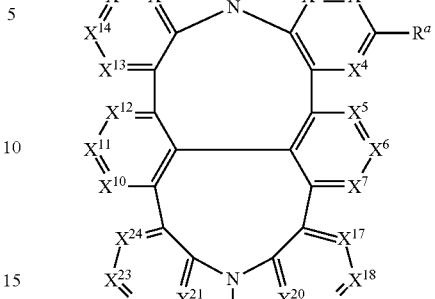

where $R^a$ is F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by —$R^2C=CR^2$—, —C≡C—, $Si(R^2)_2$, $Ge(R^2)_2$, $Sn(R^2)_2$, C=O, C=S, C=Se, C=$NR^2$, $NR^2$, $P(=O)(R^2)$, —C(=O)O—, —C(=O)$NR^2$—, —O—, —S—, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; or a combination of these systems; at the same time, the $R^a$ radical may form a ring system together with an $R^1$ radical or with the ring to which it is bonded;

the symbols $X^1, X^2, X^4, X^5, X^6, X^7, X^8, X^9, X^{10}, X^{11}, X^{12}, X^{13}, X^{14}, X^{15}, X^{16}, X^{17}, X^{18}, X^{19}, X^{20}, X^{21}, X^{22}, X^{23}, X^{24}$, $R^1, R^2$ and Ar used have the definition given above, especially for formula (I) and or (II), where preferably not more than two $X^1, X^2, X^4, X^5, X^6, X^7, X^8, X^9, X^{10}, X^{11}, X^{12}, X^{13}, X^{14}, X^{15}, X^{16}, X^{17}, X^{18}, X^{19}, X^{20}, X^{21}, X^{22}, X^{23}, X^{24}$ groups per ring are N.

It may preferably be the case that, in the structure of the formula (V), not more than three, preferably not more than one, of the symbols $X^1, X^2, X^4, X^5, X^6, X^7, X^8, X^9, X^{10}, X^{11}, X^{12}, X^{13}, X^{14}, X^{15}, X^{16}$ are not $CH_{or}$ CD or, in the structures of the formula (VI), not more than five, preferably not more than three, of the symbols $X^1, X^2, X^3, X^4, X^5, X^6, X^7, X^8, X^9, X^{10}, X^{11}, X^{12}, X^{13}, X^{14}, X^{15}, X^{16}, X^{17}, X^{18}, X^{19}, X^{20}, X^{21}, X^{22}, X^{23}, X^{24}$ are not CH or CD.

It may additionally be the case that the compounds of the invention comprise structures of the formulae (V-1) and/or (VI-1)

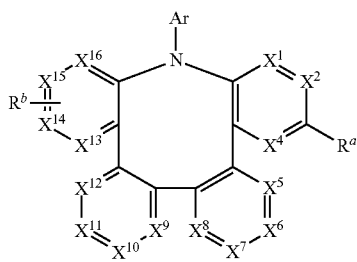

Formula (V-1)

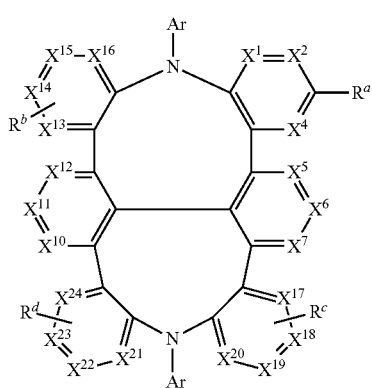

Formula (VI-1)

where $R^b$, $R^c$, $R^d$ at each instance are each independently F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $Si(R^2)_2$, $Ge(R^2)_2$, $Sn(R^2)_2$, $C=O$, $C=S$, $C=Se$, $C=NR^2$, $NR^2$, $P(=O)(R^2)$, $-C(=O)O-$, $-C(=O)NR^2-$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^2$ radicals, or an aryloxy or heteroaryloxy group which has 5 to 40 aromatic ring atoms and may be substituted by one or more $R^2$ radicals, or an aralkyl or heteroalkyl group which has 5 to 40 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; or a combination of these systems; at the same time, the $R^b$, $R^c$ and/or $R^d$ radicals may form a ring system together with an $R^1$ radical or with the ring to which they are bonded;

the symbols $X^1$, $X^2$, $X^4$, $X^5$, $X^6$, $X^7$, $X^8$, $X^9$, $X^{10}$, $X^{11}$, $X^{12}$, $R^1$, $R^2$ and Ar used have the definition given above, especially for formula (I) and/or (II), $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ are N or $CR^1$ or, in the case of the attachment site for the $R^b$, $R^c$ or $R^d$ group, are C, where preferably not more than two of the $X^1$, $X^2$, $X^4$, $X^5$, $X^6$, $X^7$, $X^8$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ groups per ring are N.

It may preferably be the case that, in the structure of the formula (V-1), not more than 2, preferably not more than 1, of the symbols $X^1$, $X^2$, $X^4$, $X^5$, $X^6$, $X^8$, $X^9$, $X^{11}$, $X^{12}$, $X^{13}$, $X^{14}$, $X^{15}$, $X^{16}$ are not C, CH or CD or, in the structures of the formula (VI), not more than 4, preferably not more than 2, of the symbols $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ are not C, CH or CD.

Furthermore, preference is given to compounds having structures of formulae (I), (II), (III-1), (II-1), (I-2), (II-2), (I-3), (II-3), (I-4), (II-4), (V), (VI), (V-1) and/or (VI-2) in which at least eight, preferably at least ten, of the symbols $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$ are $CR^1$, more preferably at least eight of the symbols $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$ are selected from C—H and C-D. More preferably, in structures of formulae (I), (II), (III-1), (II-1), (I-2), (II-2), (I-3), (II-3), (I-4), (II-4), (V), (VI), (V-1) and/or (VI-2), all the symbols $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$ are $CR^1$ or C in the case of an attachment site, where preferably at most 4 of the symbols $X^1$, $X^2$, $X^3$, $X^4$, $X^5$, $X^6$, $X^7$, $X^8$, $X^9$, $X^{10}$, $X^{11}$, $X^{12}$, $X^{11}$, $X^{14}$, $X^{15}$ are not C—H and C-D.

Furthermore, preference is given to compounds having structures of formulae (II), (II-1), (II-2), (II-3), (II-4), (VI) and/or (VI-1) which are characterized in that at least four, preferably all, symbols $X^{17}$, $X^{18}$, $X^{19}$, $X^{20}$, $X^{21}$, $X^{22}$, $X^{23}$, $X^{24}$ are $CR^1$ or C in the case of an attachment site, where at least four of the symbols $X^{17}$, $X^{18}$, $X^{19}$, $X^{20}$, $X^{21}$, $X^{22}$, $X^{23}$, $X^{24}$ are selected from C—H and C-D.

It may additionally be the case that, in structures of formulae (I), (II), (III-1), (II-1), (I-2), (II-2), (I-3), (II-3), (I-4), (II-4), (V), (VI) (V-1) and/or (VI-2), at least two of the symbols $X^1$, $X^2$, $X^3$, $X^4$, $X^5$, $X^6$, $X^7$, $X^8$, $X^8$, $X^{10}$, $X^{11}$, $X^{12}$, $X^{13}$, $X^{14}$, $X^{15}$, $X^{16}$ are N and these nitrogen atoms are nonadjacent; preferably, the structure of one of the formulae (I), (II), (III-1), (II-1), (I-2), (II-2), (I-3), (II-3), (I-4), (II-4), (V), (VI), (V-1) and/or (VI-2) does not have any two adjacent nitrogen atoms.

Preference is further given to compounds comprising structures of the formulae (V-2) and/or (VI-2)

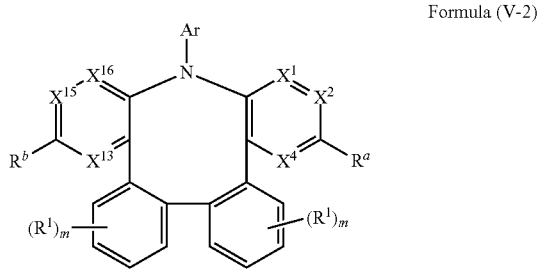

Formula (V-2)

-continued

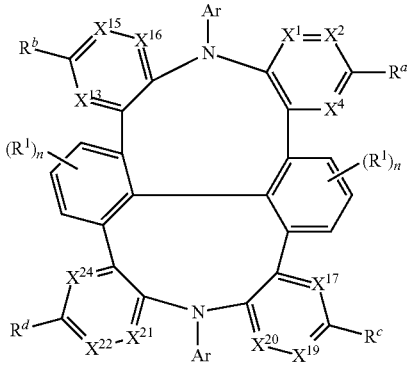

Formula (VI-2)

where the symbols $X^1$, $X^2$, $X^4$, $X^{13}$, $X^{15}$, $X^{16}$, $X^{17}$, $X^{18}$, $X^{19}$, $X^{20}$, $X^{21}$, $X^{22}$, $X^{23}$, $X^{24}$, $R^1$ and Ar have the definition given above, especially for formula (I) and/or (II), the symbols $R^a$, $R^b$, $R^c$ and $R^d$ have the definition given above, especially for formulae (V) and or (VI), and n at each instance is independently 0, 1, 2 or 3, preferably 0 or 1, where the symbols $X^1$ and $X^2$ or $X^{15}$ and $X^{16}$ or $X^{19}$ and $X^{29}$ or $X^{21}$ and $X^{22}$ are preferably not simultaneously N, such that there are preferably no two adjacent N in a heteroaromatic ring.

The preferences set out above for formula (V) and/or (VI) in relation to the $X^1$, $X^2$, $X^4$, $X^{13}$, $X^{15}$, $X^{16}$, $X^{17}$, $X^{18}$, $X^{19}$, $X^{20}$, $X^{21}$, $X^{22}$, $X^{23}$, $X^{24}$ radicals are also applicable to the formulae (V-2) and/or (VI-2), and so these radicals are preferably $CR^1$ and more preferably CH or CD.

In a further-preferred embodiment, the compounds of the invention may comprise structures of the formulae (V-3) and/or (VI-3)

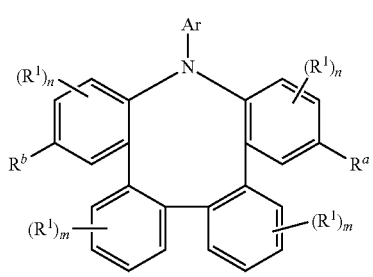

Formula (V-3)

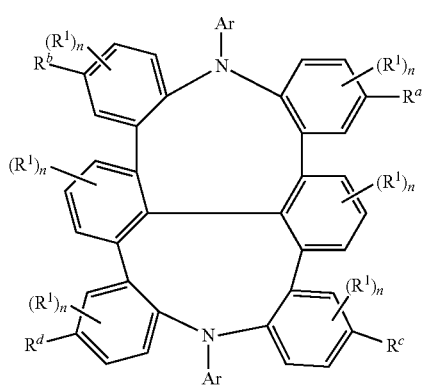

Formula (VI-3)

where the symbols $R^1$ and Ar used have the definition given above, especially for formula (I) and/or (II), the symbols $R^a$, $R^b$, $R^c$ and $R^d$ have the definition given above, especially for formula (V) and or (VI), and m at each instance is in each case independently 0, 1, 2, 3 or 4, preferably 0, 1 or 2, and n at each instance is in each case independently 0, 1, 2 or 3, preferably 0 or 1.

Especially preferably, the sum total of the indices n and m, or n in the formulae (V-3) or (VI-3), is not more than 4, more preferably not more than 2 and especially preferably 0.

Preference is further given to compounds having structures of the formulae (V), (VI), (V-1), (VI-1), (V-2), (VI-2), (V-3) and/or (VI-3) which are characterized in that at least one, preferably at least two and more preferably all of the $R^a$, $R^b$, $R^c$ and $R^d$ radicals are in each case independently a straight-chain alkyl, alkoxy or thioalkoxy group having 1 to 40 carbon atoms, preferably having 1 to 10 carbon atoms, a branched or cyclic alkyl, alkoxy or thioalkoxy group having 3 to 40 carbon atoms, preferably having 1 to 10 carbon atoms, or an aromatic or heteroaromatic ring system having 5 to 40 aromatic ring atoms, preferably having 5 to 24 aromatic ring atoms, especially preferably having 5 to 18 aromatic ring atoms, which may be substituted by one or more $R^2$ radicals, preferably an aromatic or heteroaromatic ring system having 5 to 40 aromatic ring atoms, preferably having 5 to 24 aromatic ring atoms, especially preferably having 5 to 18 aromatic ring atoms, which may be substituted by one or more $R^2$ radicals, more preferably an aryl group or a heteroaryl group having 5 to 40 aromatic ring atoms, preferably having 5 to 24 aromatic ring atoms, especially preferably having 5 to 18 aromatic ring atoms, which may be substituted by one or more $R^2$ radicals, very particular preference being given to aryl groups having 6 to 40 aromatic ring atoms, preferably having 5 to 24 aromatic ring atoms, especially preferably having 5 to 18 aromatic ring atoms.

Preference is also given to compounds having structures of the formulae (V), (VI), (V-1), (VI-1), (V-2), (VI-2), (V-3) and/or (VI-3) in which at least two, preferably all, of the $R^a$, $R^b$, $R^c$ and $R^d$ radicals are the same.

In a preferred embodiment, a compound of the invention may have two or more structural units of the formula (I) and/or (II) or preferred embodiments thereof. In this case, the structural unit, rather than a hydrogen atom or a substituent, may have one or more bonds to a further group having a structural unit of the formula (I) and/or (II).

Preferably, a joining group may be joined in each case to the nitrogen atom of the heterocycle shown in formula (I) and/or to one of the nitrogen atoms in the heterocycle shown in formula (II), such that the joining group constitutes a substructure of the Ar group or the Ar group can be represented by the joining group, where a further heterocycle having at least 4 aromatic or heteroaromatic rings and one nitrogen atom is bonded to this joining group. The joining group is preferably an aromatic or heteroaromatic ring system having 5 to 30 aromatic or heteroaromatic ring atoms, preferably an aromatic ring system which has 6 to 12 carbon atoms and may be substituted by one or more $R^1$ radicals.

It may preferably be the case that the compounds of the invention comprise structures of the formula (VII)

Formula (VII)

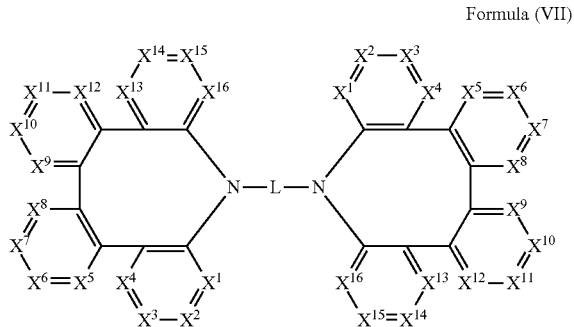

where L is aromatic or heteroaromatic ring system which has 5 to 30 aromatic or heteroaromatic ring atoms and may be substituted by one or more $R^1$ radicals and the symbols $R^1$, $X^1, X^2, X^3, X^4, X^5, X^6, X^7, X^8, X^9, X^{10}, X^{11}, X^{12}, X^{13}, X^{14}, X^{15}$ and $X^{16}$ used have the definition given above, especially for formulae (I) and/or (II), where preferably not more than two $X^5, X^6, X^7, X^8, X^9, X^{10}, X^{11}, X^{12}, X^{13}, X^{14}, X^{15}, X^{16}, X^{17}, X^{18}, X^{19}, X^{20}, X^{21}, X^{22}, X^{23}, X^{24}$ groups per ring are N.

In a further preferred embodiment of the invention, L is a bond or an aromatic or heteroaromatic ring system which has 5 to 24, preferably 5 to 18, more preferably 6 to 13, aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formula (I) and/or (II).

Preferably, the L group may form through-conjugation with the nitrogen atom to which the L group of formula (VII) is bonded.

Further preferably, the symbol L shown in formula (VII) inter alia is the same or different at each instance and is a bond or an aryl or heteroaryl radical having 5 to 24 ring atoms, preferably 6 to 13 ring atoms, more preferably 6 to 12 ring atoms, such that an aromatic or heteroaromatic group of an aromatic or heteroaromatic ring system is bonded to the respective atom of the further group directly, i.e. via an atom of the aromatic or heteroaromatic group.

The preferred embodiments set out above especially with regard to compounds having structures of the formula (I), as set out, for example, in the formulae (I-1), (I-2), (I-3), (I-4), (III), (V), (V-1), (V-2) and (V-3), are also correspondingly applicable to compounds of formula (VII). For example, compounds of formula (VII) may likewise have radicals of the formulae $R^a$ and/or $R^b$ in place of the radicals mentioned. In this case, these compounds may preferably comprise structures in which two groups of the above-detailed formulae (I-1), (I-2), (I-3), (I-4), (III), (V), (V-1), (V-2) and (V-3) are bonded via an L group, where the groups of the formulae (I-1), (I-2), (I-3), (I-4), (III), (V), (V-1), (V-2) and (V-3) do not comprise an Ar radical but are bonded to one another via the L group.

It may additionally be the case that the $R^1$ substituents of the heteroaromatic ring system of the formulae (I), (II), (III-1), (II-1), (I-2), (II-2), (I-3), (II-3), (I-4), (II-4), (III), (IV), (V), (VI), (V-1), (VI-1), (V-2), (VI-2), (V-3), (VI-3) and/or (VII) do not form a fused aromatic or heteroaromatic ring system, preferably any fused ring system, with the ring atoms of the heteroaromatic ring system. This includes the formation of a fused ring system with possible $R^2$, $R^3$ substituents which may be bonded to the $R^1$ radicals. It may preferably be the case that the $R^1$ substituents of the heteroaromatic ring system of the formulae (I), (II), (III-1), (II-1), (I-2), (II-2), (I-3), (II-3), (I-4), (II-4), (III), (IV), (V), (VI), (V-1), (VI-1), (V-2), (VI-2), (V-3), (VI-3) and/or (VII) do not form any ring system with the ring atoms of the heteroaromatic ring system. This includes the formation of a ring system with possible $R^2$, $R^3$ substituents which may be bonded to the $R^1$ radicals.

It may further be the case that the $R^a$, $R^b$, $R^c$ and/or $R^d$ substituents of the heteroaromatic ring system of the formulae (V), (VI), (V-1), (VI-1), (V-2), (VI-2), (V-3) and/or (VI-3) do not form a fused aromatic or heteroaromatic ring system, preferably any fused ring system, with the ring atoms of the heteroaromatic ring system. This includes the formation of a fused ring system with possible $R^2$, $R^3$ substituents which may be bonded to the $R^a$, $R^b$, $R^c$ and/or $R^d$ radicals. It may preferably be the case that the $R^a$, $R^b$, $R^c$ and/or $R^d$ substituents heteroaromatic ring system of the formulae (V), (VI), (V-1), (VI-1), (V-2), (VI-2), (V-3) and/or (VI-3) do not form any fused ring system with the ring atoms of the heteroaromatic ring system. This includes the formation of a ring system with possible $R^2$, $R^3$ substituents which may be bonded to the $R^a$, $R^b$, $R^c$ and/or $R^d$ radicals.

When two radicals that may especially be selected from $R^1, R^2, R^3, R^a, R^b, R^c$ and/or $R^d$ form a ring system with one another, this ring system may be mono- or polycyclic, aliphatic, heteroaliphatic, aromatic or heteroaromatic.

In this case, the radicals which together form a ring system may be adjacent, meaning that these radicals are bonded to the same carbon atom or to carbon atoms directly bonded to one another, or they may be further removed from one another.

In a preferred configuration, inventive compounds can be represented by structures of the formula (I), (II), (III-1), (II-1), (I-2), (II-2), (I-3), (II-3), (I-4), (II-4), (III), (IV), (V), (VI), (V-1), (VI-1), (V-2), (VI-2), (V-3), (VI-3) and/or (VII). Accordingly, preference is given to compounds of a structure of the formula (I), (II), (III-1), (II-1), (I-2), (II-2), (I-3), (II-3), (I-4), (II-4), (III), (IV), (V), (VI), (V-1), (VI-1), (V-2), (VI-2), (V-3), (VI-3) and/or (VII). Preferably, compounds comprising structures of formula (I), (II), (III-1), (II-1), (I-2), (II-2), (I-3), (II-3), (I-4), (II-4), (III), (IV), (V), (VI), (V-1), (VI-1), (V-2), (VI-2), (V-3), (VI-3) and/or (VII) have a molecular weight of not more than 5000 g/mol, preferably not more than 4000 g/mol, particularly preferably not more than 3000 g/mol, especially preferably not more than 2000 g/mol and most preferably not more than 1200 g/mol.

In addition, it is a feature of preferred compounds of the invention that they are sublimable. These compounds generally have a molar mass of less than about 1200 g/mol.

In a further preferred embodiment, it may be the case that the Ar, $R^a$, $R^b$, $R^c$ and/or $R^d$ group in the structures shown above is selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, pyrenyl, triazinyl, imidazolyl, benzimidazolyl, benzoxazolyl, benzothiazolyl, 1-, 2-, 3- or 4-carbazolyl, 1- or 2-naphthyl, anthracenyl, preferably 9-anthracenyl, phenanthrenyl and/or triphenylenyl, each of which may be substituted by one or more $R^2$ radicals, except fluorenyl and carbazolyl, but are preferably unsubstituted, particular preference being given to spirobifluorene, fluorene, dibenzofuran, dibenzothiophene, anthracene, phenanthrene, triphenylene groups.

In a further embodiment, the Ar group and/or one of the $R^1$, $R^a$, $R^b$, $R^c$ and/or $R^d$ radicals is a group selected from arylamino groups, preferably di- or triarylamino groups, heteroarylamino groups, preferably di- or triheteroarylamino groups, carbazole groups, preference being given to carbazole groups. These groups may also be regarded as a hole-transporting group.

It may preferably be the case that the Ar group and/or one of the $R^1$, $R^a$, $R^b$, $R^c$ and/or $R^d$ radicals comprises a group, preferably is a group, selected from the group consisting of the formulae (H-1) to (H-3)

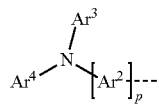

Formula (H-1)

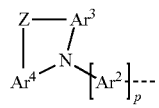

Formula (H-2)

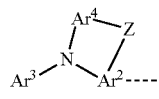

Formula (H-3)

where the dotted bond marks the position of attachment and $Ar^2$, $Ar^3$, $Ar^4$ are each independently an aryl group having 6 to 40 carbon atoms or a heteroaryl group having 3 to 40 carbon atoms, each of which may be substituted by one or more $R^2$ radicals;

p is 0 or 1, and

Z is a bond, $C(R^2)_2$, $Si(R^2)_2$, C=O, N—$Ar^1$, $BR^2$, $PR^2$, $POR^2$, SO, $SO_2$, Se, O or S, preferably $C(R^2)_2$, N—$Ar^2$, O or S, where the $R^2$ radical has the definition given above, especially for formula (I) and/or (II), and $Ar^1$ represents an aromatic or heteroaromatic ring system which has 5 to 40 aromatic ring atoms and may be substituted in each case by one or more $R^2$ radicals, an aryloxy group which has 5 to 40 aromatic ring atoms and may be substituted in each case by one or more $R^2$ radicals, or an aralkyl group which has 5 to 40 aromatic ring atoms and may be substituted in each case by one or more $R^2$ radicals, where it is optionally possible for two or more, preferably adjacent $R^2$ substituents to form a mono- or polycyclic, aliphatic, heteroaliphatic, aromatic or heteroaromatic ring system which may be substituted by one or more $R^3$ radicals.

If the Ar group is a radical of the formulae (H-1) to (H-3), p is preferably 1, such that no N—N bond is formed. The nitrogen atom of the groups formula (H-1) and (H-2) may bind directly to a ring in a structure of formula (I) and/or formula (II), in which case the index p is 0.

It may additionally be the case that the Ar group and/or one of the $R^1$, $R^a$, $R^b$, $R^c$ and/or $R^d$ radicals comprises a group, preferably is a group, selected from the group consisting of the formulae (H-4) to (H-26)

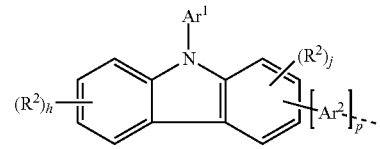

Formula (H-4)

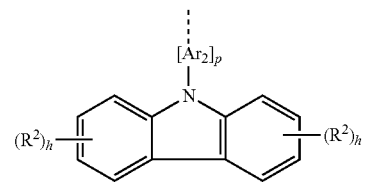

Formula (H-5)

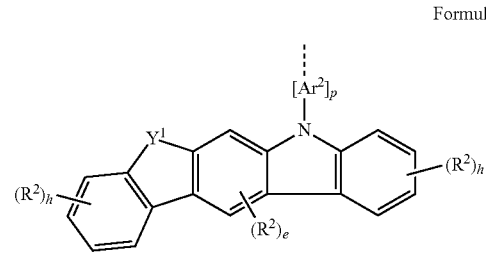

Formula (H-6)

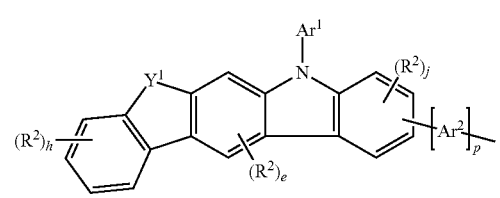

Formula (H-7)

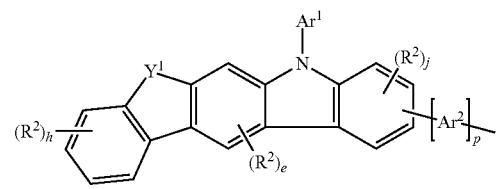

Formula (H-8)

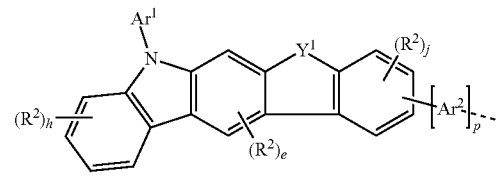

Formula (H-9)

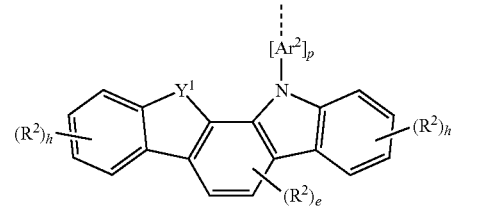

Formula (H-10)

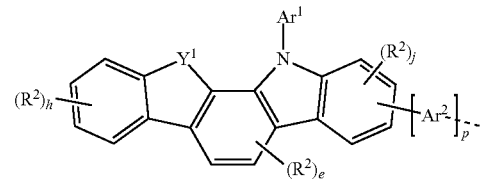

Formula (H-11)
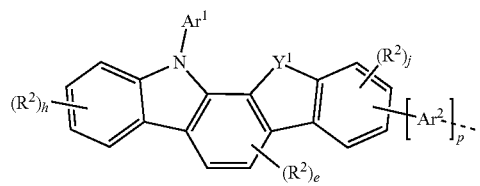
Formula (H-12)
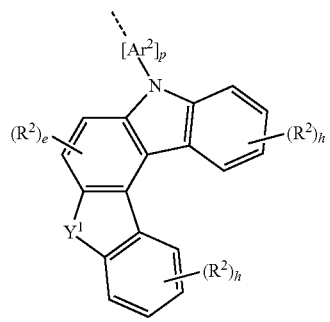
Formula (H-13)
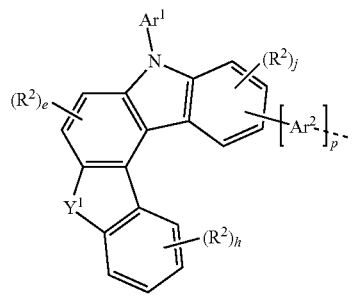
Formula (H-14)
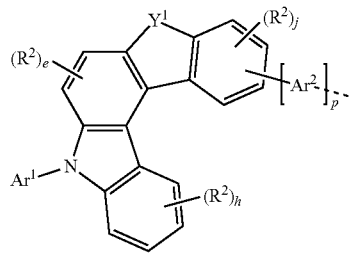
Formula (H-15)
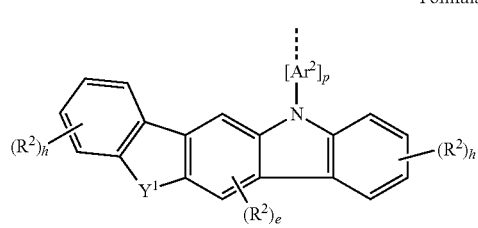
Formula (H-16)
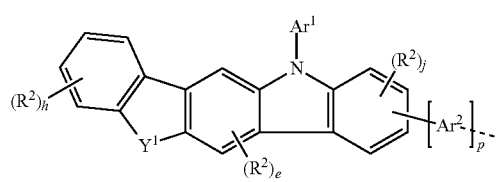
Formula (H-17)
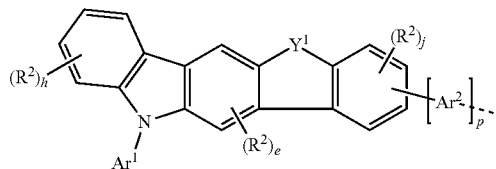
Formula (H-18)
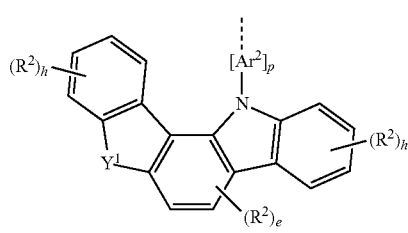
Formula (H-19)
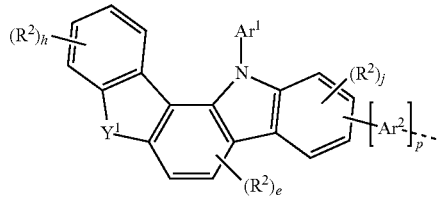
Formula (H-20)
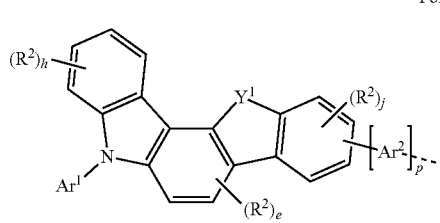
Formula (H-21)
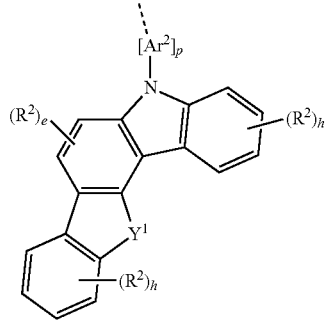
Formula (H-22)
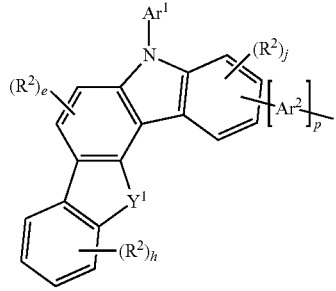

Formula (H-23)

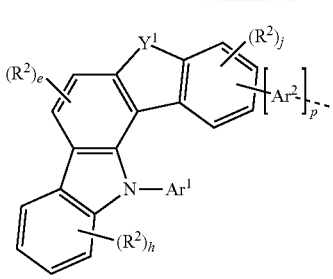

Formula (H-24)

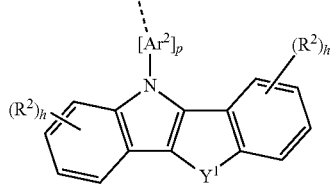

Formula (H-25)

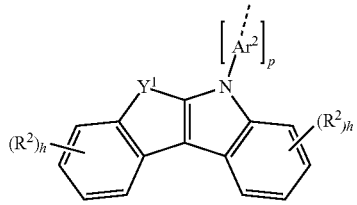

Formula (H-26)

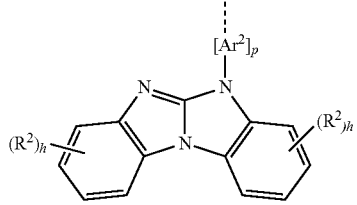

where $Y^1$ is O, S, $C(R^2)_2$ or $NAr^1$, the dotted bond marks the attachment position, e is 0, 1 or 2, j is 0, 1, 2 or 3, h is 0, 1, 2, 3 or 4, p is 0, 1, 2, 3, 4, 5 or 6, preferably 0, 1, 2 or 3 and more preferably 0, 1 or 2, $Ar^1$ and $Ar^2$ have the definition given above, especially for formula (H-1) or (H-2), and $R^2$ has the definition given above, especially for formula (I) and/or (II).

If the Ar group is a radical of the formulae (H-1), (H-2), (H-3), (H-5), (H-6), (H-9), (H-12), (H-15), (H-18), (H-21) and/or (H-24) to (H-26), p is preferably 1, such that no N—N bond is formed.

Of the groups (H-1) to (H-26), preference is given to carbazole groups, especially the groups (H-4) to (H-26).

Preferably, the $Ar^2$ group may form through-conjugation with the aromatic or heteroaromatic radical or the nitrogen atom to which the $Ar^2$ group of the formulae (H-1) to (H-26) may be bonded.

In a further preferred embodiment of the invention, $Ar^2$ is an aromatic or heteroaromatic ring system which has 5 to 14 aromatic or heteroaromatic ring atoms, preferably an aromatic ring system which has 6 to 12 carbon atoms, and which may be substituted by one or more $R^2$ radicals, but is preferably unsubstituted, where $R^2$ may have the definition given above, especially for formula (I) and/or (II). More preferably, $Ar^2$ is an aromatic ring system having 6 to 10 aromatic ring atoms or a heteroaromatic ring system having 6 to 13 heteroaromatic ring atoms, each of which may be substituted by one or more $R^2$ radicals, but is preferably unsubstituted, where $R^2$ may have the definition given above, especially for formula (I) and/or (II).

Further preferably, the symbol $Ar^2$ shown in formulae (H-1) to (H-26) inter alia is an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded to the respective atom of the further group directly, i.e. via an atom of the aromatic or heteroaromatic group.

It may further be the case, for compounds that are used as hole transport materials or host materials, that the $Ar^2$ group shown in formulae (H-1) to (H-26) comprises an aromatic ring system having not more than two fused aromatic and/or heteroaromatic rings, preferably does not comprise any fused aromatic or heteroaromatic ring system. Accordingly, naphthyl structures are preferred over anthracene structures. In addition, fluorenyl, spirobifluorenyl, dibenzofuranyl and/or dibenzothienyl structures are preferred over naphthyl structures. Particular preference is given to structures having no fusion, for example phenyl, biphenyl, terphenyl and/or quaterphenyl structures.

In compounds that find use as fluorescent emitters, it is also possible for more highly fused ring systems than $Ar^2$ to occur, for example phenanthrene, anthracene or pyrene groups.

Examples of suitable aromatic or heteroaromatic ring systems $Ar^2$ are selected from the group consisting of ortho-, meta- or para-phenylene, ortho-, meta- or para-biphenylene, terphenylene, especially branched terphenylene, quaterphenylene, especially branched quaterphenylene, fluorenylene, spirobifluorenylene, dibenzofuranylene, dibenzothienylene and carbazolylene, each of which may be substituted by one or more $R^2$ radicals, but are preferably unsubstituted.

It may further be the case that the $Ar^2$ group shown in formulae (H-1) to (H-26) inter alia has not more than 1 nitrogen atom, preferably not more than 2 heteroatoms, particularly preferably not more than one heteroatom and especially preferably no heteroatom.

In a further preferred embodiment of the invention, $Ar^3$ and/or $Ar^4$ are the same or different at each instance and are an aromatic or heteroaromatic ring system having 6 to 24 aromatic ring atoms, preferably 6 to 18 aromatic ring atoms, and are more preferably an aromatic ring system having 6 to 12 aromatic ring atoms or a heteroaromatic ring system having 6 to 13 aromatic ring atoms, each of which may be substituted by one or more $R^2$ radicals, but is preferably unsubstituted, where $R^2$ may have the definition given above, especially in formula (I) and/or (II). Examples of suitable $Ar^3$ and/or $Ar^4$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^3$ radicals, but are preferably unsubstituted.

Preferably, the $R^2$ radicals do not form a fused ring system with the ring atoms of the aryl group or heteroaryl group $Ar^1$, $Ar^2$, $Ar^3$ and/or $Ar^4$ to which the $R^2$ radicals in the formulae (H-1) to (H-26) may be bonded. This includes the formation of a fused ring system with possible $R^3$ substituents which may be bonded to the $R^2$ radicals.

In a preferred embodiment, the Ar group and/or one of the $R^1$, $R^a$, $R^b$, $R^c$ and/or $R^d$ radicals may comprise, preferably constitute, an electron transport group. Electron transport groups are widely known in the technical field and promote the ability of compounds to transport and/or conduct electrons.

Furthermore, surprising advantages are exhibited by compounds comprising at least one structure of formula (I) and/or (II) or preferred embodiments thereof, in which the Ar group in formulae (V) and/or (VI) or the preferred embodiments thereof, or one of the $R^1$, $R^a$, $R^b$, $R^c$ and/or $R^d$ radicals, comprises at least one structure selected from the group of the pyridines, pyrimidines, pyrazines, pyridazines, triazines, quinazolines, quinoxalines, quinolines, isoquinolines, imidazoles and/or benzimidazoles, particular preference being given to pyrimidines, triazines and quinazolines.

In a preferred configuration of the present invention, it may be the case that the Ar group and/or one of the $R^1$, $R^a$, $R^b$, $R^c$ and/or $R^d$ radicals is a group that can be represented by the formula (QL)

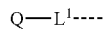

Formula (QL)

in which $L^1$ represents a bond or an aromatic or heteroaromatic ring system which has 5 to 40, preferably 5 to 30, aromatic ring atoms and may be substituted by one or more $R^2$ radicals, and Q is an electron transport group, where $R^2$ has the definition given above, especially for formula (I) and/or (II).

Preferably, the Q group shown in the formula (QL) inter alia may be selected from structures of the formulae (Q-1), (Q-2), (Q-3), (Q-4) and/or (Q-5)

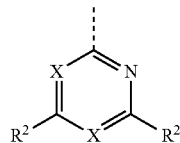

Formula (Q-1)

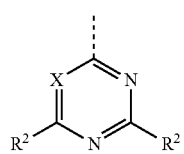

Formula (Q-2)

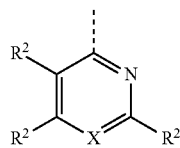

Formula (Q-3)

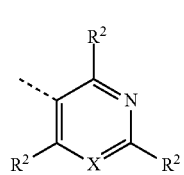

Formula (Q-4)

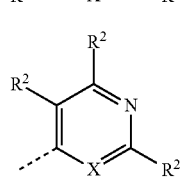

Formula (Q-5)

where the symbol $R^2$ has the definition given for formula (I) and/or (II) inter alia, X is N or $CR^2$ and the dotted bond marks the attachment position, where X is preferably a nitrogen atom.

In a further embodiment, the Q group shown in the formula (QL) inter alia may be selected from structures of the formulae (Q-6), (Q-7), (Q-8), (Q-9), (Q-10), (Q-11) and/or (Q-12)

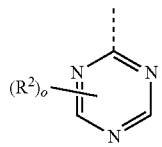

Formula (Q-6)

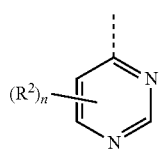

Formula (Q-7)

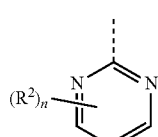

Formula (Q-8)

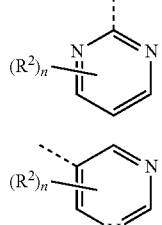

Formula (Q-9)

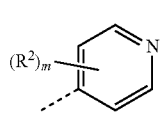

Formula (Q-10)

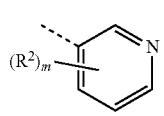

Formula (Q-11)

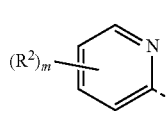

Formula (Q-12)

in which the symbol $R^2$ has the definition detailed above for formula (I) and/or (II) inter alia, the dotted bond marks the attachment position and m is 0, 1, 2, 3 or 4, preferably 0, 1 or 2, n is 0, 1, 2 or 3, preferably 0, 1 or 2, and o is 0, 1 or 2, preferably 1 or 2. Preference is given here to the structures of the formulae (Q-6), (Q-7), (Q-8) and (Q-9).

In a further embodiment, the Q group shown in the formula (QL) inter alia may be selected from structures of the formulae (Q-13), (Q-14) and/or (Q-15)

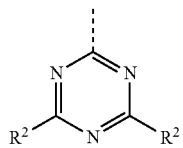

Formula (Q-13)

Formula (Q-14)

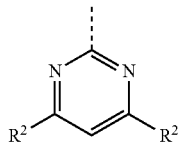

Formula (Q-15)

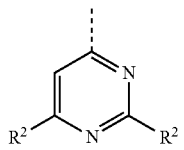

in which the symbol R² has the definition set out above for formula (I) and/or (II) inter alia, and the dotted bond marks the position of attachment.

In a further embodiment, the Q group shown in the formula (QL) inter alia may be selected from structures of the formulae (Q-16), (Q-17), (Q-18), (Q-19) and/or (Q-20)

Formula (Q-16)

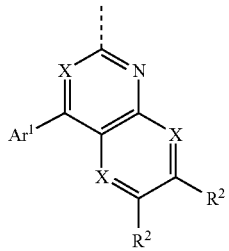

Formula (Q-17)

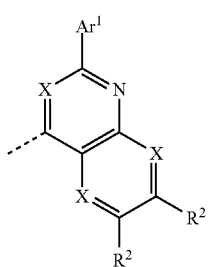

Formula (Q-18)

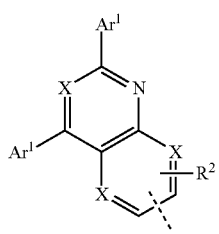

Formula (Q-19)

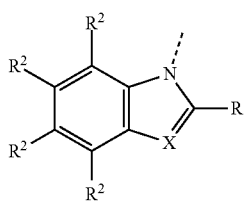

Formula (Q-20)

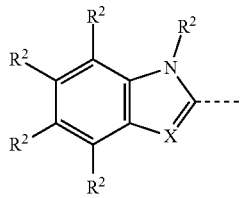

where X is N or CR², the symbol R² has the definition given above for formula (I) and/or (II) inter alia, the dotted bond marks the attachment position and Ar¹ represents an aromatic or heteroaromatic ring system which has 5 to 40 aromatic ring atoms and may be substituted in each case by one or more R² radicals, an aryloxy group which has 5 to 40 aromatic ring atoms and may be substituted by one or more R² radicals, or an aralkyl group which has 5 to 40 aromatic ring atoms and may be substituted in each case by one or more R² radicals, where it is optionally possible for two or more, preferably adjacent R² substituents to form a mono- or polycyclic, aliphatic ring system which may be substituted by one or more R³ radicals.

Preferably, the Q group shown in the formula (QL) inter alia may be selected from structures of the formulae (Q-21), (Q-22), (Q-23), (Q-24), (Q-25), (Q-26), (Q-27), (Q-28), (Q-29), (Q-30), (Q-31), (Q-32), (Q-33) and/or (Q-34)

Formula (Q-21)

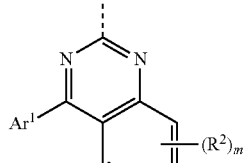

Formula (Q-22)

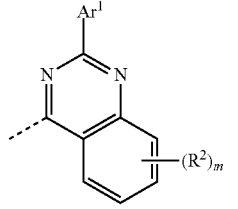

Formula (Q-23)

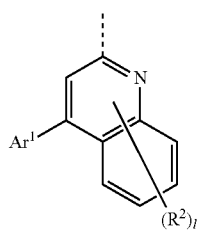

Formula (Q-24)

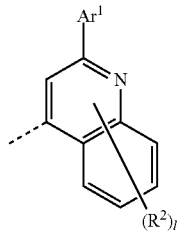

Formula (Q-25)
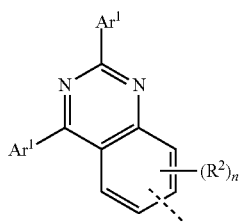

Formula (Q-26)
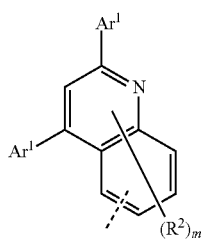

Formula (Q-27)
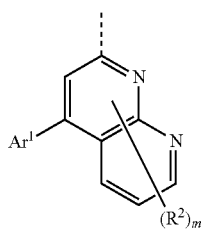

Formula (Q-28)
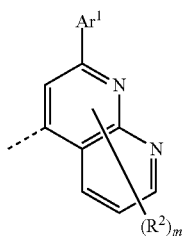

Formula (Q-29)
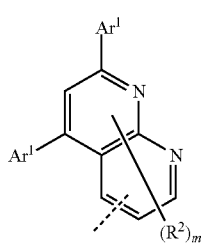

Formula (Q-30)
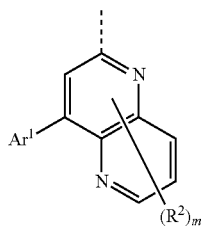

Formula (Q-31)
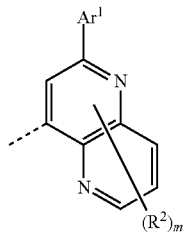

Formula (Q-32)
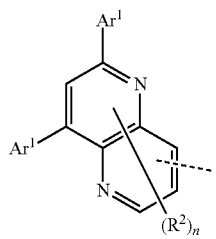

Formula (Q-33)

Formula (Q-34)
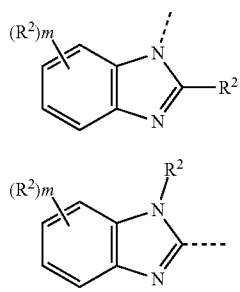

in which the symbols $Ar^1$ have the definition set out above for formula (Q-16), (Q-17) or (Q-18) inter alia and $R^2$ has the definition set out above for formula (I) and/or (II) inter alia, the dotted bond marks the attachment position and m is 0, 1, 2, 3 or 4, preferably 0, 1 or 2, n is 0, 1, 2 or 3, preferably 0, 1 or 2, and l is 1, 2, 3, 4 or 5, preferably 0, 1 or 2.

Preferably, the symbol $Ar^1$ is an aryl or heteroaryl radical, such that an aromatic or heteroaromatic group of an aromatic or heteroaromatic ring system is bonded directly, i.e. via an atom of the aromatic or heteroaromatic group, to the respective atom of the further group, for example a carbon or nitrogen atom of the (H-1) to (H-26) or (Q-16) to (Q-34) groups shown above.

In a further preferred embodiment of the invention, $Ar^1$ is the same or different at each instance and is an aromatic or heteroaromatic ring system having 6 to 24 aromatic ring atoms, preferably 6 to 18 aromatic ring atoms, and is more preferably an aromatic ring system having 6 to 12 aromatic ring atoms or a heteroaromatic ring system having 6 to 13 aromatic ring atoms, each of which may be substituted by one or more $R^2$ radicals, but is preferably unsubstituted, where $R^2$ may have the definition given above, especially in formula (I) and/or (II). Examples of suitable $Ar^1$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^3$ radicals, but are preferably unsubstituted.

Advantageously, $Ar^1$ in the formulae (H-1) to (H-26) or (Q-16) to (Q-34) is an aromatic ring system which has 6 to 12 aromatic ring atoms and may be substituted by one or more $R^2$ radicals, but is preferably unsubstituted, where $R^2$ may have the definition detailed above, especially for formula (I).

Preferably, the $R^2$ radicals in the formulae (H-1) to (H-26) or (Q-1) to (Q-34) do not form a fused ring system with the ring atoms of the heteroaryl group or the $Ar^1$ and/or Are group to which the $R^2$ radicals are bonded. This includes the formation of a fused ring system with possible $R^3$ substituents which may be bonded to the $R^2$ radicals.

When $X^1, X^2, X^3, X^4, X^5, X^6, X^7, X^8, X^9, X^{10}, X^{11}, X^{12}, X^{13}, X^{14}, X^{15}, X^{16}, X^{17}, X^{18}, X^{19}, X^{20}, X^{21}, X^{22}, X^{23}, X^{24}$ is $CR^1$ or when the aromatic and/or heteroaromatic group is substituted by substituents $R^1$, these substituents $R^1$ are preferably selected from the group consisting of H, D, F, CN, $N(Ar^1)_2$, $C(=O)Ar^1$, $P(=O)(Ar^1)_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^2$ radicals, where one or more nonadjacent $CH_2$ groups may be replaced by 0 and where one or more hydrogen atoms may be replaced by D or F, an aromatic or heteroaromatic ring system having 5 to 24 aromatic ring atoms, each of which may be substituted by one or more $R^2$ radicals, but is preferably unsubstituted, or an aralkyl or heteroaralkyl group which has 5 to 25 aromatic ring atoms and may be substituted by one or more $R^2$ radicals; it is optionally possible here for two substituents $R^1$ bonded to the same carbon atom or to adjacent carbon atoms to form a monocyclic or polycyclic, aliphatic, aromatic or heteroaromatic ring system which may be substituted by one or more $R^1$ radicals; where $Ar^1$ is the same or different at each instance and represents an aromatic or heteroaromatic ring system which has 5 to 40 aromatic ring atoms and may be substituted in each case by one or more $R^2$ radicals, an aryloxy group which has 5 to 40 aromatic ring atoms and may be substituted in each case by one or more $R^2$ radicals, or an aralkyl group which has 5 to 40 aromatic ring atoms and may be substituted in each case by one or more $R^2$ radicals, where two or more, preferably adjacent, substituents $R^2$ may optionally form a mono- or polycyclic, aliphatic, heteroaliphatic, aromatic or heteroaromatic ring system, preferably a mono- or polycyclic, aliphatic ring system, which may be substituted by one or more $R^3$ radicals, where the symbol $R^2$ may have the definition given above, especially for formula (I) and/or (II). Preferably, $Ar^1$ is the same or different at each instance and is an aryl or heteroaryl group which has 5 to 24 and preferably 5 to 12 aromatic ring atoms, and which may be substituted in each case by one or more $R^2$ radicals, but is preferably unsubstituted.

Examples of suitable $Ar^1$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted.

More preferably, these $R^1$ substituents are selected from the group consisting of H, D, F, CN, $N(Ar^1)_2$, a straight-chain alkyl group having 1 to 8 carbon atoms, preferably having 1, 2, 3 or 4 carbon atoms, or a branched or cyclic alkyl group having 3 to 8 carbon atoms, preferably having 3 or 4 carbon atoms, or an alkenyl group having 2 to 8 carbon atoms, preferably having 2, 3 or 4 carbon atoms, each of which may be substituted by one or more $R^2$ radicals, but is preferably unsubstituted, or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more nonaromatic $R^1$ radicals, but is preferably unsubstituted; at the same time, it is optionally possible for two $R^1$ substituents bonded to the same carbon atom or to adjacent carbon atoms to form a monocyclic or polycyclic aliphatic ring system which may be substituted by one or more $R^2$ radicals, but is preferably unsubstituted, where $Ar^1$ may have the definition set out above.

Most preferably, the $R^1$ substituents are selected from the group consisting of H and an aromatic or heteroaromatic ring system which has 6 to 18 aromatic ring atoms, preferably 6 to 13 aromatic ring atoms, and may be substituted in each case by one or more nonaromatic $R^2$ radicals, but is preferably unsubstituted. Examples of suitable $R^1$ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted.

It may additionally be the case that, in the structure of formula (I), (II), (III-1), (II-1), (I-2), (II-2), (I-3), (II-3), (I-4), (II-4), (III), (IV), (V), (VI), (V-1), (VI-1), (V-2), (VI-2), (V-3), (VI-3) and/or (H1) to (H-26), at least one $R^1$, Ar, $Ar^1$, Ara, $Ar^4$, $R^a$, $R^b$, $R^c$, $R^d$ radical comprises a group, preferably is a group, selected from the formulae ($R^1$-1) to ($R^1$-95)

Formula ($R^1$-1)

Formula ($R^1$-2)

Formula ($R^1$-3)

Formula ($R^1$-4)

-continued

Formula (R¹-5)

Formula (R¹-6)

Formula (R¹-7)

Formula (R¹-8)

Formula (R¹-9)

Formula (R¹-10)

-continued

Formula (R¹-11)

Formula (R¹-12)

Formula (R¹-13)

Formula (R¹-14)

Formula (R¹-15)

Formula (R¹-16)
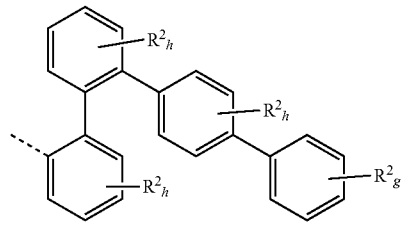
Formula (R¹-17)
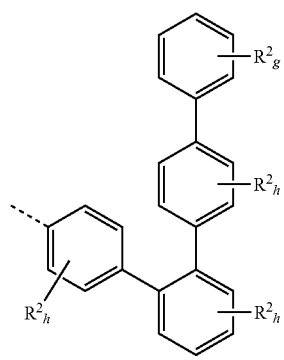
Formula (R¹-18)
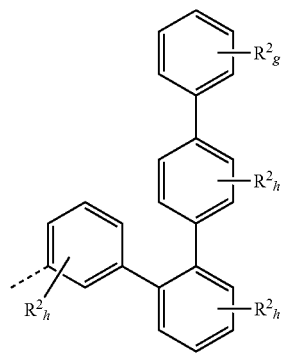
Formula (R¹-19)
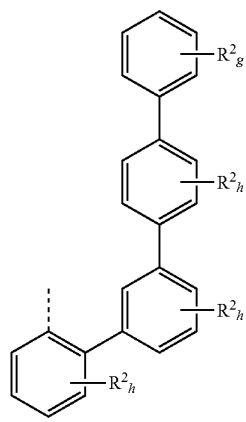
Formula (R¹-20)
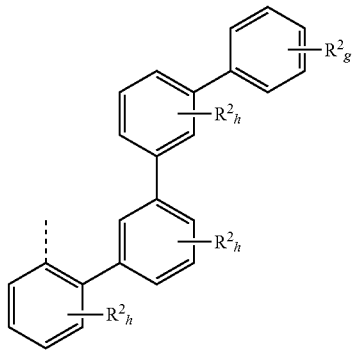
Formula (R¹-21)
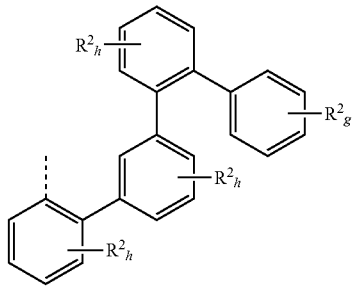
Formula (R¹-22)
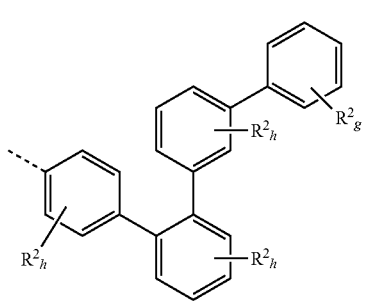
Formula (R¹-23)
Formula (R¹-24)
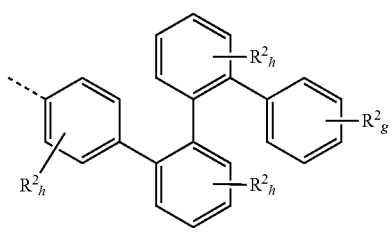

-continued
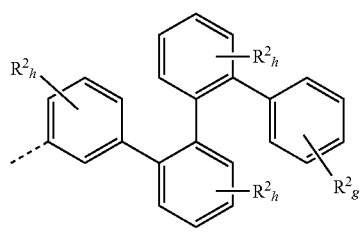
Formula (R¹-25)
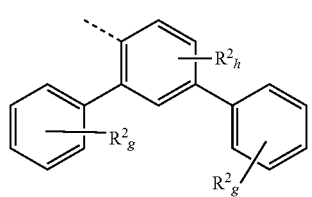
Formula (R¹-26)
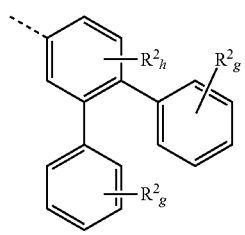
Formula (R¹-27)
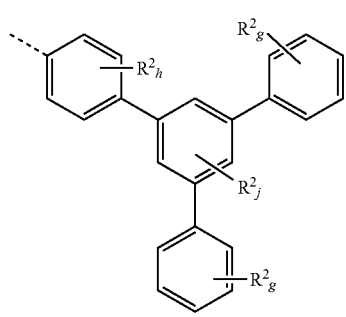
Formula (R¹-28)
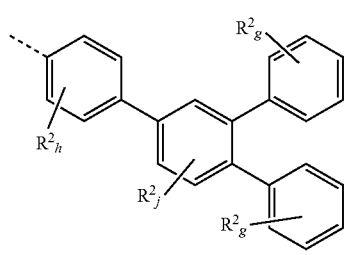
Formula (R¹-29)
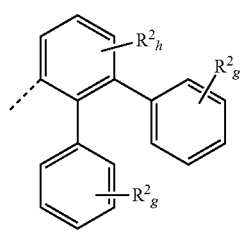
Formula (R¹-30)
-continued
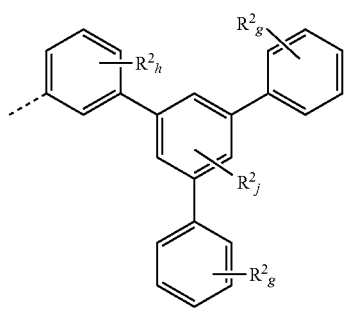
Formula (R¹-31)
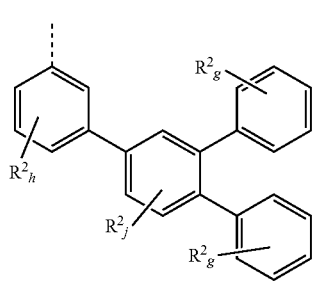
Formula (R¹-32)
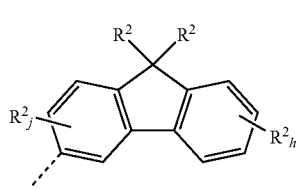
Formula (R¹-33)
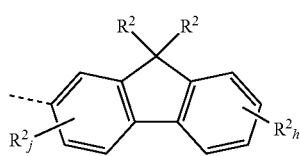
Formula (R¹-34)
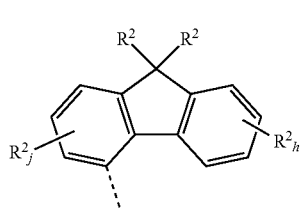
Formula (R¹-35)
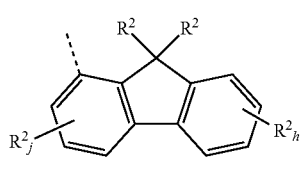
Formula (R¹-36)
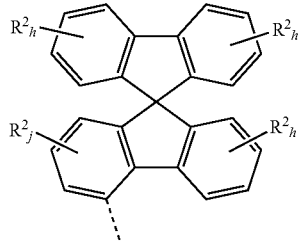
Formula (R¹-37)

Formula (R¹-38)
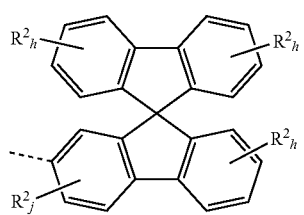
Formula (R¹-39)
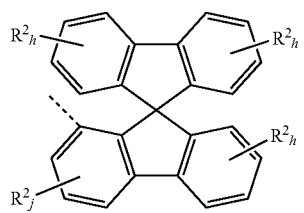
Formula (R¹-40)
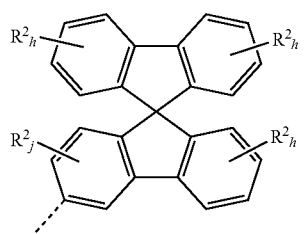
Formula (R¹-41)
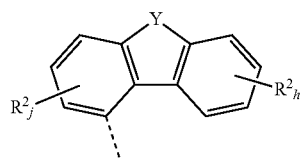
Formula (R¹-42)
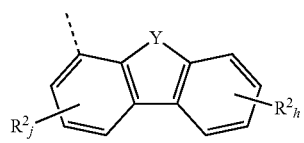
Formula (R¹-43)
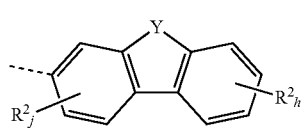
Formula (R¹-44)
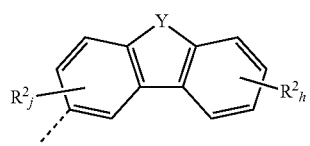
Formula (R¹-45)
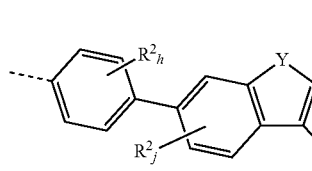
Formula (R¹-46)
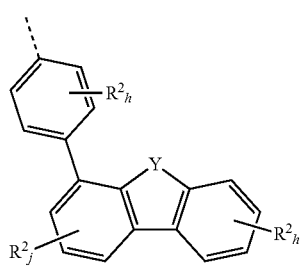
Formula (R¹-47)
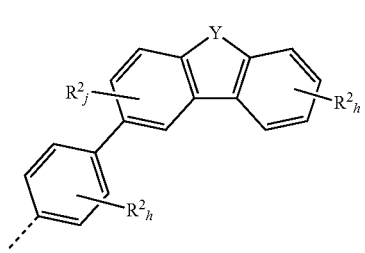
Formula (R¹-48)
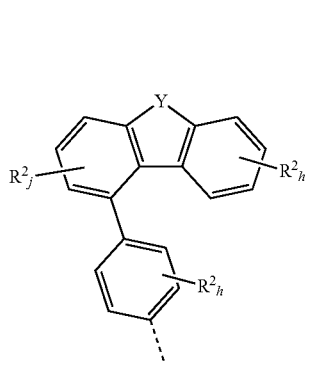
Formula (R¹-49)
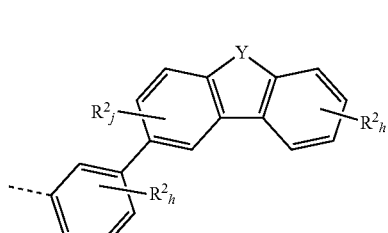
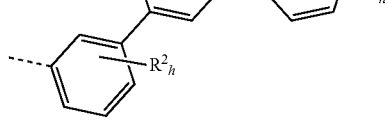
Formula (R¹-50)
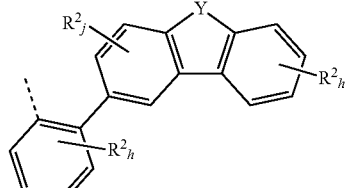
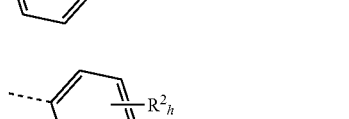
Formula (R¹-51)
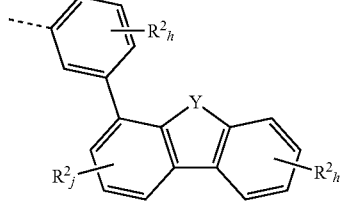

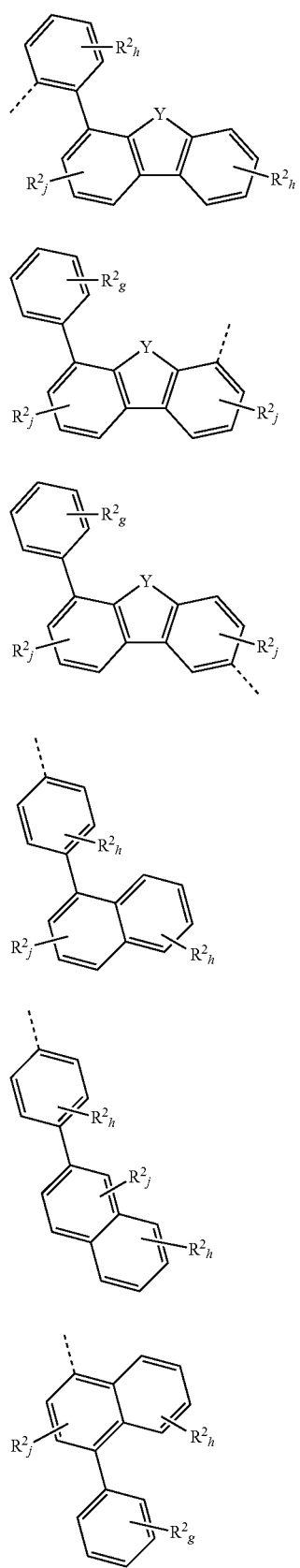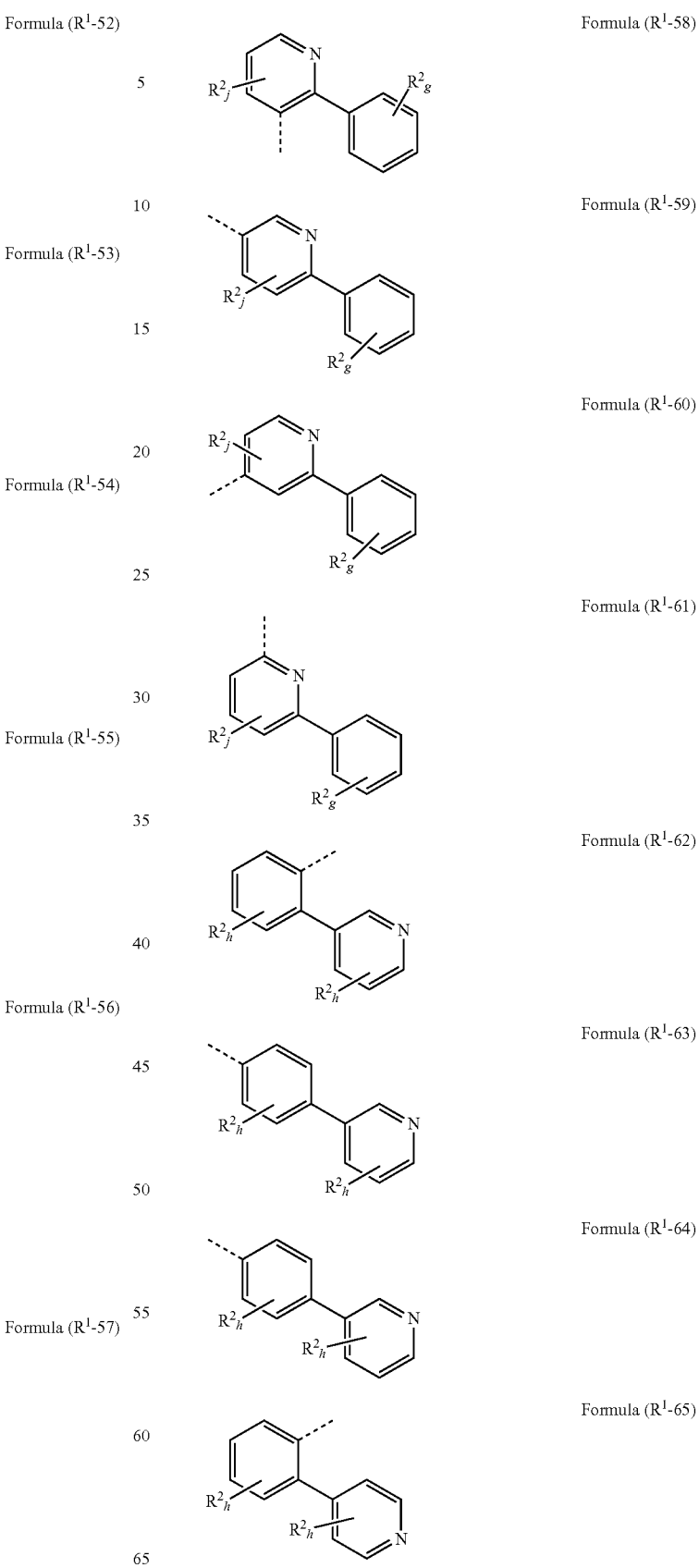

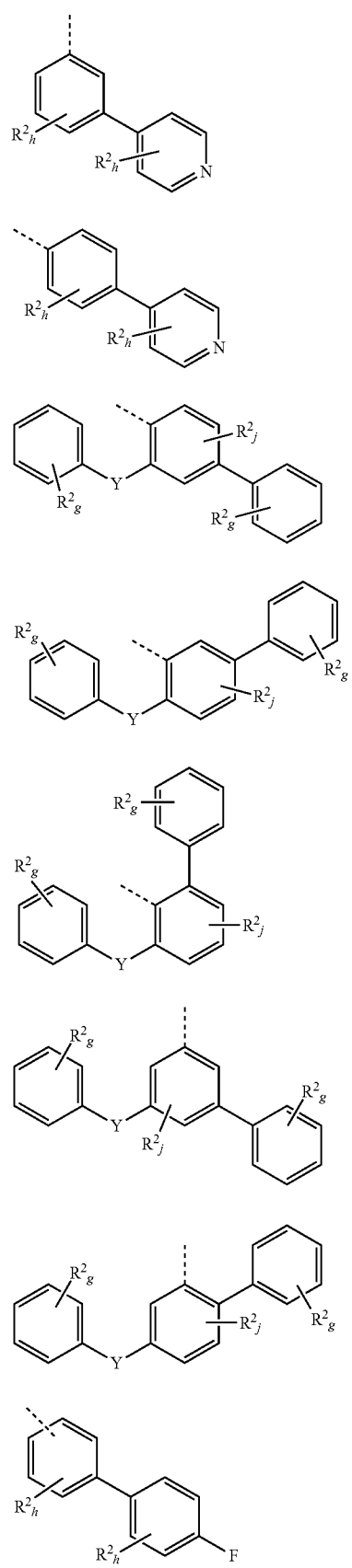
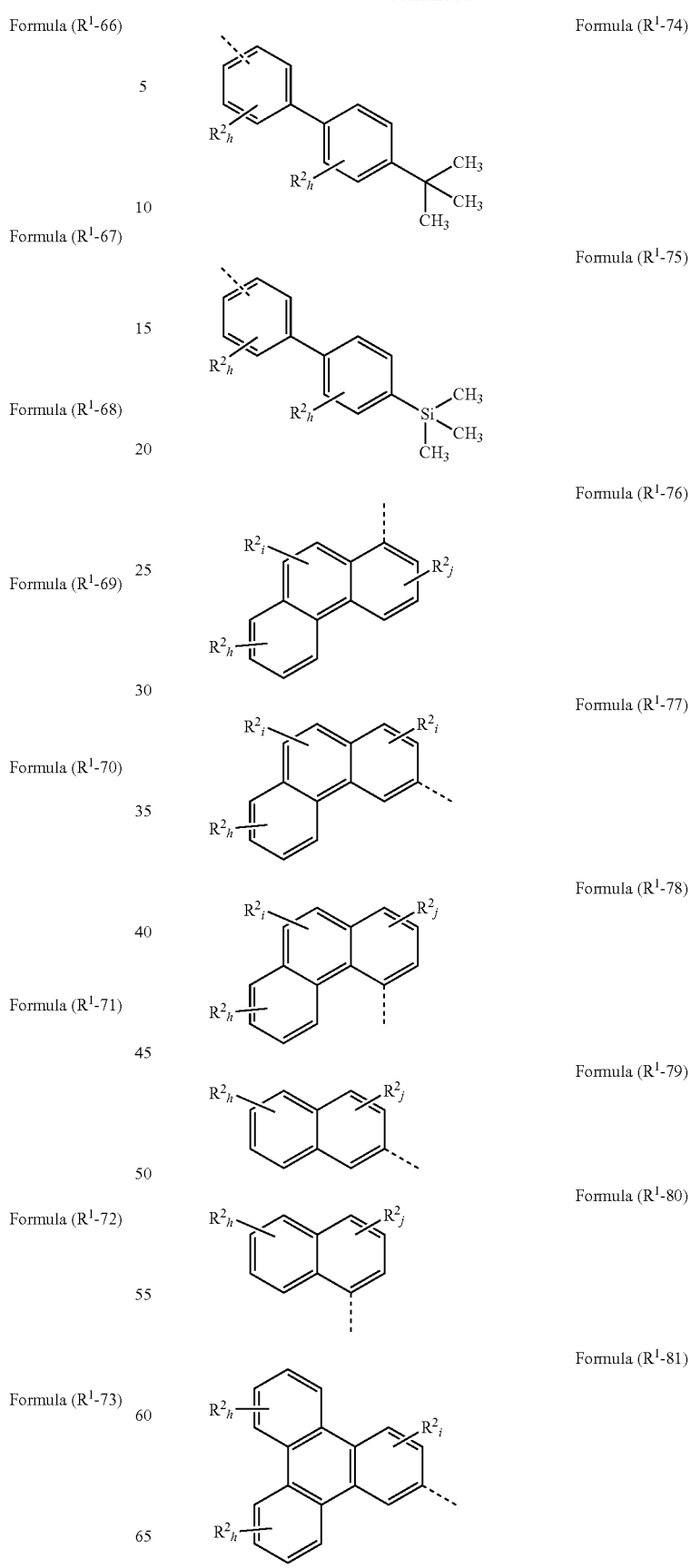

Formula (R¹-82)
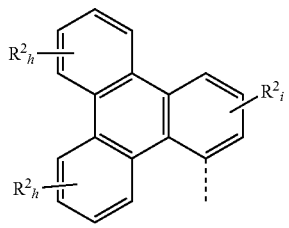

Formula (R¹-83)
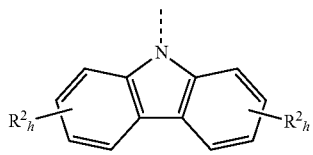

Formula (R¹-84)
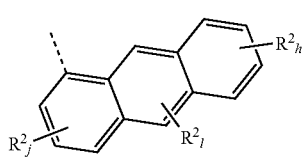

Formula (R¹-85)
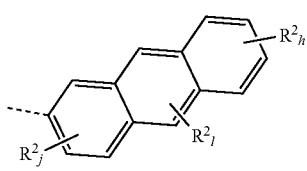

Formula (R¹-86)
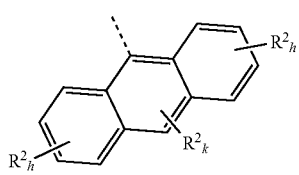

Formula (R¹-87)
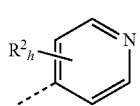

Formula (R¹-88)
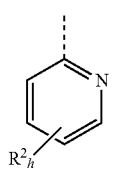

Formula (R¹-89)
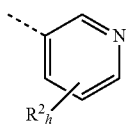

Formula (R¹-90)
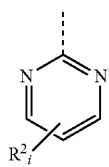

Formula (R¹-91)
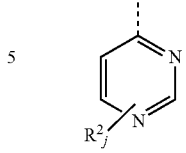

Formula (R¹-92)
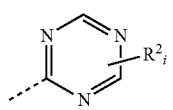

Formula (R¹-93)
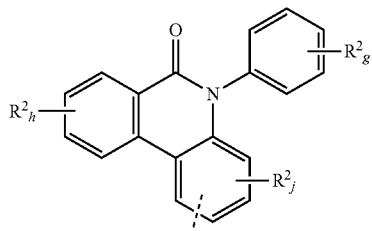

Formula (R¹-94)
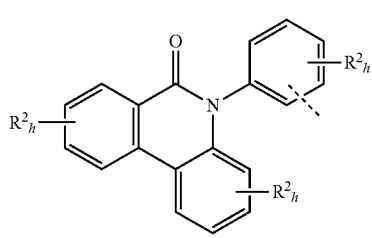

Formula (R¹-95)
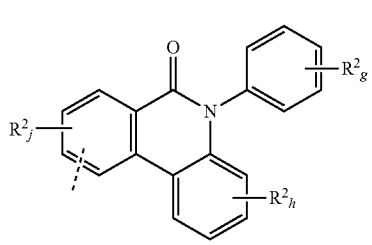

where the symbols used are as follows:
Y is O, S or NR², preferably O or S;
i at each instance is independently 0, 1 or 2;
j at each instance is independently 0, 1, 2 or 3;
h at each instance is independently 0, 1, 2, 3 or 4;
g at each instance is independently 0, 1, 2, 3, 4 or 5;
R² may have the definition given above, especially for formula (I) and/or (II), and
the dotted bond marks the position of attachment.

It may preferably be the case that the sum total of the indices i, j, h and g in the structures of the formula (R¹-1) to (R¹-95) is not more than 3 in each case, preferably not more than 2 and more preferably not more than 1.

Preferably, the R² radicals in the formulae (R¹-1) to (R¹-95) do not form a fused aromatic or heteroaromatic ring system, and preferably do not form any fused ring system, with the ring atoms of the aryl group or heteroaryl group to which the R² radicals are bonded. This includes the formation of a fused ring system with possible R³ substituents which may be bonded to the R² radicals.

It may preferably be the case that, in the structure of the formula (I), (V) or (VII), at most 2 of the symbols $X^1$, $X^2$, $X^3$, $X^4$, $X^5$, $X^6$, $X^7$, $X^8$, $X^9$, $X^{10}$, $X^{12}$, $X^{13}$, $X^{14}$, $X^{15}$, $X^{16}$ are not CH or CD or, in the structure of the formula (II) or (VI), at most 4 of the symbols $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ are not CH or CD; preferably, the sum total of the indices m and n in the structure of the formula (III) is not more than 2 or in the structure of the formula (IV) is not more than 4 and in the structure of the formula (V-3) or (VI-3) is 0, where the $R^1$ radicals that are not H or D, or the $R^a$, $R^b$, $R^c$, $R^d$ radicals are selected from the above-detailed groups of the formulae ($R^1$-1) to ($R^1$-95), preferably ($R^1$-1) to ($R^1$-54), more preferably ($R^1$-1) to ($R^1$-4), where the ($R^1$-1) group is especially preferred, and the Ar radical is preferably selected from the above-detailed groups of the formulae ($R^1$-1) to ($R^1$-95), preferably ($R^1$-1) to ($R^1$-54), more preferably ($R^1$-3) and/or ($R^1$-46).

Preferably, the $L^1$ group may form through-conjugation with the Q group and the aromatic or heteroaromatic radical or the nitrogen atom to which the $L^1$ group of formula (QL) is bonded. Through-conjugation of the aromatic or heteroaromatic systems is formed as soon as direct bonds are formed between adjacent aromatic or heteroaromatic rings. A further bond between the aforementioned conjugated groups, for example via a sulfur, nitrogen or oxygen atom or a carbonyl group, is not detrimental to conjugation. In the case of a fluorene system, the two aromatic rings are bonded directly, where the spa-hybridized carbon atom in position 9 does prevent fusion of these rings, but conjugation is possible, since this $sp^3$-hybridized carbon atom in position 9 does not necessarily lie between the electron-transporting Q group and the fluorene structure. In contrast, in the case of a second spirobifluorene structure, through-conjugation can be formed if the bond between the Q group and the aromatic or heteroaromatic radical to which the $L^1$ group of formula (QL) is bonded is via the same phenyl group in the spirobifluorene structure or via phenyl groups in the spirobifluorene structure that are bonded directly to one another and are in one plane. If the bond between the Q group and the aromatic or heteroaromatic radical to which the $L^1$ group of formula (QL) is bonded is via different phenyl groups in the second spirobifluorene structure bonded via the spa-hybridized carbon atom in position 9, the conjugation is interrupted.

In a further preferred embodiment of the invention, $L^1$ is a bond or an aromatic or heteroaromatic ring system which has 5 to 14 aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formula (I) and/or (II). More preferably, $L^1$ is an aromatic ring system having 6 to 10 ring atoms or a heteroaromatic ring system having 6 to 13 heteroaromatic ring atoms, each of which may be substituted by one or more $R^2$ radicals, but is preferably unsubstituted, where $R^2$ may have the definition given above, especially for formula (I) and/or (II).

Further preferably, the symbol $L^1$ shown in formula (QL) inter alia is the same or different at each instance and is a bond or an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded to the respective atom of the further group directly, i.e. via an atom of the aromatic or heteroaromatic group.

It may additionally be the case that the L group shown in formula (VII) and/or the $L^1$ group shown in formula (QL) comprises an aromatic ring system having not more than two fused aromatic and/or heteroaromatic rings, preferably does not comprise any fused aromatic or heteroaromatic ring system. Accordingly, naphthyl structures are preferred over anthracene structures. In addition, fluorenyl, spirobifluorenyl, dibenzofuranyl and/or dibenzothienyl structures are preferred over naphthyl structures.

Particular preference is given to structures having no fusion, for example phenyl, biphenyl, terphenyl and/or quaterphenyl structures.

Examples of suitable aromatic or heteroaromatic ring systems L (formula (VII)) or L' (formula (QL)) are selected from the group consisting of ortho-, meta- or para-phenylene, ortho-, meta- or para-biphenylene, terphenylene, especially branched terphenylene, quaterphenylene, especially branched quaterphenylene, fluorenylene, spirobifluorenylene, dibenzofuranylene, dibenzothienylene and carbazolylene, each of which may be substituted by one or more $R^2$ radicals, but are preferably unsubstituted.

It may further be the case that the L group shown in formula (VII) and/or the $L^1$ group shown in formula (QL) inter alia has not more than 1 nitrogen atom, preferably not more than 2 heteroatoms, especially preferably not more than one heteroatom and more preferably no heteroatom.

Preference is given to compounds comprising at least one structure of the formulae (H-1) to (H-26) in which the Are group is a group selected from the formulae ($L^1$-1) to ($L^1$-108), and/or compounds comprising structures of the formula (VII) in which the L group is a group selected from the formulae ($L^1$-1) to ($L^1$-108), and/or compounds comprising structures of the formula (QL) in which the $L^1$ group is a bond or a group selected from the formulae ($L^1$-1) to ($L^1$-108)

Formula ($L^1$-1)

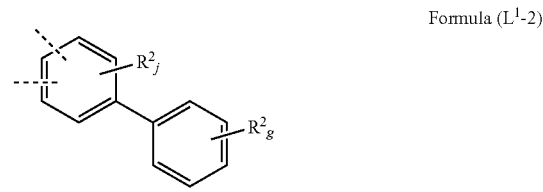

Formula ($L^1$-2)

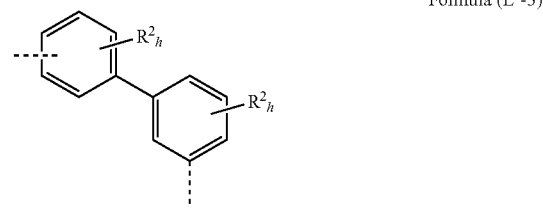

Formula ($L^1$-3)

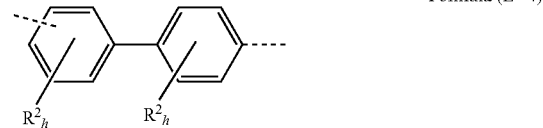

Formula ($L^1$-4)

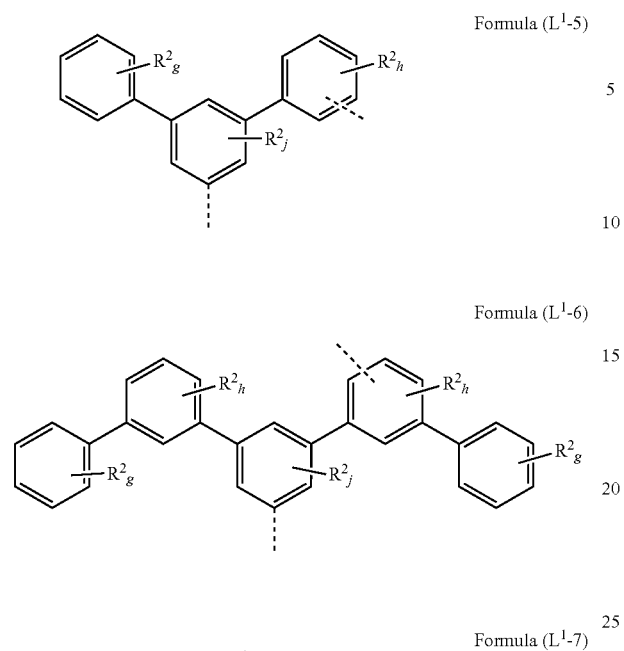

Formula (L¹-16)
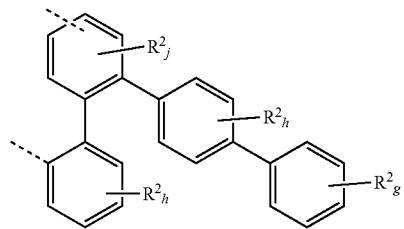
Formula (L¹-17)
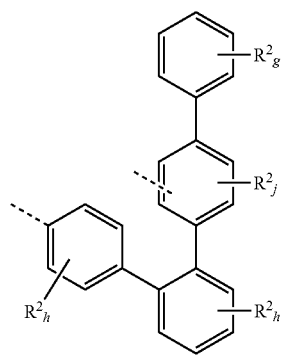
Formula (L¹-18)
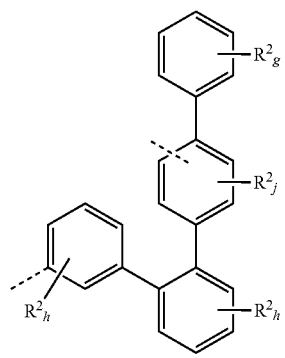
Formula (L¹-19)
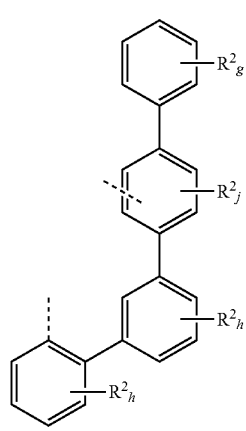
Formula (L¹-20)
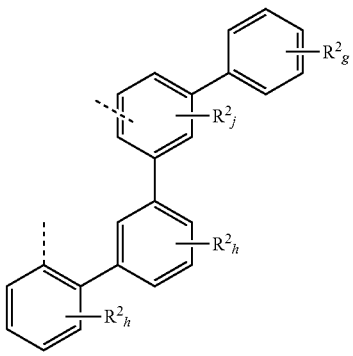
Formula (L¹-21)
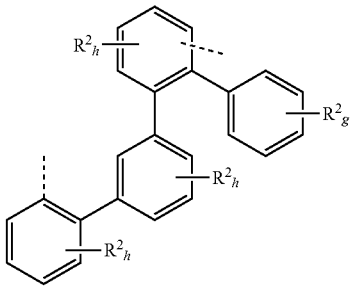
Formula (L¹-22)
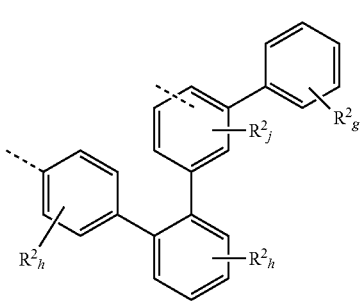
Formula (L¹-23)
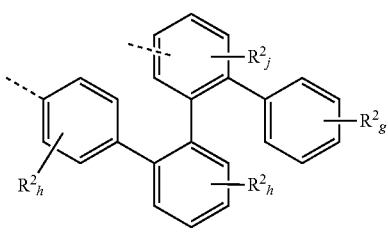
Formula (L¹-24)
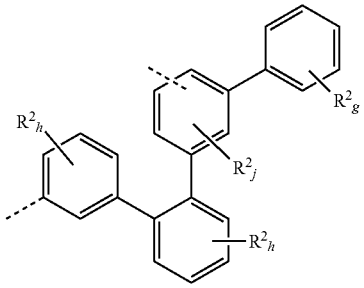

Formula (L¹-25)
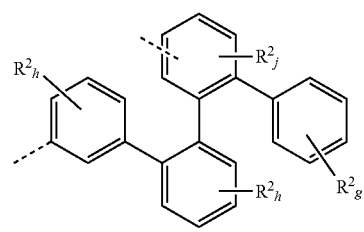
Formula (L¹-26)
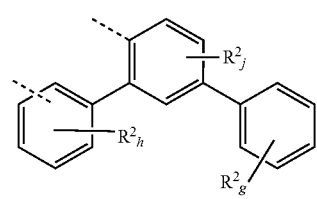
Formula (L¹-27)
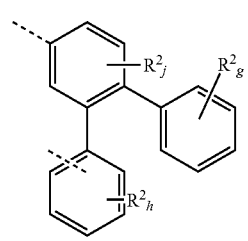
Formula (L¹-28)
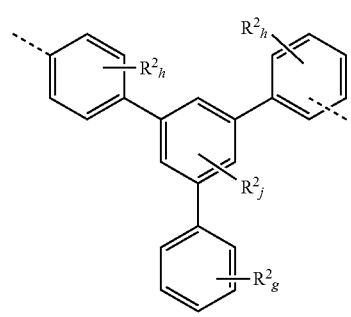
Formula (L¹-29)
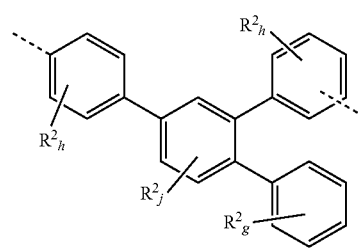
Formula (L¹-30)
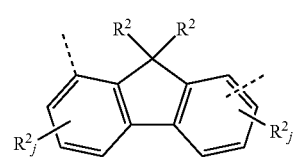
Formula (L¹-31)
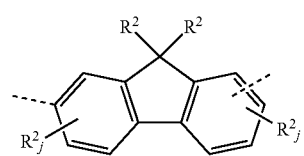
Formula (L¹-32)
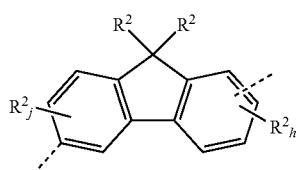
Formula (L¹-33)
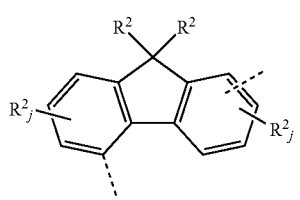
Formula (L¹-34)
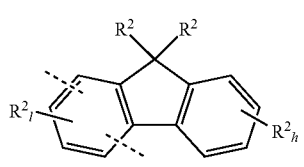
Formula (L¹-35)
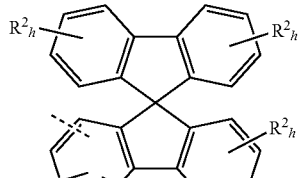
Formula (L¹-36)
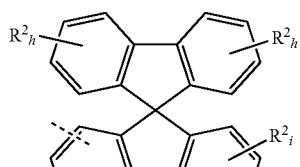
Formula (L¹-37)
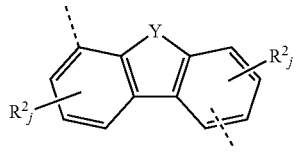
Formula (L¹-38)
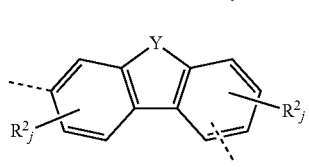
Formula (L¹-39)
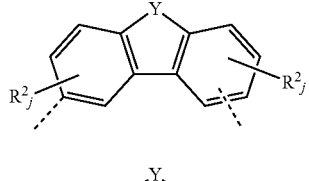
Formula (L¹-40)
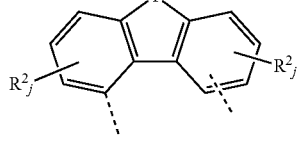

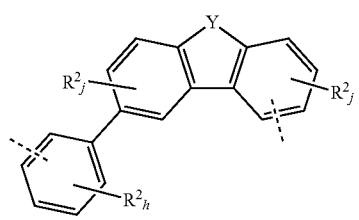
Formula (L¹-41)
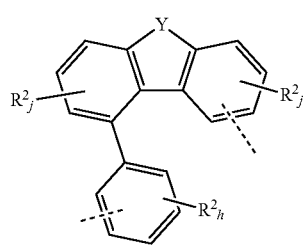
Formula (L¹-42)
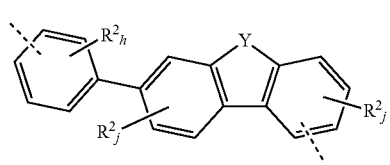
Formula (L¹-43)
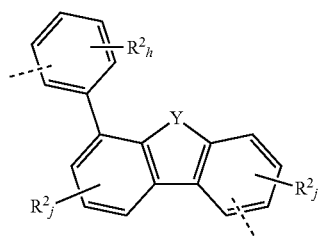
Formula (L¹-44)
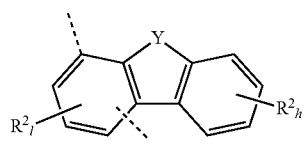
Formula (L¹-45)
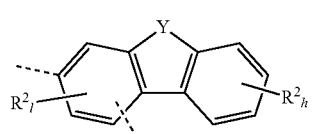
Formula (L¹-46)
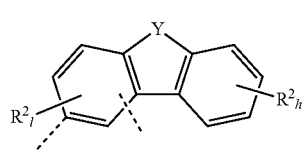
Formula (L¹-47)
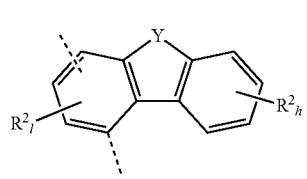
Formula (L¹-48)
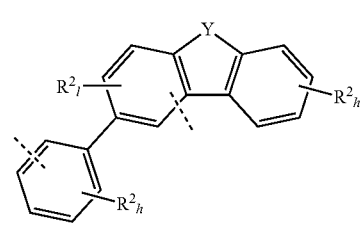
Formula (L¹-49)
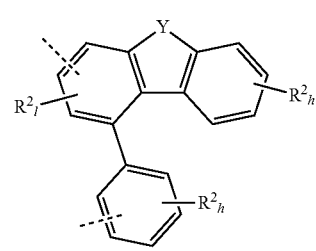
Formula (L¹-50)
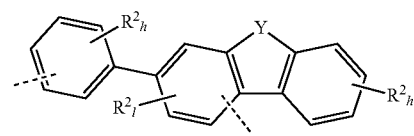
Formula (L¹-51)
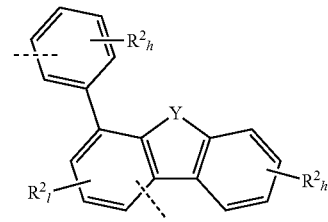
Formula (L¹-52)
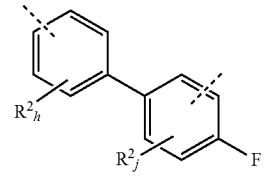
Formula (L¹-53)
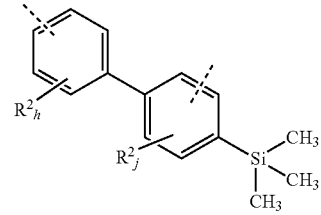
Formula (L¹-54)
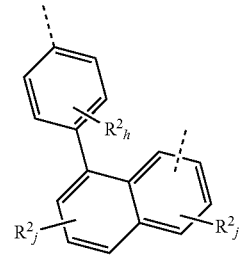
Formula (L¹-55)

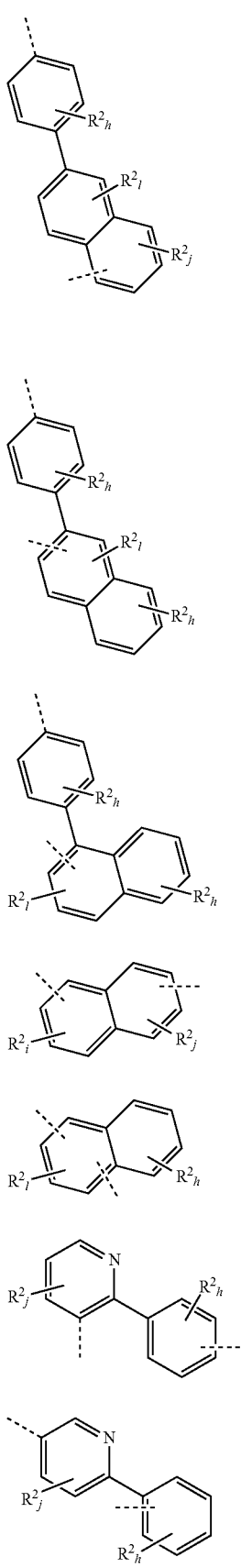
Formula (L¹-56)
Formula (L¹-57)
Formula (L¹-58)
Formula (L¹-59)
Formula (L¹-60)
Formula (L¹-61)
Formula (L¹-62)
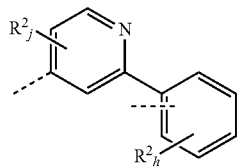
Formula (L¹-63)
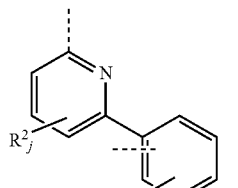
Formula (L¹-64)
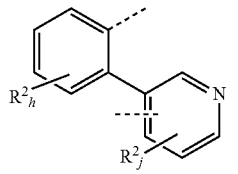
Formula (L¹-65)
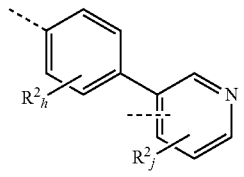
Formula (L¹-66)
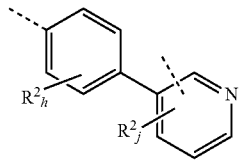
Formula (L¹-67)
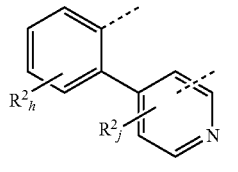
Formula (L¹-68)
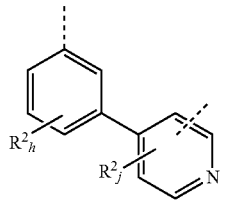
Formula (L¹-69)
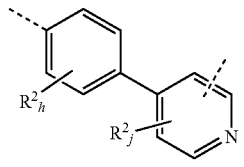
Formula (L¹-70)

Formula (L¹-71)
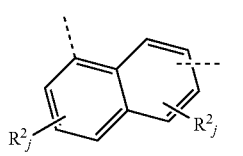
Formula (L¹-72)
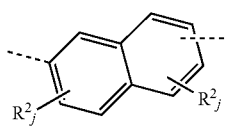
Formula (L¹-73)
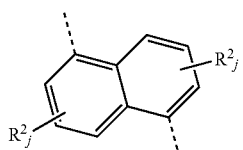
Formula (L¹-74)
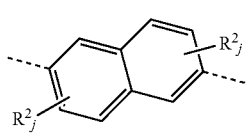
Formula (L¹-75)
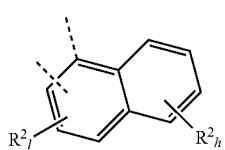
Formula (L¹-76)
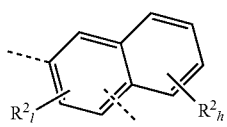
Formula (L¹-77)
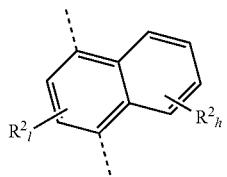
Formula (L¹-78)
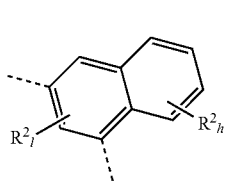
Formula (L¹-79)
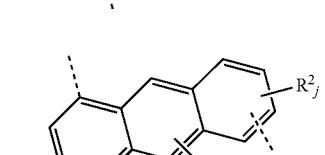
Formula (L¹-80)
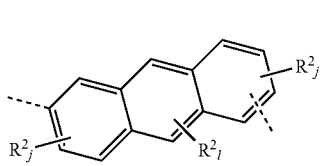
Formula (L¹-81)
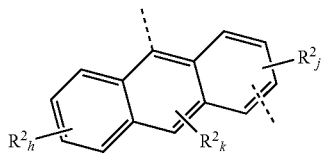
Formula (L¹-82)
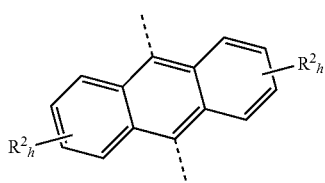
Formula (L¹-83)

Formula (L¹-84)
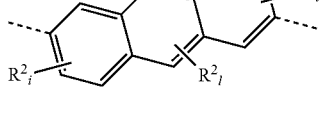
Formula (L¹-85)
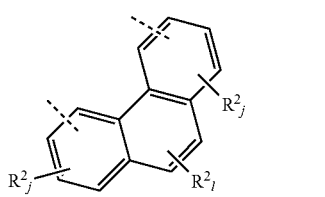
Formula (L¹-86)
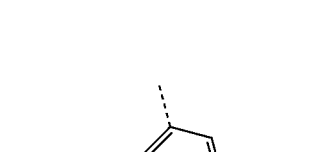
Formula (L¹-87)
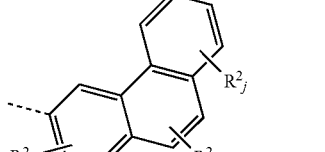

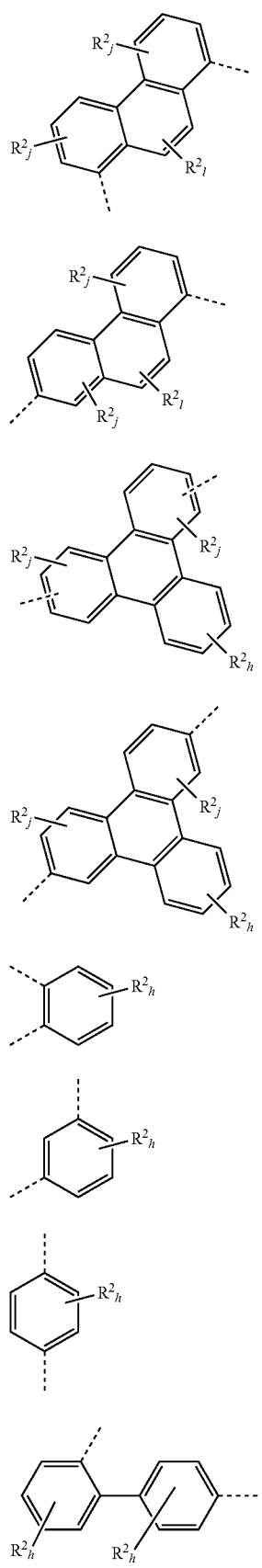

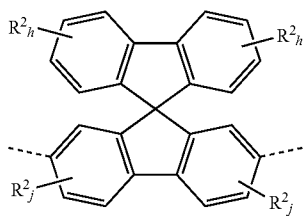

Formula (L¹-105)

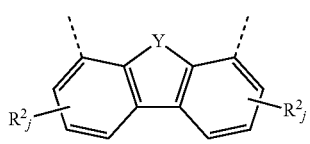

Formula (L¹-106)

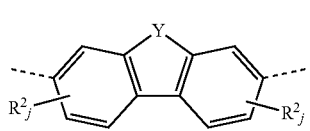

Formula (L¹-107)

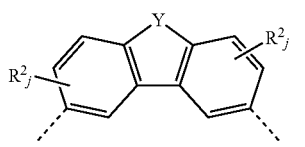

Formula (L¹-108)

where the dotted bonds in each case mark the attachment positions, the index k is 0 or 1, the index l is 0, 1 or 2, the index j at each instance is independently 0, 1, 2 or 3; the index h at each instance is independently 0, 1, 2, 3 or 4, the index g is 0, 1, 2, 3, 4 or 5; the symbol Y is O, S or $NR^2$, preferably O or S; and the symbol $R^2$ has the definition given above, especially for formula (I).

It may preferably be the case that the sum total of the indices k, l, g, h and j in the structures of the formula ($L^1$-1) to ($L^1$-108) is at most 3 in each case, preferably at most 2 and more preferably at most 1.

Preferred compounds of the invention having a group of the formula (QL) comprise an L group which represents a bond or which is selected from one of the formulae ($L^1$-1) to ($L^1$-78)- and/or ($L^1$-92) to ($L^1$-108), preferably of the formula ($L^1$-1) to ($L^1$-54) and/or ($L^1$-92) to ($L^1$-108), especially preferably of the formula ($L^1$-1) to ($L^1$-29) and/or ($L^1$-92) to ($L^1$-103). Advantageously, the sum total of the indices k, l, g, h and j in the structures of the formulae ($L^1$-1) to ($L^1$-78) and/or ($L^1$-92) to ($L^1$-108), preferably of the formula ($L^1$-1) to ($L^1$-54) and/or ($L^1$-92) to ($L^1$-108), especially preferably of the formula ($L^1$-1) to ($L^1$-29) and/or ($L^1$-92) to ($L^1$-103), may in each case be not more than 3, preferably not more than 2 and more preferably not more than 1.

Preferred compounds of the invention having a group of the formulae (H-1) to (H-26) comprise an Are group selected from one of the formulae ($L^1$-1) to ($L^1$-78) and/or ($L^1$-92) to ($L^1$-108), preferably of the formula ($L^1$-1) to ($L^1$-54) and/or ($L^1$-92) to ($L^1$-108), especially preferably of the formula ($L^1$-1) to ($L^1$-29) and/or ($L^1$-92) to ($L^1$-103). Advantageously, the sum total of the indices k, l, g, h and j in the structures of the formulae ($L^1$-1) to ($L^1$-78) and/or ($L^1$-92) to ($L^1$-108), preferably of the formula ($L^1$-1) to ($L^1$-54) and/or ($L^1$-92) to ($L^1$-108), especially preferably of the formula ($L^1$-1) to ($L^1$-29) and/or ($L^1$-92) to ($L^1$-103), may in each case be not more than 3, preferably not more than 2 and more preferably not more than 1.

Preferably, the $R^2$ radicals in the formulae ($L^1$-1) to ($L^1$-108) do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible $R^3$ substituents which may be bonded to the $R^2$ radicals.

It may further be the case that, in the structure of the formula (I), (V) or (VII), at most 2 of the symbols $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$ are not CH or CD or, in the structure of the formula (II) or (VI), at most 4 of the symbols $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ are not CH or CD; preferably, the sum total of the indices m and n in the structure of the formula (III) is not more than 2 or in the structure of the formula (IV) is not more than 4 and in the structure of the formula (V-3) or (VI-3) is 0, where the Ar radical is selected from the above-detailed groups of the formulae ($R^1$-1) to ($R^1$-95), preferably ($R^1$-1) to ($R^1$-54), more preferably ($R^1$-3) and/or ($R^1$-46), or the Ar radical is selected from the structures of the formulae (H-1) to (H-26) and the $Ar^1$, Ara and $Ar^4$ radicals are selected from groups of the formulae ($R^1$-1) to ($R^1$-95), preferably ($R^1$-1) to ($R^1$-54), more preferably ($R^1$-1) to ($R^1$-4), where the ($R^1$-1) group is especially preferred, and the Are radical is selected from the above-detailed groups of the formulae ($L^1$-1) to ($L^1$-108), preferably ($L^1$-1) to ($L^1$-54), more preferably ($L^1$-1) to ($L^1$-4), where the ($L^1$-1) group is especially preferred.

When the compound of the invention is substituted by aromatic or heteroaromatic $R^1$ or $R^2$ groups, especially in the case of configuration thereof as host material, electron transport material or hole transport material, it is preferable when they do not have any aryl or heteroaryl groups having more than two aromatic six-membered rings fused directly to one another. More preferably, the substituents do not have any aryl or heteroaryl groups having six-membered rings fused directly to one another at all. The reason for this preference is the low triplet energy of such structures. Fused aryl groups which have more than two aromatic six-membered rings fused directly to one another but are nevertheless also suitable in accordance with the invention are phenanthrene and triphenylene, since these also have a high triplet level.

In the case of configuration of the compounds of the invention for use as fluorescent emitters, preferred compounds may contain corresponding groups, for example fluorene, anthracene and/or pyrene groups which may be substituted by $R^2$ groups or which are formed by corresponding substitution of the ($R^1$-1) to ($R^1$-95) groups, preferably ($R^1$-33) to ($R^1$-57) and ($R^1$-76) to ($R^1$-86), or ($L^1$-1) to ($L^1$-108), preferably ($L^1$-30) to ($R^1$-60) and ($R^1$-71) to ($R^1$-91), by the $R^2$ substituents.

In a further preferred embodiment of the invention, $R^2$, for example in a structure of formula (I) and/or (II) and preferred embodiments of this structure or the structures where reference is made to these formulae, is the same or different at each instance and is selected from the group consisting of H, D, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

In a further preferred embodiment of the invention, $R^3$, for example in a structure of formula (I) and/or (II) and preferred embodiments of this structure or the structures where reference is made to these formulae, is the same or different at each instance and is selected from the group consisting of H, D, F, CN, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

Particular preference is given to compounds of the invention having structures of the formula (I) or (II) where a total of not more than 6, preferably not more than 4 and, in the case of structures of formula (I), not more than 2 radicals of the formulae $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ are not CH or CD and having the following properties:

| $R^1$, not H or D | preferably | Ar | preferably |
|---|---|---|---|
| $R^1$-1 to $R^1$-95 | $R^1$-1 to $R^1$-54 | $R^1$-1 to $R^1$-95 | $R^1$-1 to $R^1$-54 |
| $R^1$-1 to $R^1$-95 | $R^1$-1 to $R^1$-54 | H-1 to H-26 | H1-H-5 |
| $R^1$-1 to $R^1$-4 | $R^1$-1 | $R^1$-1 to $R^1$-54 | $R^1$-3 or $R^1$-46 |
| $R^1$-1 to $R^1$-4 | $R^1$-1 | H-1 to H-26 | H-4 or H-5 |
| $R^1$-1 to $R^1$-95 | $R^1$-1 to $R^1$-54 | QL | |
| $R^1$-1 to $R^1$-4 | $R^1$-1 | QL | |

Particular preference is given to compounds of the invention having structures of the formula (III) or (IV), where the sum total of the indices m and n is not more than 3, preferably not more than 1 and especially preferably 0, and having the following properties:

| $R^1$, not H or D (if present) | preferably | Ar | preferably |
|---|---|---|---|
| $R^1$-1 to $R^1$-95 | $R^1$-1 to $R^1$-54 | $R^1$-1 to $R^1$-95 | $R^1$-1 to $R^1$-54 |
| $R^1$-1 to $R^1$-95 | $R^1$-1 to $R^1$-54 | H-1 to H-26 | H4-H-26 |
| $R^1$-1 to $R^1$-4 | $R^1$-1 | $R^1$-1 to $R^1$-54 | $R^1$-3 or $R^1$-46 |
| $R^1$-1 to $R^1$-4 | $R^1$-1 | H-1 to H-26 | H-4 or H-5 |
| $R^1$-1 to $R^1$-95 | $R^1$-1 to $R^1$-54 | QL | |
| $R^1$-1 to $R^1$-4 | $R^1$-1 | QL | |

Particular preference is given to compounds of the invention having structures of the formula (V) or (VI) where a total of not more than 5, preferably not more than 3 and, in the case of structures of formula (I), not more than 1 radicals of the formulae $X^1$, $X^2$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ are not CH or CD, and having the following properties:

| $R^1$, not H or D (if present) | $R^a$ | Ar | preferably |
|---|---|---|---|
| $R^1$-1 to $R^1$-95 | $R^1$-1 to $R^1$-95 | $R^1$-1 to $R^1$-95 | $R^1$-1 to $R^1$-54 |
| $R^1$-1 to $R^1$-54 | $R^1$-1 to $R^1$-54 | $R^1$-1 to $R^1$-95 | $R^1$-1 to $R^1$-54 |
| $R^1$-1 to $R^1$-95 | $R^1$-1 to $R^1$-95 | H-1 to H-26 | H4-H-26 |
| $R^1$-1 to $R^1$-54 | $R^1$-1 to $R^1$-54 | H-1 to H-26 | H4-H-26 |
| $R^1$-1 to $R^1$-4 | $R^1$-1 to $R^1$-4 | $R^1$-1 to $R^1$-54 | $R^1$-3 or $R^1$-46 |
| $R^1$-1 | $R^1$-1 | $R^1$-1 to $R^1$-54 | $R^1$-3 or $R^1$-46 |
| $R^1$-1 to $R^1$-4 | $R^1$-1 to $R^1$-4 | H-1 to H-26 | H-4 or H-5 |
| $R^1$-1 | $R^1$-1 | H-1 to H-26 | H-4 or H-5 |
| $R^1$-1 to $R^1$-95 | $R^1$-1 to $R^1$-95 | QL | |
| $R^1$-1 to $R^1$-54 | $R^1$-1 to $R^1$-54 | QL | |
| $R^1$-1 to $R^1$-4 | $R^1$-1 to $R^1$-4 | QL | |
| $R^1$-1 | $R^1$-1 | QL | |

Particular preference is given to compounds of the invention having structures of the formula (V-3) or (VI-3), where the sum total of the indices m and n is not more than 3, preferably not more than 1 and especially preferably 0, and having the following properties:

| $R^1$, not H or D (if present) | $R^a$, $R^b$, $R^c$, $R^d$ | Ar | preferably |
|---|---|---|---|
| $R^1$-1 to $R^1$-95 | $R^1$-1 to $R^1$-95 | $R^1$-1 to $R^1$-95 | $R^1$-1 to $R^1$-54 |
| $R^1$-1 to $R^1$-54 | $R^1$-1 to $R^1$-54 | $R^1$-1 to $R^1$-95 | $R^1$-1 to $R^1$-54 |
| $R^1$-1 to $R^1$-95 | $R^1$-1 to $R^1$-95 | H-1 to H-26 | H4-H-26 |
| $R^1$-1 to $R^1$-54 | $R^1$-1 to $R^1$-54 | H-1 to H-26 | H4-H-26 |
| $R^1$-1 to $R^1$-4 | $R^1$-1 to $R^1$-4 | $R^1$-1 to $R^1$-54 | $R^1$-3 or $R^1$-46 |
| $R^1$-1 | $R^1$-1 | $R^1$-1 to $R^1$-54 | $R^1$-3 or $R^1$-46 |
| $R^1$-1 to $R^1$-4 | $R^1$-1 to $R^1$-4 | H-1 to H-26 | H-4 or H-5 |
| $R^1$-1 | $R^1$-1 | H-1 to H-26 | H-4 or H-5 |
| $R^1$-1 to $R^1$-95 | $R^1$-1 to $R^1$-95 | QL | |
| $R^1$-1 to $R^1$-54 | $R^1$-1 to $R^1$-54 | QL | |
| $R^1$-1 to $R^1$-4 | $R^1$-1 to $R^1$-4 | QL | |
| $R^1$-1 | $R^1$-1 | | |

The radicals of the formulae H-1 to H-26 in the tables shown above are preferably selected according to the following criteria:

| $Ar^1$ (if present) | $Ar^2$ | $Ar^3$, $Ar^4$ | preferably |
|---|---|---|---|
| $R^1$-1 to $R^1$-95 | $L^1$-1 to $L^1$-108 | $R^1$-1 to $R^1$-95 | $R^1$-1 to $R^1$-54 |
| $R^1$-1 to $R^1$-54 | $L^1$-1 to $L^1$-4 | $R^1$-1 to $R^1$-95 | $R^1$-1 to $R^1$-54 |
| $R^1$-1 to $R^1$-54 | $L^1$-30 to $L^1$-52 | $R^1$-1 to $R^1$-95 | $R^1$-1 to $R^1$-54 |

The radicals of the formula QL in the tables shown above are preferably selected according to the following criteria:

| $L^1$ | preferably | Q | preferably |
|---|---|---|---|
| A bond or $L^1$-1 to $L^1$-108 | A bond or $L^1$-1 to $L^1$-4 | $Q^1$-1 to $Q^1$-34 | $Q^1$-1 to $Q^1$-9 |

The index g in formula $R^1$-1 in the tables given above is preferably 0, 1, 2 or 3, more preferably 0 or 1, especially preferably 0; the sum total of the indices i, j, h and g in the structures of the formula ($R^1$-1) to ($R^1$-95) is in each case not more than 3, preferably not more than 2 and more preferably not more than 1.

In the tables set out above, the assignment that $R^a$, $R^b$, $R^c$, $R^d$ is $R^1$-1 to $R^1$-95 means that both the $R^a$ group and the $R^b$, $R^c$, $R^d$ groups are selected from the radicals of the above-detailed formulae $R^1$-1 to $R^1$-95, preferably $R^1$-1. The assignment that Ar is $R^1$-1 to $R^1$-95, preferably $R^1$-1 to $R^1$-54, or Ar is H-1 to H-26, preferably H4-H-26, means that the Ar group in the above-detailed formulae can be represented by a group of the above-detailed structures ($R^1$-1) to ($R^1$-95) or (H-1) to (H-26). The further assignments apply correspondingly.

Examples of suitable compounds of the invention are the structures of the following formulae 1 to 180 shown below:
Formula 1
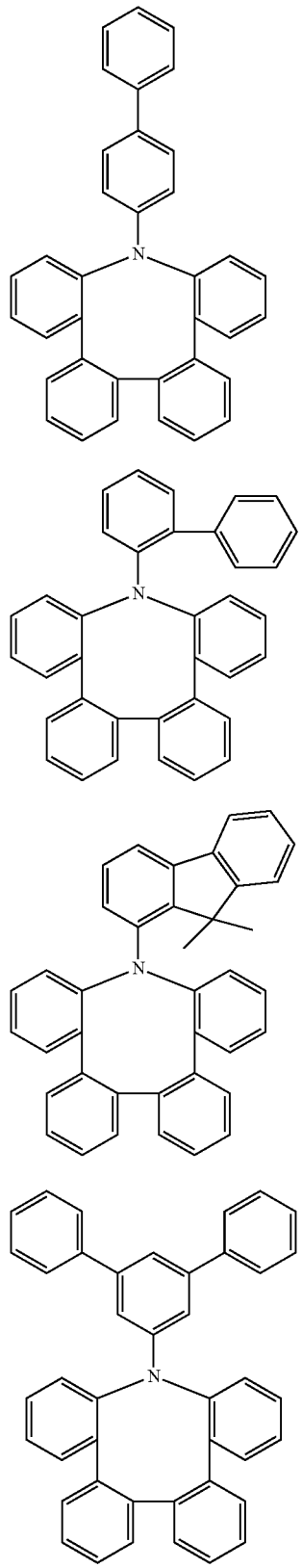
Formula 2
Formula 3
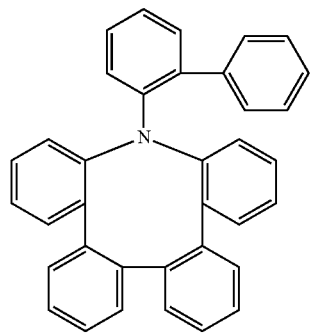
Formula 4
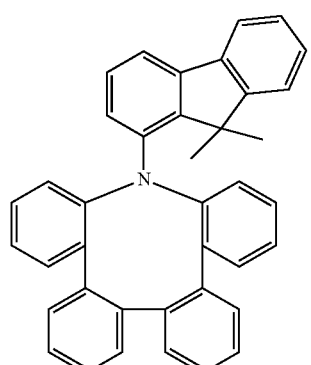
Formula 5
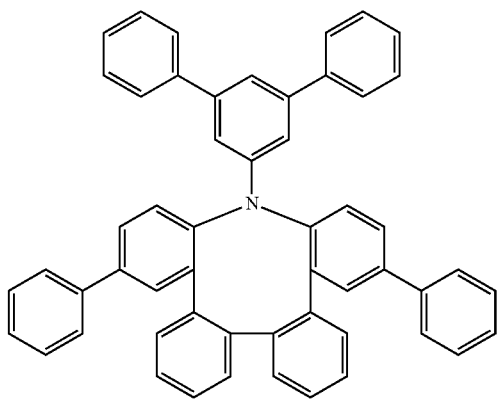
Formula 6
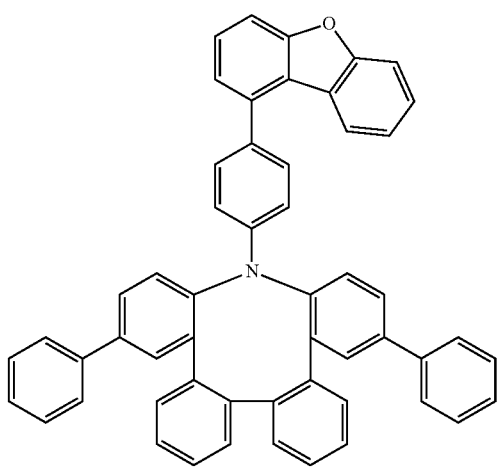
Formula 7
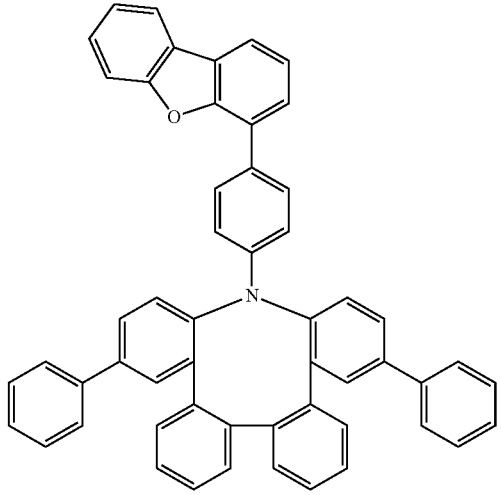

Formula 8
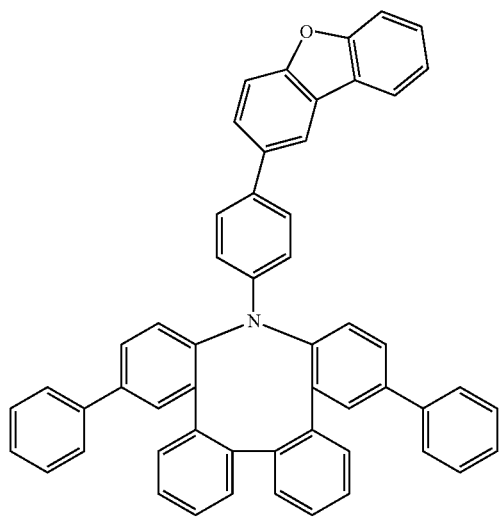
Formula 9
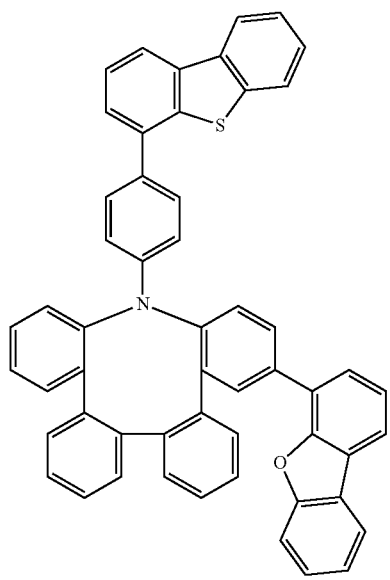
Formula 10
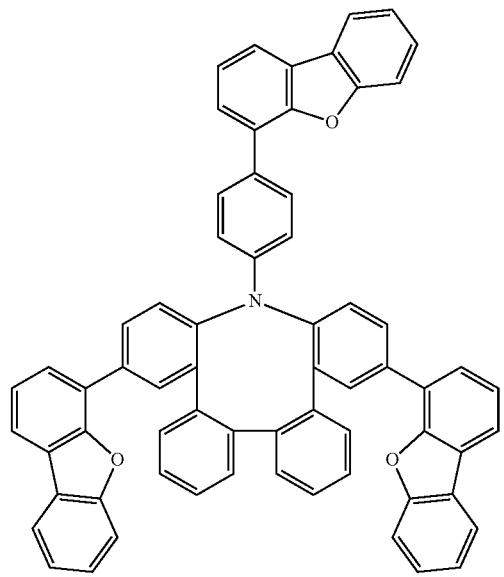
Formula 11
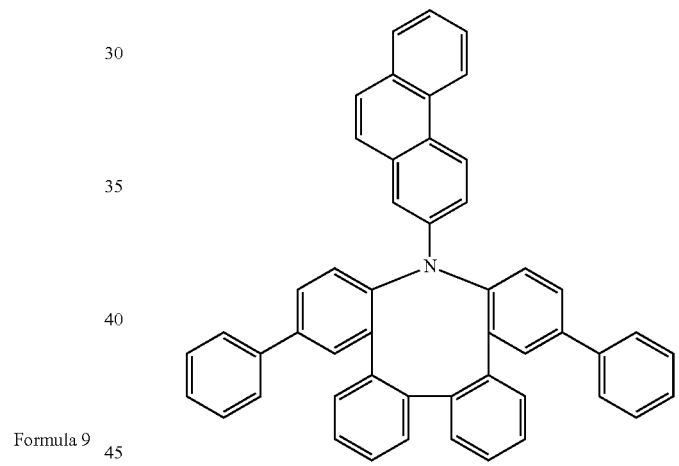
Formula 12
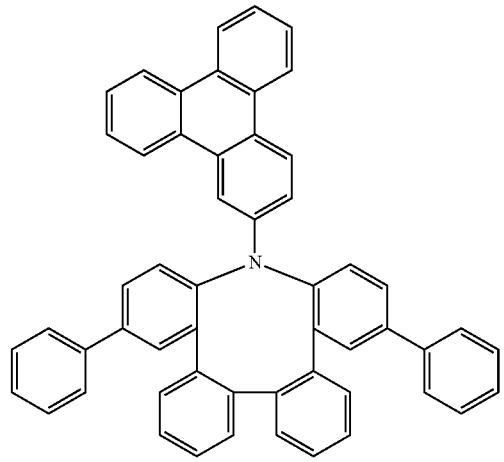

Formula 13
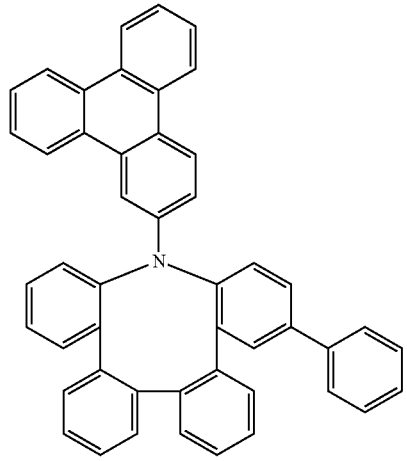
Formula 14
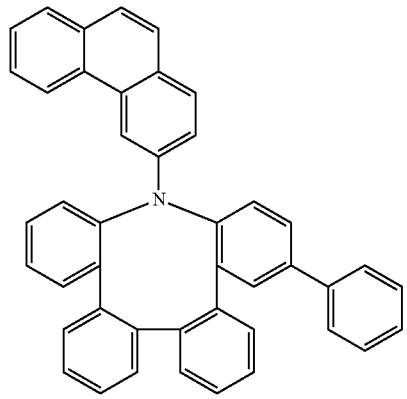
Formula 15
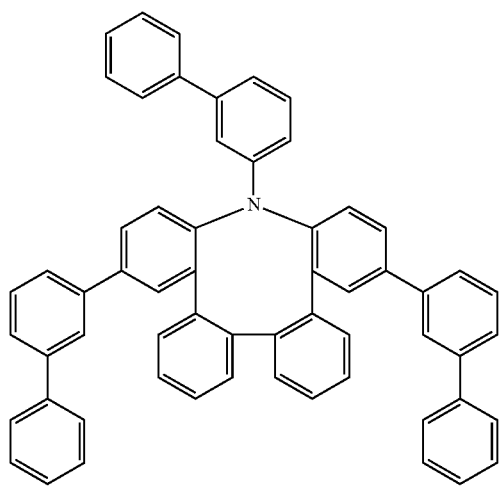
Formula 16
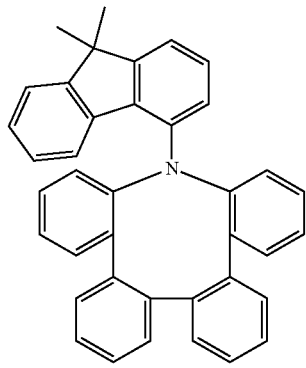
Formula 17
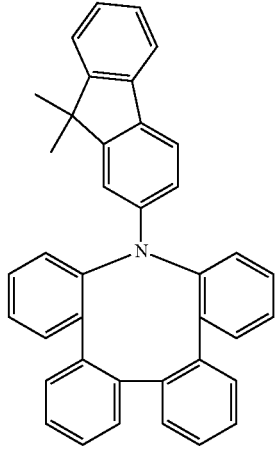
Formula 18
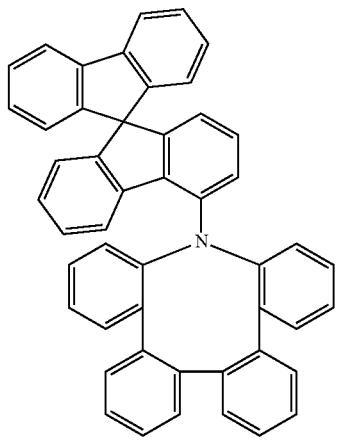

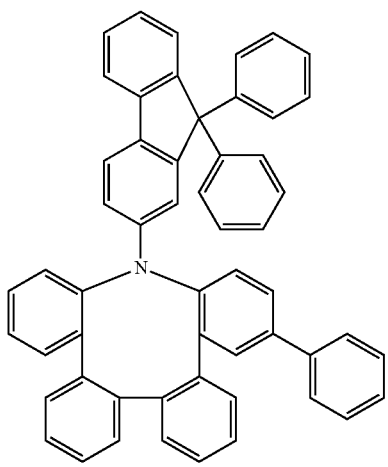
Formula 19
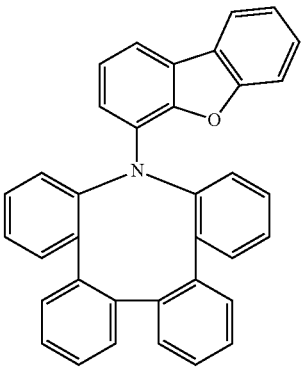
Formula 22
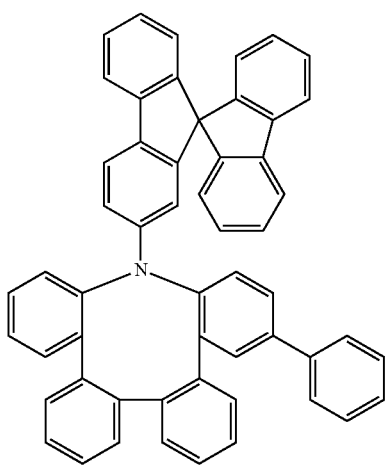
Formula 20
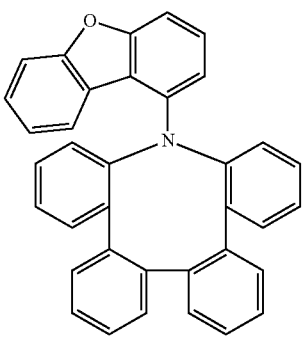
Formula 23
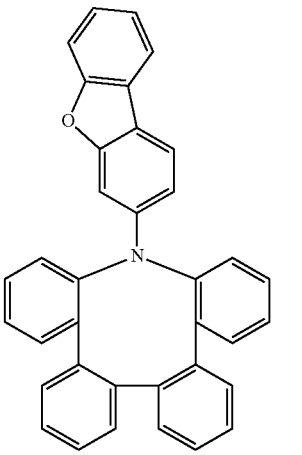
Formula 24
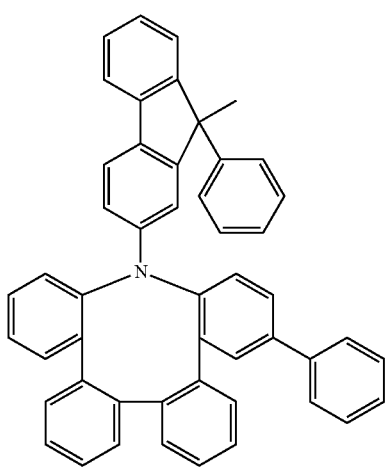
Formula 21
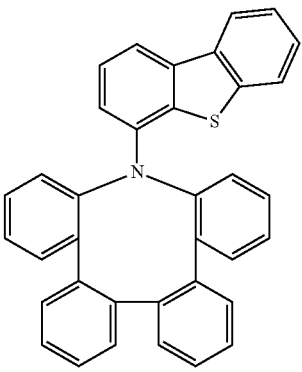
Formula 25

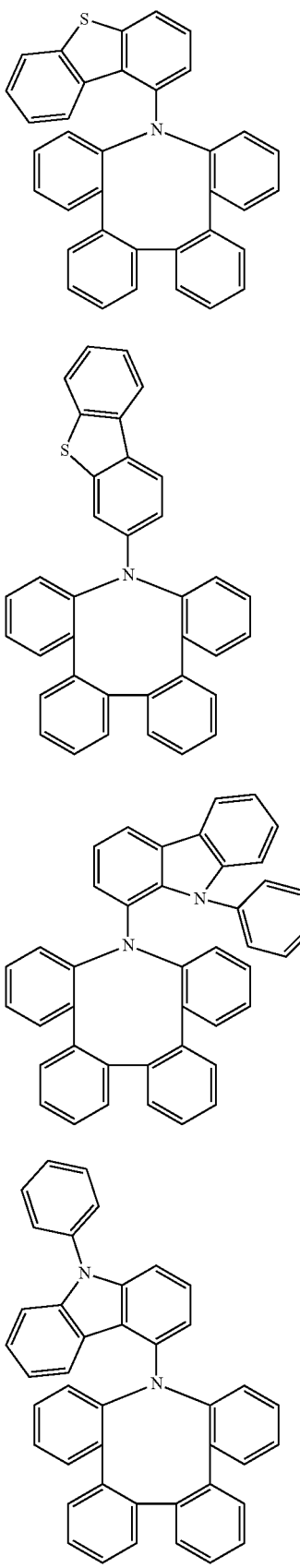
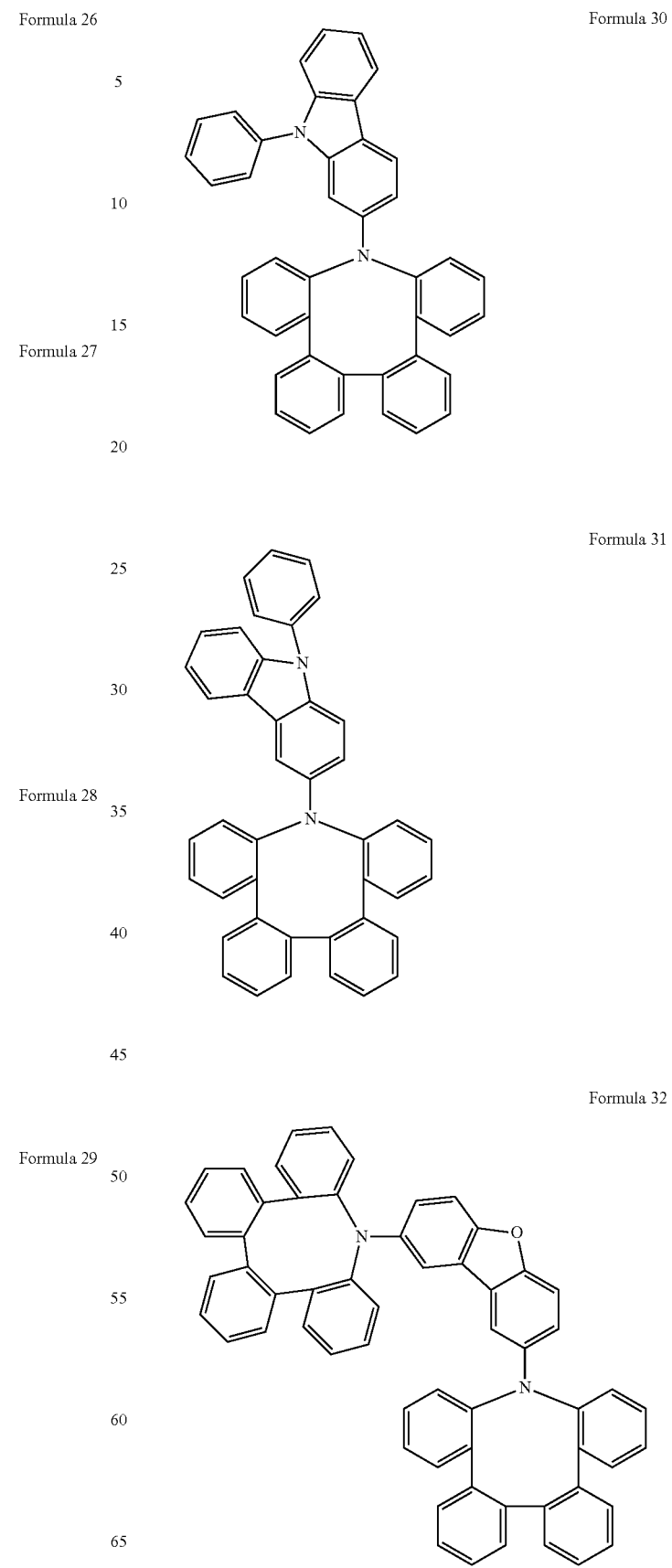

Formula 33
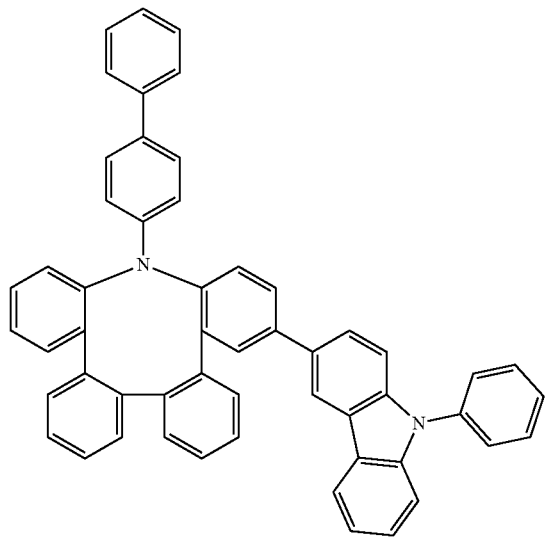
Formula 36
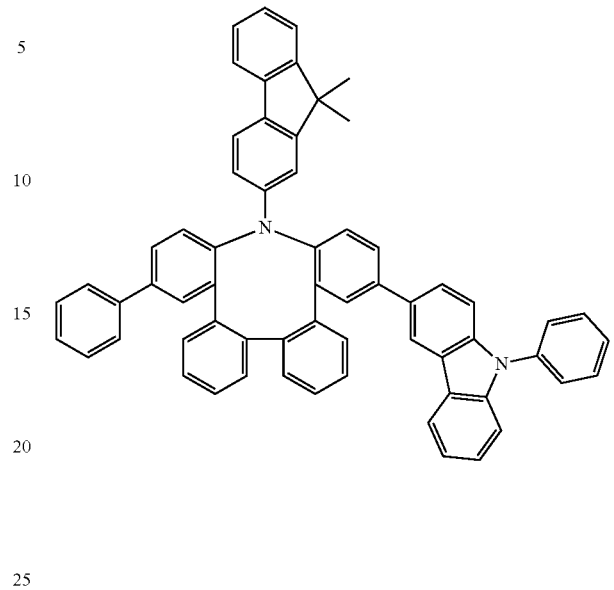
Formula 34
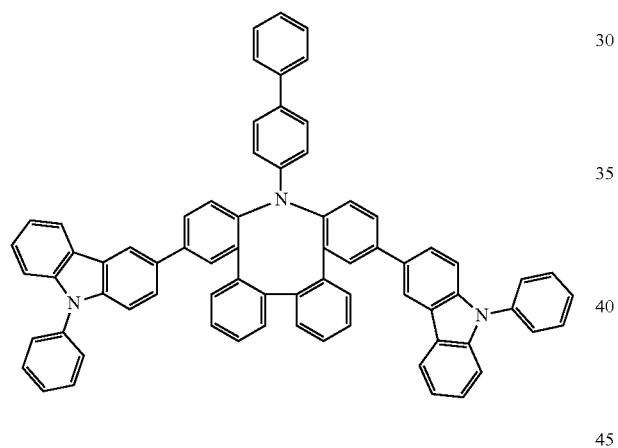
Formula 37
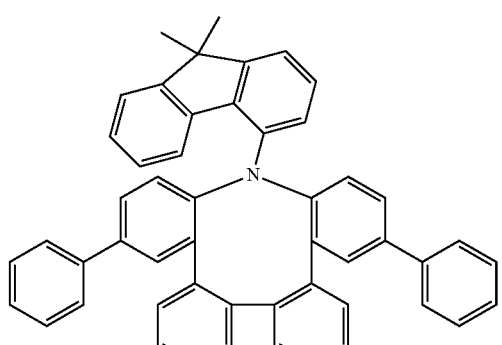
Formula 35
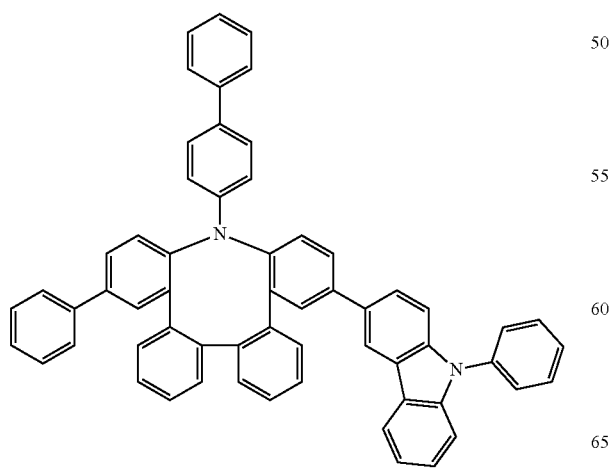
Formula 38
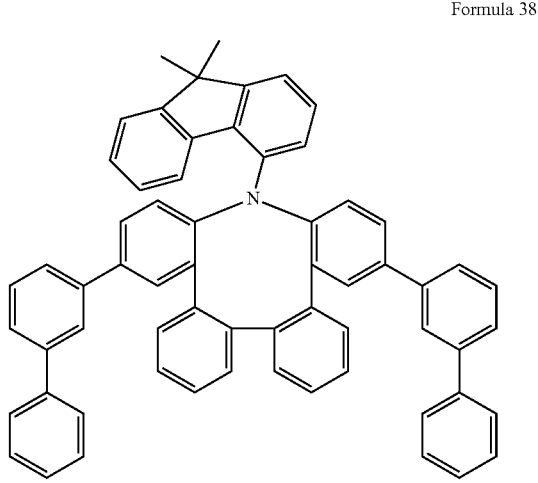

Formula 39
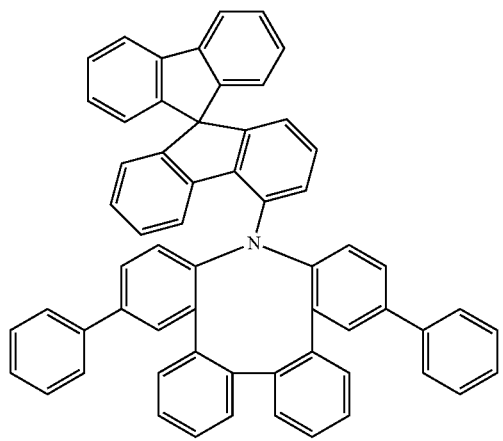
Formula 42
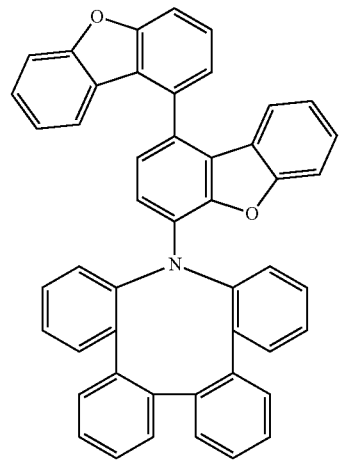
Formula 40
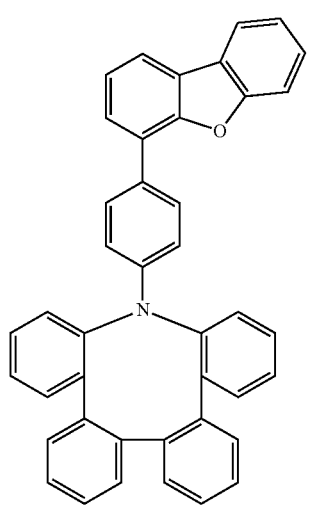
Formula 43
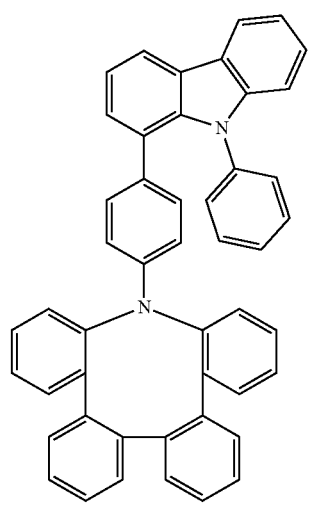
Formula 41
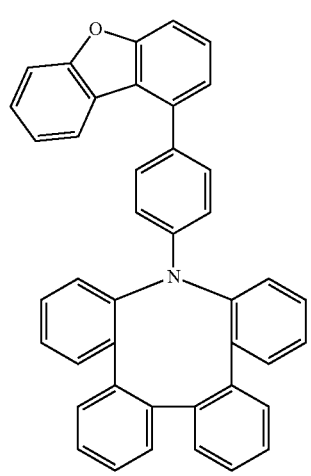
Formula 44
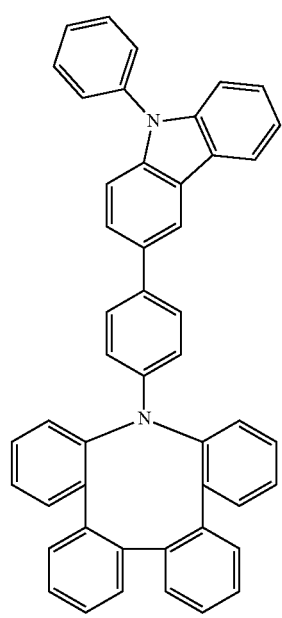

Formula 45
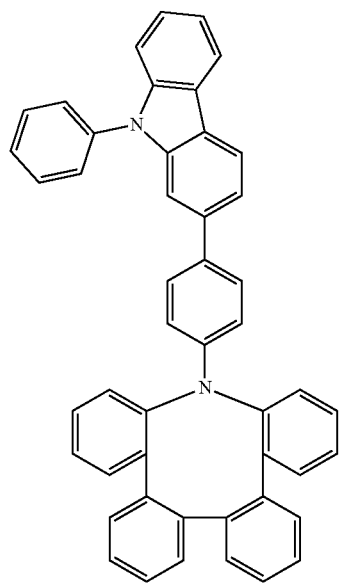
Formula 47
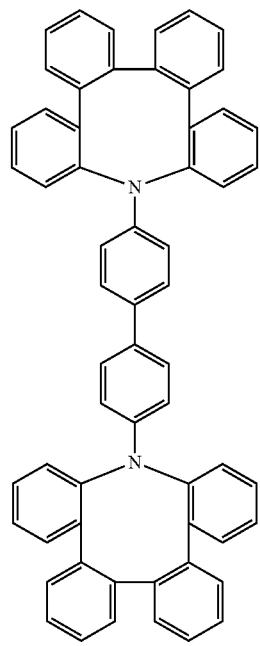
Formula 46
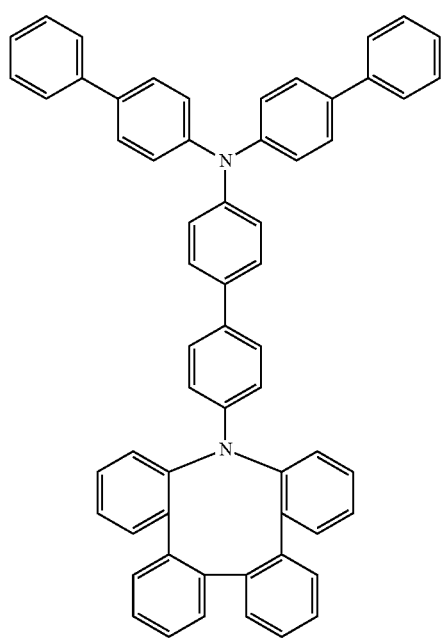
Formula 48
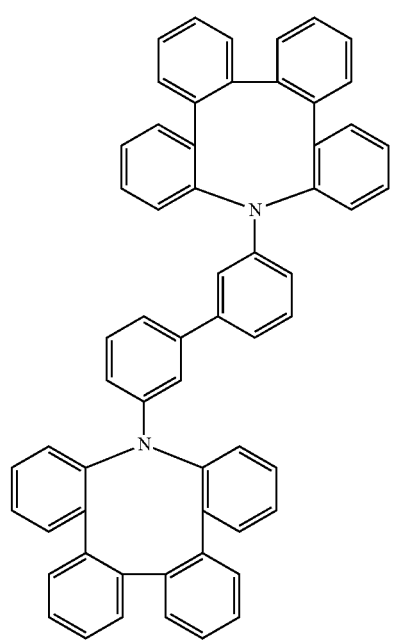

Formula 49
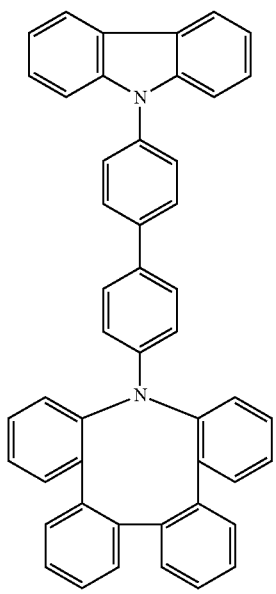
Formula 50
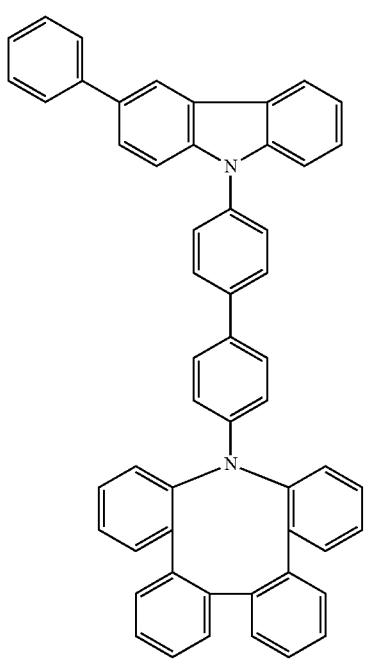
Formula 51
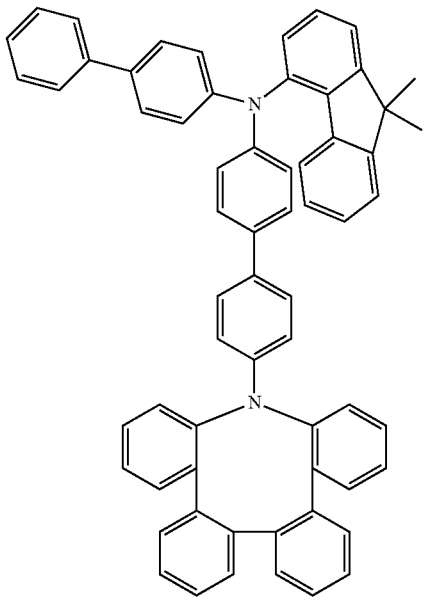
Formula 52
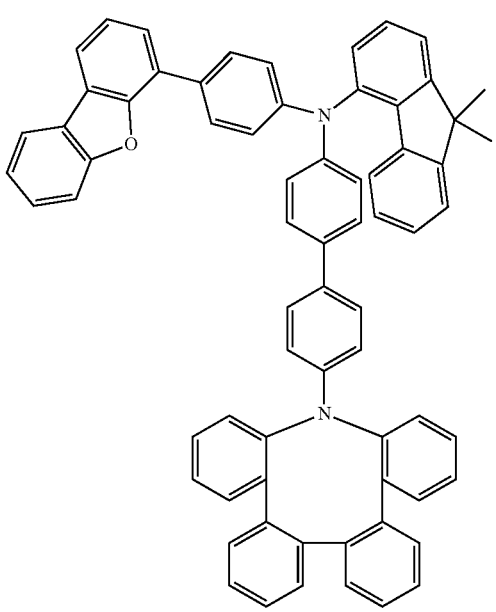

Formula 53
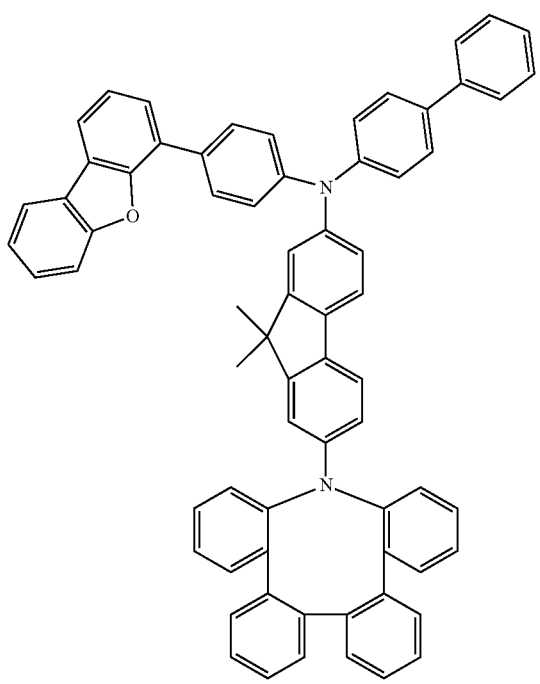
Formula 54
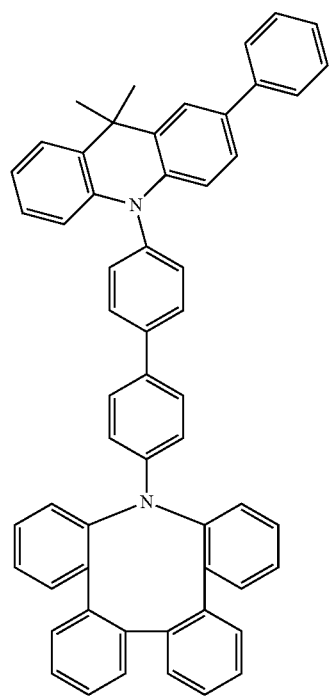
Formula 55
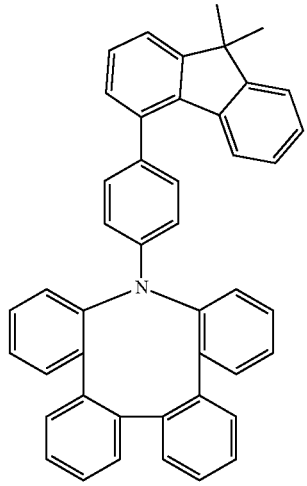
Formula 56
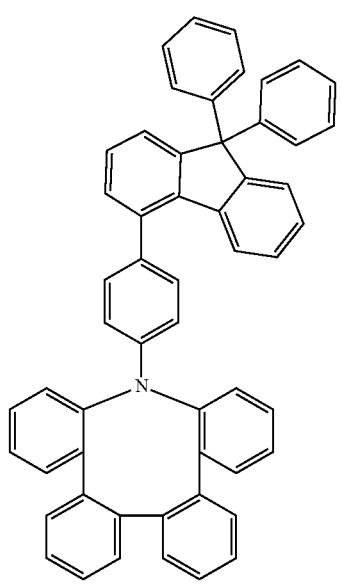
Formula 57
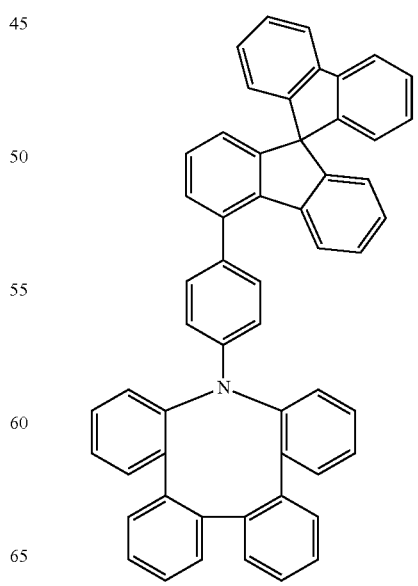

Formula 58
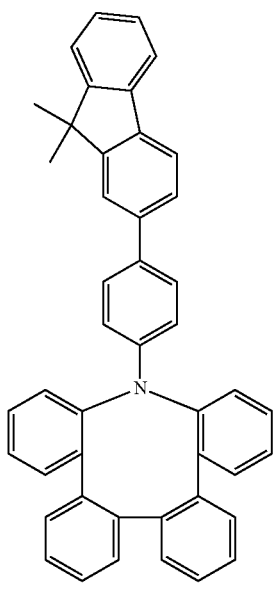
Formula 59
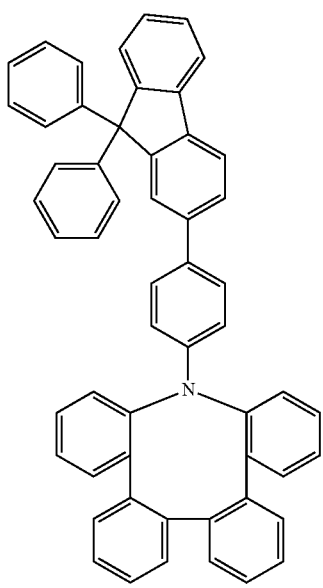
Formula 60
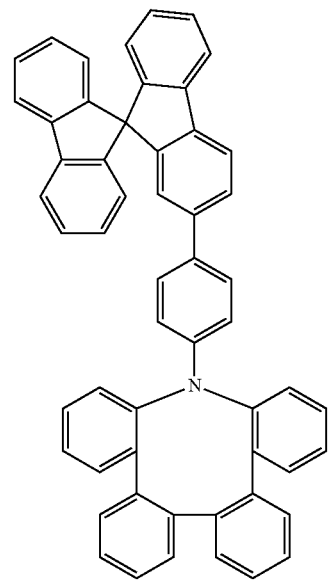
Formula 61
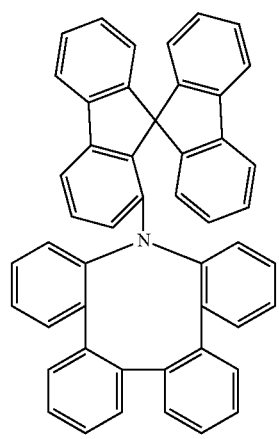
Formula 62
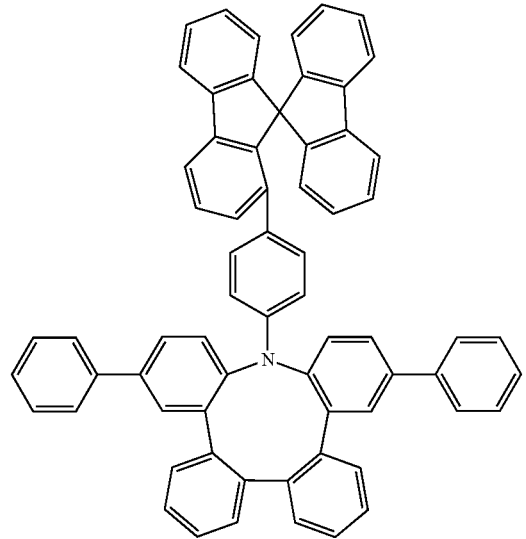

Formula 63
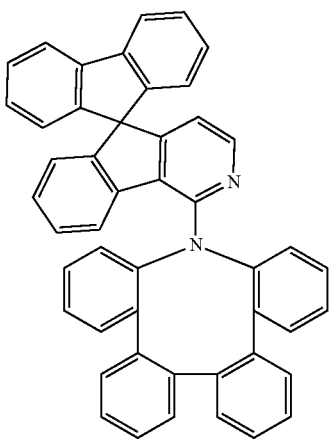
Formula 64
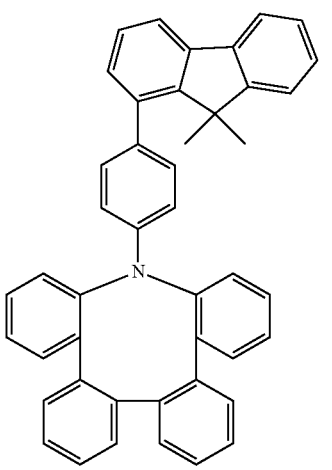
Formula 65
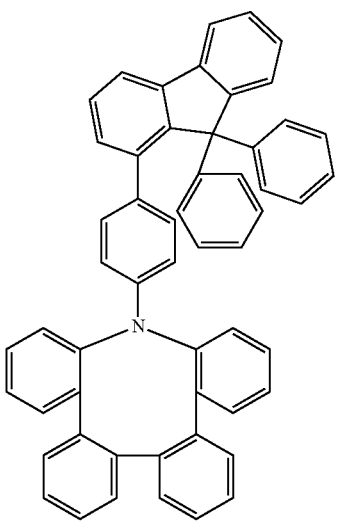
Formula 66
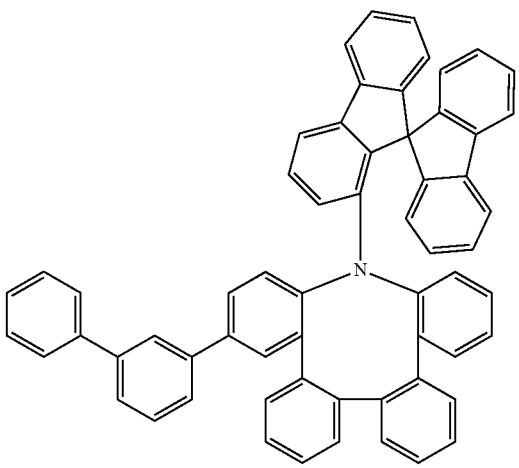
Formula 67
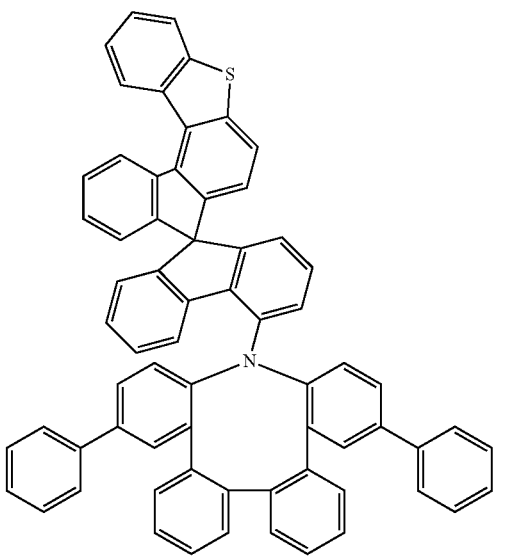
Formula 68
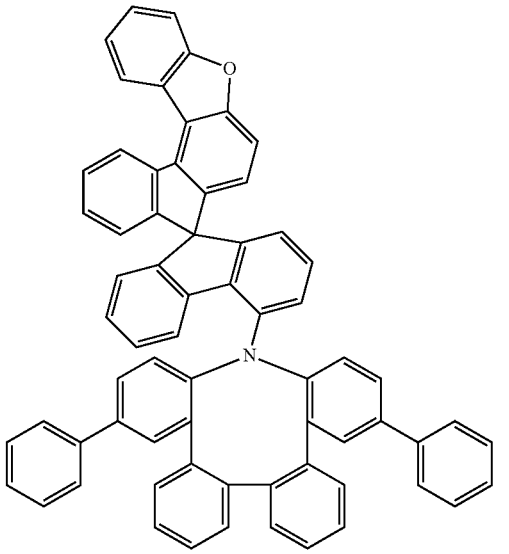

-continued
Formula 69
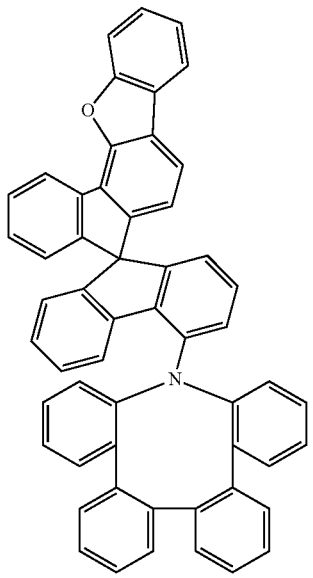
Formula 70
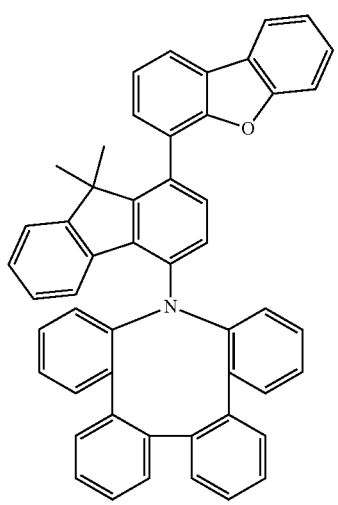
Formula 71
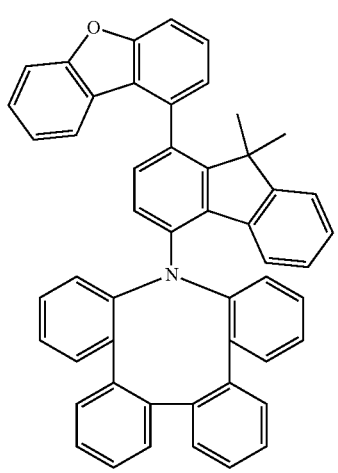
Formula 72
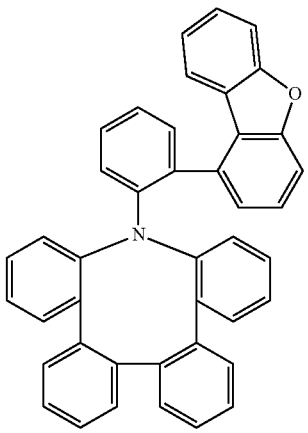
Formula 73
Formula 74
Formula 75
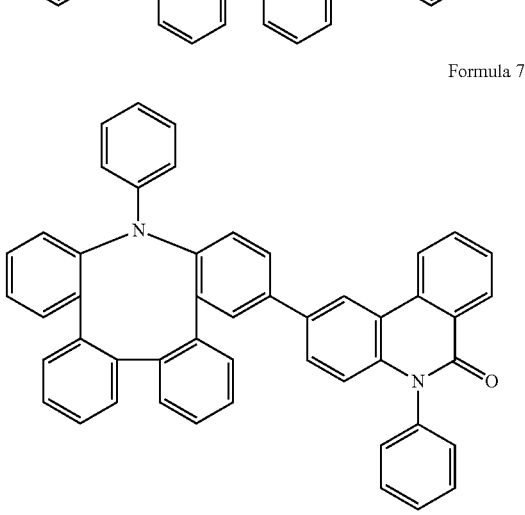

Formula 76
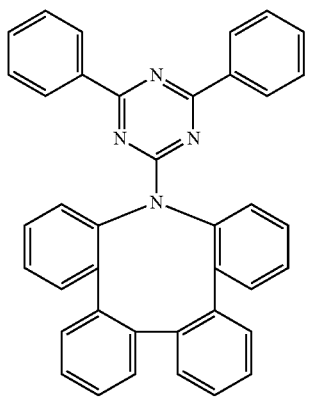
Formula 77
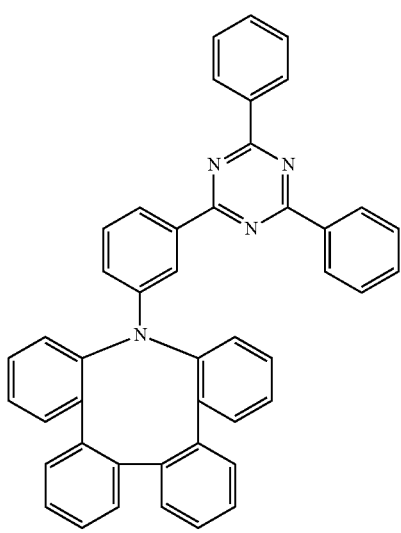
Formula 78
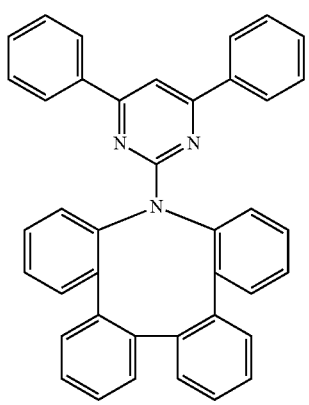
Formula 79
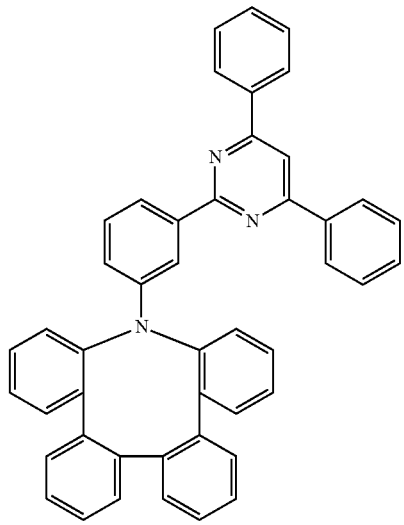
Formula 80
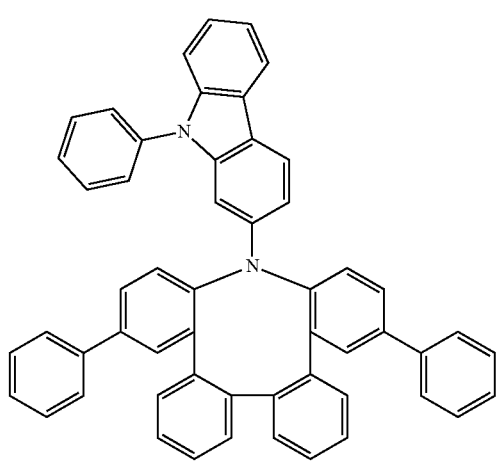
Formula 81
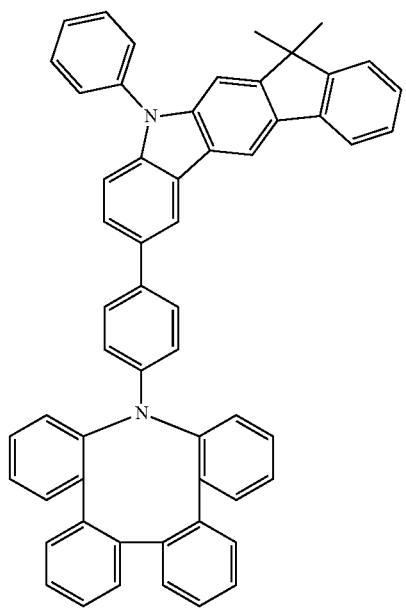

Formula 82
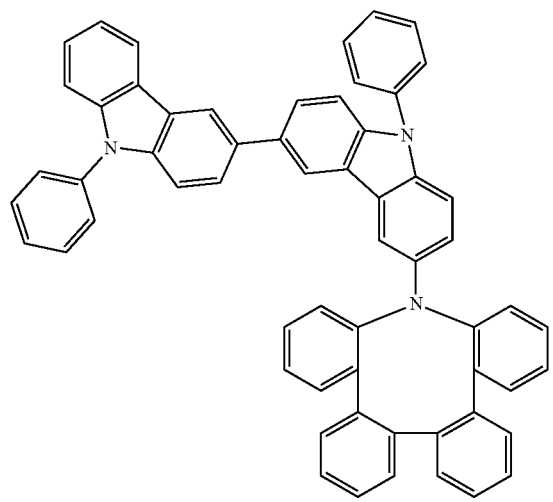
Formula 83
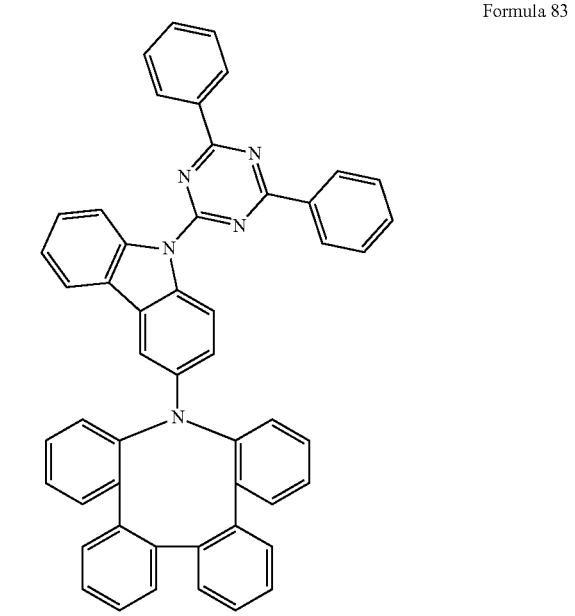
Formula 84
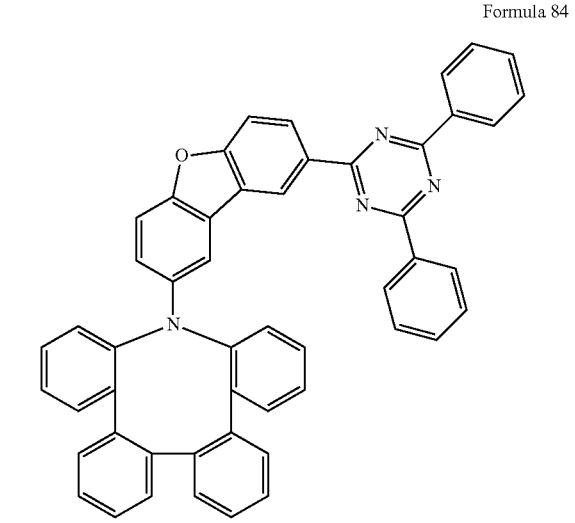
Formula 85
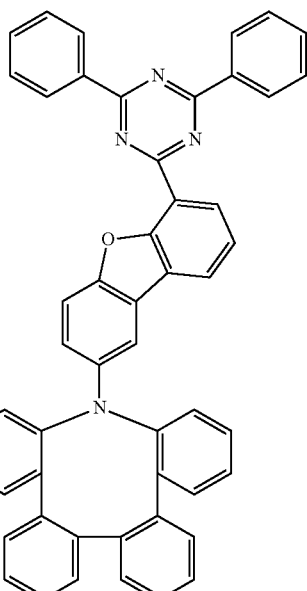
Formula 86
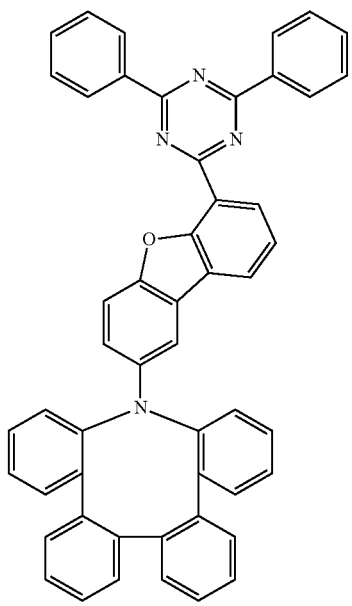
Formula 87
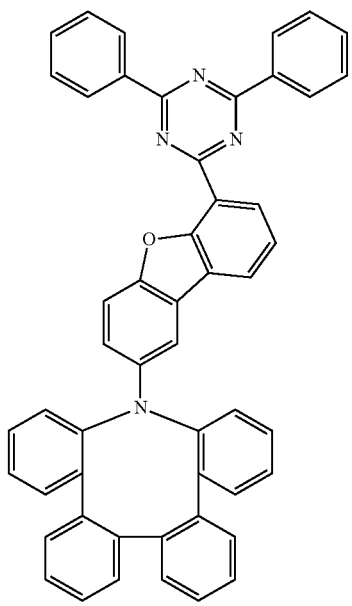

-continued
Formula 88
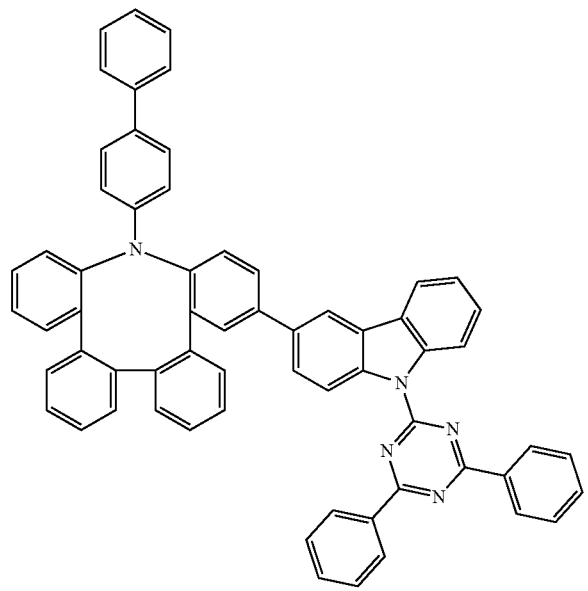
Formula 89
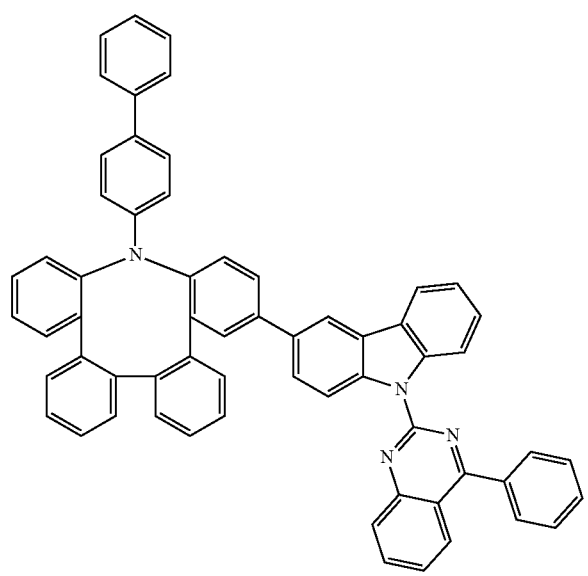
Formula 90
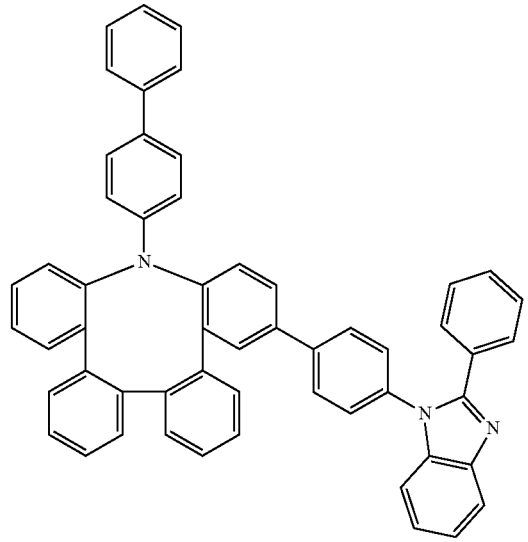
Formula 91
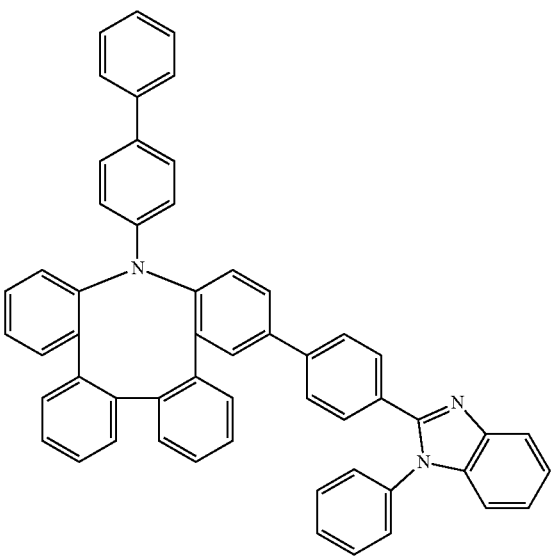
Formula 92

-continued
Formula 93
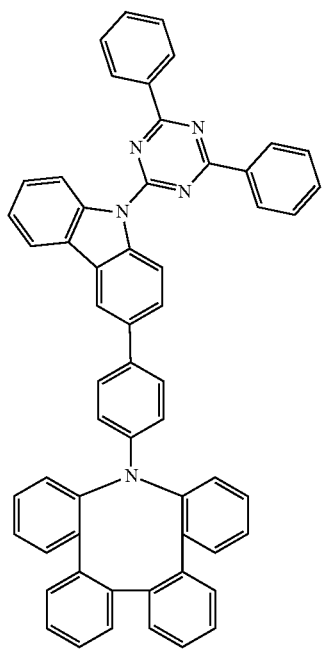
Formula 94
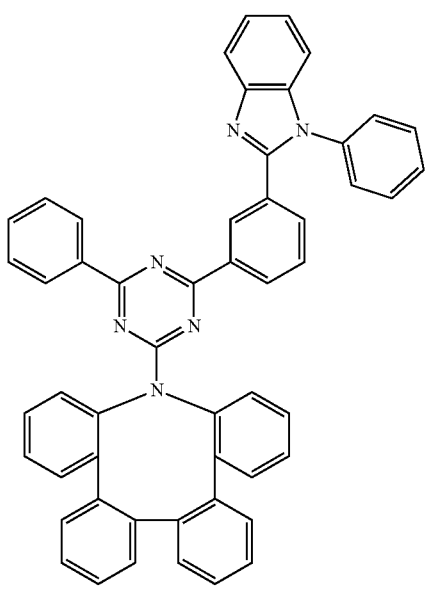
Formula 95
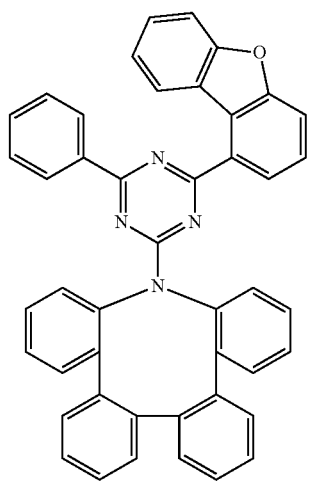
Formula 96
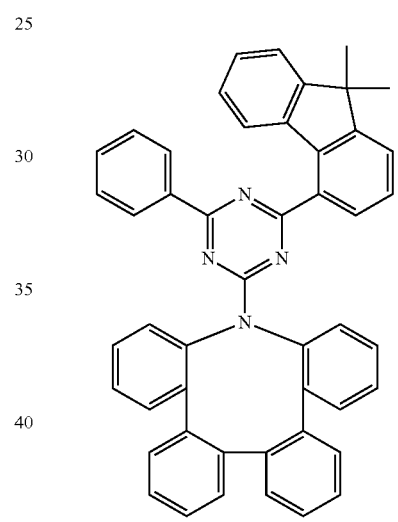
Formula 97
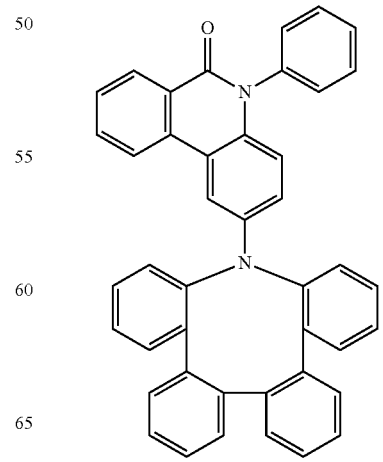

Formula 98
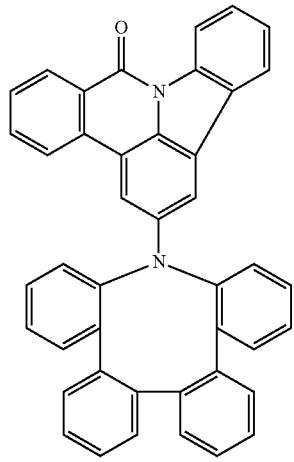
Formula 99
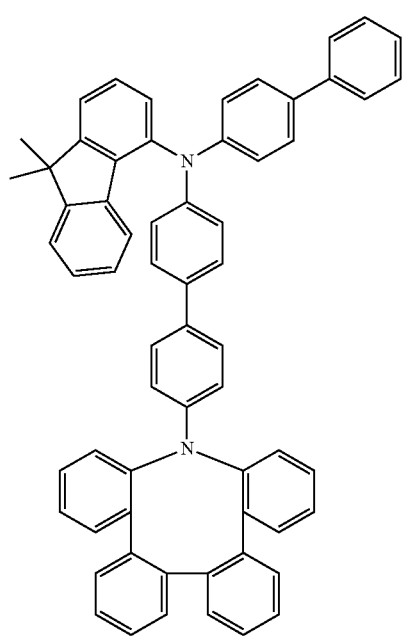
Formula 100
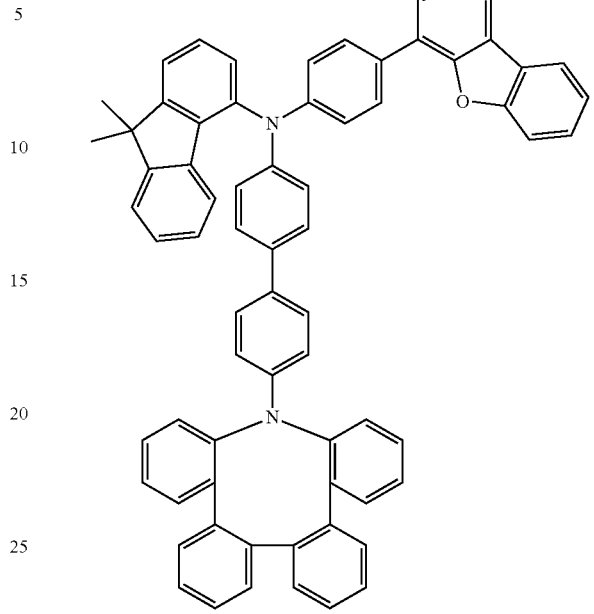
Formula 101
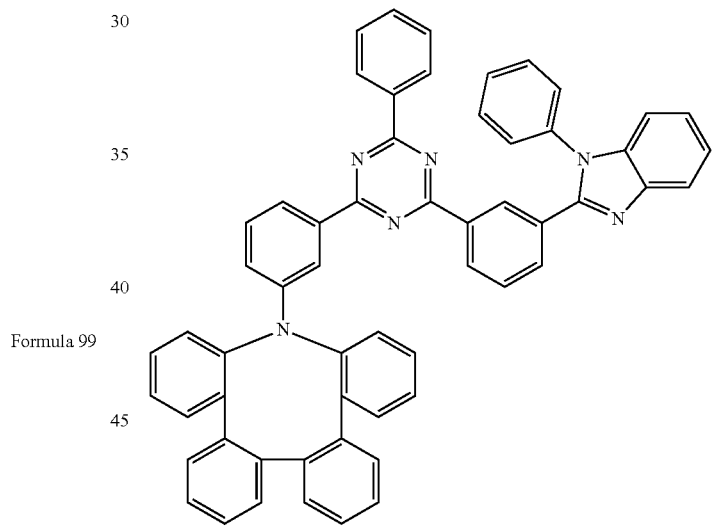
Formula 102
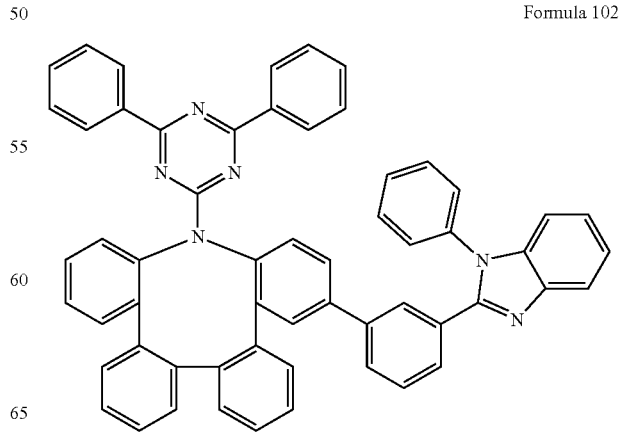

Formula 103
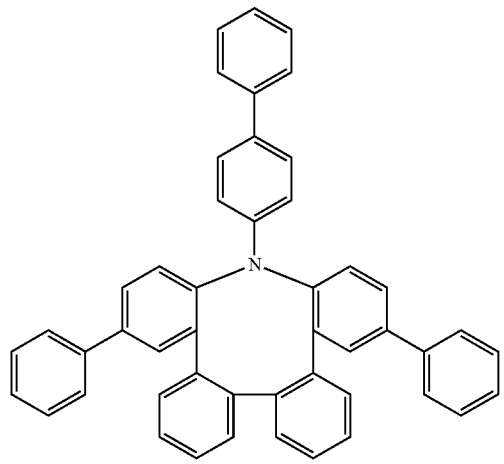
Formula 106
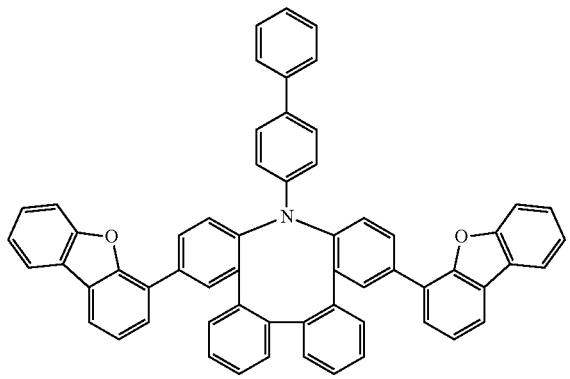
Formula 104
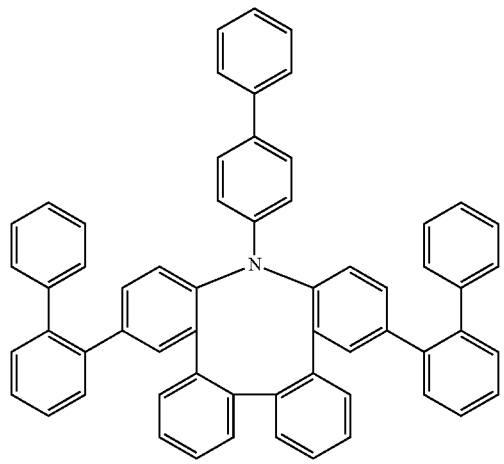
Formula 107
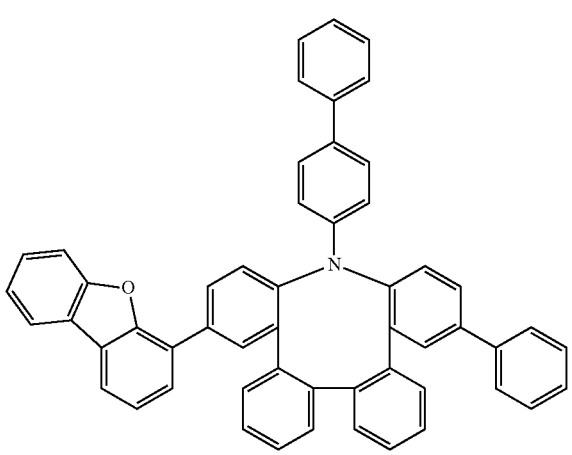
Formula 105
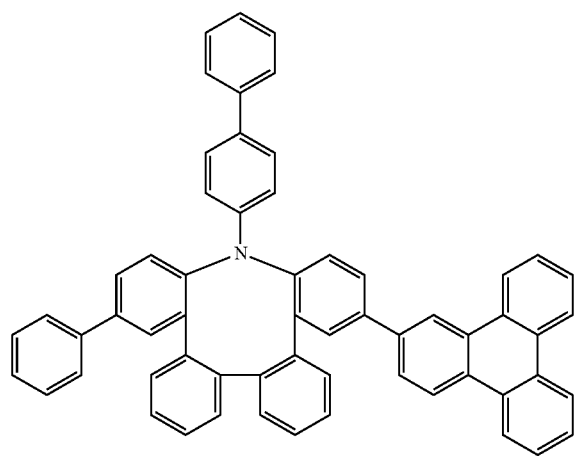
Formula 108
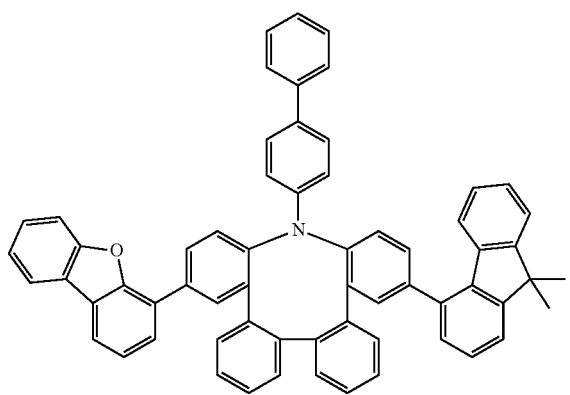

-continued
Formula 109
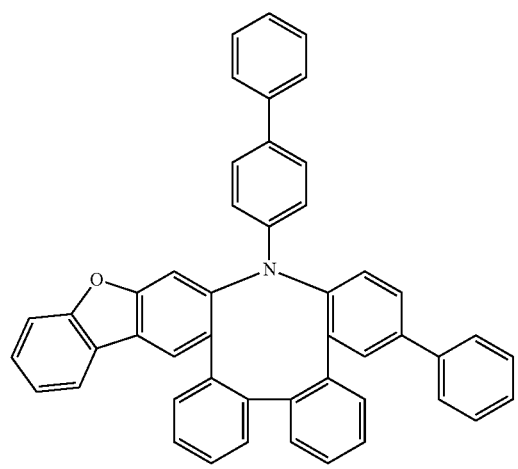
Formula 110
Formula 111
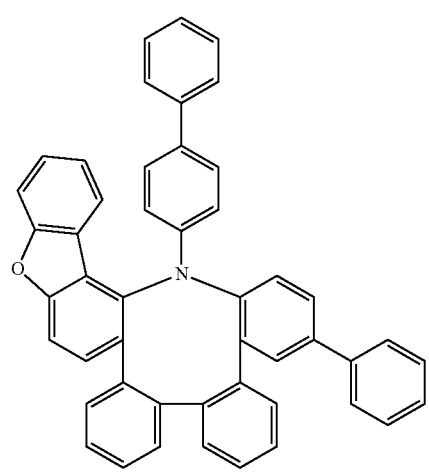
-continued
Formula 112
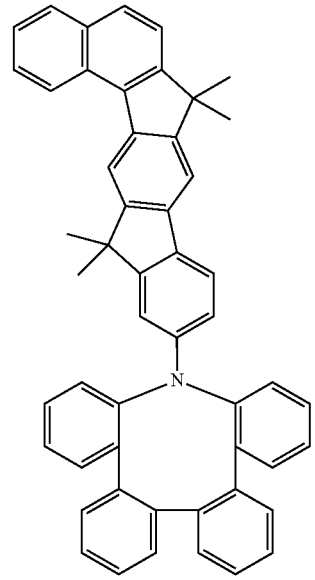
Formula 113
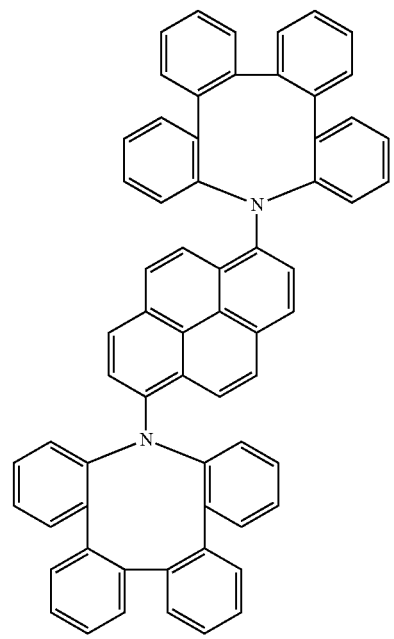

Formula 114
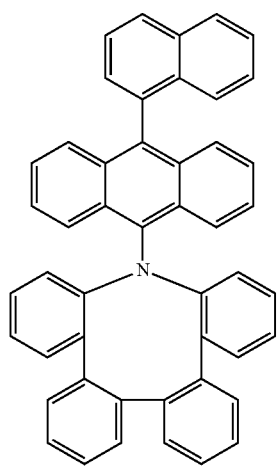
Formula 115
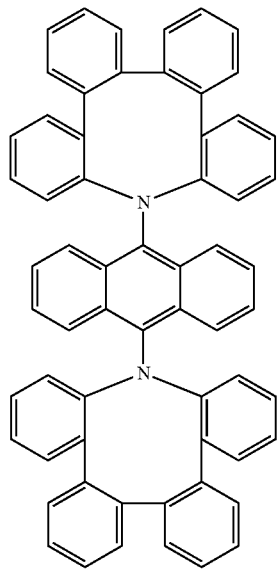
Formula 116
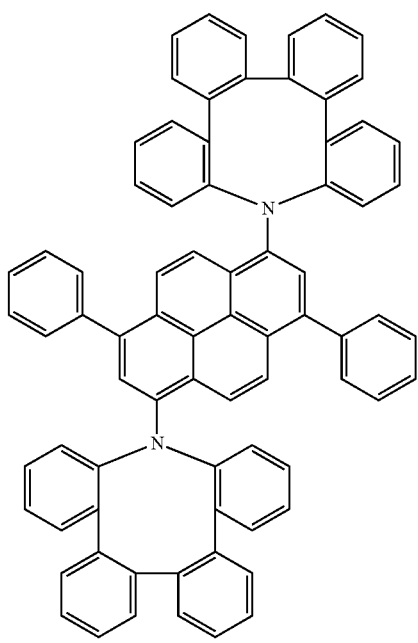
Formula 117
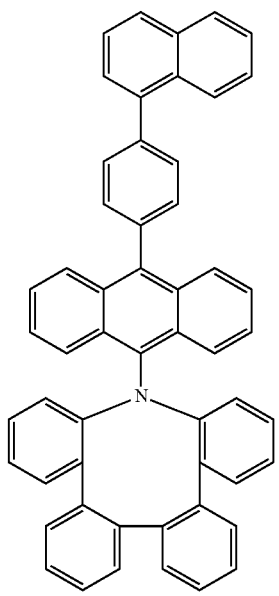
Formula 118
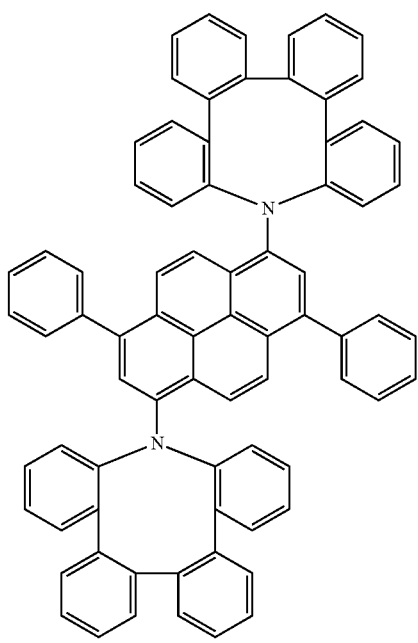

Formula 119
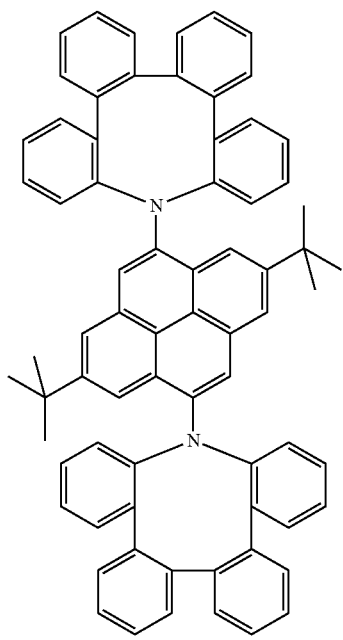
Formula 121
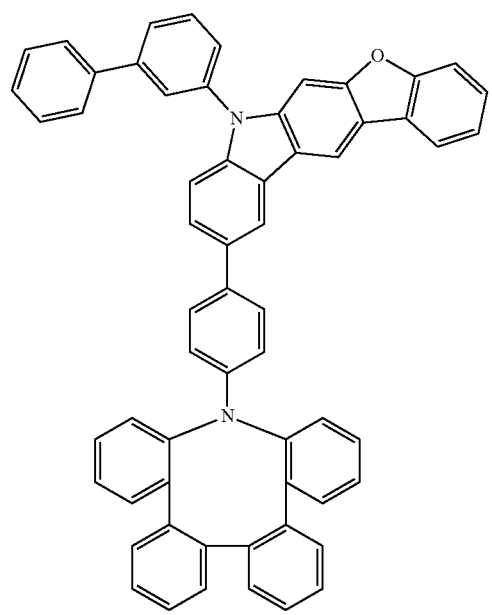
Formula 120
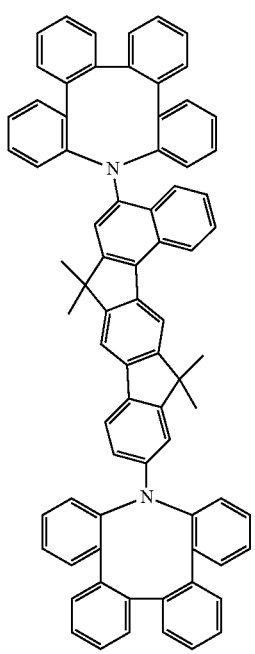
Formula 122
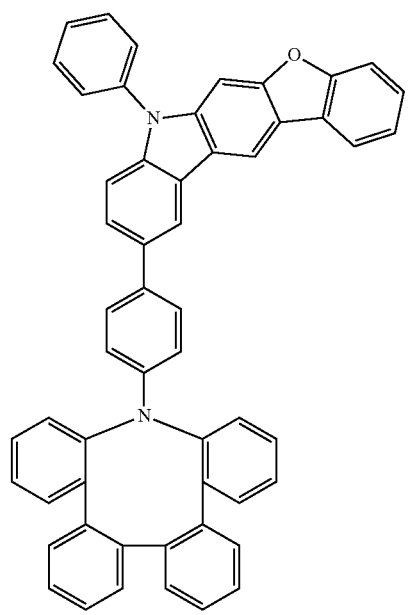

Formula 123
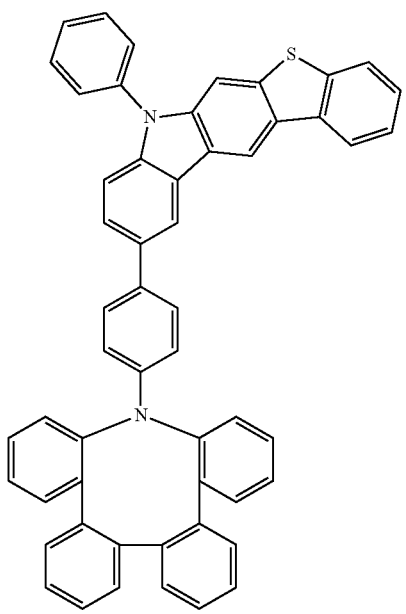
Formula 124
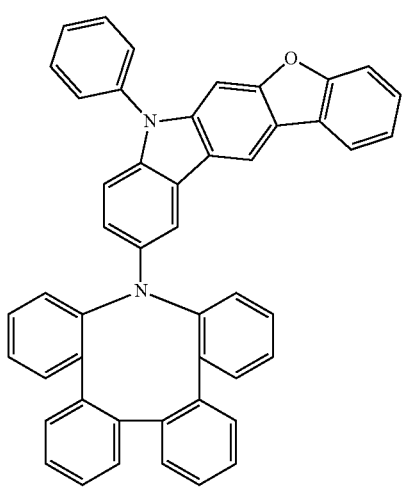
Formula 125
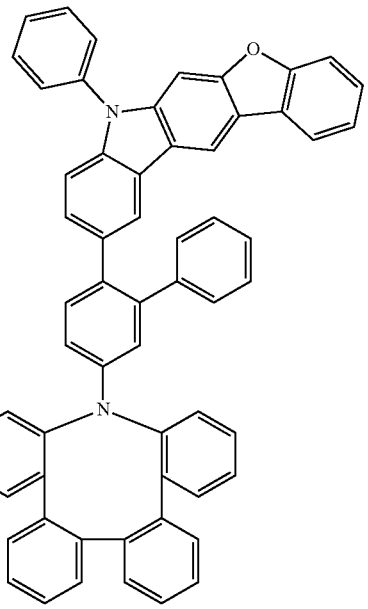
Formula 126
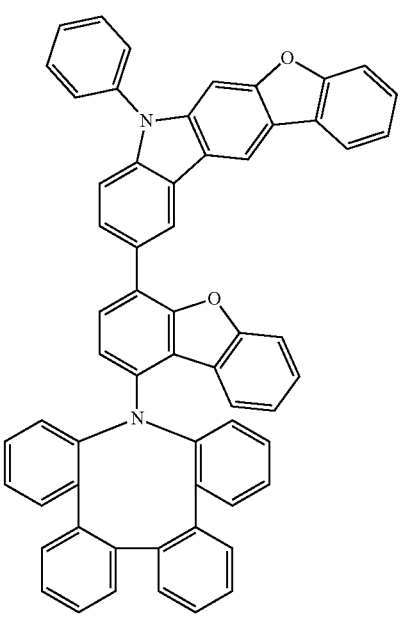

Formula 127
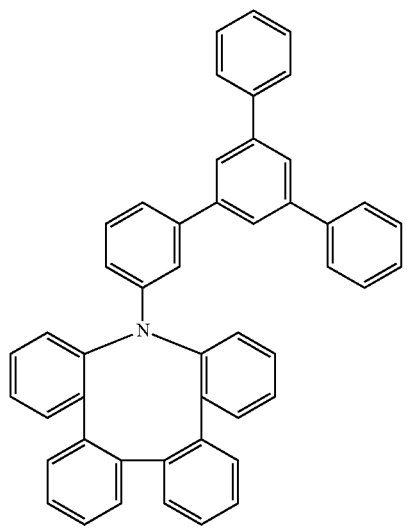
Formula 128
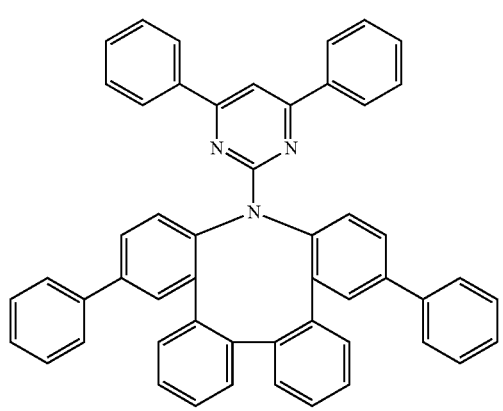
Formula 129
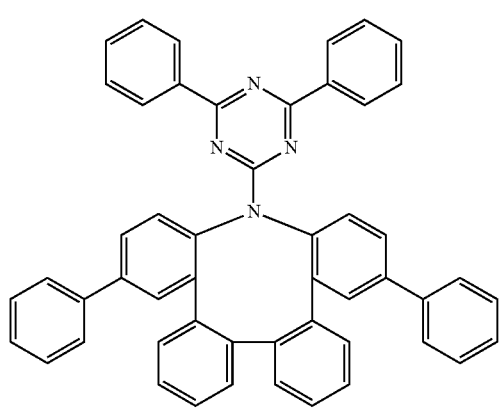
Formula 130
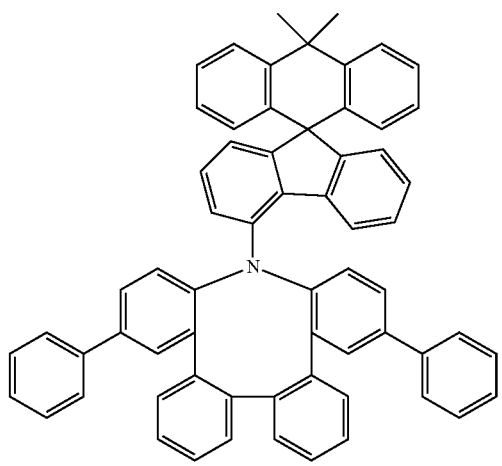
Formula 131
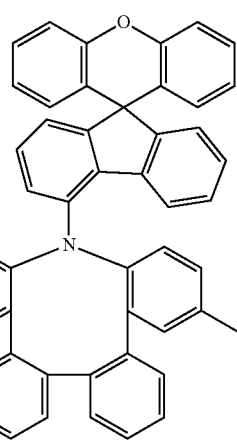
Formula 132
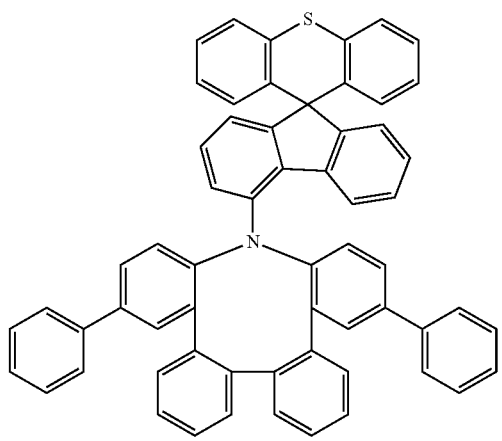

Formula 133
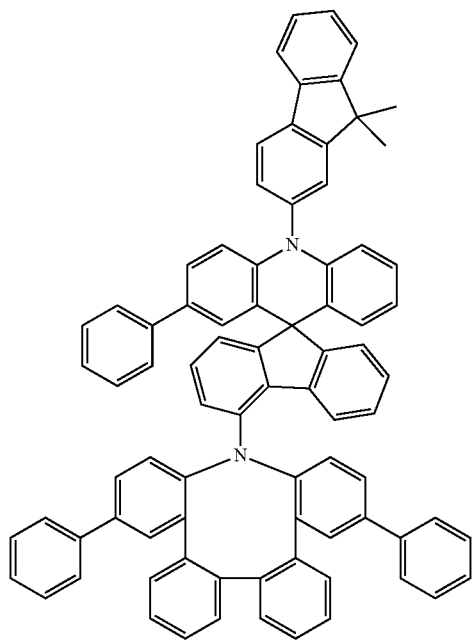
Formula 134
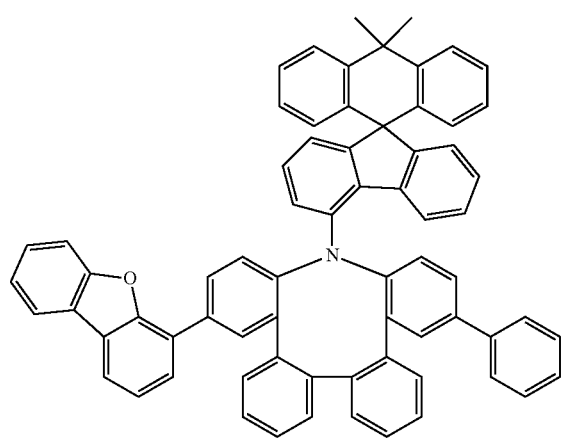
Formula 135
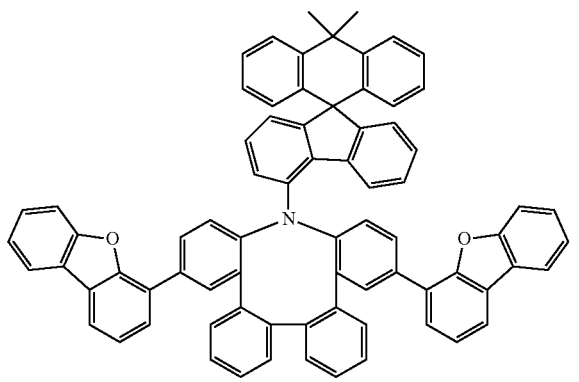
Formula 136
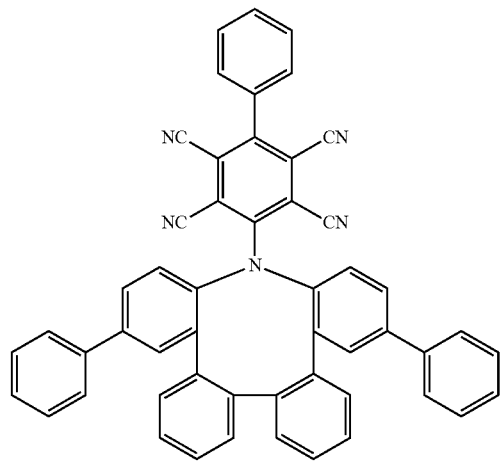
Formula 137
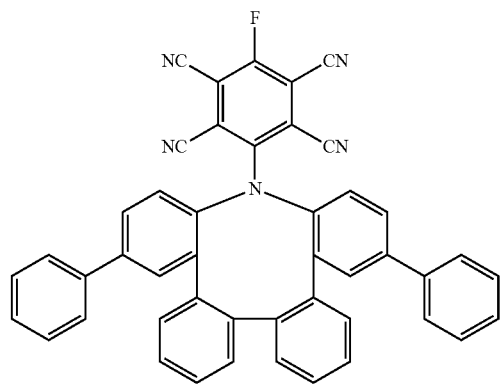
Formula 138
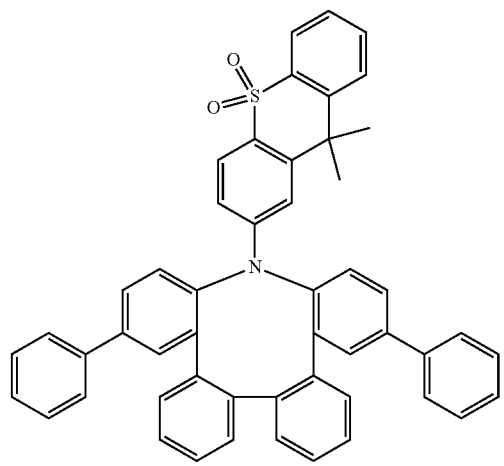

Formula 139
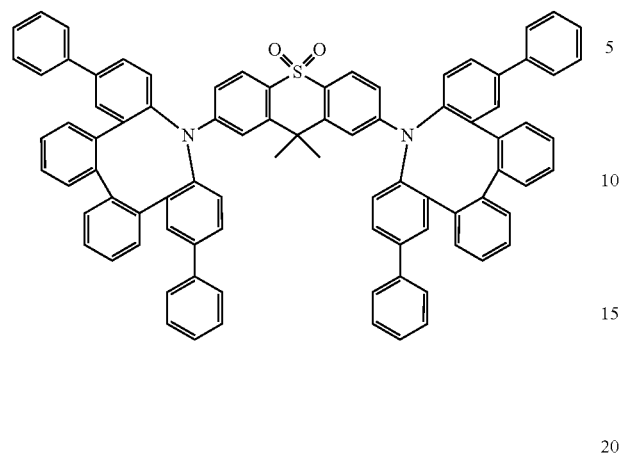
Formula 140
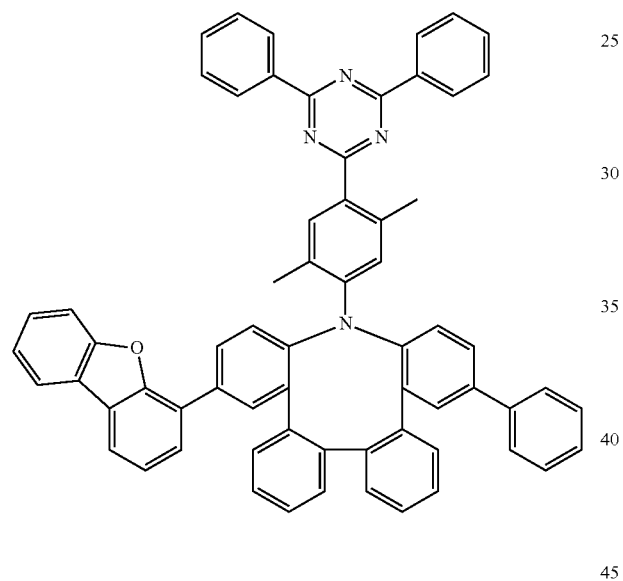
Formula 141
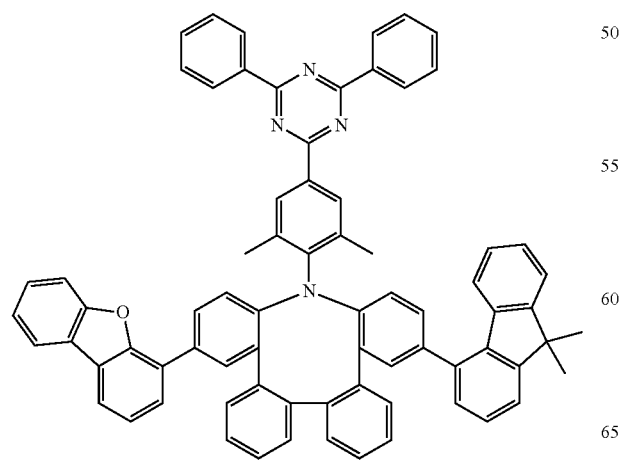
Formula 142
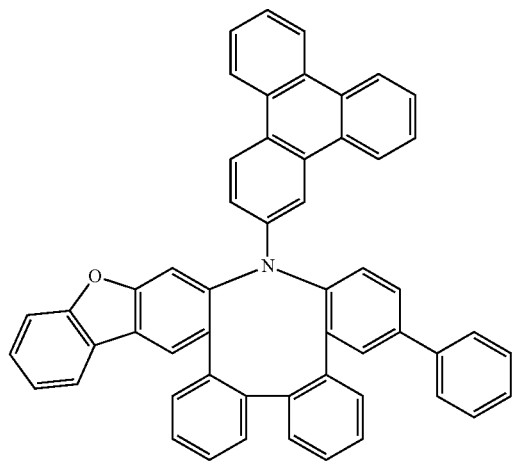
Formula 143
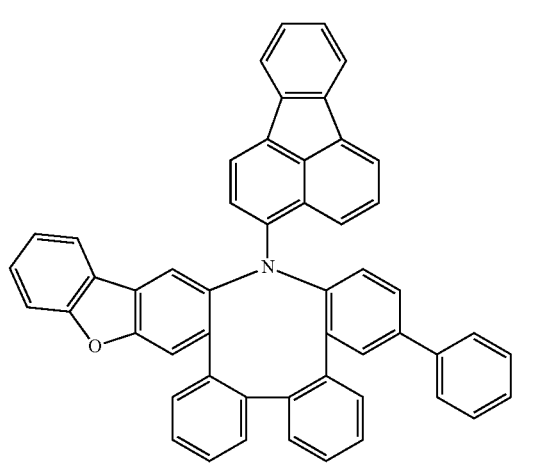
Formula 144
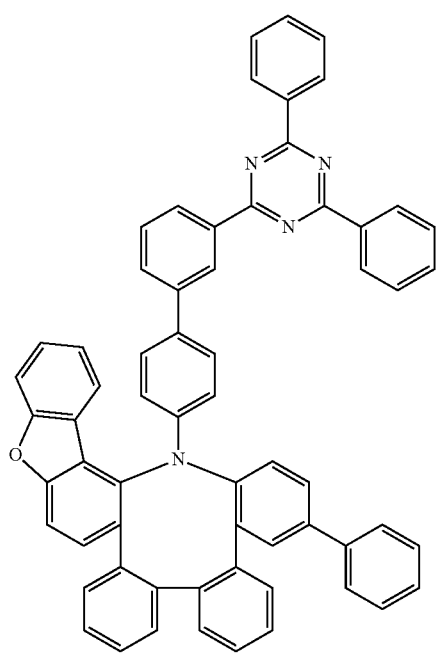

-continued
Formula 145
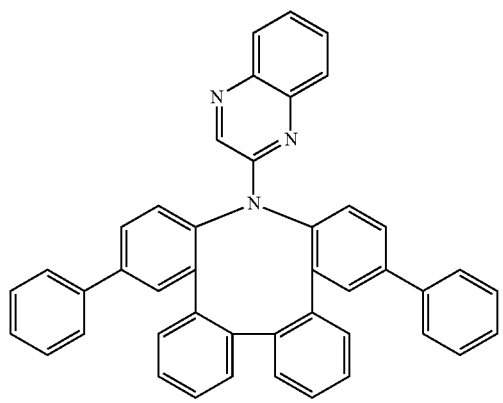
Formula 146
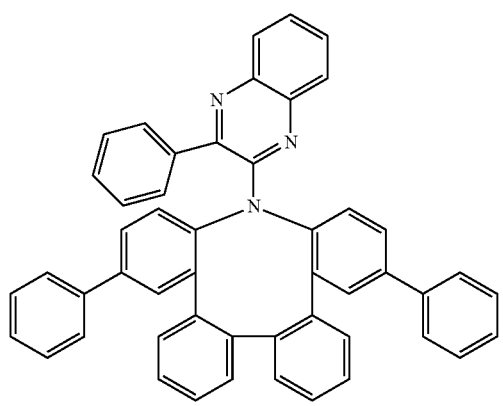
Formula 147
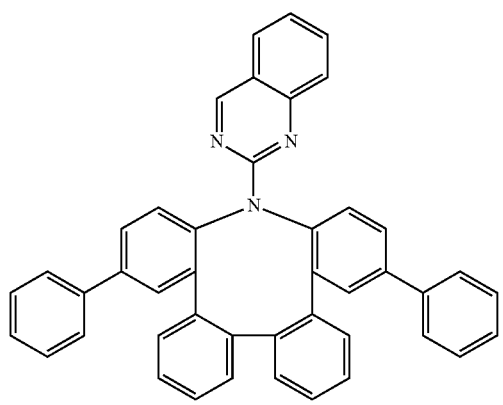
-continued
Formula 148
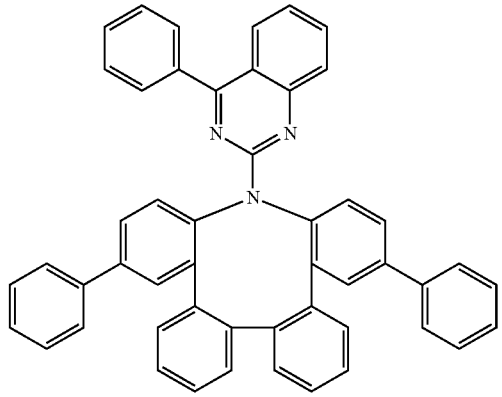
Formula 149
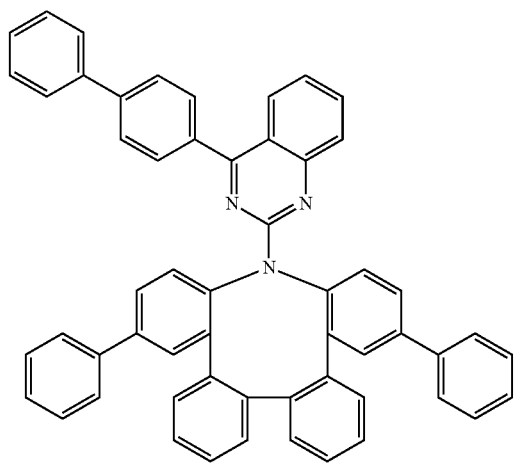
Formula 150
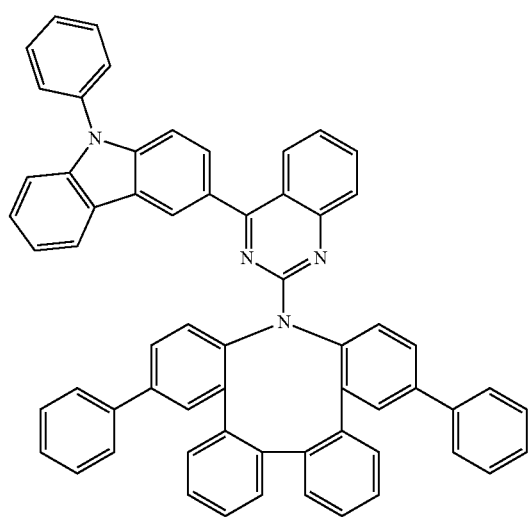

Formula 151
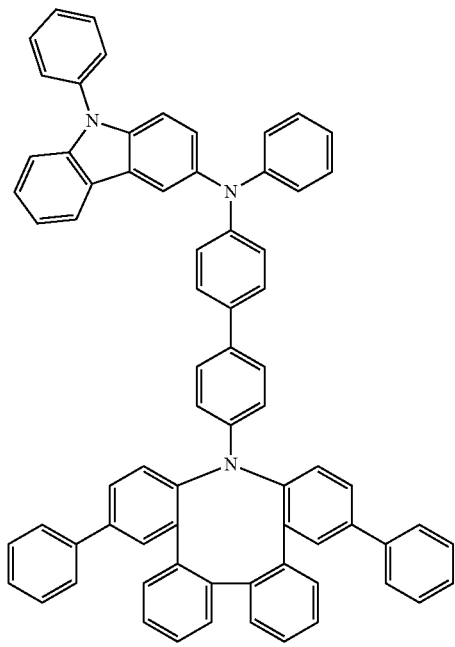
Formula 152
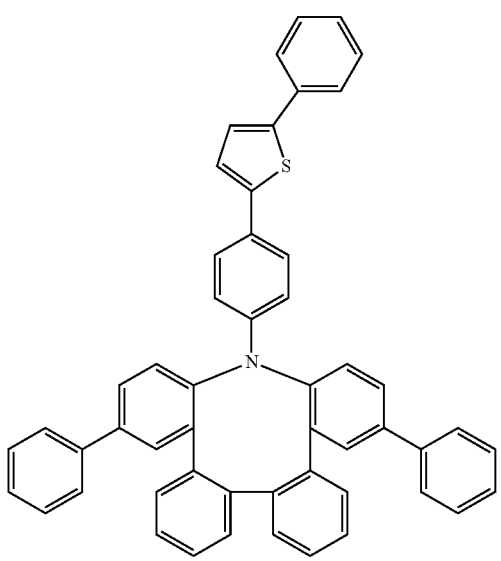
Formula 153
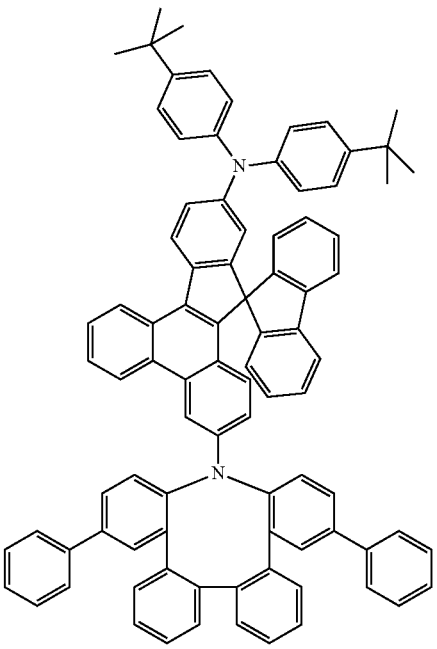
Formula 154
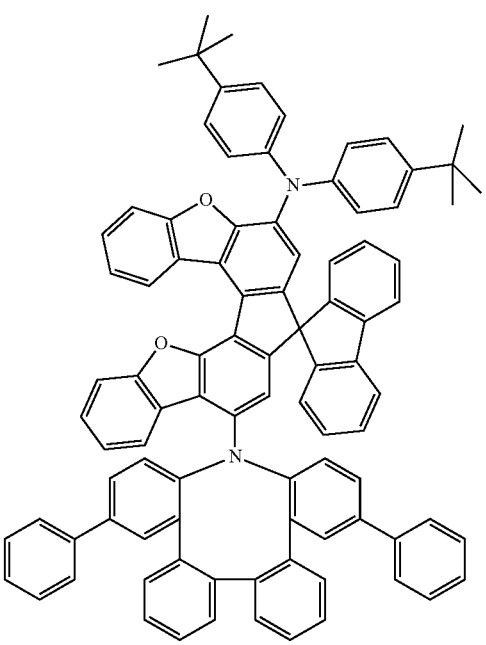

Formula 155
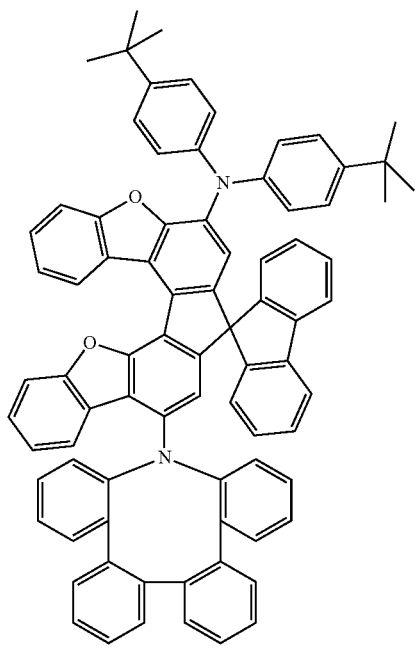
Formula 156
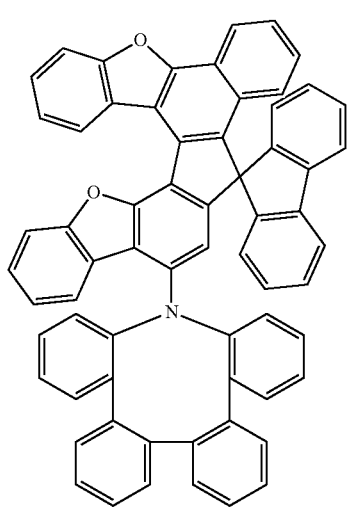
Formula 157
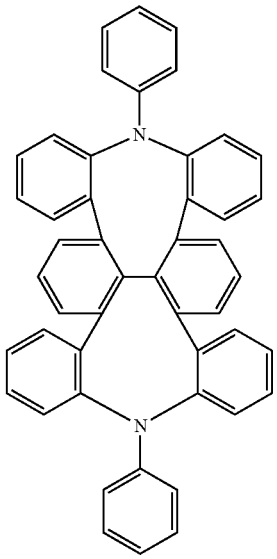
Formula 158
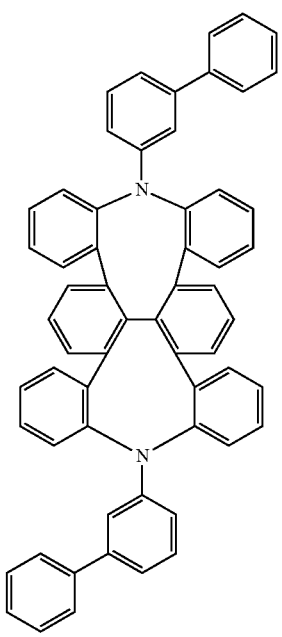

123
-continued
Formula 159
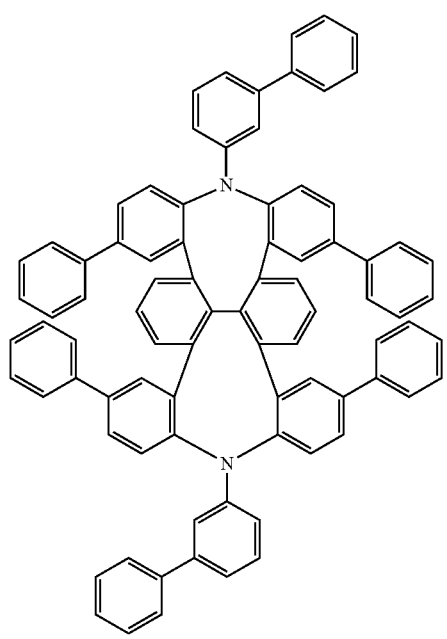
Formula 160
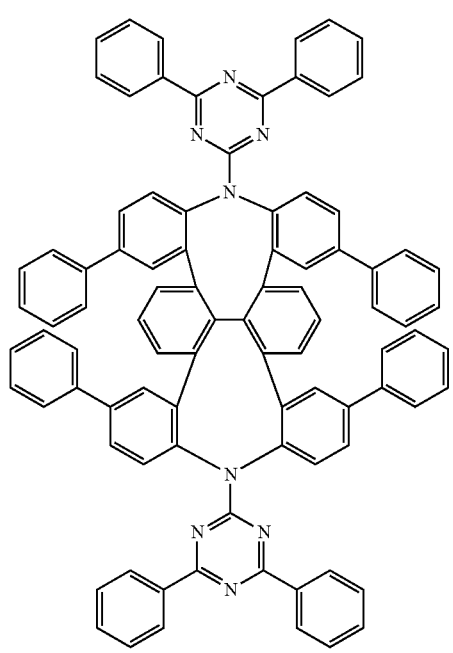
124
-continued
Formula 161
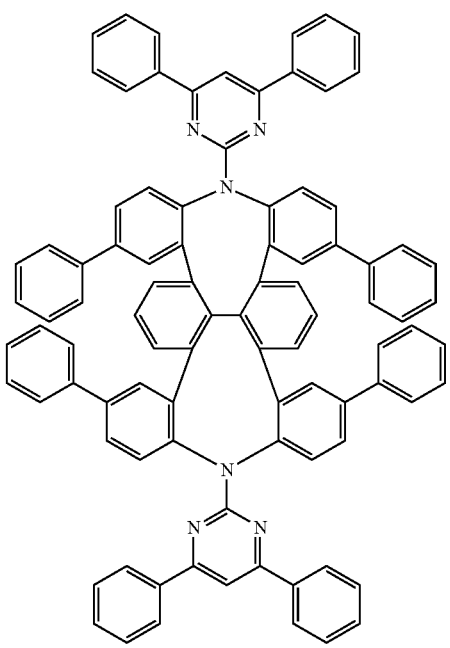
Formula 162
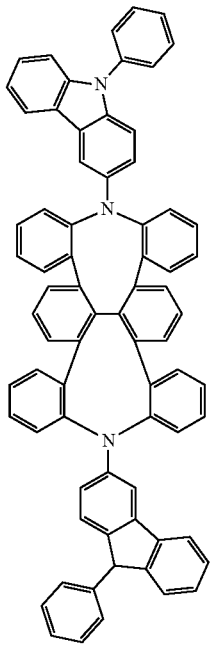

Formula 163
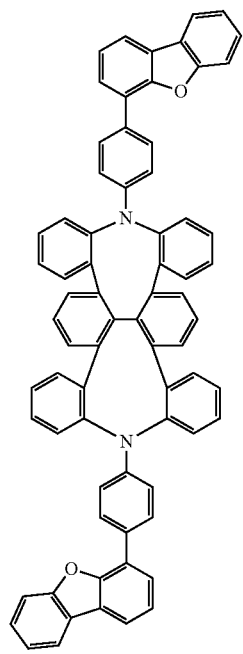
Formula 164
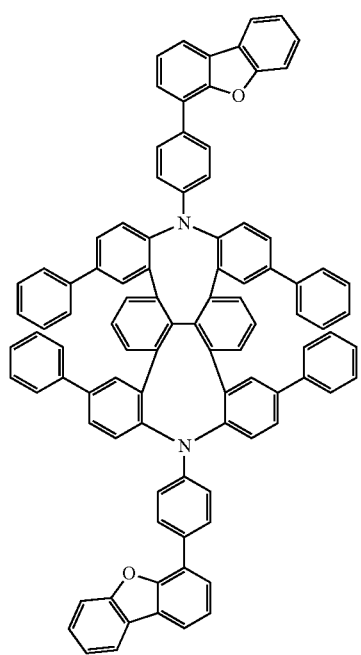
Formula 165
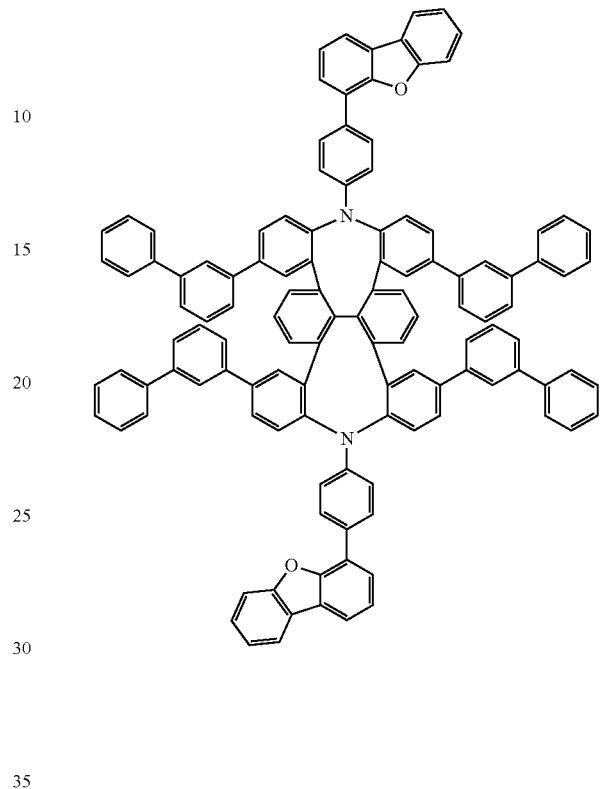
Formula 166
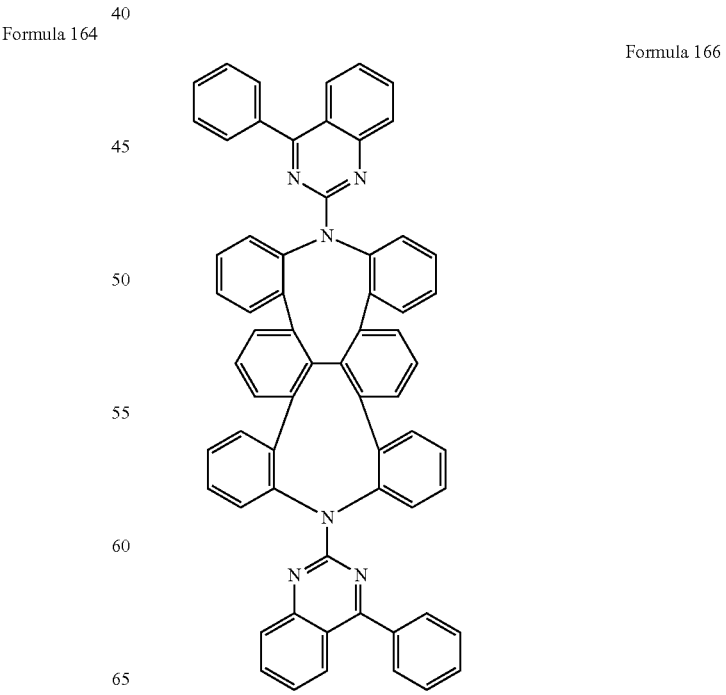

-continued
Formula 167
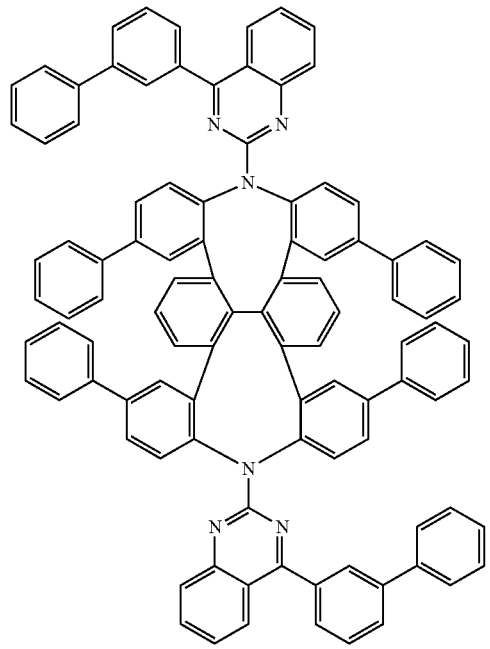
Formula 168
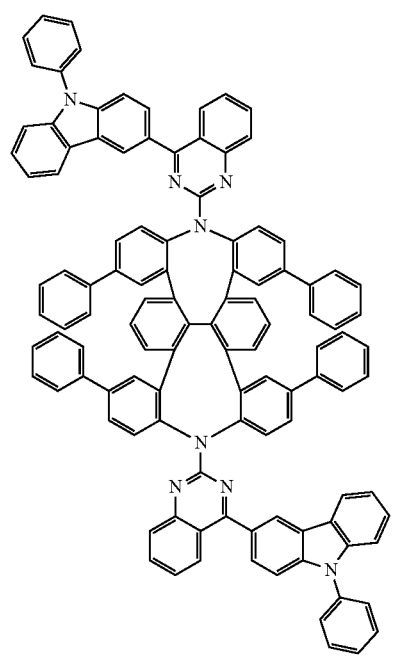
Formula 169
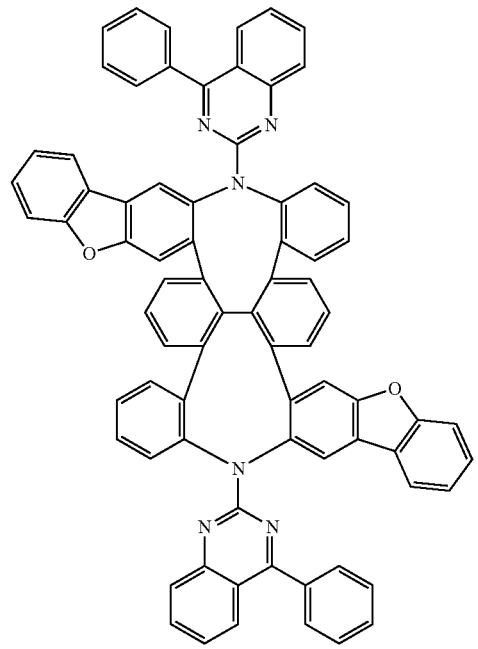
Formula 170
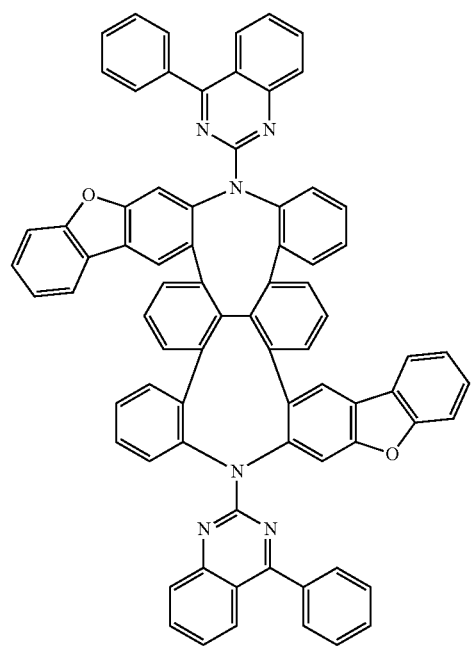

Formula 171
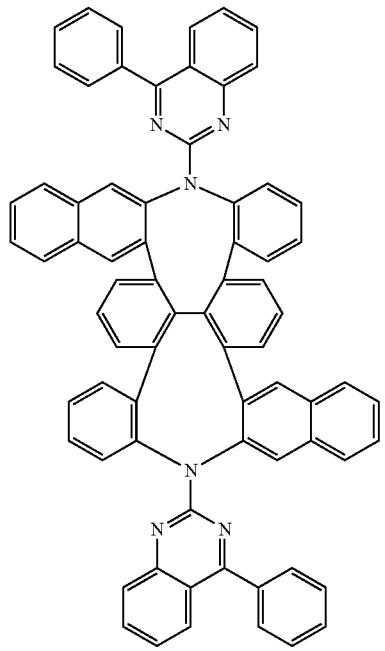
Formula 173
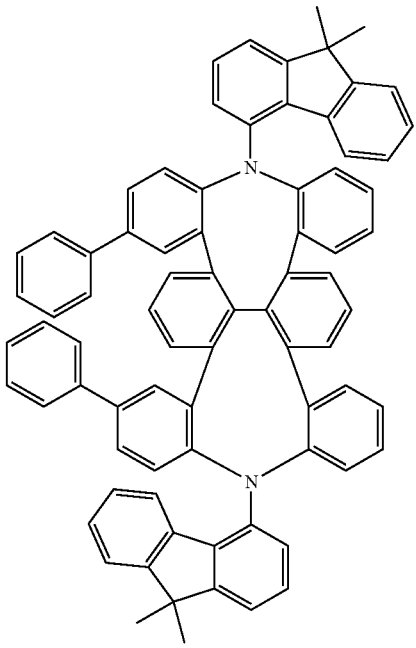
Formula 172
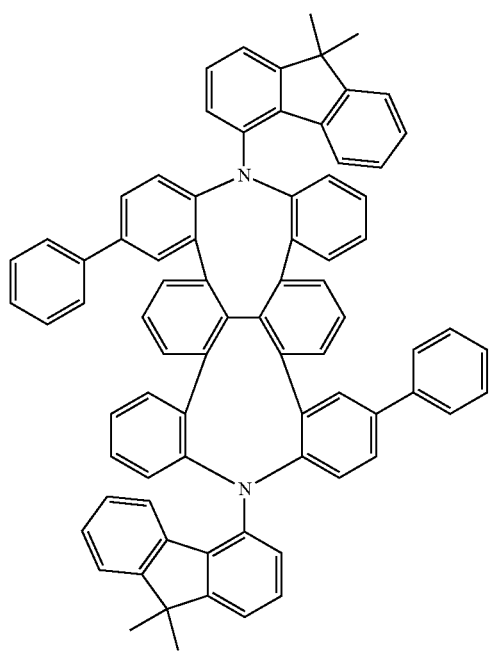
Formula 174
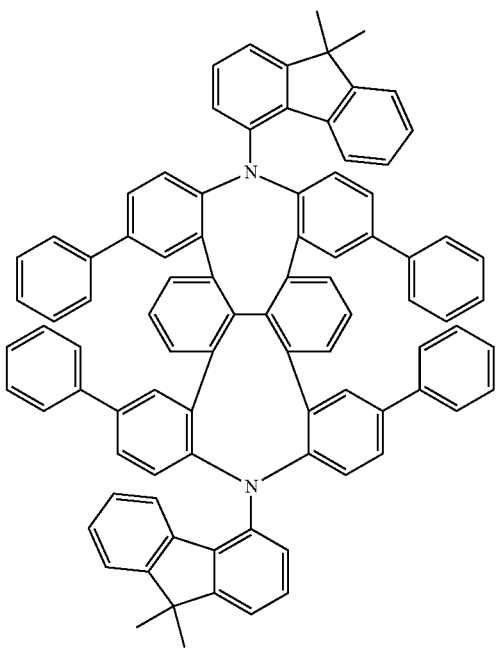

Formula 175
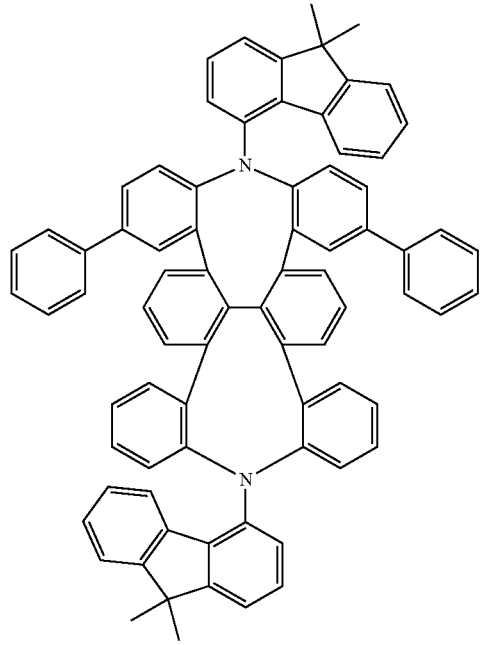
Formula 176
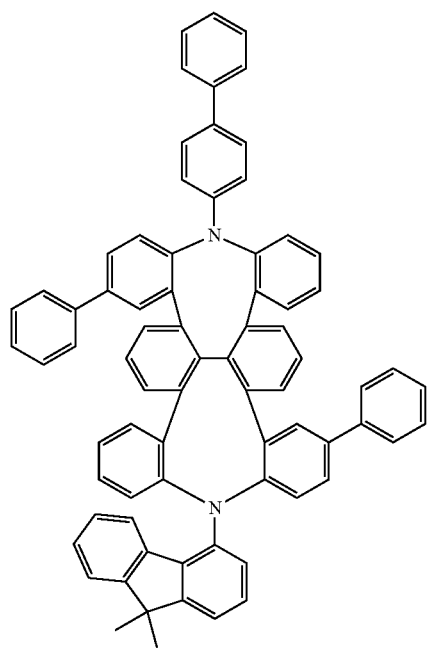
Formula 177
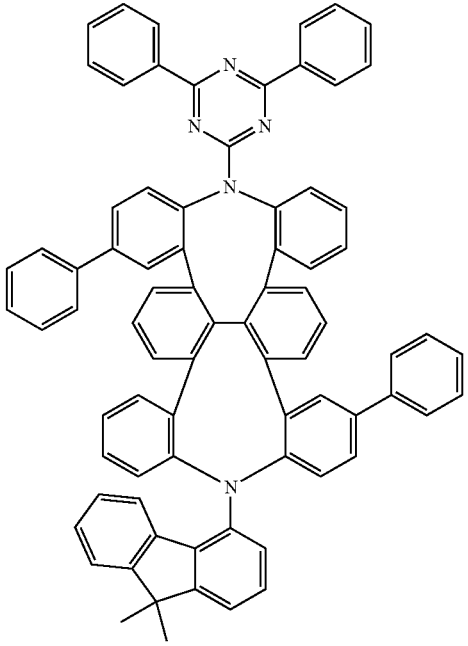
Formula 178
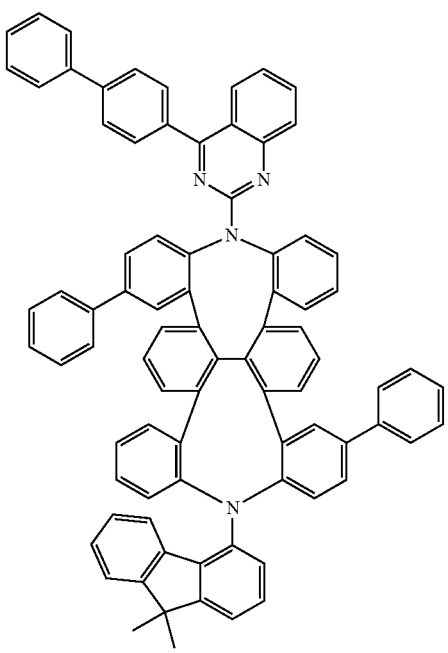

-continued

Formula 179

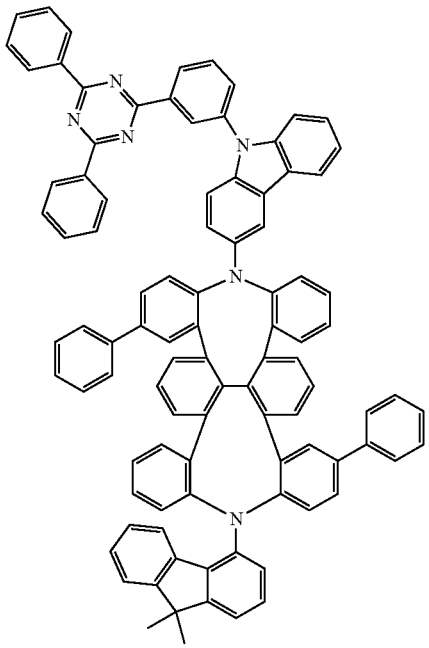

Formula 180

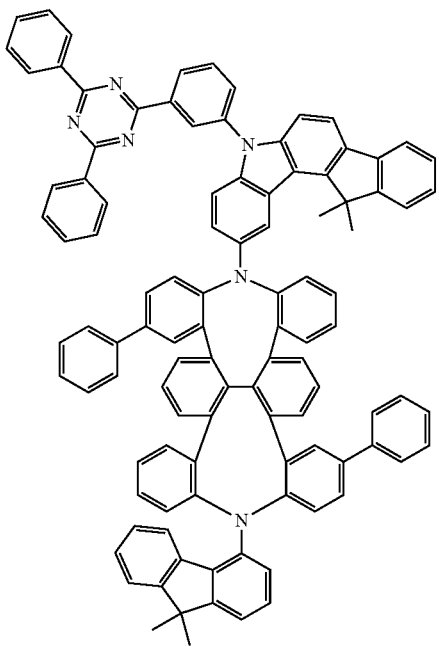

Preferred embodiments of compounds of the invention are recited specifically in the examples, these compounds being usable alone or in combination with further compounds for all purposes of the invention.

Provided that the conditions specified in claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds comprising structures of formula (I) in which, in a coupling reaction, a compound comprising at least one diarylamine group is joined to a group comprising at least one aryl or heteroaryl radical.

Suitable compounds having a diarylamine group are in many cases commercially available, and the starting compounds detailed in the examples are obtainable by known processes, and so reference is made thereto.

For example, compounds having a diarylamine group that are suitable for preparation of a compound of the invention can be obtained from known compounds by appropriate coupling reactions.

Compounds having a diarylamine group can be reacted with further aryl or heteroaryl compounds by known coupling reactions, the necessary conditions for this purpose being known to the person skilled in the art, and detailed specifications in the examples give support to the person skilled in the art in conducting these reactions.

Particularly suitable and preferred coupling reactions which all lead to C—C bond formation and/or C—N bond formation are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

In all the synthesis schemes which follow, the compounds are shown with a small number of substituents to simplify the structures. This does not rule out the presence of any desired further substituents in the processes.

An illustrative implementation is given by the schemes which follow, without any intention that these should impose a restriction. The component steps of the individual schemes may be combined with one another as desired.

Scheme 1: Formation of a suitable cyclic diarylamine compound

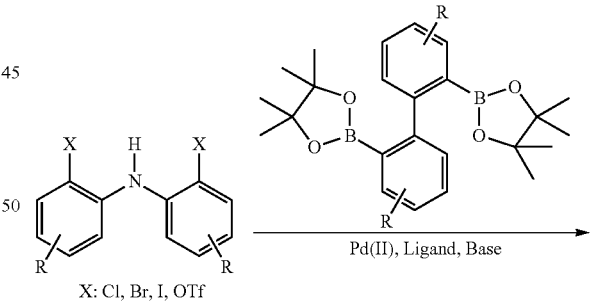

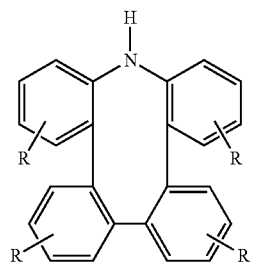

Scheme 2: Buchwald or Ullmann coupling to give the compound of the invention

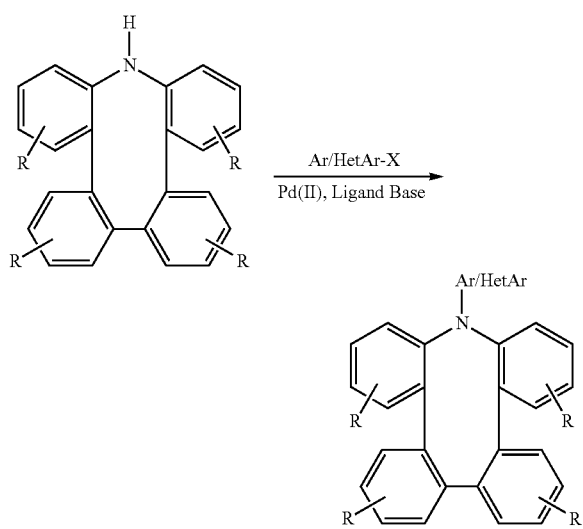

Scheme 3: S$_N$Ar reaction to give the compound of the invention

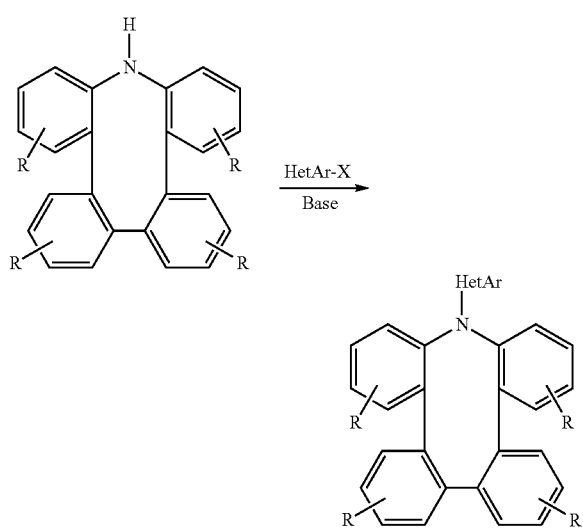

The definition of the symbols used in Schemes 1 to 3 corresponds essentially to those defined for formula (I) or (II), dispensing with numbering for reasons of clarity. The abbreviation Ar here represents an aryl radical, and HetAr a heteroaryl radical.

Proceeding from 2,2'-dihalo- or triflate-substituted secondary arylamines, it is possible in a first step to prepare a 2,7-bispinacolatoborane-substituted biphenyl via palladium-catalyzed Suzuki coupling. For this type of reaction, it is possible to use catalyst systems known from the literature, consisting of a Pd source (e.g. Pd(ac)$_2$, PdCl$_2$, Pd(dba)$_2$, etc.), a phosphine (e.g. triphenylphosphine, tri-o-tolylphosphine, tricyclohexylphosphine, bisdiphenylphosphinoferrocene, S-Phos, X-Phos, Ru-Phos, etc.) and a base (KAc, K$_3$PO$_4$, Cs(CO$_3$)$_2$, etc.).

The secondary amine thus obtained can be converted to the tertiary amines of the invention by reaction with aryl/heteroaryl halides or triflates in a palladium-catalyzed Buchwald or copper-catalyzed Ullmann coupling to give the tertiary amines of the invention.

The reaction of the secondary amine with can alternatively be effected with electron-deficient heterocycles (pyridines, diazines, triazines) in the presence of a base to give the tertiary amines of the invention.

The tertiary amines thus obtained, if they have a hydrogen atom in the p position to the nitrogen atom, can be brominated by standard methods, for example with bromine or N-bromosuccinimide. Bromides thus obtained can be functionalized further by standard methods (Grignard cross-coupling, Heck coupling, Suzuki coupling, Negishi coupling, Sonogashira coupling, Yamamoto coupling, Buchwald coupling, Ullmann coupling, etc.), or converted to oligomers, dendrimers or polymers.

The processes shown for synthesis of the compounds of the invention should be understood by way of example. The person skilled in the art will be able to develop alternative synthesis routes within the scope of his common knowledge in the art.

The principles of the preparation processes detailed above are known in principle from the literature for similar compounds and can be adapted easily by the person skilled in the art to the preparation of the compounds of the invention. Further information can be found in the examples.

It is possible by these processes, if necessary followed by purification, for example recrystallization or sublimation, to obtain the compounds of the invention comprising structures of formula (I) in high purity, preferably more than 99% (determined by means of $^1$H NMR and/or HPLC).

The compounds of the invention may also have suitable substituents, for example be substituted by relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, such that the compounds are soluble at room temperature in toluene or xylene, for example, in sufficient concentration to be able to process the compounds from solution. These soluble compounds are of particularly good suitability for processing from solution, for example by printing methods. In addition, it should be emphasized that the compounds of the invention comprising at least one structure of the formula (I) and/or (II) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds and polymers of the invention may be used in the form of a crosslinked or uncrosslinked layer.

The invention therefore further provides oligomers, polymers or dendrimers containing one or more of the above-detailed structures of the formula (I) and/or (II) or compounds of the invention, wherein one or more bonds in the compounds of the invention or in the structures of the formula (I) to the polymer, oligomer or dendrimer are present. According to the linkage of the structures of the formula (I) and/or (II) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

Additionally of particular interest are compounds of the invention which feature a high glass transition temperature. In this connection, preference is given especially to compounds of the invention comprising structures of the general formula (I) and/or (II) or the preferred embodiments recited above and hereinafter which have a glass transition temperature of at least 70° C., more preferably of at least 110° C., even more preferably of at least 125° C. and especially preferably of at least 150° C., determined in accordance with DIN 51005 (2005-08 version).

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound, especially a phosphorescent dopant, and/or a further matrix material. This further compound may also be polymeric.

The present invention therefore still further provides a composition comprising a compound of the invention and at least one further organic functional material. Functional materials are generally the organic or inorganic materials introduced between the anode and cathode. Preferably, the organically functional material is selected from the group consisting of fluorescent emitters, phosphorescent emitters, emitters that exhibit TADF (thermally activated delayed fluorescence), host materials, electron transport materials, electron injection materials, hole transport materials, hole injection materials, electron blacker materials, hole blocker materials, wide band gap materials and n-dopants.

In a particular aspect of the present invention, the compounds of the invention can be used as emitter, preferably as fluorescent emitter, where emitters are in many cases used in combination with suitable matrix materials. In addition, the compounds of the invention can be used as matrix material, especially for phosphorescent emitters, and matrix materials are in many cases used in combination with further matrix materials.

The present invention therefore also relates to a composition comprising at least one compound comprising structures of formula (I) and/or (II) or the preferred embodiments recited above and hereinafter and at least one further matrix material. According to a particular aspect of the present invention, the further matrix material has electron-transporting properties.

The present invention further provides a composition comprising at least one compound comprising at least one structure of formula (I) and/or (II) or the preferred embodiments recited above and hereinafter and at least one wide band gap material, a wide band gap material being understood to mean a material in the sense of the disclosure of U.S. Pat. No. 7,294,849. These systems exhibit exceptional advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state Ti and that of the lowest excited singlet state Si of the materials are determined via quantum-chemical calculations. For calculation of organic substances, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). The HOMO energy level HEh or LUMO energy level LEh is obtained from the energy calculation in Hartree units. This is used to determine the HOMO and LUMO energy levels in electron volts, calibrated by cyclic voltammetry measurements, as follows:

HOMO(eV)=((HEh*27.212)−0.9899)/1.1206

LUMO(eV)=((LEh*27.212)−2.0041)/1.385

These values are to be regarded as HOMO and LUMO energy levels of the materials in the context of this application.

The lowest triplet state Ti is defined as the energy of the triplet state having the lowest energy, which is apparent from the quantum-chemical calculation described.

The lowest excited singlet state Si is defined as the energy of the excited singlet state having the lowest energy, which is apparent from the quantum-chemical calculation described.

The method described herein is independent of the software package used and always gives the same results. Examples of frequently utilized programs for this purpose are "Gaussian09W" (Gaussian Inc.) and Q-Chem 4.1 (Q-Chem, Inc.).

The present invention also relates to a composition comprising at least one compound comprising structures of formula (I) and/or (II) or the preferred embodiments recited above and hereinafter and at least one phosphorescent emitter, the term "phosphorescent emitter" also being understood to mean phosphorescent dopants.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in matrix systems, preferably mixed matrix systems, are the preferred phosphorescent dopants specified hereinafter.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent compounds.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2016/124304, WO 2016/015815, WO 2016/000803, WO 2015117718, WO 2015104045 and WO 2015036074. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Explicit examples of phosphorescent dopants are adduced in the following table:

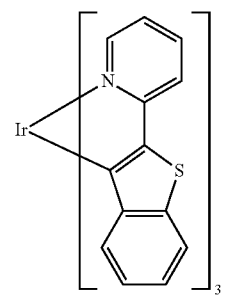

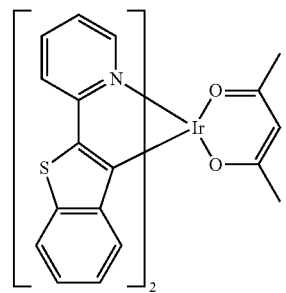

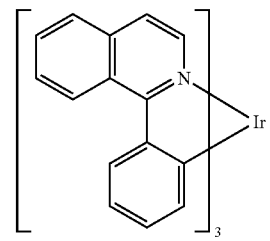

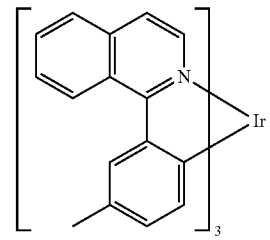

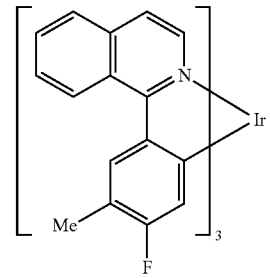

141
-continued
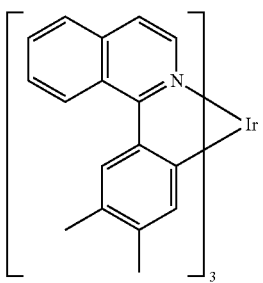
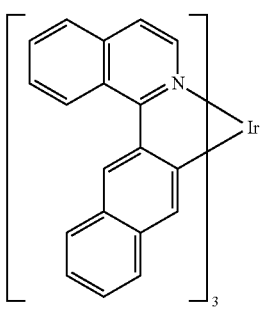
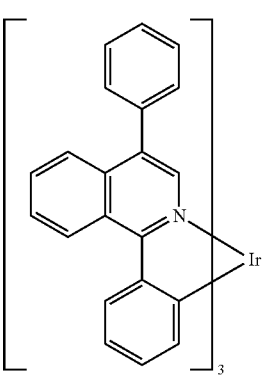
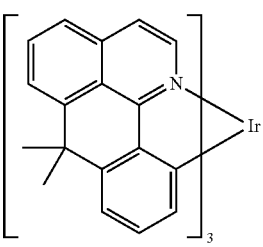
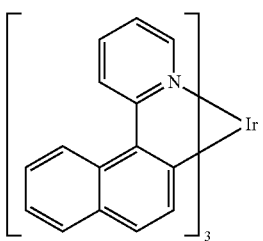
142
-continued
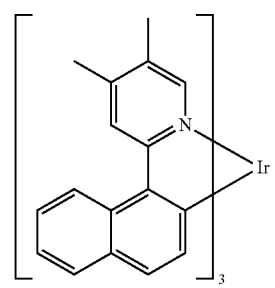
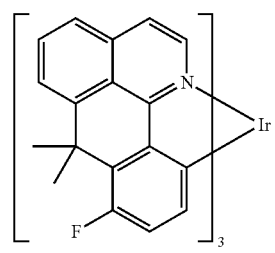
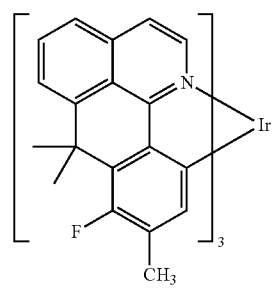
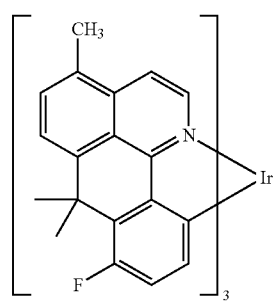
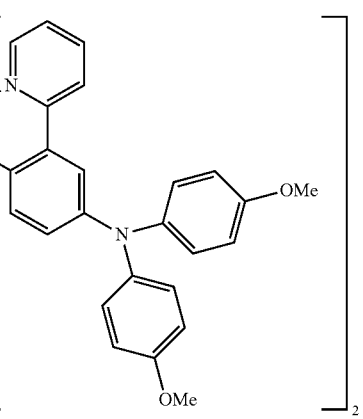

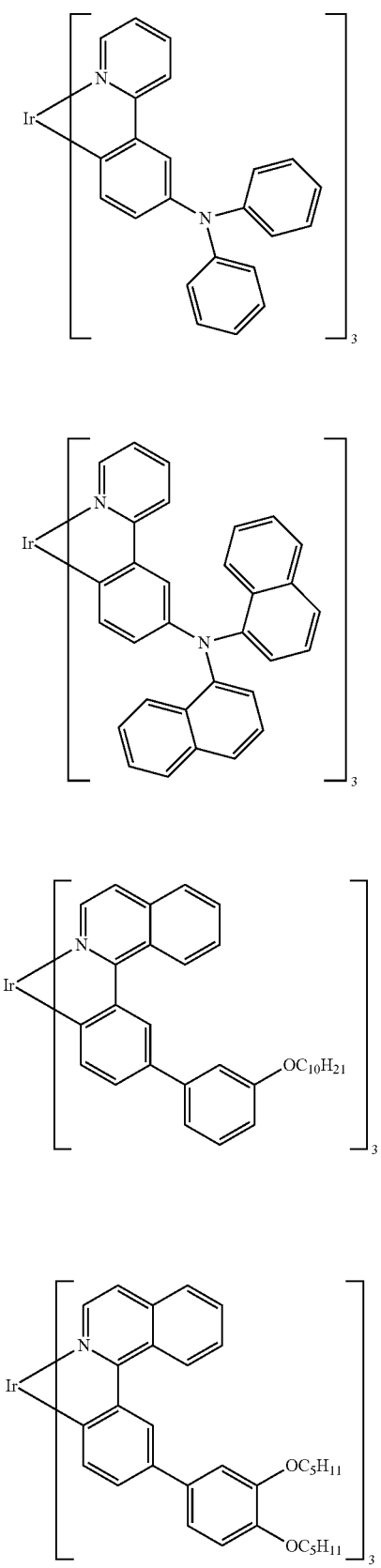
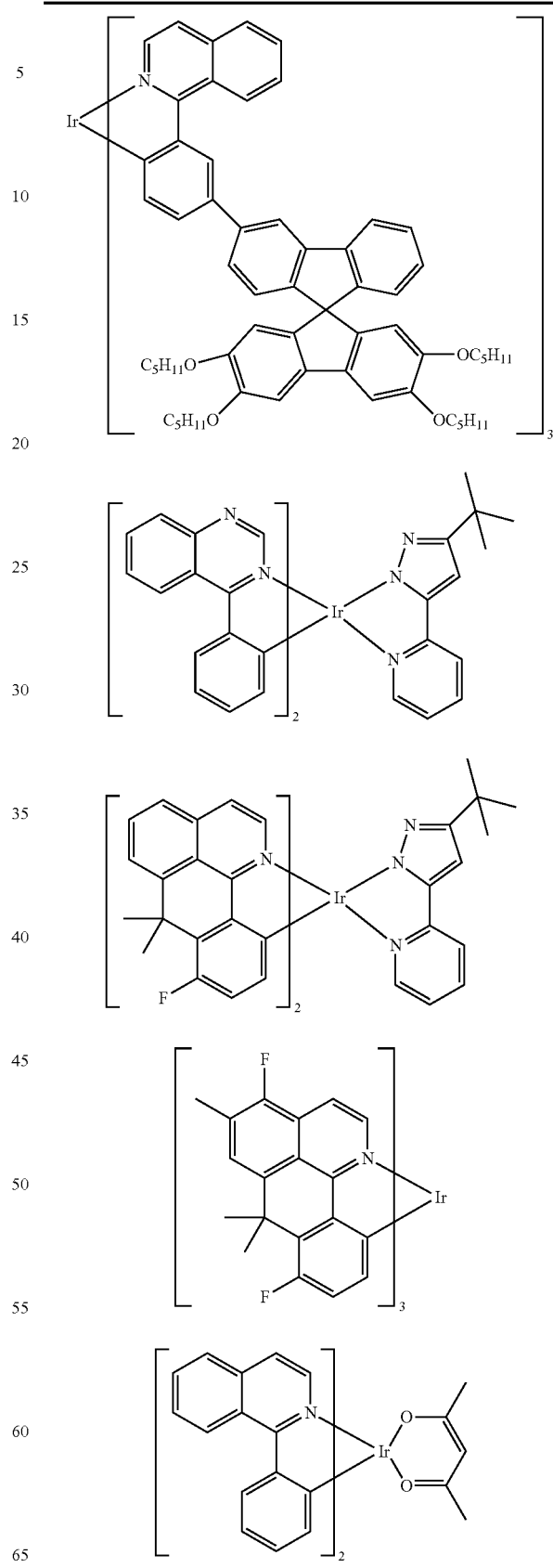

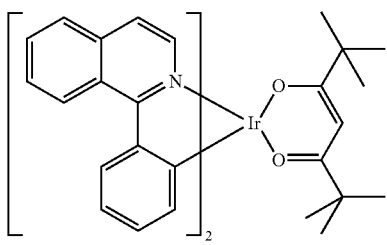
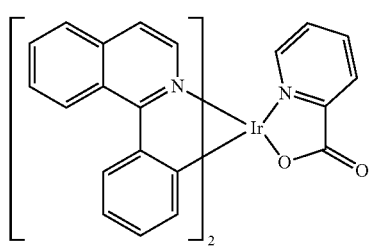
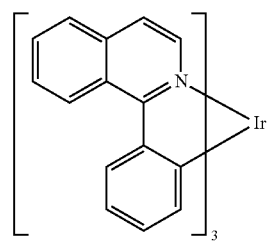
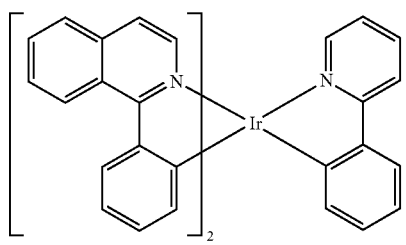
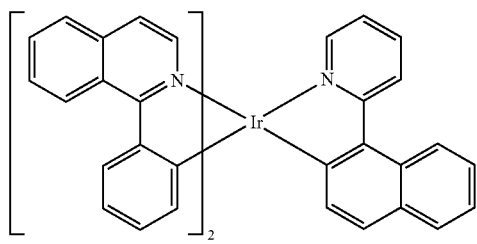
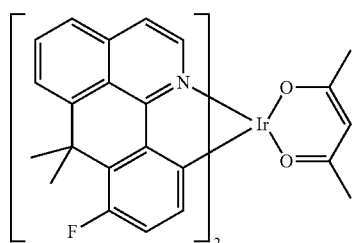
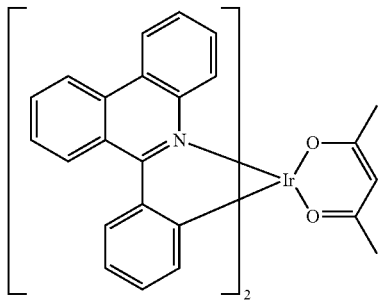
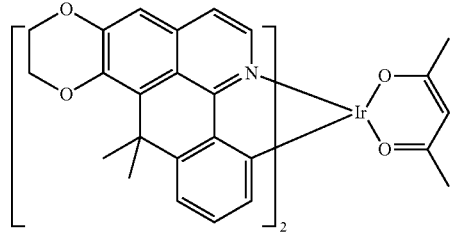
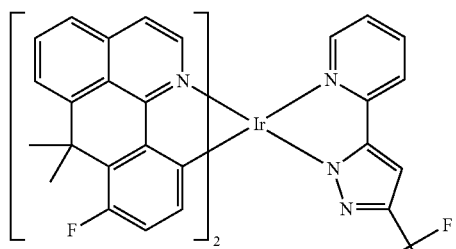
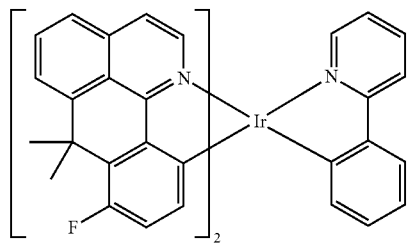
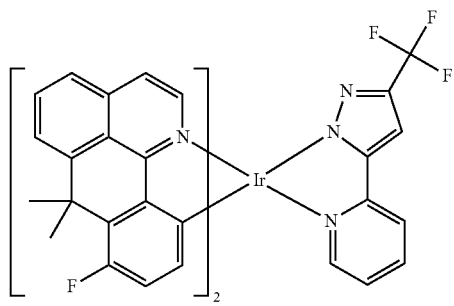

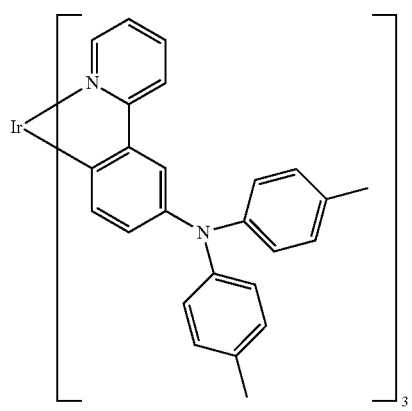
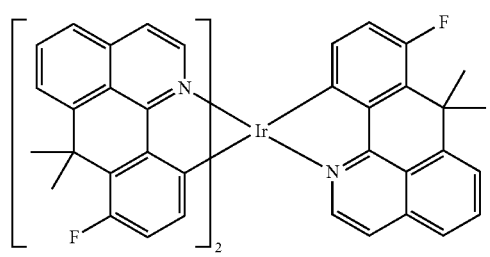
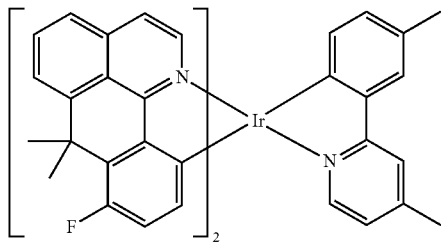
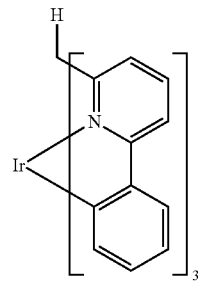
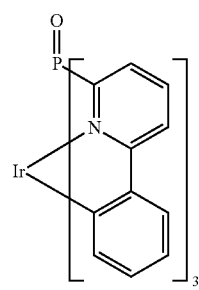
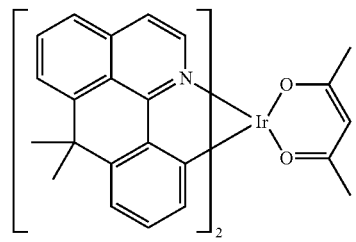
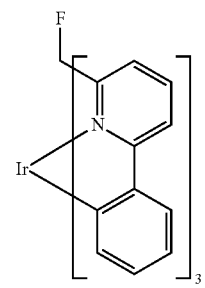
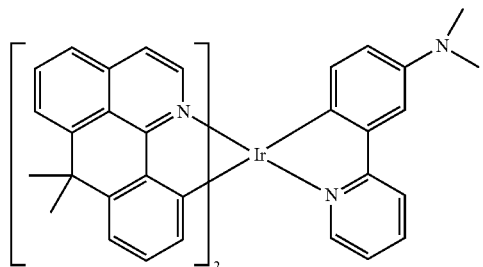
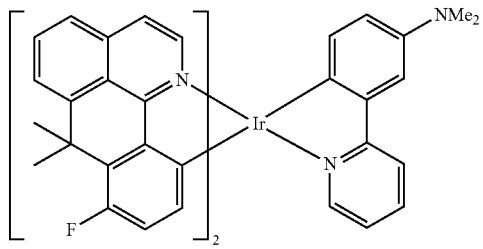
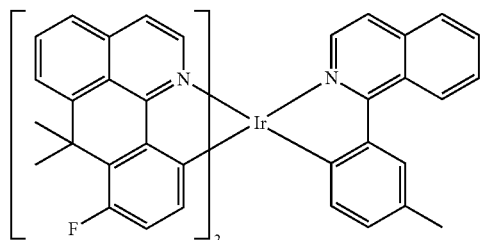
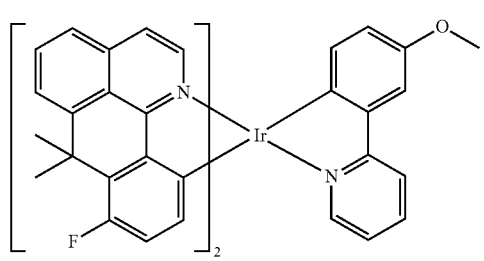

149
-continued
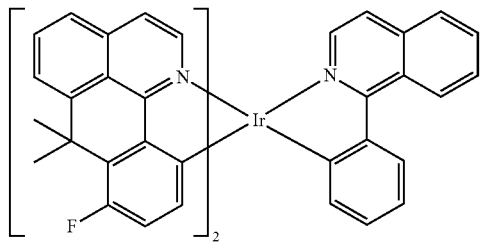
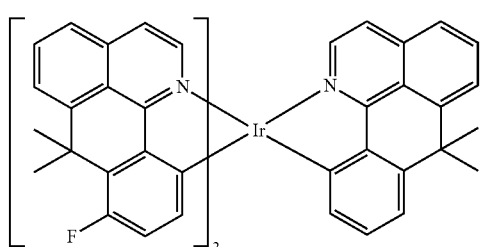
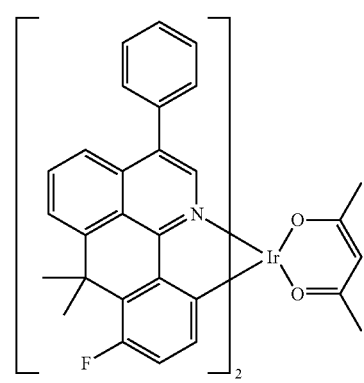
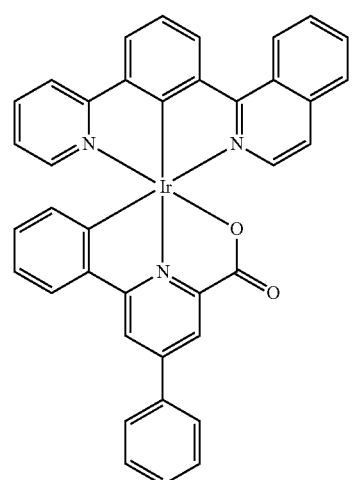
150
-continued
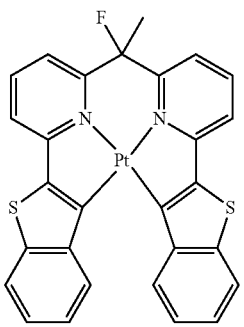
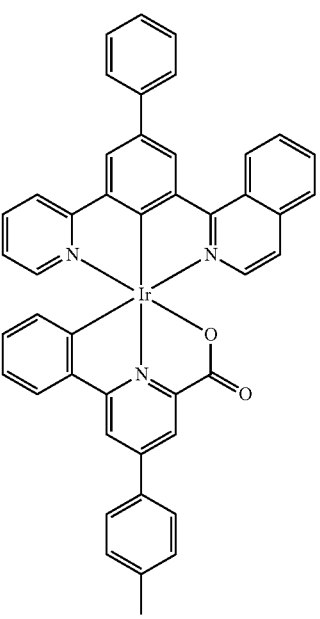
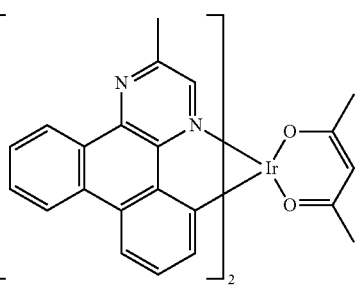
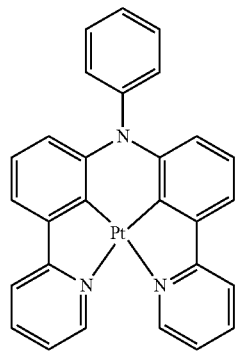

| 151 -continued | 152 -continued |
|---|---|
| 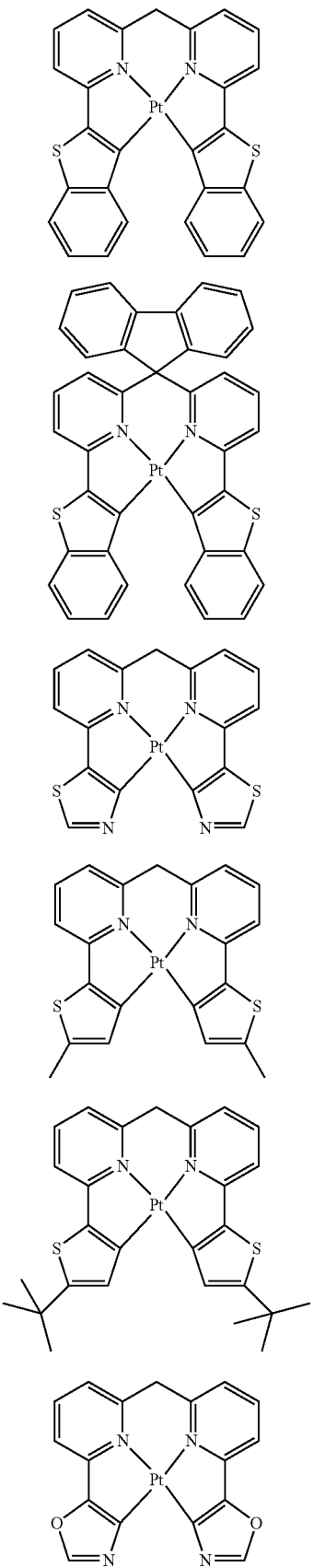 | 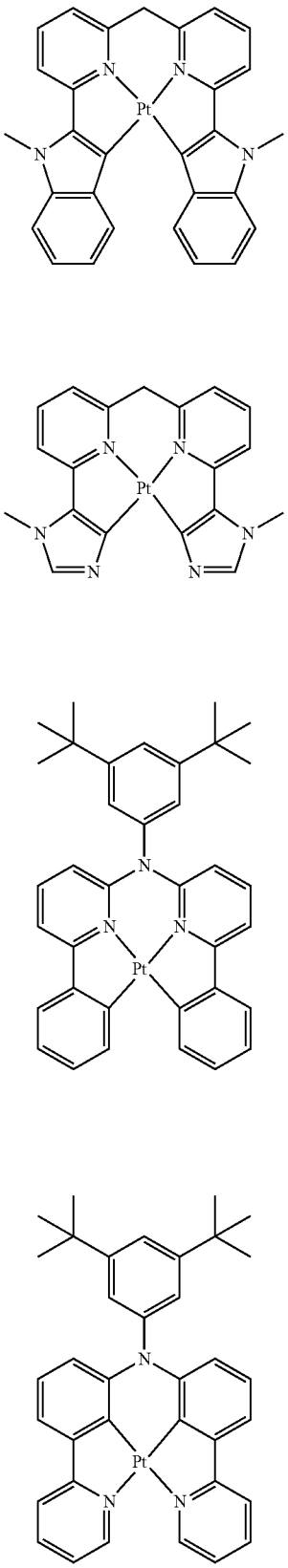 |

153
-continued
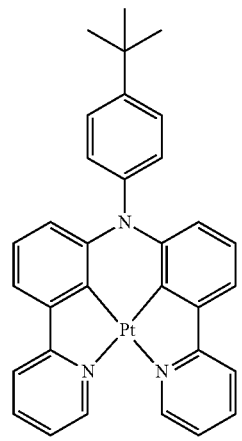
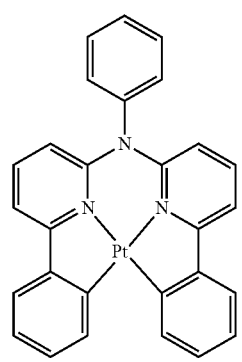
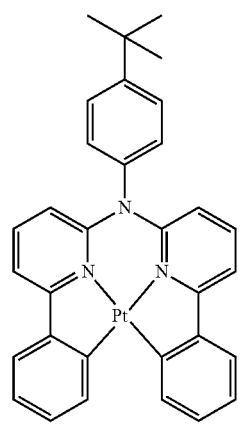
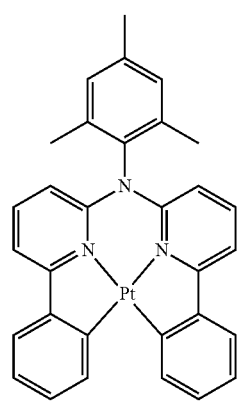
154
-continued
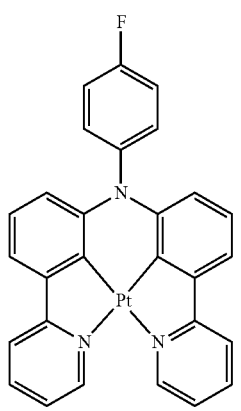
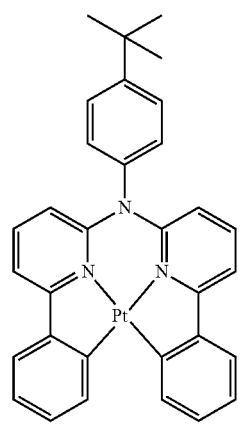
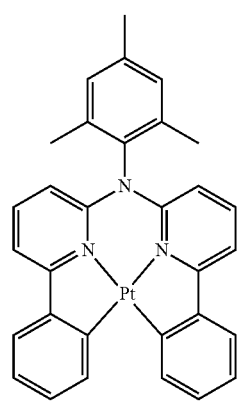

155
-continued
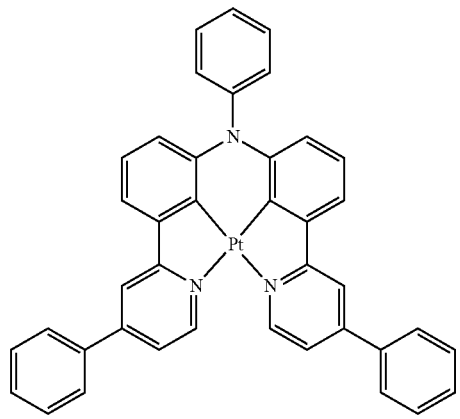
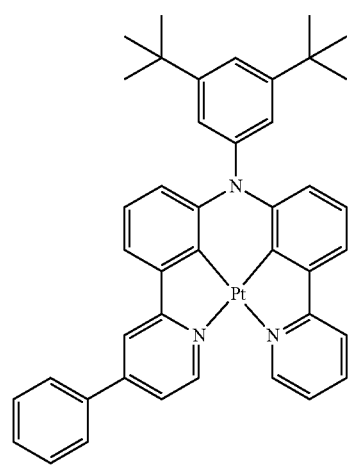
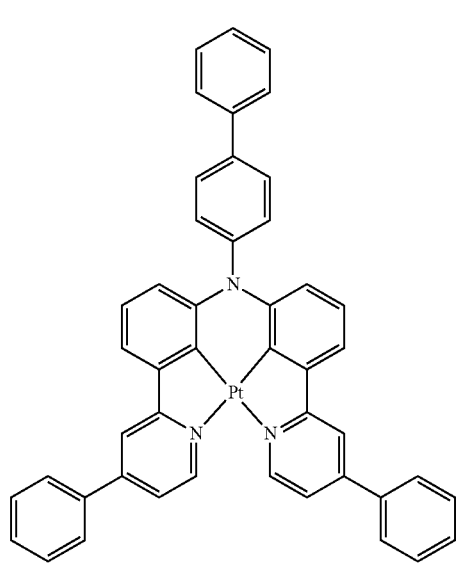
156
-continued
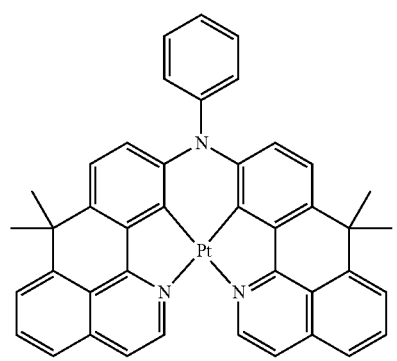
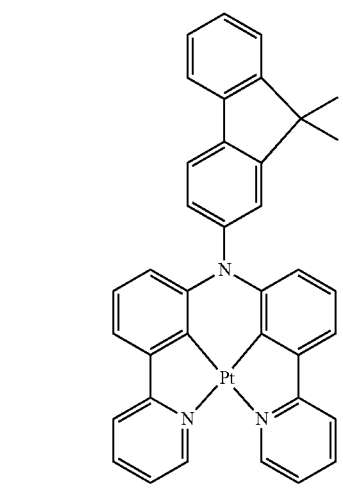
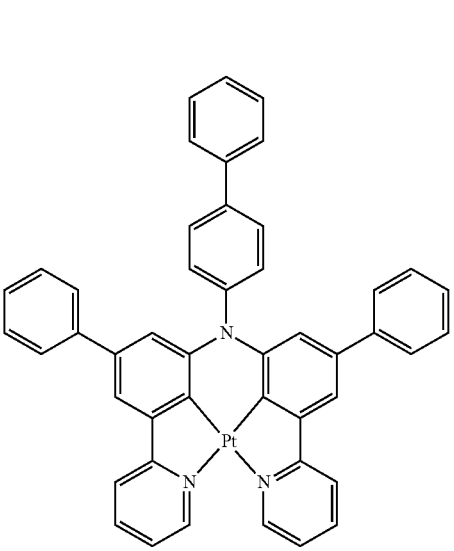

-continued
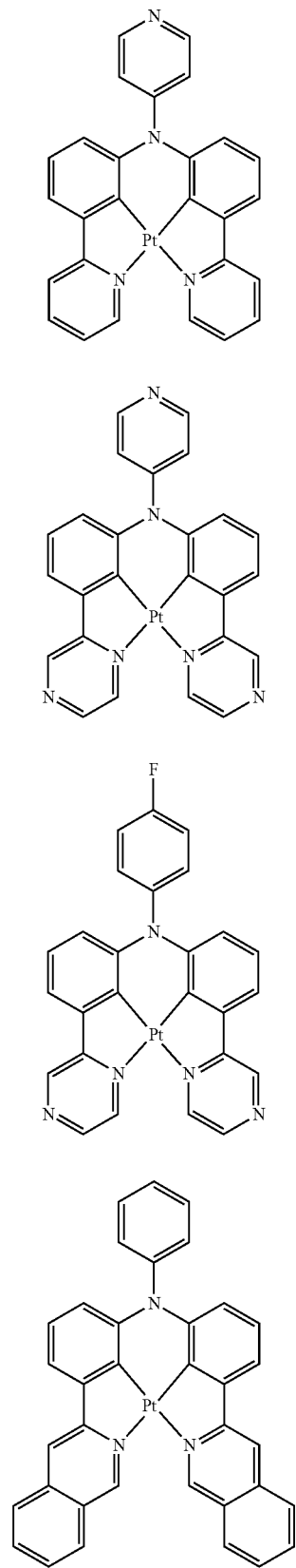
-continued
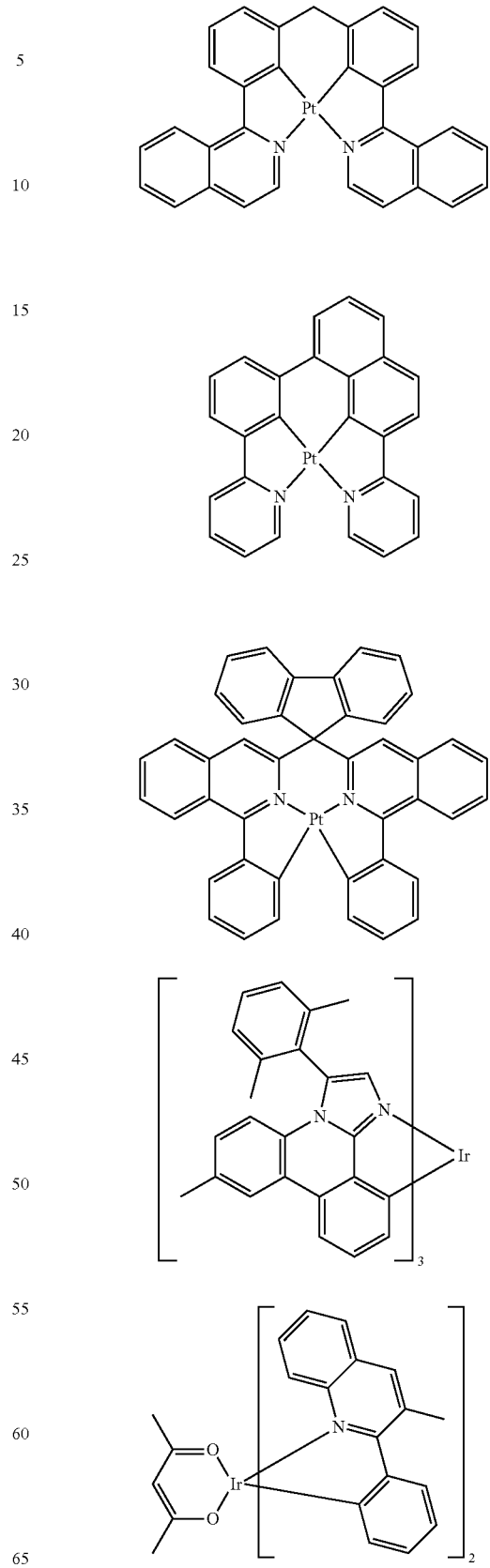

-continued
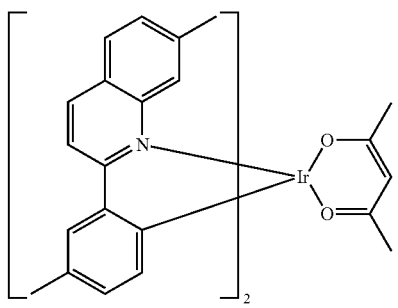
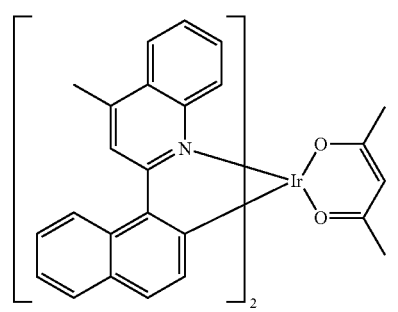
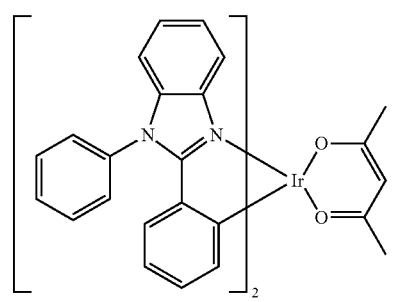
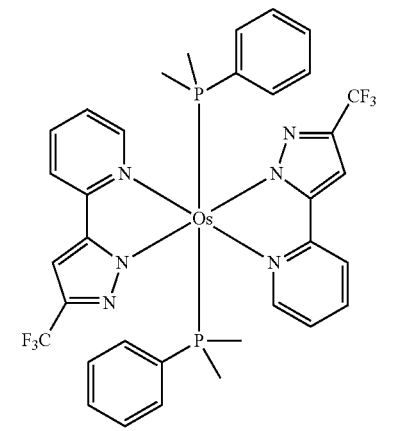
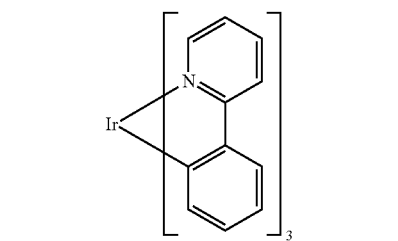
-continued
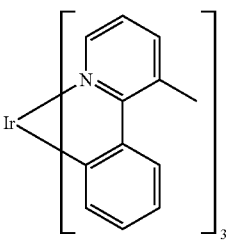
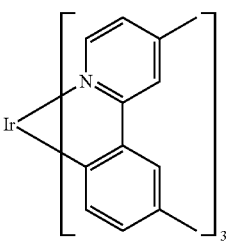
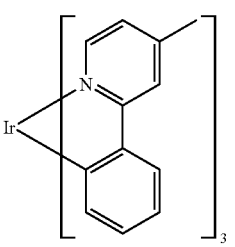
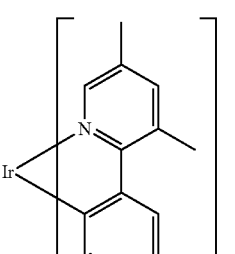
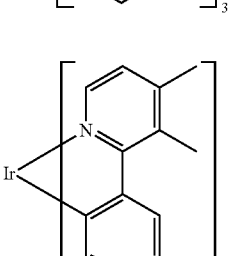
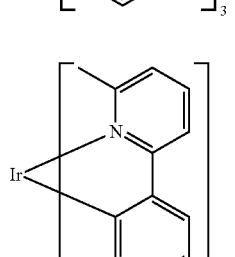

161
-continued
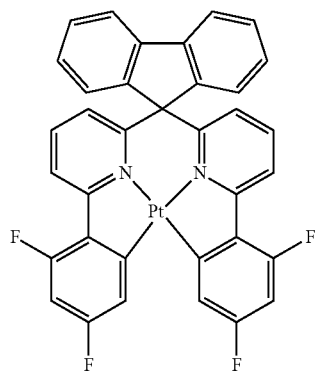
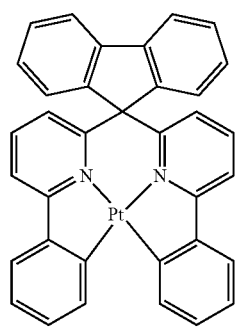
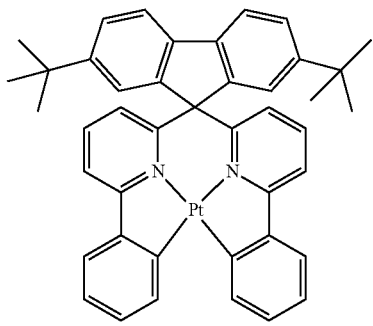
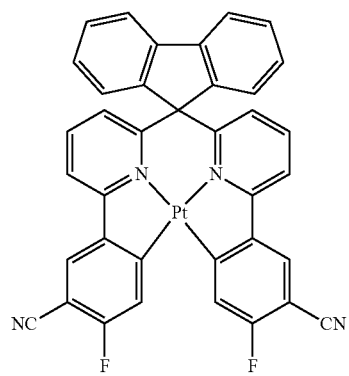
162
-continued
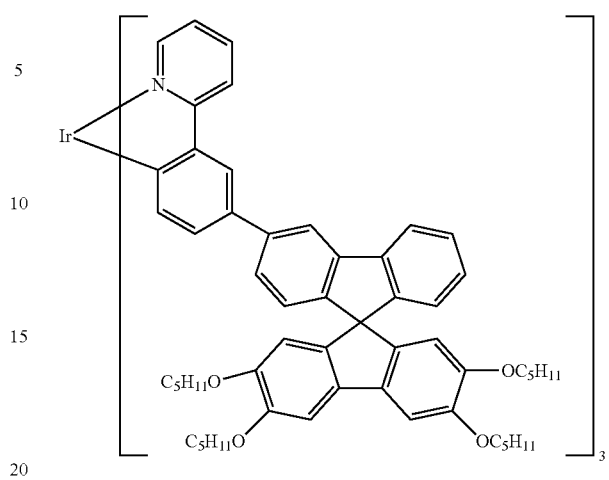
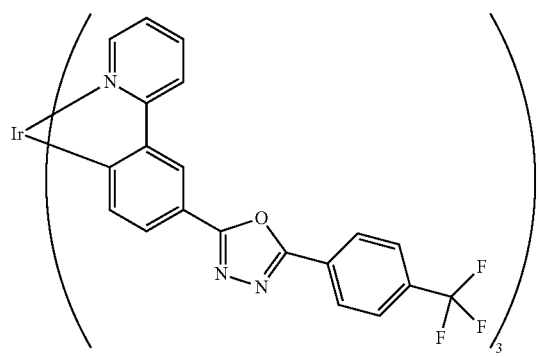
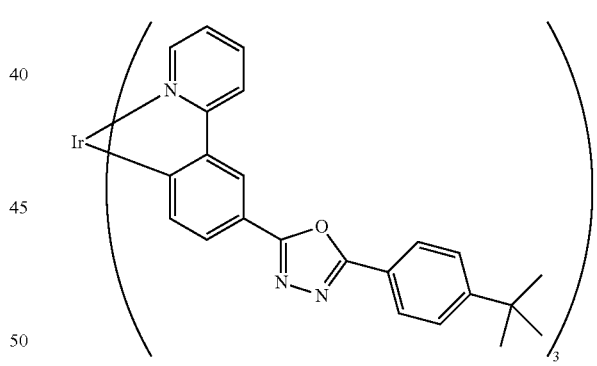
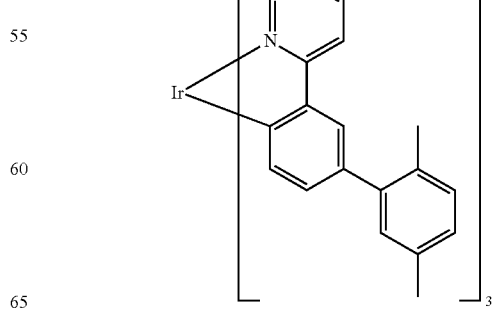

163
-continued
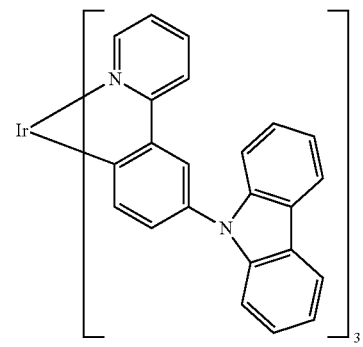
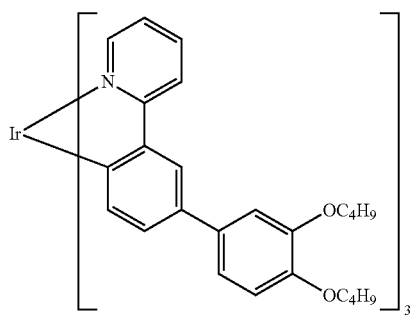
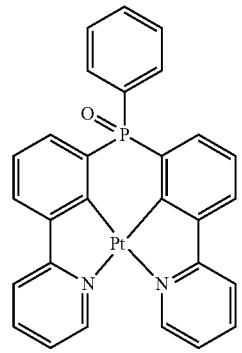
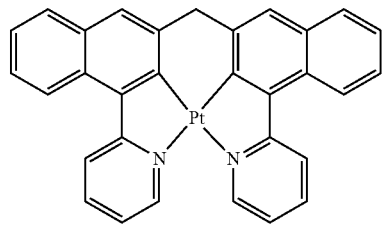
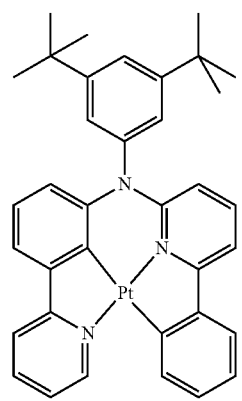
164
-continued
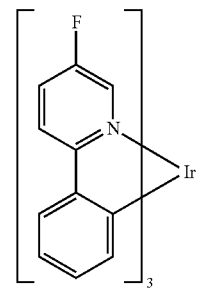
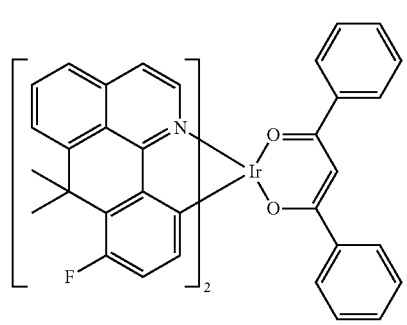
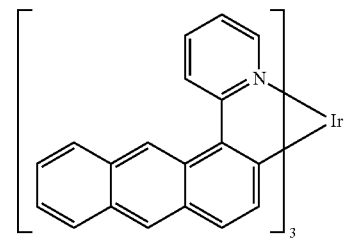
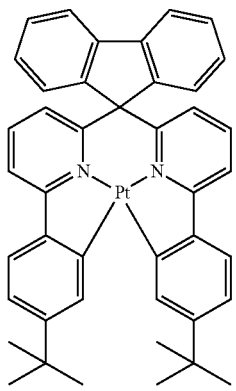
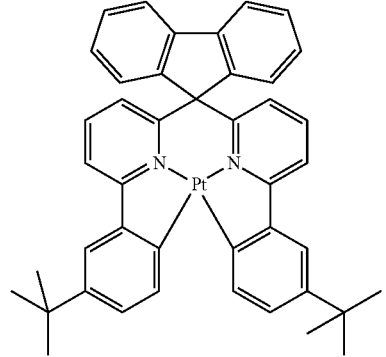

165
-continued
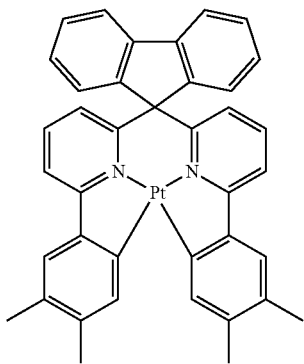
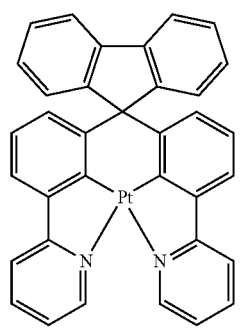
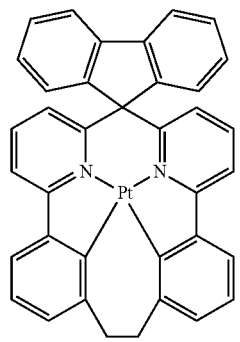
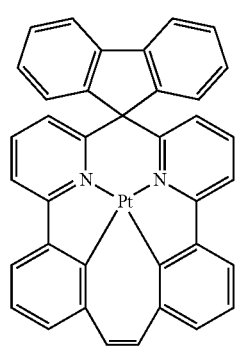
166
-continued
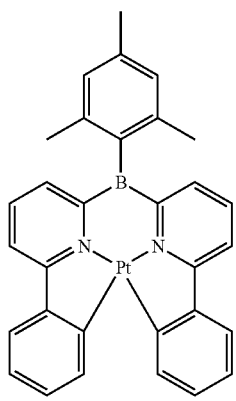
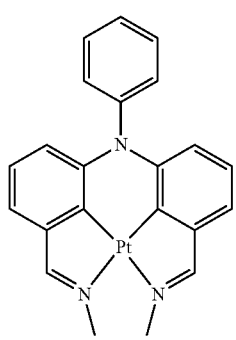
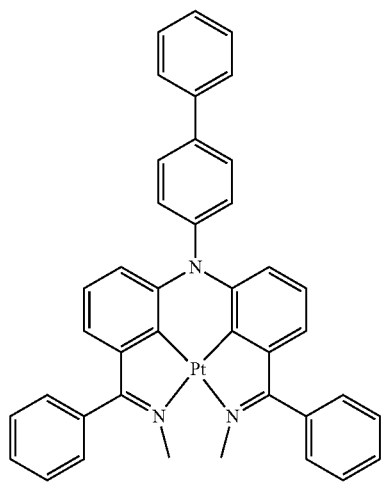
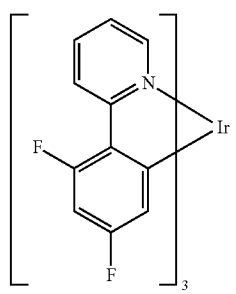

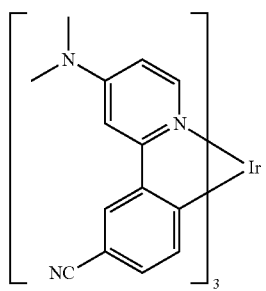
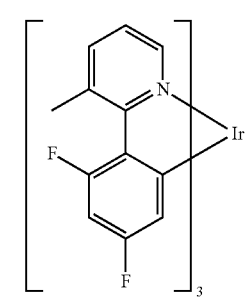
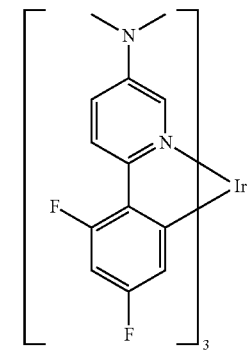
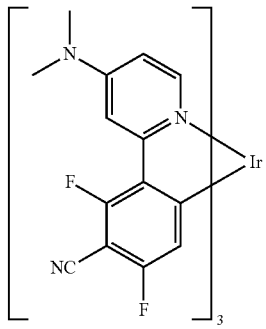
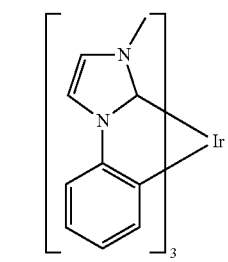
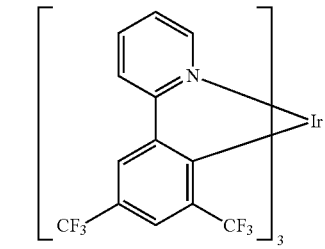
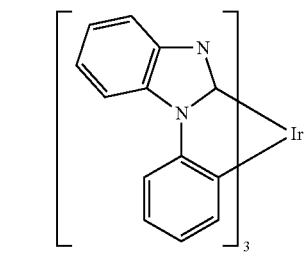
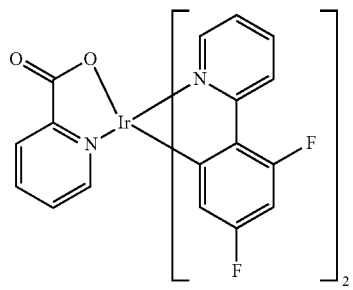
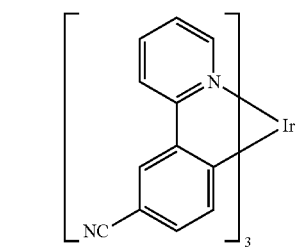
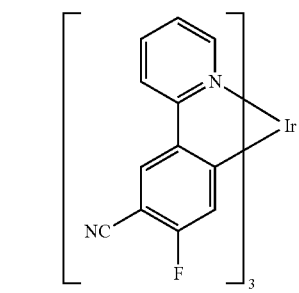
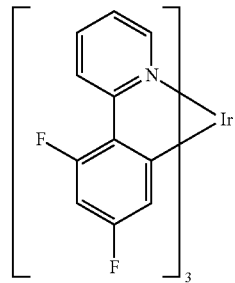

169
-continued
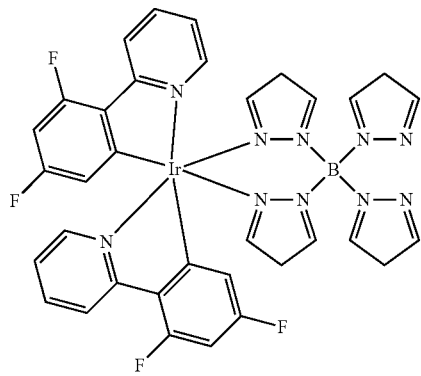
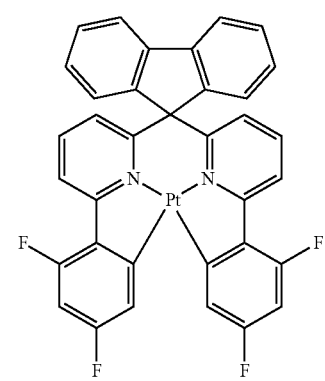
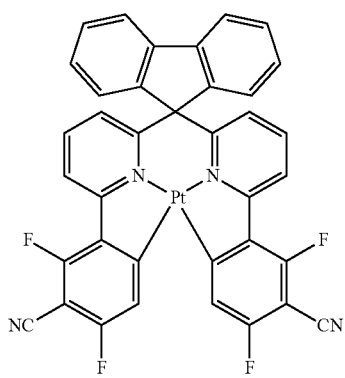
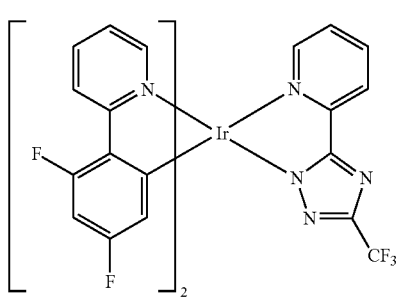
170
-continued
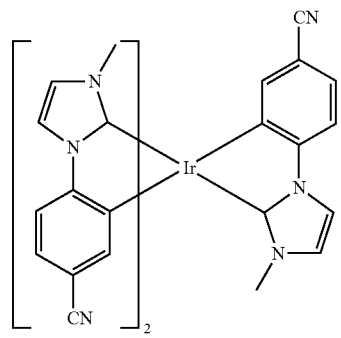
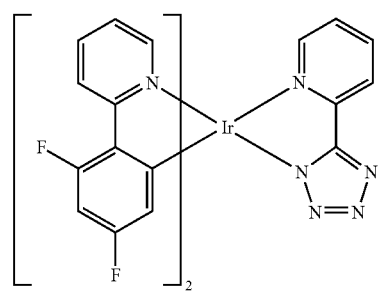
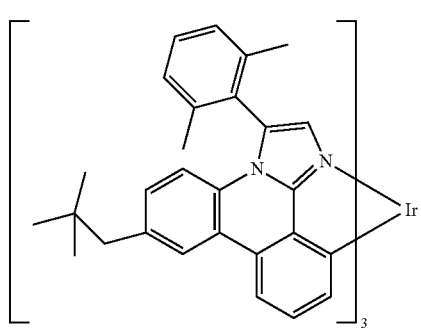
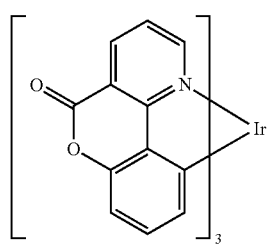
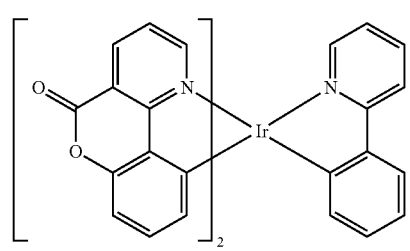

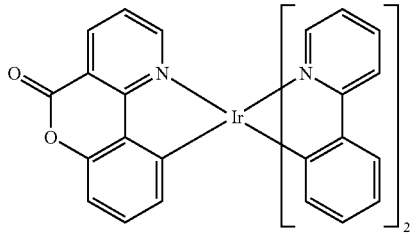
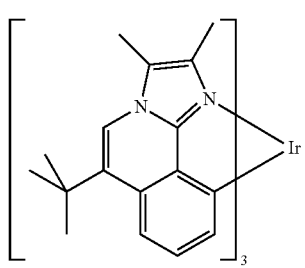
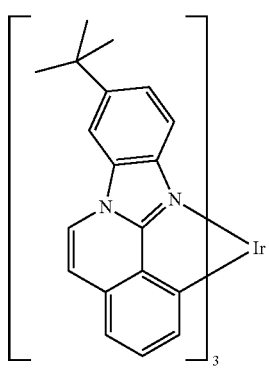
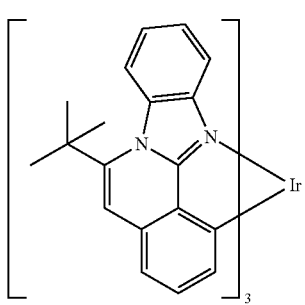
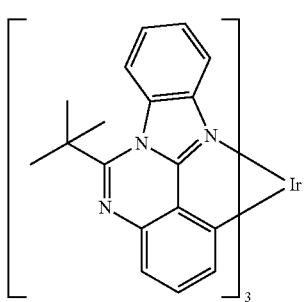
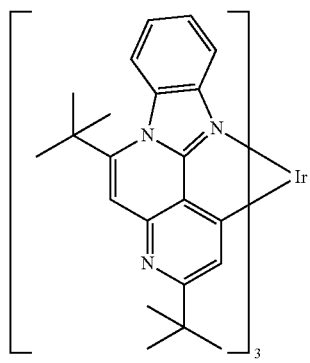
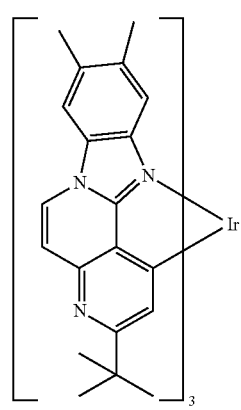
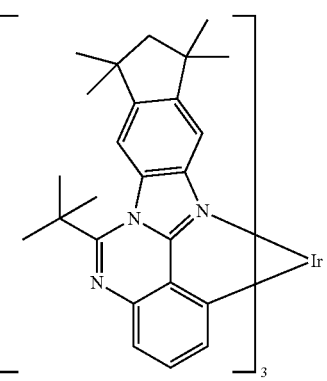
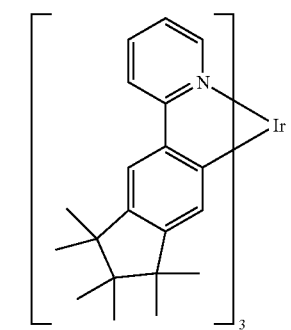

173
-continued
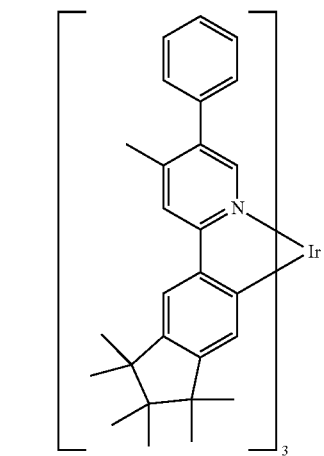
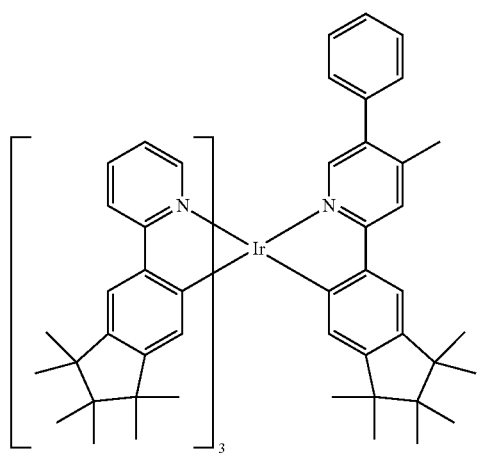
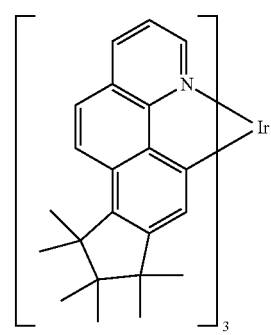
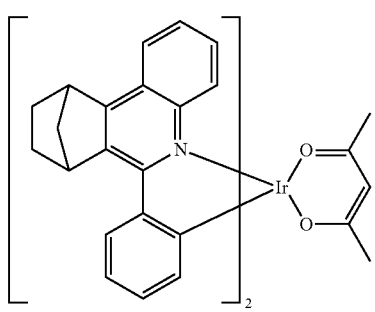
174
-continued
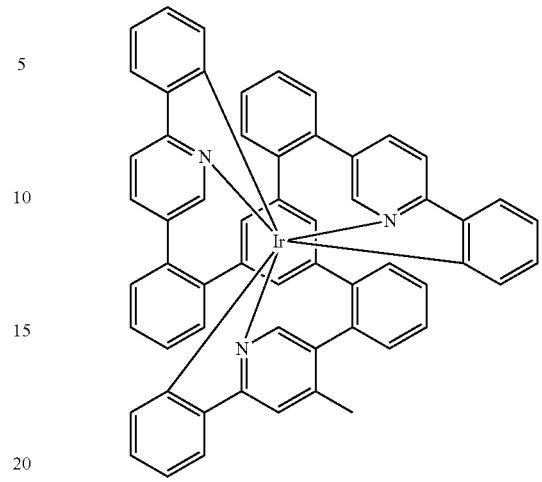
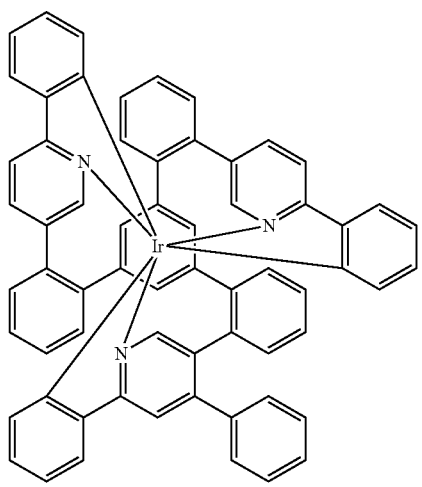
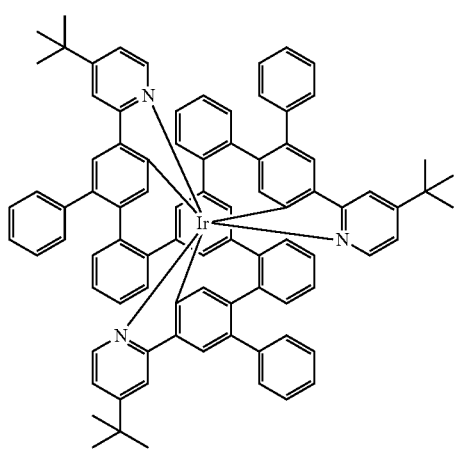

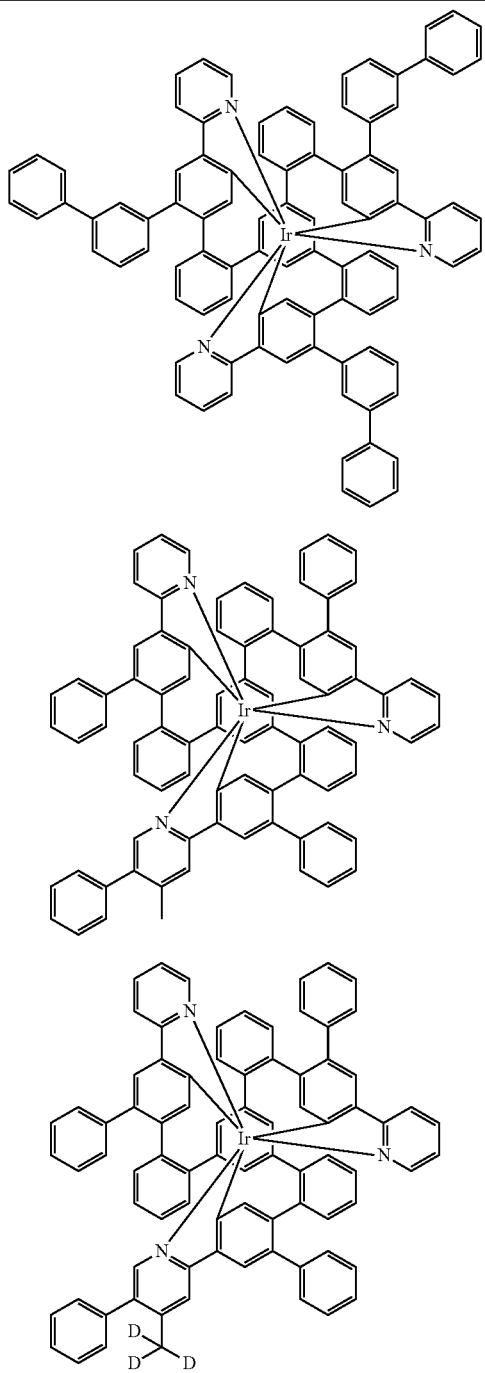

The above-described compounds comprising structures of the formula (I) and/or (II) or the above-detailed preferred embodiments can preferably be used as active component in an electronic device. An electronic device is understood to mean any device comprising anode, cathode and at least one layer between anode and cathode, said layer comprising at least one organic or organometallic compound. The electronic device of the invention thus comprises anode, cathode and at least one layer in between containing at least one compound comprising structures of the formula (I) and/or (II). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices (D. M. Koller et al., *Nature Photonics* 2008, 1-4), preferably organic electroluminescent devices (OLEDs, PLEDs), especially phosphorescent OLEDs, containing at least one compound comprising structures of the formula (I) in at least one layer. Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce.

In a preferred embodiment of the invention, the organic electroluminescent device contains the compound of the invention comprising structures of formula (I) and/or (II) or the above-detailed preferred embodiments as matrix material, preferably as hole-conducting matrix material, in one or more emitting layers, preferably in combination with a further matrix material, preferably an electron-conducting matrix material. In a further preferred embodiment of the invention, the further matrix material is a hole-transporting compound. In yet a further preferred embodiment, the further matrix material is a compound having a large band gap which is not involved to a significant degree, if at all, in the hole and electron transport in the layer. An emitting layer comprises at least one emitting compound.

Suitable matrix materials which can be used in combination with the compounds of formula (I) and/or (II) or according to the preferred embodiments are aromatic ketones, aromatic phosphine oxides or aromatic sulfoxides or sulfones, for example according to WO 2004/013080, WO 2004/093207, WO 2006/005627 or WO 2010/006680, triarylamines, especially monoamines, for example according to WO 2014/015935, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, lactams, for example according to WO 2011/116865, WO 2011/137951 or WO 2013/064206, or 4-spirocarbazole derivatives, for example according to WO 2014/094963 or WO 2015/192939. It is likewise possible for a further phosphorescent emitter which emits at a shorter wavelength than the actual emitter to be present as co-host in the mixture.

Preferred co-host materials are triarylamine derivatives, especially monoamines, indenocarbazole derivatives, 4-spirocarbazole derivatives, lactams and carbazole derivatives.

Preferred triarylamine derivatives which are used as co-host materials together with the compounds of the invention are selected from the compounds of the following formula (TA-1):

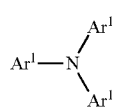

Formula (TA-1)

where $Ar^1$ is the same or different at each instance and is an aromatic or heteroaromatic ring system which has 6 to 40 carbon atoms and may be substituted in each case by one or more $R^2$ radicals, an aryloxy group which has 5 to 60 aromatic ring atoms and may be substituted by one or more $R^2$ radicals, or an aralkyl group which has 5 to 60 aromatic ring atoms and may be substituted in each case by one or more $R^2$ radicals, where two or more adjacent $R^2$ substituents may optionally form a mono- or polycyclic aliphatic, heteroaliphatic, aromatic or heteroaromatic ring system, preferably a mono- or polycyclic aliphatic ring system, which may be substituted by one or more $R^3$ radicals, where the symbol $R^2$ has the definition given above, especially for formula (I). Preferably, $Ar^1$ is the same or different at each instance and is an aryl or heteroaryl group which has 5 to 24 and preferably 5 to 12 aromatic ring atoms, and which may be substituted in each case by one or more $R^2$ radicals, but is preferably unsubstituted.

Examples of suitable $Ar^1$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted.

Preferably, the $Ar^1$ groups are the same or different at each instance and are selected from the abovementioned $R^1$-1 to $R^1$-95 groups, more preferably $R^1$-1 to $R^1$-54.

In a preferred embodiment of the compounds of the formula (TA-1), at least one $Ar^1$ group is selected from a biphenyl group, which may be an ortho-, meta- or para-biphenyl group. In a further preferred embodiment of the compounds of the formula (TA-1), at least one $Ar^1$ group is selected from a fluorene group or spirobifluorene group, where these groups may each be bonded to the nitrogen atom in the 1, 2, 3 or 4 position. In yet a further preferred embodiment of the compounds of the formula (TA-1), at least one $Ar^1$ group is selected from a phenylene or biphenyl group, where the group is an ortho-, meta- or para-bonded group, substituted by a dibenzofuran group, a dibenzothiophene group or a carbazole group, especially a dibenzofuran group, where the dibenzofuran or dibenzothiophene group is bonded to the phenylene or biphenyl group via the 1, 2, 3 or 4 position and where the carbazole group is bonded to the phenylene or biphenyl group via the 1, 2, 3 or 4 position or via the nitrogen atom.

In a particularly preferred embodiment of the compounds of the formula (TA-1), one $Ar^1$ group is selected from a fluorene or spirobifluorene group, especially a 4-fluorene or 4-spirobifluorene group, and one $Ar^1$ group is selected from a biphenyl group, especially a para-biphenyl group, or a fluorene group, especially a 2-fluorene group, and the third $Ar^1$ group is selected from a para-phenylene group or a para-biphenyl group, substituted by a dibenzofuran group, especially a 4-dibenzofuran group, or a carbazole group, especially an N-carbazole group or a 3-carbazole group.

Preferred indenocarbazole derivatives which are used as co-host materials together with the compounds of the invention are selected from the compounds of the following formula (TA-2):

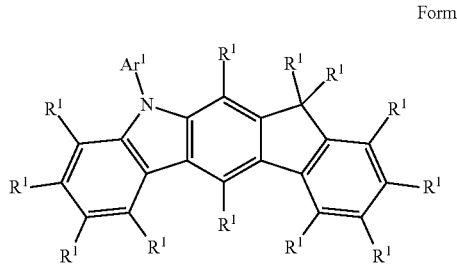

Formula (TA-2)

where $Ar^1$ and $R^1$ have the definitions listed above, especially for formulae (I) and/or (TA-1). Preferred embodiments of the $Ar^1$ group are the above-listed structures $R^1$-1 to $R^1$-95, more preferably $R^1$-1 to $R^1$-54.

A preferred embodiment of the compounds of the formula (TA-2) is the compounds of the following formula (TA-2a):

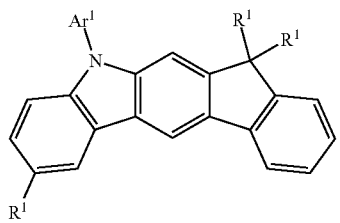

Formula (TA-2a)

where Ar$^1$ and R$^1$ have the definitions listed above, especially for formulae (I) and/or (TA-1). The two R$^1$ groups bonded to the indeno carbon atom here are preferably the same or different and are an alkyl group having 1 to 4 carbon atoms, especially methyl groups, or an aromatic ring system having 6 to 12 carbon atoms, especially phenyl groups. More preferably, the two R$^1$ groups bonded to the indeno carbon atom are methyl groups. Further preferably, the R$^1$ substituent bonded to the indenocarbazole base skeleton in formula (TA-2a) is H or a carbazole group which may be bonded to the indenocarbazole base skeleton via the 1, 2, 3 or 4 position or via the nitrogen atom, especially via the 3 position.

Preferred 4-spirocarbazole derivatives which are used as co-host materials together with the compounds of the invention are selected from the compounds of the following formula (TA-3):

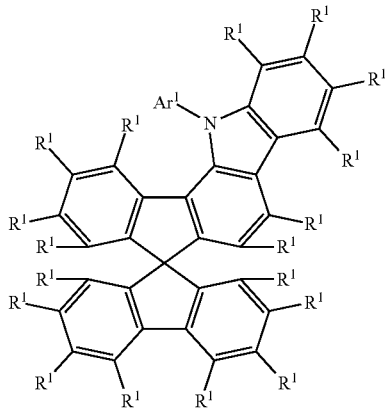

Formula (TA-3)

where Ar$^1$ and R$^1$ have the definitions listed above, especially for formulae (I), (II) and/or (Q-1). Preferred embodiments of the Ar$^1$ group are the above-listed structures R$^1$-1 to R$^1$-95, more preferably R$^1$-1 to R$^1$-54.

A preferred embodiment of the compounds of the formula (TA-3) is the compounds of the following formula (TA-3a):

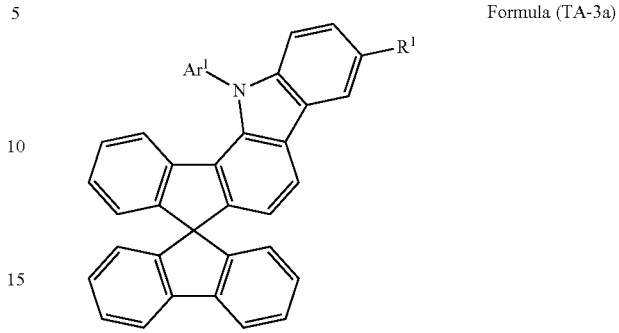

Formula (TA-3a)

where Ar$^1$ and R$^1$ have the definitions listed above, especially for formulae (I), (II) and/or (Q-1). Preferred embodiments of the Ar$^1$ group are the above-listed structures R$^1$-1 to R$^1$-95, more preferably R$^1$-1 to R$^1$-54.

Preferred lactams which are used as co-host materials together with the compounds of the invention are selected from the compounds of the following formula (LAC-1):

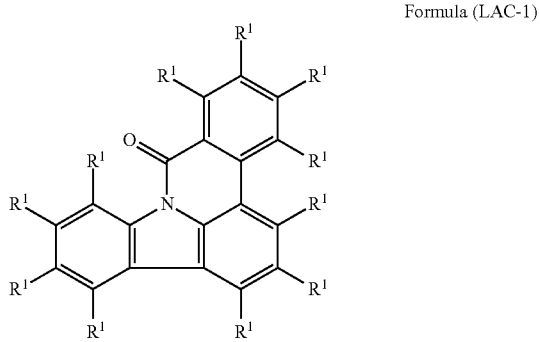

Formula (LAC-1)

where R$^1$ has the definition listed above, especially for formula (I) and/or (II).

A preferred embodiment of the compounds of the formula (LAC-1) is the compounds of the following formula (LAC-1a):

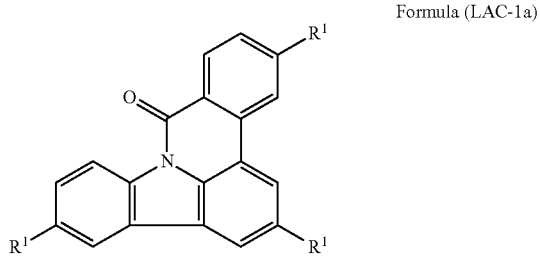

Formula (LAC-1a)

where R$^1$ has the definition given above, especially for formula (I) and/or (II). R$^1$ here is preferably the same or different at each instance and is H or an aromatic or heteroaromatic ring system which has 5 to 40 aromatic ring atoms and may be substituted by one or more R$^2$ radicals, where R$^2$ may have the definition given above, especially for formula (I) and/or (II). Most preferably, the R$^1$ substituents are selected from the group consisting of H and an aromatic or heteroaromatic ring system which has 6 to 18 aromatic ring atoms, preferably 6 to 13 aromatic ring atoms, and may be substituted in each case by one or more nonaromatic $R^2$ radicals, but is preferably unsubstituted. Examples of suitable $R^1$ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted. Suitable $R^1$ structures here are the same structures as depicted above for R-1 to R-95, more preferably $R^1$-1 to $R^1$-54.

It may also be preferable to use a plurality of different matrix materials as a mixture, especially at least one electron-conducting matrix material and at least one hole-conducting matrix material. Preference is likewise given to the use of a mixture of a charge-transporting matrix material and an electronically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, a compound of the invention comprising structures of formula (I) and/or (II), in a preferred embodiment, can be used as matrix material in an emission layer of an organic electronic device, especially in an organic electroluminescent device, for example in an OLED or OLEC. In this case, the matrix material containing a compound comprising structures of formula (I) and/or (II) or the preferred embodiments recited above and hereinafter is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising structures of formula (I) and/or (II) or the preferred embodiments recited above and hereinafter is used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfil(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more hole-conducting layers, as hole-conducting compound.

The present invention additionally provides an electronic device, preferably an organic electroluminescent device, comprising one or more compounds of the invention and/or at least one oligomer, polymer or dendrimer of the invention in emitting layers, as emitting compound, preferably as fluorescent emitter, or as matrix material, preferably in combination with a phosphorescent emitter.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapor deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example M. S. Arnold et al., *Appl. Phys. Lett.* 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device, can also be produced as a hybrid system by applying one or more layers from solution and applying one or more other layers by vapor deposition. For example, it is possible to apply an emitting layer comprising a compound of the invention comprising structures of formula (I) and/or (II) and a matrix material from solution, and to apply a hole blocker layer and/or an electron transport layer thereto by vapor deposition under reduced pressure.

These methods are known in general terms to those skilled in the art and can be applied by those skilled in the art without difficulty to electronic devices, especially organic electroluminescent devices comprising compounds of the invention comprising structures of formula (I) and/or (II) or the above-detailed preferred embodiments.

The electronic devices of the invention, especially organic electroluminescent devices, are notable for one or more of the following surprising advantages over the prior art:

1, Electronic devices, especially organic electroluminescent devices, comprising compounds, oligomers, polymers or dendrimers having structures of formula (I) and/or (II) or the preferred embodiments recited above and hereinafter, especially as fluorescent emitter, as host material or as electron-conducting materials and/or hole-conducting materials, have a very good lifetime. In this context, these compounds especially bring about low roll-off, i.e. a small drop in power efficiency of the device at high luminances.

2, Electronic devices, especially organic electroluminescent devices, comprising compounds, oligomers, polymers or dendrimers having structures of formula (I) and/or (II) or the preferred embodiments recited above and hereinafter, as fluorescent emitter or as electron-conducting materials, hole-conducting materials and/or host materials, have excellent efficiency. In this context, compounds, oligomers, polymers or dendrimers of the invention having structures of formula (I) and/or (II) or the preferred embodiments recited above and hereinafter bring about a low operating voltage when used in electronic devices.

3. The compounds, oligomers, polymers or dendrimers of the invention having structures of formula (I) and/or (II) or the preferred embodiments recited above and hereinafter exhibit very high stability and lifetime.

4. With compounds, oligomers, polymers or dendrimers having structures of formula (I) and/or (II) or the preferred embodiments recited above and hereinafter, it is possible to avoid the formation of optical loss channels in electronic devices, especially organic electroluminescent devices. As a result, these devices feature a high PL efficiency and hence high EL efficiency of emitters, and excellent energy transmission of the matrices to dopants.

5. The use of compounds, oligomers, polymers or dendrimers having structures of formula (I) and/or (II) or the preferred embodiments recited above and hereinafter in layers of electronic devices, especially organic electroluminescent devices, leads to high mobility of the electron conductor structures.

6. Compounds, oligomers, polymers and dendrimers having structures of formula (I) and/or (II) or the preferred embodiments recited above and hereinafter feature excellent thermal stability, and compounds having a molar mass of less than about 1200 g/mol have good sublimability.

7. Compounds, oligomers, polymers and dendrimers having structures of formula (I) and/or (II) or the preferred embodiments recited above and hereinafter have excellent glass film formation.

8. Compounds, oligomers, polymers and dendrimers having structures of formula (I) and/or (II) or the preferred embodiments detailed above and hereinafter form very good films from solutions.

9. The compounds, oligomers, polymers or dendrimers comprising structures of formula (I) and/or (II) or the preferred embodiments recited above and hereinafter have a surprisingly high triplet level Ti.

These abovementioned advantages are not accompanied by a deterioration in the further electronic properties.

The compounds and mixtures of the invention are suitable for use in an electronic device. An electronic device is understood here to mean a device containing at least one layer containing at least one organic compound. The component may, however, also comprise inorganic materials or else layers formed entirely from inorganic materials.

The present invention therefore further provides for the use of the compounds or mixtures of the invention in an electronic device, especially in an organic electroluminescent device.

The present invention still further provides for the use of a compound of the invention and/or of an oligomer, polymer or dendrimer of the invention in an electronic device as fluorescent emitter, host material for phosphorescent emitters, electron transport material and/or hole transport material, preferably as host material for phosphorescent emitters or as hole transport material.

The present invention still further provides an electronic device comprising at least one of the above-detailed compounds or mixtures of the invention.

In this case, the preferences detailed above for the compound also apply to the electronic devices. More preferably, the electronic device is selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices (D. M. Koller et al., Nature Photonics 2008, 1-4), preferably organic electroluminescent devices (OLEDs, PLEDs), especially phosphorescent OLEDs.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds of formula (I) and/or (II) or according to the preferred embodiments.

The compounds of the invention generally have very good properties on use in organic electroluminescent devices. Especially in the case of use of the compounds of the invention in organic electroluminescent devices, the lifetime is significantly better compared to similar compounds according to the prior art. At the same time, the further properties of the organic electroluminescent device, especially the efficiency and voltage, are likewise better or at least comparable.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in more detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The reactants can be sourced from ALDRICH. The numbers for the reactants known from the literature, some of which are stated in square brackets, are the corresponding CAS numbers.

Synthesis Examples

Stage 1:

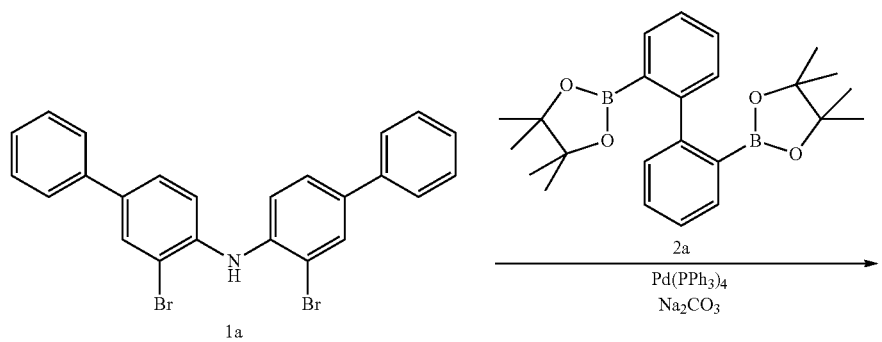

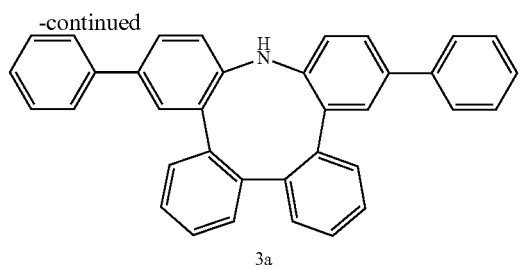

3a

Variant A:

18.0 g (37.6 mmol, 1.0 eq) of 3-bromo-N-(3-bromo[1,1'-biphenyl]-4-yl)-[1,1-biphenyl]-4-amine [1388152-32-6] 1a, together with 15.3 g (37.6 mmol, 1.0 eq) of 2,2'-[1,1'-biphenyl]-2,2'-diylbis[4,4,5,5-tetramethyl-1,3,2-dioxaborolane [398128-09-1] 2a, are dissolved in 200 ml each of toluene and 1,4-dioxane, and 100 ml of water are added. The mixture is degassed with argon for 30 minutes. Subsequently, 12.0 g (106 mmol, 3.0 eq) of sodium carbonate and 2.17 g (1.88 mmol, 0.05 eq) of tetrakis(triphenylphosphine) are added and the mixture is stirred at 100° C. for two days. After the reaction has ended, the aqueous phase is removed and extracted twice with toluene, and the combined organic phases are washed once again with water. This is followed by drying over sodium sulfate and removal of the solvents on a rotary evaporator. The residue is recrystallized from toluene/heptane. 7.27 g (15.4 mmol, 41%) of the desired product 3a are obtained.

Variant B:

0.02 eq of palladium(II) acetate, 0.05 eq of tri-o-tolylphosphine, 2.25 eq of potassium phosphate; in toluene/dioxane/water 2:2:1 as solvent Variant C:

0.03 eq of palladium(II) acetate, 0.05 eq of tri-t-butylphosphine, 3.0 eq of potassium fluoride anhydr.; in THF as solvent The following are prepared analogously:

| Entry | Reactant 1 | Reactant 2 | Product 3 | Yield | Variant |
|---|---|---|---|---|---|
| 3b | 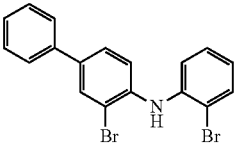 [101875-58-5] | 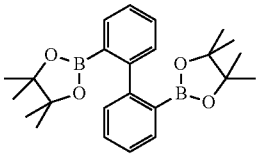 [398128-09-1] | 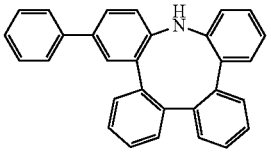 [SMILES: c1ccc(-c2ccc3[nH]c4ccccc4c4ccccc4c4ccccc4c3c2)cc1] | 34% | C |
| 3c | 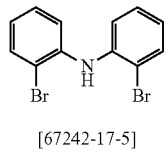 [67242-17-5] | 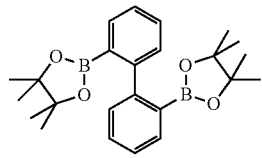 [398128-09-1] | 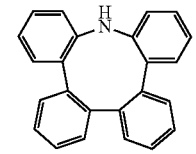 [SMILES: c1ccc2c(c1)[nH]c1ccccc1c1ccccc1c1ccccc21] | 55% | B |
| 3d | 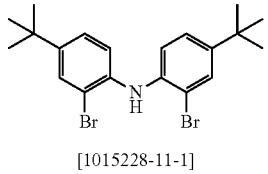 [SMILES: CC(C)(C)c1ccc(Nc2ccc(C(C)(C)C)cc2Br)c(Br)c1] [1015228-11-1] | 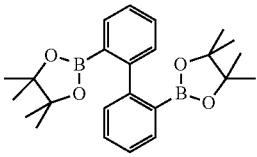 [398128-09-1] | 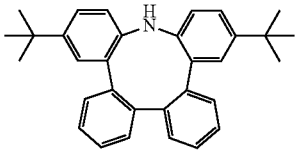 [SMILES: CC(C)(C)c1ccc2[nH]c3ccc(C(C)(C)C)cc3c3ccccc3c3ccccc3c2c1] | 28% | C |

Stage 2:

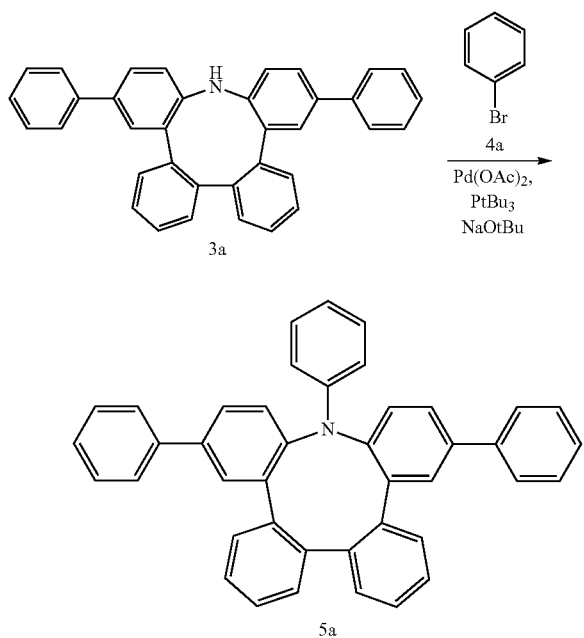

Variant A:

10.0 g (21.2 mmol, 1.0 eq) of the prepared compound 3a together with 4.00 g (25.4 mmol, 1.2 eq) of bromobenzene [108-86-1] 4a are dissolved in 200 ml of toluene and degassed with argon for 30 minutes. Subsequently, 4.07 g (42.4 mmol, 2.0 eq) of sodium t-butoxide, 238 mg (1.06 mmol, 0.05 eq) of palladium(II) acetate and 2.1 ml (2.12 mmol, 0.10 eq) of tri-t-butylphosphine (1.0M in toluene) are added and the mixture is stirred under reflux overnight. After the reaction has ended, 200 ml of water are added to the mixture, and the organic phase is removed and extracted twice with water. The organic phase is dried over sodium sulfate and concentrated to about 80 ml on a rotary evaporator. The precipitated solids are filtered off with suction and purified by means of hot extraction in toluene. The product is recrystallized three times with toluene/heptane and then sublimed. 6.59 g (12.0 mmol, 57%) of the desired target compound 5a are obtained with an HPLC purity of >99.9%.

Variant B:

0.05 eq of tris(dibenzylideneacetone)dipalladium(0), 0.10 eq of dicyclohexyl(2',6'-dimethoxybiphenyl-2-yl)phosphine/S-Phos, 2.0 eq sodium t-butoxide; in toluene as solvent Variant C:

0.05 eq of 1,1'-bis(diphenylphosphino)ferrocenedichloropalladium(II) complex with dichloromethane, 2.0 eq of sodium t-butoxide; in toluene as solvent The following are prepared analogously:

| Entry | Reactant 3 | Reactant 4 | Product 5 | Yield [%] | Variant |
|---|---|---|---|---|---|
| 5b | | | | 31 | A |
| 5c | | | | 56 | C |

| Entry | Reactant 3 | Reactant 4 | Product 5 | Yield [%] | Variant |
|---|---|---|---|---|---|
| 5d | | | | 45 | A |
| 5e | | | | 41 | B |

| Entry | Reactant 3 | Reactant 4 | Product 5 | Yield [%] | Variant |
|---|---|---|---|---|---|
| 5f | 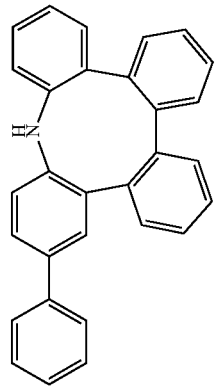 | 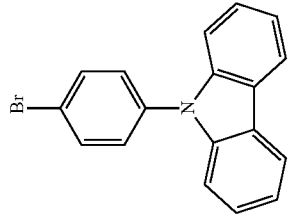 | 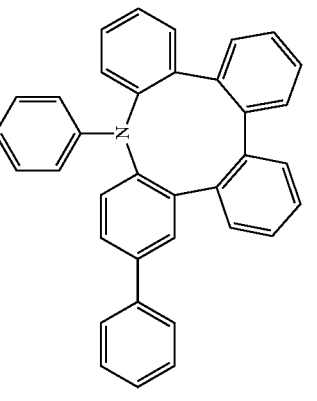 | 66 | B |
| 5g | 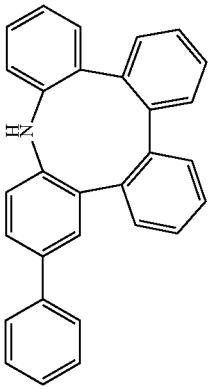 | 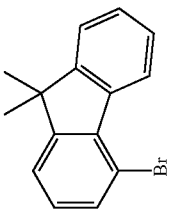 | 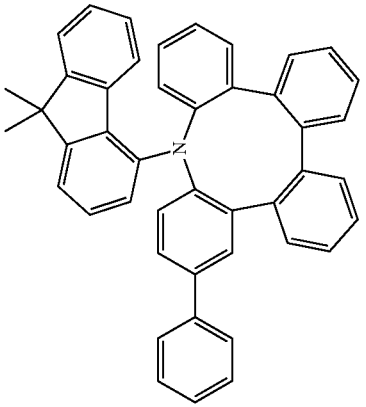 | 38 | B |

| Entry | Reactant 3 | Reactant 4 | Product 5 | Yield [%] | Variant |
|---|---|---|---|---|---|
| 5h | 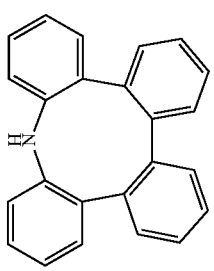 | 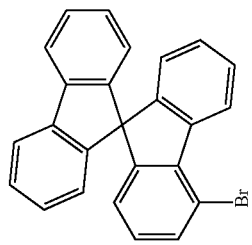 | 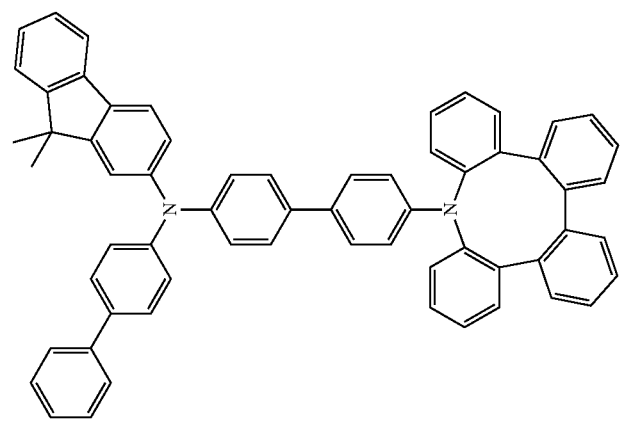 | 46 | B |
| 5i | 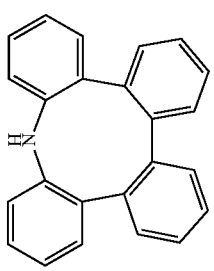 | 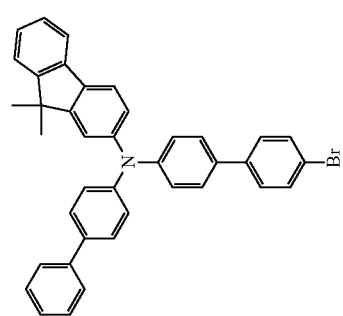 | 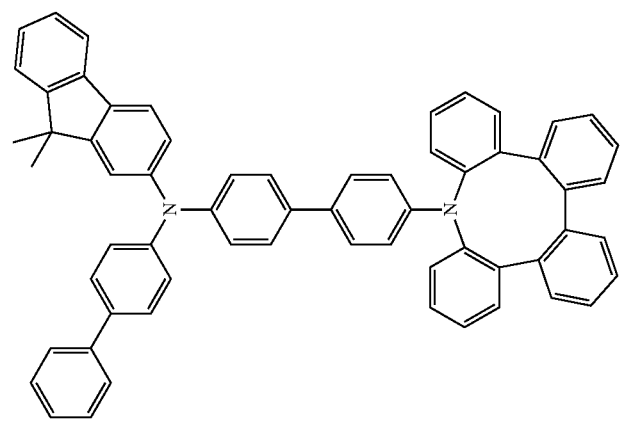 | 71 | A |

| Entry | Reactant 3 | Reactant 4 | Product 5 | Yield [%] | Variant |
|---|---|---|---|---|---|
| 5j | | | | 54 | B |
| 5k | | | | 33 | B |

-continued

| Entry | Reactant 3 | Reactant 4 | Product 5 | Yield [%] | Variant |
|---|---|---|---|---|---|
| 51 | | | | 41 | A |

-continued

| Entry | Reactant 3 | Reactant 4 | Product 5 | Yield [%] | Variant |
|---|---|---|---|---|---|
| 5m | | | | 21 | B |
| 5n | | | | 52 | C |

-continued

| Entry | Reactant 3 | Reactant 4 | Product 5 | Yield [%] | Variant |
|---|---|---|---|---|---|
| 5o | | | | 39 | A |
| 5p | | | | 11 | C |

-continued
| Entry | Reactant 3 | Reactant 4 | Product 5 | Yield [%] | Variant |
|---|---|---|---|---|---|
| 5q | 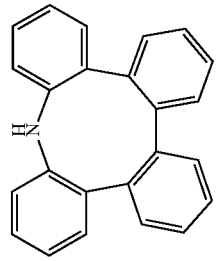 | 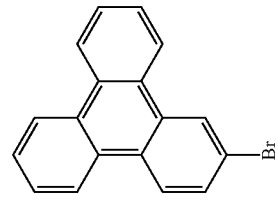 | 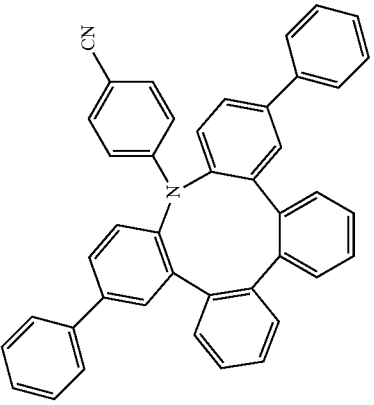 | 53 | B |
| 5r | 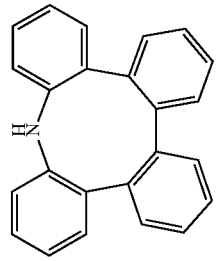 | 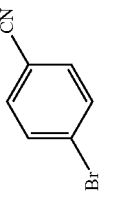 | 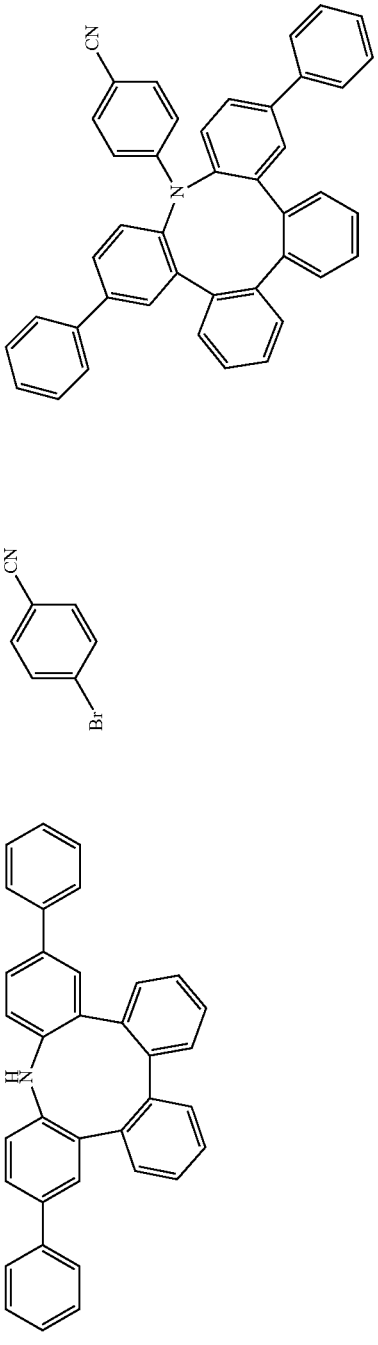 | 31 | B |

-continued

| Entry | Reactant 3 | Reactant 4 | Product 5 | Yield [%] | Variant |
|---|---|---|---|---|---|
| 5s | | | | 13 | B |

Stage 3:

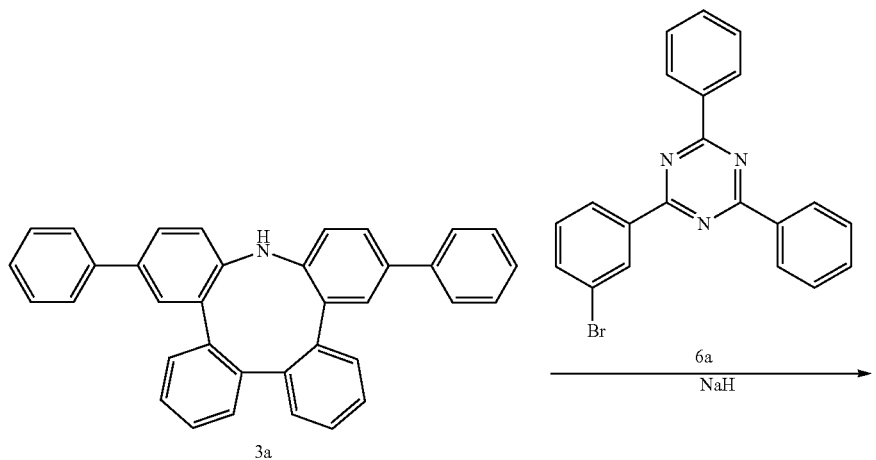

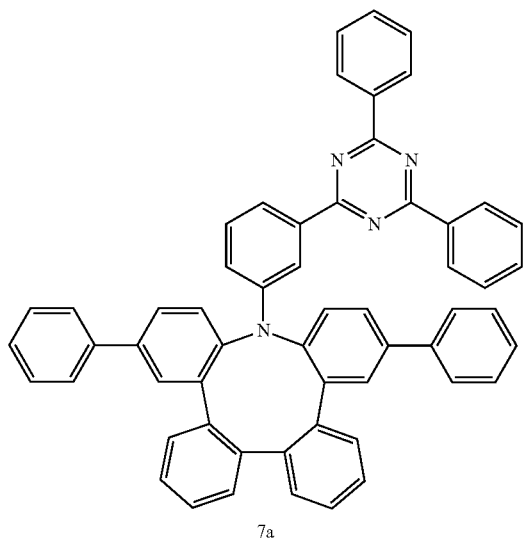

Variant A:

A solution of 8.0 g (17 mmol, 1.0 eq) of 3a in 75 ml of dried DMF is slowly added dropwise to a suspension of 820 mg (20.4 mmol, 1.2 eq) of sodium hydride (60% suspension in mineral oil) in 50 ml of dried DMF and stirred for two hours. Subsequently, 7.9 g (20 mmol, 1.2 eq) of 2-(3-bromophenyl)-4,6-diphenyl-[1,3,5]triazine 6a in 50 ml of dried THF are added dropwise and the mixture is stirred at room temperature overnight. After the reaction has ended, the mixture is added to 300 ml of a 1:1 water/ice mixture and the resultant solids are filtered off with suction. The crude product is purified by means of hot extraction from toluene and recrystallization three times from heptane/toluene and sublimed twice. 8.2 g (10.5 mmol, 62%) of the desired product 7a are obtained with an HPLC purity of >99%.

Variant B:

5.0 eq of cesium carbonate in dimethylacetamide

The following are prepared analogously:

| Entry | Reactant 3 | Reactant 6 | Product 7 | Yield [%] | Variant |
|---|---|---|---|---|---|
| 7b | | | | 73 | A |
| 7c | | | | 65 | A |

-continued
| Entry | Reactant 3 | Reactant 6 | Product 7 | Yield [%] | Variant |
|---|---|---|---|---|---|
| 7d | 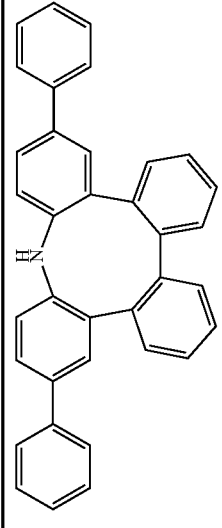 | 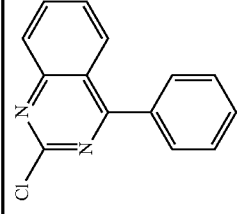 | 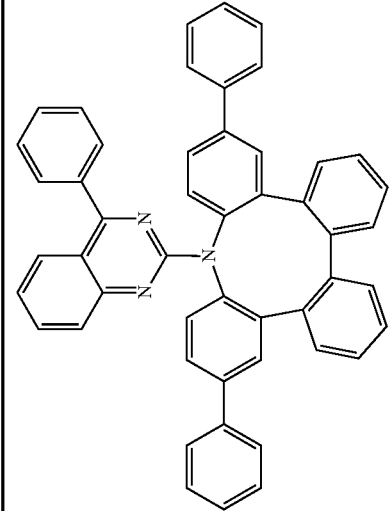 | 69 | A |
| 7e | 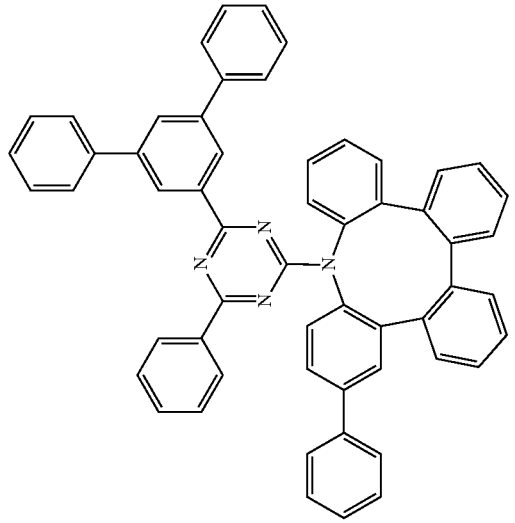 | | | 44 | B |

-continued
| Entry | Reactant 3 | Reactant 6 | Product 7 | Yield [%] | Variant |
|---|---|---|---|---|---|
| 7f | 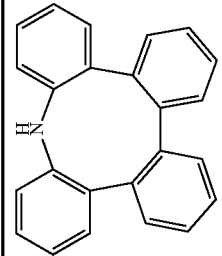 | 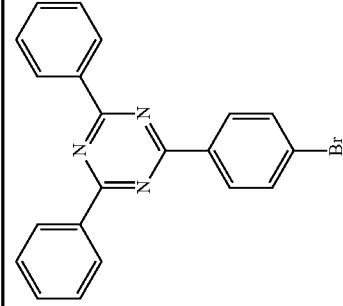 | 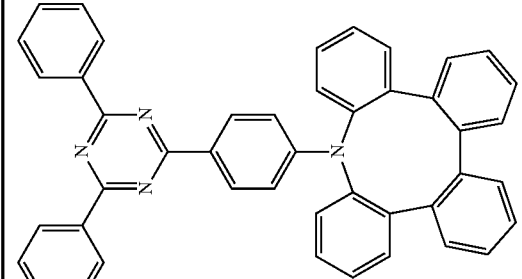 | 52 | B |
| 7g | 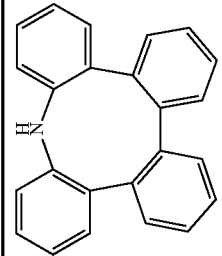 | 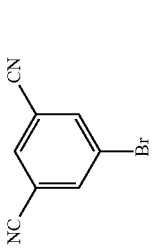 | 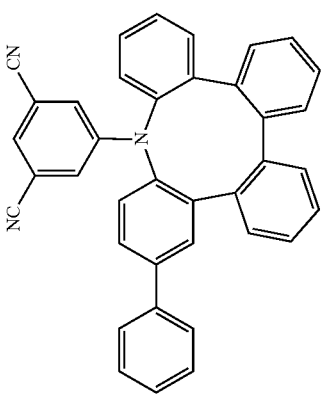 | 38 | A |

Production of the OLEDs

OLEDs of the invention and OLEDs according to the prior art are produced by a general method according to WO 2004/058911, which is adapted to the circumstances described here (variation in layer thickness, materials used).

In the examples which follow, the results for various OLEDs are presented. Glass plaques with structured ITO (50 nm, indium tin oxide) form the substrates to which the OLEDs are applied. The OLEDs basically have the following layer structure: substrate/hole transport layer 1 (HTL1) consisting of HTM doped with 5% NDP-9 (commercially available from Novaled), 20 nm/hole transport layer 2 (HTL2)/optional electron blocker layer (EBL)/emission layer (EML)/optional hole blocker layer (HBL)/electron transport layer (ETL) and finally a cathode. The cathode is formed by an aluminum layer of thickness 100 nm.

First of all, vacuum-processed OLEDs are described. For this purpose, all the materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as M3:M2:Ir(L1)$_3$ (55%:35%:10%) mean here that the material M3 is present in the layer in a proportion by volume of 55%, M2 in a proportion of 35% and Ir(L1)$_3$ in a proportion of 10%. Analogously, the electron transport layer may also consist of a mixture of two materials. The exact structure of the OLEDs can be found in Table 1. The materials used for production of the OLEDs are shown in Table 3.

The OLEDs are characterized in a standard manner. The lifetime is defined as the time after which the luminance has fallen from a particular starting luminance to a certain proportion. The figure LT50 means that the lifetime specified is the time at which the luminance has dropped to 50% of the starting luminance, i.e. from, for example, 1000 cd/m$^2$ to 500 cd/m$^2$. According to the emission color, different starting brightnesses are chosen. The values for the lifetime can be converted to a figure for other starting luminances with the aid of conversion formulae known to those skilled in the art. In this context, the lifetime for a starting luminance of 1000 cd/m$^2$ is a standard figure.

The compounds of the invention can be used inter alia as hole conductor (HTL) and as hole-conducting material (h-TMM) in the emission layer in OLEDs (see table 1). The results for the OLEDs are collated in Table 2.

TABLE 1

Structure of the OLEDs

| Ex. | HTL2 thickness | EBL thickness | EML thickness | HBL thickness | ETL thickness |
|---|---|---|---|---|---|
| Red OLEDs | | | | | |
| D-R1 | 5b 280 nm | — | M5:M6:Ir-R1 (65%:30%:5%) 35 nm | — | ETM1:ETM2 (50%:50%) 40 nm |
| D-R2 | HTM 280 nm | — | M5:5c:Ir-R1 (60%:35%:5%) 35 nm | — | ETM1:ETM2 (50%:50%) 40 nm |
| D-R3 | 5b 280 nm | — | M5:5c:Ir-R1 (60%:35%:5%) 35 nm | — | ETM1:ETM2 (50%:50%) 40 nm |
| D-R4 | 5l 280 nm | — | 7d:Ir-R1 (60%:35%:5%) 35 nm | — | ETM1:ETM2 (50%:50%) 40 nm |
| Yellow OLEDs | | | | | |
| D-Y1 | 5b 250 nm | — | M5:M6:Ir-Y1 (62%:30%:8%) 30 nm | — | ETM1:ETM2 (50%:50%) 45 nm |
| D-Y2 | 5c 250 nm | — | M5:5c:Ir-Y1 (60%:30%:10%) 30 nm | — | ETM1:ETM2 (50%:50%) 45 nm |
| Green OLEDs | | | | | |
| D-G1 | HTM 220 nm | 5c 10 nm | M5:5c:Ir-G1 (60%:30%:10%) 30 nm | HBM2 10 nm | ETM1:ETM2 (50%:50%) 35 nm |
| D-G2 | 5c 220 nm | 5c 10 nm | M5:5c:Ir-G1 (60%:30%:10%) 30 nm | HBM2 10 nm | ETM1:ETM2 (50%:50%) 35 nm |
| D-G3 | HTM 220 nm | 5a 10 nm | M5:M6:Ir-G1 (45%:40%:15%) 30 nm | HBM2 10 nm | ETM1:ETM2 (50%:50%) 35 nm |
| D-G4 | HTM 220 nm | 5b 10 nm | M5:M6:Ir-G1 (45%:40%:15%) 30 nm | HBM2 10 nm | ETM1:ETM2 (50%:50%) 35 nm |
| D-G5 | HTM 220 nm | 5c 10 nm | M5:5e:Ir-G1 (55%:30%:15%) 30 nm | HBM2 10 nm | ETM1:ETM2 (50%:50%) 35 nm |
| D-G6 | HTM 220 nm | 5g 10 nm | M5:5f:Ir-G1 (65%:20%:15%) 30 nm | HBM2 10 nm | ETM1:ETM2 (50%:50%) 35 nm |
| D-G7 | HTM 220 nm | 5g 10 nm | M5:5k:Ir-G1 (45%:40%:15%) 30 nm | HBM2 10 nm | ETM1:ETM2 (50%:50%) 35 nm |
| D-G8 | 5i 220 nm | 5c 10 nm | M5:M6:Ir-G1 (55%:30%:15%) 30 nm | HBM2 10 nm | ETM1:ETM2 (50%:50%) 35 nm |
| D-G9 | HTM 220 nm | 5c 10 nm | M5:5q:Ir-G1 (55%:30%:15%) 30 nm | HBM2 10 nm | ETM1:ETM2 (50%:50%) 35 nm |
| D-G10 | HTM 220 nm | 5c 10 nm | 7f:Ir-G1 (80%:20%) 30 nm | HBM2 10 nm | ETM1:ETM2 (50%:50%) 35 nm |
| Blue OLEDs | | | | | |
| D-B1 | 5b 190 nm | EBM 10 nm | M1:M4:Ir-B1 (60%:35%:5%) 25 nm | HBM1 10 nm | ETM1:ETM2 (50%:50%) 15 nm |
| D-B2 | 5c 190 nm | EBM 10 nm | M2:M4:Ir-B1 (60%:35%:5%) 25 nm | HBM1 10 nm | ETM1:ETM2 (50%:50%) 15 nm |
| D-B3 | 5m 190 nm | EBM 10 nm | M2:M4:Ir-B1 (60%:35%:5%) 25 nm | HBM1 10 nm | ETM1:ETM2 (50%:50%) 15 nm |
| D-B4 | 5l 190 nm | EBM 10 nm | M2:M4:Ir-B1 (60%:30%:10%) 25 nm | HBM1 10 nm | ETM1:ETM2 (50%:50%) 15 nm |

TABLE 2

Results for the vacuum-processed OLEDs

| Ex. | EQE (%) 1000 cd/m$^2$ | Voltage (V) 1000 cd/m$^2$ | CIE x/y 1000 cd/m$^2$ | LT80 (h) 1000 cd/m$^2$ |
|---|---|---|---|---|
| Red OLEDs | | | | |
| D-R1 | 15.3 | 3.0 | 0.67/0.33 | 15000 |
| D-R2 | 16.2 | 3.1 | 0.67/0.33 | 16000 |
| D-R3 | 15.9 | 3.0 | 0.67/0.33 | 14500 |
| D-R4 | 15.9 | 2.9 | 0.67/0.33 | 18000 |

TABLE 2-continued
Results for the vacuum-processed OLEDs
Yellow OLEDs
| | | | | |
|---|---|---|---|---|
| D-Y1 | 22.7 | 3.1 | 0.44/0.55 | 73000 |
| D-Y2 | 23.1 | 3.2 | 0.48/0.51 | 62000 |
Green OLEDs
| | | | | |
|---|---|---|---|---|
| D-G1 | 20.6 | 3.3 | 0.32/0.64 | 33000 |
| D-G2 | 19.0 | 3.2 | 0.33/0.63 | 35000 |
| D-G3 | 19.5 | 3.2 | 0.32/0.64 | 41000 |
| D-G4 | 19.8 | 3.1 | 0.32/0.64 | 38000 |
| D-G5 | 20.2 | 3.3 | 0.33/0.63 | 35000 |
| D-G6 | 19.2 | 3.2 | 0.33/0.63 | 26000 |
| D-G7 | 19.6 | 3.2 | 0.33/0.63 | 36000 |
| D-G8 | 19.4 | 3.3 | 0.32/0.64 | 38000 |
| D-G9 | 20.0 | 3.2 | 0.32/0.64 | 40000 |
| D-G10 | 19.8 | 3.1 | 0.32/0.64 | 32000 |
Blue OLEDs
| | | | | LT50 (h) 1000 cd/m² |
|---|---|---|---|---|
| D-B1 | 22.3 | 4.4 | 0.16/0.33 | 900 |
| D-B2 | 17.8 | 4.5 | 0.15/0.34 | 1100 |
| D-B3 | 18.8 | 4.8 | 0.15/0.33 | 1000 |
| D-B4 | 19.4 | 4.4 | 0.15/0.33 | 1100 |
TABLE 3
Structural formulae of the materials used
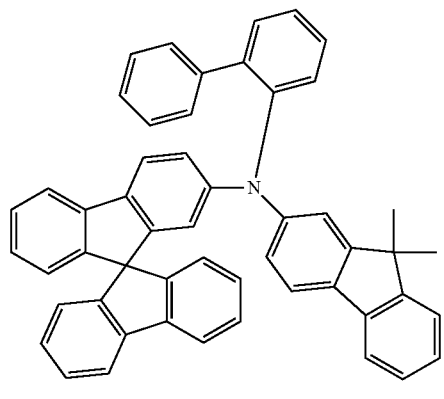
HTM
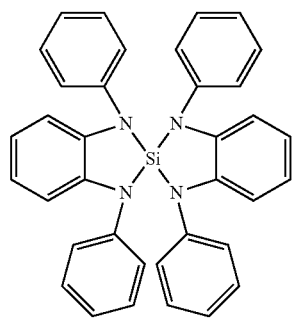
EBM
TABLE 3-continued
Structural formulae of the materials used
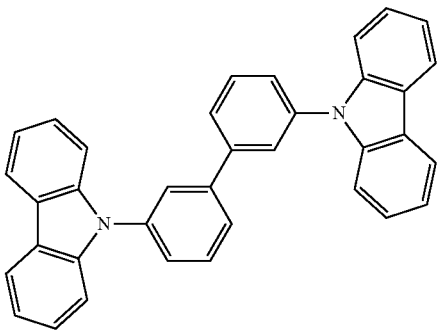
M1
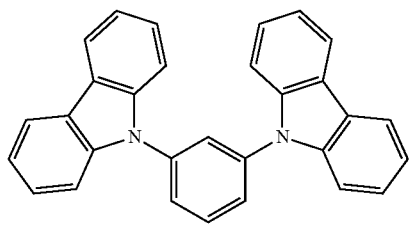
M2
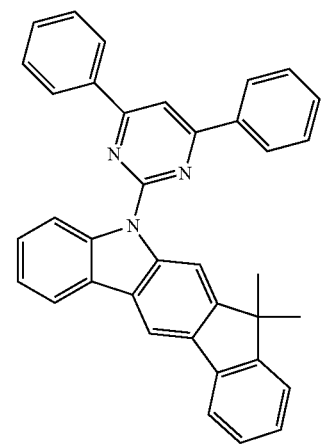
HBM2

TABLE 3-continued
Structural formulae of the materials used
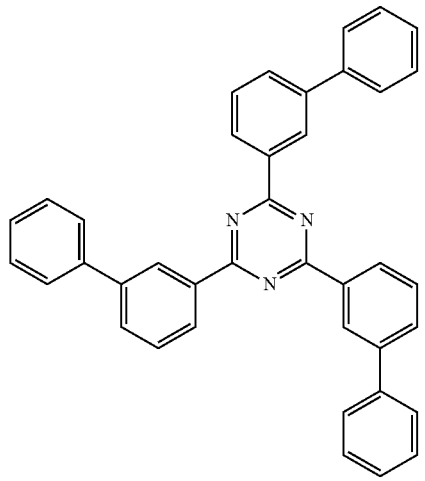
M4 = HBM1
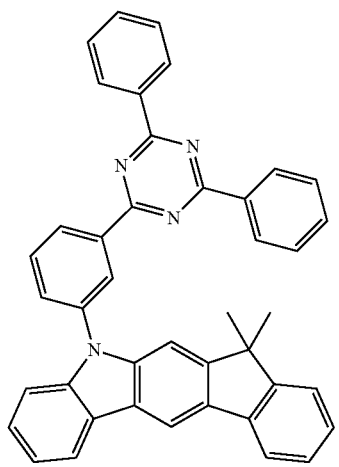
M5
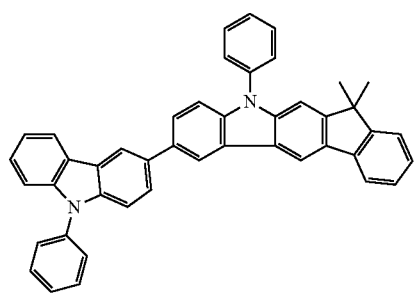
M6
TABLE 3-continued
Structural formulae of the materials used
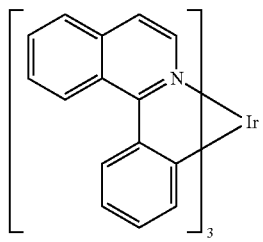
435293-93-9
Ir-R1
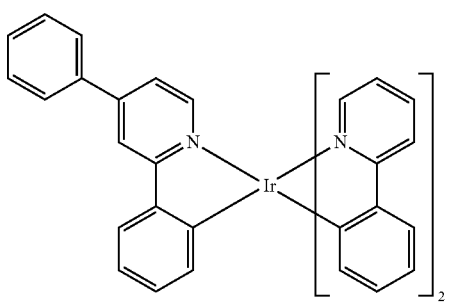
1215281-24-5
Ir-Y1
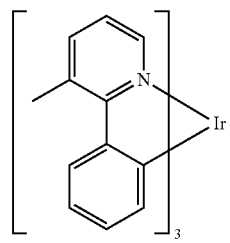
359014-71-4
Ir-G1
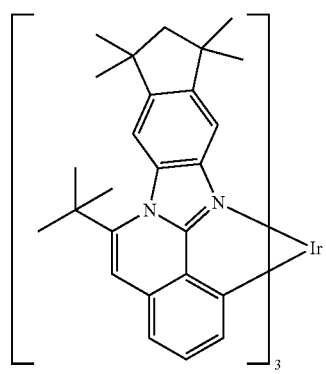
1541114-98-0
Ir-B1

TABLE 3-continued

Structural formulae of the materials used

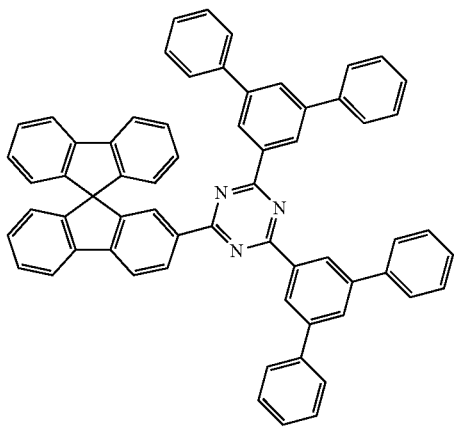

ETM1

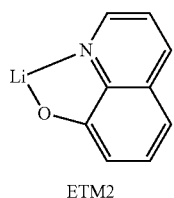

ETM2

The invention claimed is:

1. A compound comprising at least one structure of the formula (I) and/or (II):

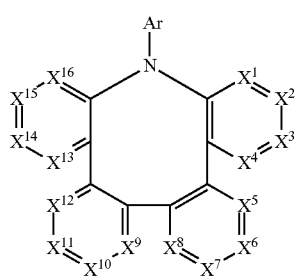
Formula (I)

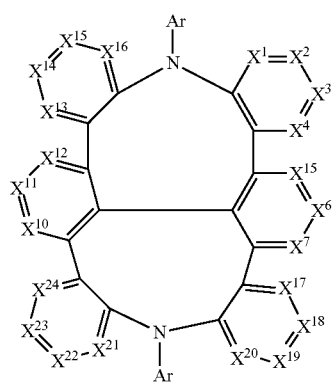
Formula (II)

where the symbols used are as follows:
$X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ is N or $CR^1$, Ar is the same or different at each instance and is an aromatic or heteroaromatic ring system which has 5 to 60 aromatic ring atoms and may be substituted by one or more $R^1$ radicals;

$Ar^{10}$ is the same or different at each instance and is of the formula (H-1)

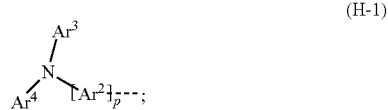
(H-1)

$Ar^2$ is an aromatic or heteroaromatic ring system which has 5 to 14 aromatic or heteroaromatic ring atoms, which may be substituted by one or more $R^{21}$ radicals;

p is 0 or 1, $Ar^3$ and $Ar^4$ are the same or different at each instance and are an aromatic or heteroaromatic ring system having 6 to 24 aromatic ring atoms, each of which may be substituted by one or more $R^{21}$ radicals;

$R^1$ is the same or different at each instance and is H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $NR^2$, $P(=O)(R^2)$, $-C(=O)O-$, $-C(=O)NR^2-$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; or a combination of these systems; at the same time, two or more $R^1$ radicals together may form a ring system;

$R^2$ is the same or different at each instance and is H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $-R^3C=CR^3-$, $-C\equiv C-$, $Si(R^3)_2$, $Si(R^3)_2$, $Ge(R^3)_2$, $Sn(R^3)_2$, $C=O$, $C=S$, $C=Se$, $C=NR^3$, $NR^3$, $P(=O)(R^3)$, $-C(=O)O-$, $-C(=O)NR^3-$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^3$ radicals, or an aryloxy or heteroaryloxy group which has 5 to 40 aromatic ring atoms and may be substituted by one or more $R^3$ radicals, or an aralkyl or heteroaralkyl group which has 5 to 40 aromatic ring atoms and may be substituted by one or more $R^3$ radicals, or a diarylamino group, diheteroarylamino group or arylheteroarylamino group which has 10 to 40 aromatic ring atoms and may be substituted by one or more $R^3$ radicals, or a combination of these systems; at the same time, two or more $R^2$ substituents together may also form a ring system;

$R^{21}$ is the same or different at each instance and is H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $-R^3C=CR^3-$, $-C\equiv C-$, $Si(R^3)_2$, $Si(R^3)_2$, $Ge(R^3)_2$, $Sn(R^3)_2$, C=O, C=S, C=Se, $C=NR^3$, $P(=O)(R^3)$, $-C(=O)O-$, $-C(=O)NR^3-$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^3$ radicals, or an aryloxy or heteroaryloxy group which has 5 to 40 aromatic ring atoms and may be substituted by one or more $R^3$ radicals, or an aralkyl or heteroaralkyl group which has 5 to 40 aromatic ring atoms and may be substituted by one or more $R^3$ radicals and with the proviso that the aromatic or heteroaromatic ring system does not contain triarylamine;

$R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more $R^3$ substituents together may also form a ring system.

2. A compound as claimed in claim 1, comprising at least one structure of the formula (III) and/or (IV)

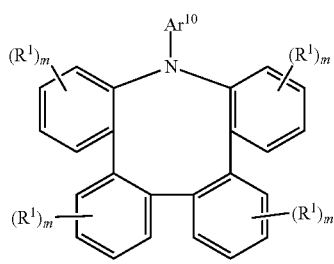

Formula (III)

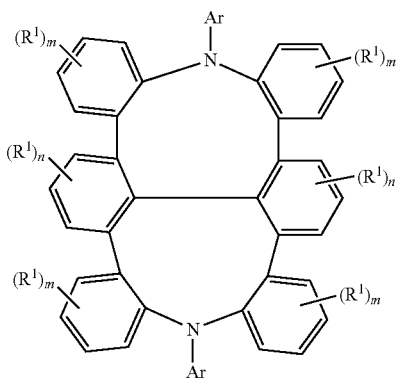

Formula (IV)

where the symbols $R^1$, $Ar^{10}$ and Ar used have the definition given in claim 1 and m at each instance is in each case independently 0, 1, 2, 3 or 4, and n at each instance is in each case independently 0, 1, 2 or 3.

3. A compound as claimed in claim 1, comprising at least one structure of the formula (V) and/or (VI)

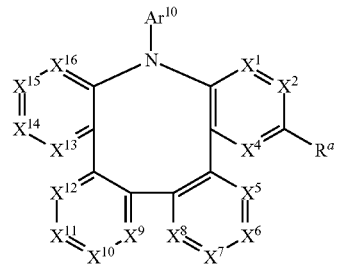

Formula (V)

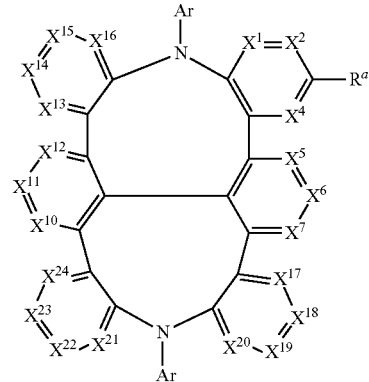

Formula (VI)

where $R^a$ is F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, C=O, C=S, C=Se, $C=NR^2$, $NR^2$, $P(=O)(R^2)$, $-C(=O)O-$, $-C(=O)NR^2-$, $-O-$, $-S-$, SO or $SO_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^2$ radicals, or an aryloxy or heteroaryloxy group which has 5 to 40 aromatic ring atoms and may be substituted by one or more R$^2$ radicals, or an aralkyl or heteroaralkyl group which has 5 to 40 aromatic ring atoms and may be substituted by one or more R$^2$ radicals, or a diarylamino group, diheteroarylamino group or arylheteroarylamino group which has 10 to 40 aromatic ring atoms and may be substituted by one or more R$^2$ radicals; or a combination of these systems; at the same time, the R$^a$ radical may form a ring system together with an R$^1$ radical or with the ring to which it is bonded; the symbols X$^1$, X$^2$, X$^4$, X$^5$, X$^6$, X$^7$, X$^8$, X$^9$, X$^{10}$, X$^{11}$, X$^{12}$, X$^{13}$, X$^{14}$, X$^{15}$, X$^{16}$, X$^{17}$, X$^{18}$, X$^{19}$, X$^{20}$, X$^{21}$, X$^{22}$, X$^{23}$, X$^{24}$, R$^1$, R$^2$, Ar$^{10}$ and Ar used to have the definition given in claim 1.

4. A compound as claimed in claim 3, comprising at least one structure of the formula (V-3) and/or (VI-3)

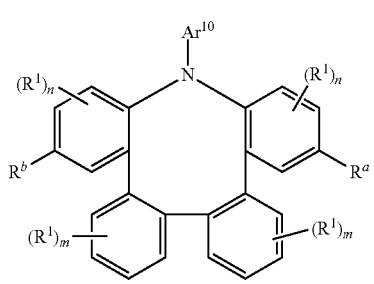

Formula (V-3)

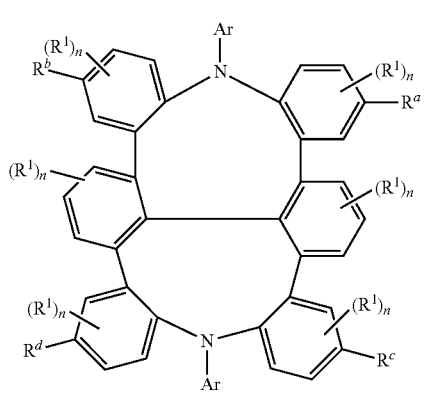

Formula (VI-3)

where the symbols R$^1$, Ar$^{10}$ and Ar have the definition given in claim 1, and the symbol R$^a$ has the definition given in claim 3, and R$^b$, R$^c$ and R$^d$ are as defined for R$^a$, and m at each instance is in each case independently 0, 1, 2, 3 or 4, and n at each instance is in each case independently 0, 1, 2 or 3.

5. A compound as claimed in claim 1, characterized in that the R$^1$ radical comprises a group, selected from the group consisting of the formulae (H-4) to (H-26)

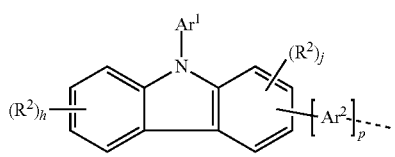

Formula (H-4)

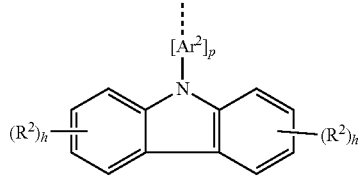

Formula (H-5)

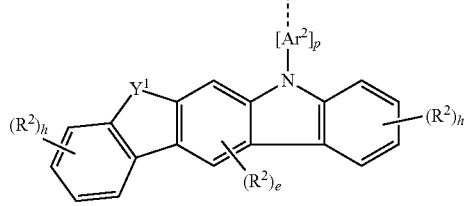

Formula (H-6)

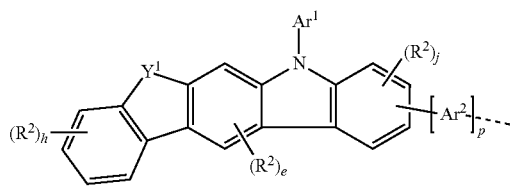

Formula (H-7)

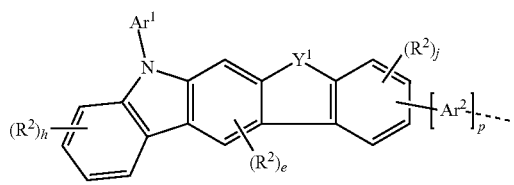

Formula (H-8)

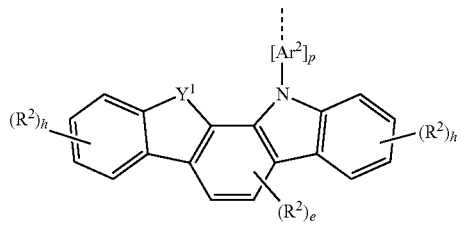

Formula (H-9)

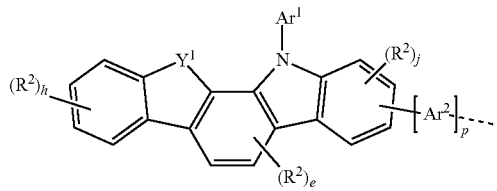

Formula (H-10)

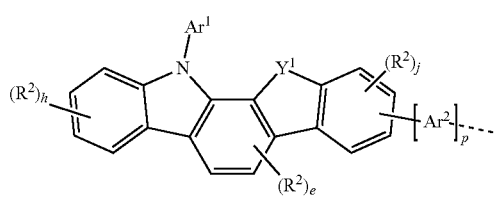

Formula (H-11)

Formula (H-12)
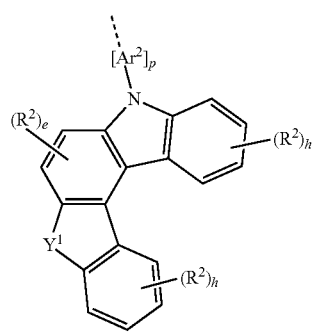
Formula (H-13)
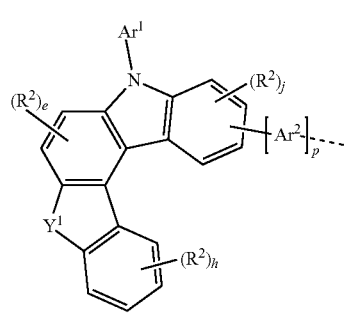
Formula (H-14)
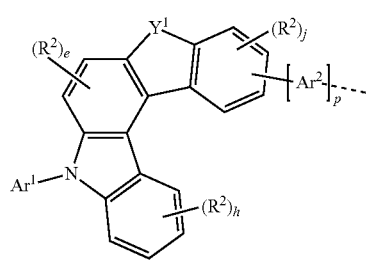
Formula (H-15)
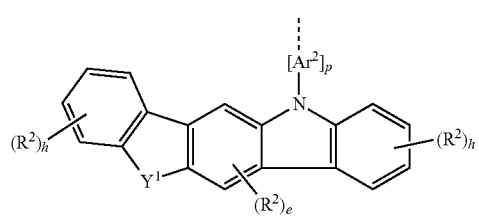
Formula (H-16)
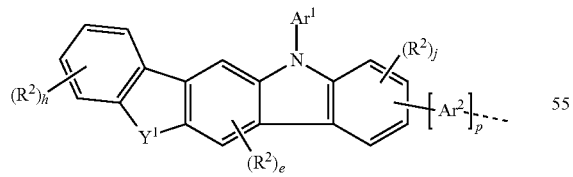
Formula (H-17)
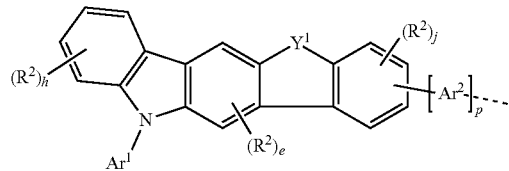
Formula (H-18)
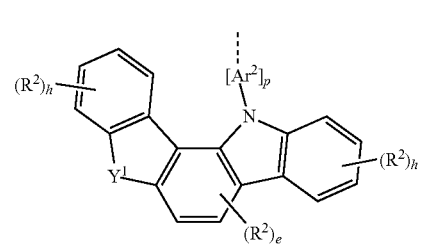
Formula (H-19)
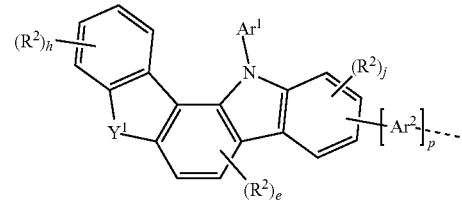
Formula (H-20)
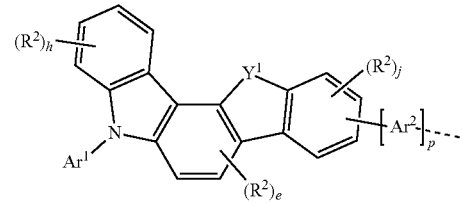
Formula (H-21)
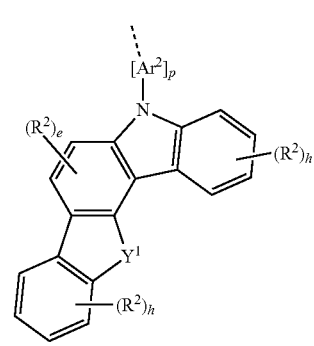
Formula (H-22)
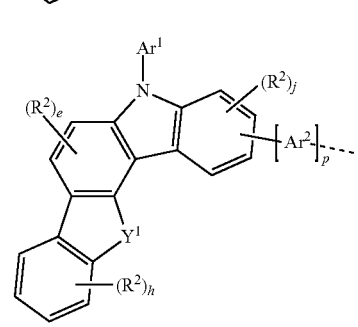
Formula (H-23)
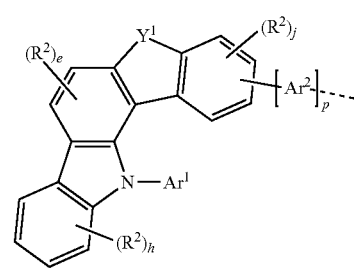

Formula (H-24)
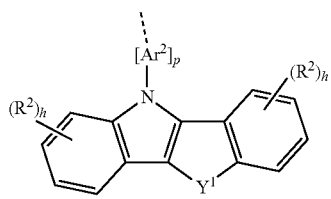

Formula (H-25)
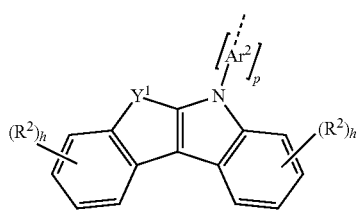

Formula (H-26)
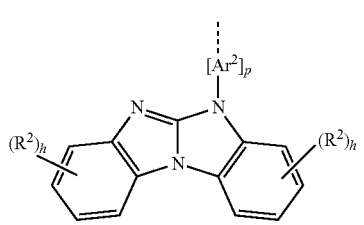

Formula (III)
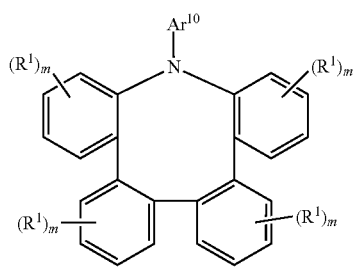

Formula (IV)
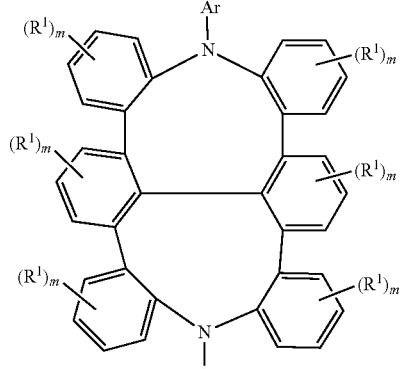

Formula (V)
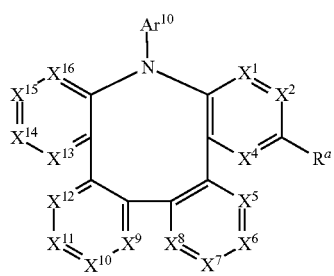

Formula (VI)
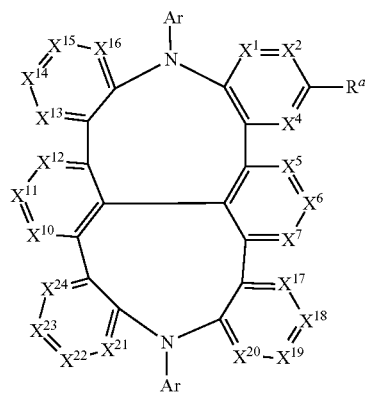

Formula (V-3)
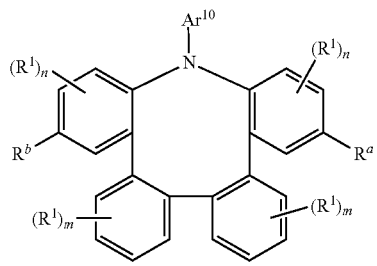

where $Y^1$ represents O, S, $C(R^2)_2$ or $NAr^1$, the dotted bond marks the attachment position, e is 0, 1 or 2, j is 0, 1, 2 or 3, h is 0, 1, 2, 3 or 4, p is 0 or 1, $Ar^1$ represents an aromatic or heteroaromatic ring system which has 5 to 40 aromatic ring atoms and may be substituted in each case by one or more $R^2$ radicals, an aryloxy group which has 5 to 40 aromatic ring atoms and may be substituted in each case by one or more $R^2$ radicals, or an aralkyl group which has 5 to 40 aromatic ring atoms and may be substituted in each case by one or more $R^2$ radicals, where it is optionally possible for two or more $R^2$ substituents to form a mono- or polycyclic, aliphatic, heteroaliphatic, aromatic or heteroaromatic ring system which may be substituted by one or more $R^3$ radicals and $Ar^2$ are each independently an aryl group having 6 to 40 carbon atoms or a heteroaryl group having 3 to 40 carbon atoms, each of which may be substituted by one or more $R^2$ radicals; and $R^2$ has the definition given in claim 1 and $R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more $R^3$ substituents together may also form a ring system.

6. A compound as claimed in claim 1, characterized in that, in the structure of formula (I), (II), (III), (IV), (V), (VI), (V-3), (VI-3) and/or (H4) to (H-26), -continued Formula (VI-3)

Formula (H-4)

Formula (H-5)

Formula (H-6)

Formula (H-7)

Formula (H-8)

Formula (H-9)

Formula (H-10)

Formula (H-11)

Formula (H-12)

Formula (H-13)

Formula (H-14)

Formula (H-15)
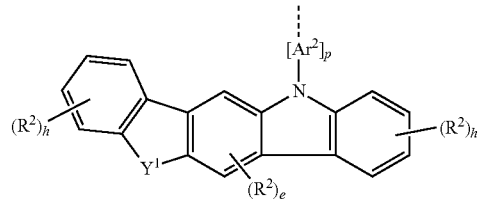
Formula (H-16)
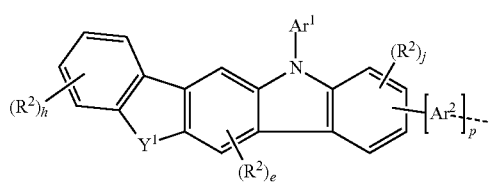
Formula (H-17)
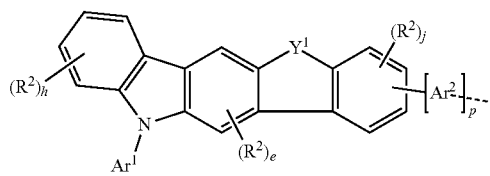
Formula (H-18)
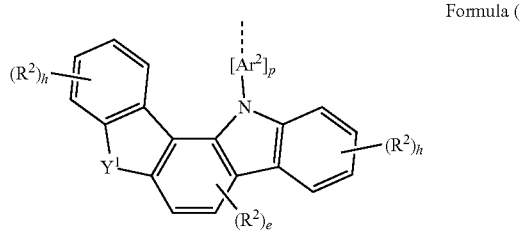
Formula (H-19)
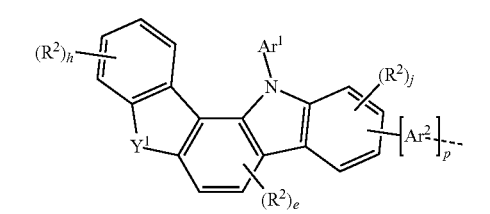
Formula (H-20)
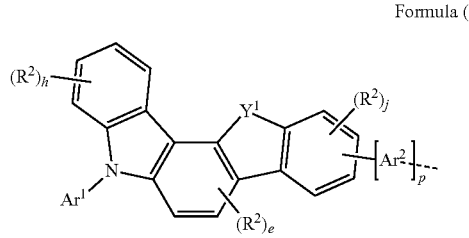
Formula (H-21)
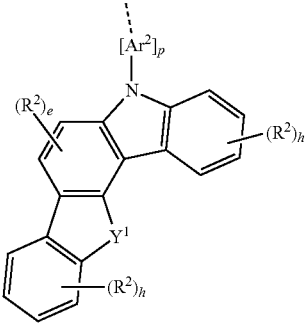
Formula (H-22)
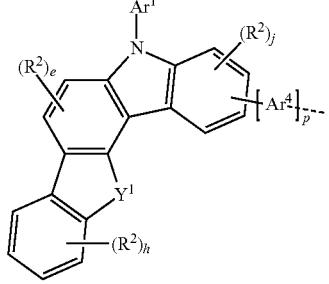
Formula (H-23)
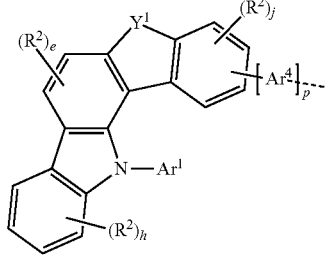
Formula (H-24)
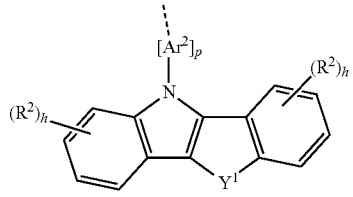
Formula (H-25)
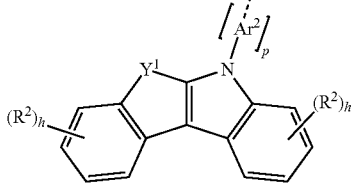
Formula (H-26)
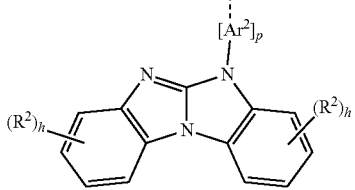

at least one R[1] radical comprises a group selected from the formulae (R[1]-1) to (R[1]-95)
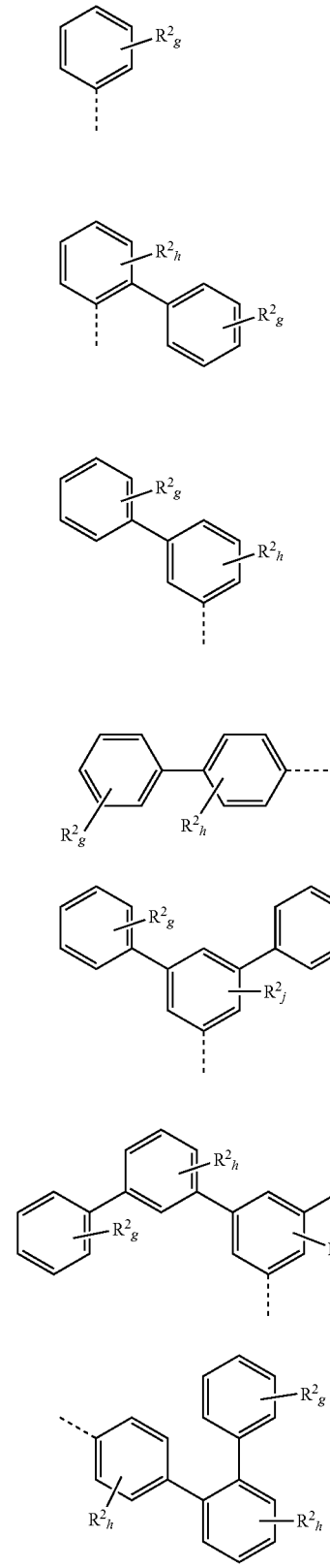

Formula (R¹-14)
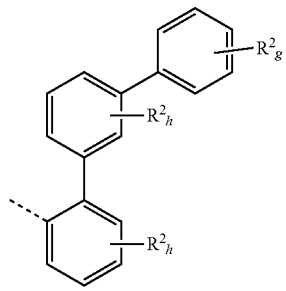
Formula (R¹-15)
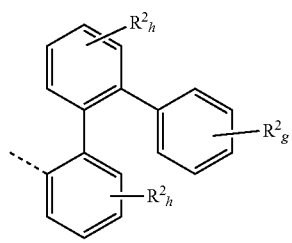
Formula (R¹-16)
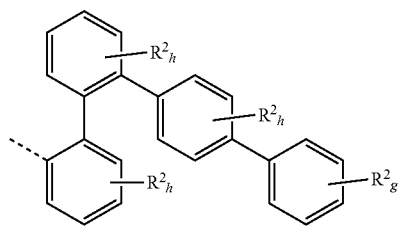
Formula (R¹-17)
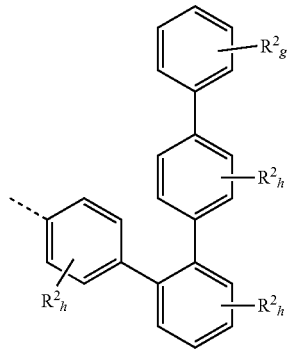
Formula (R¹-18)
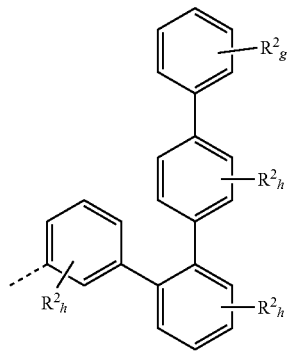
Formula (R¹-19)
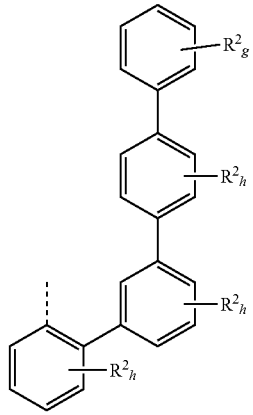
Formula (R¹-20)
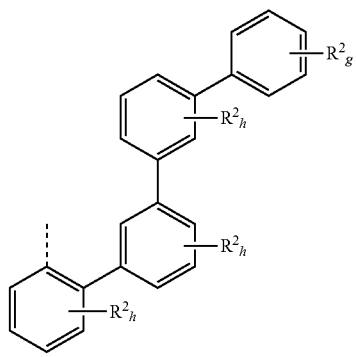
Formula (R¹-21)
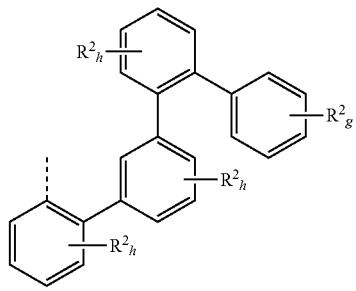
Formula (R¹-22)
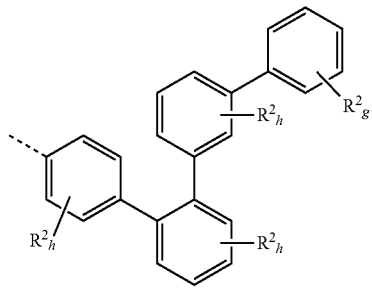
Formula (R¹-23)
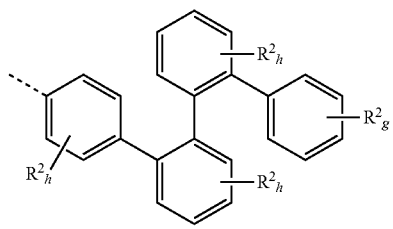

Formula (R¹-24)
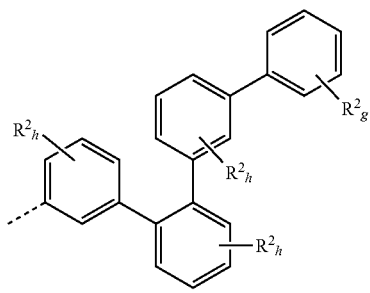
Formula (R¹-25)
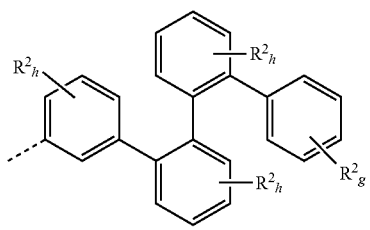
Formula (R¹-26)
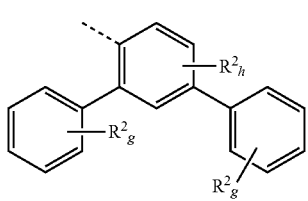
Formula (R¹-27)
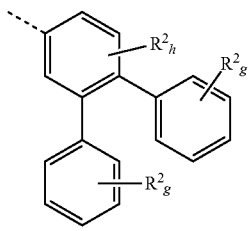
Formula (R¹-28)
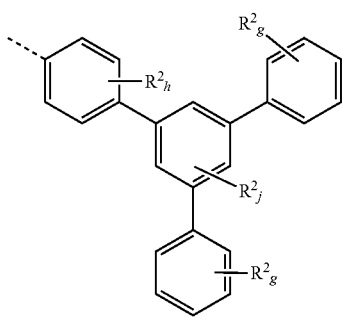
Formula (R¹-29)
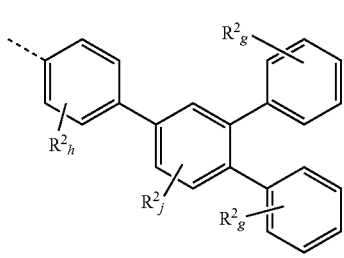
Formula (R¹-30)
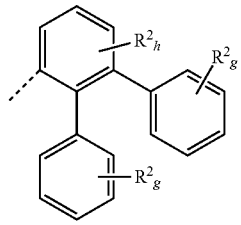
Formula (R¹-31)
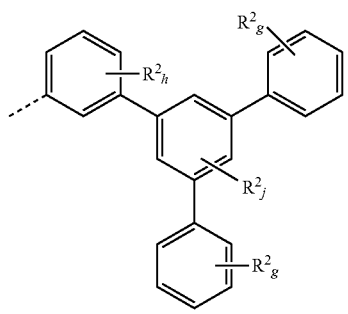
Formula (R¹-32)
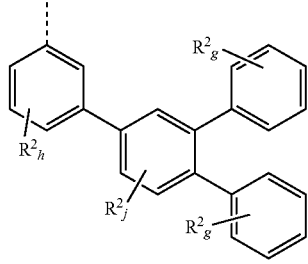
Formula (R¹-33)
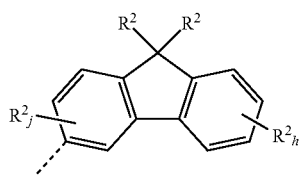
Formula (R¹-34)
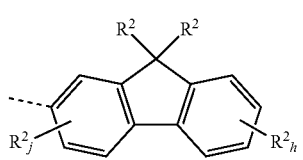
Formula (R¹-35)
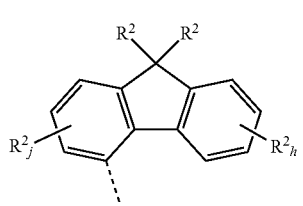
Formula (R¹-36)
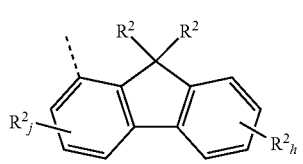

Formula (R¹-37)
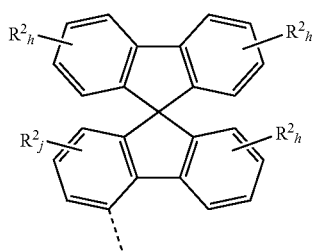
Formula (R¹-38)
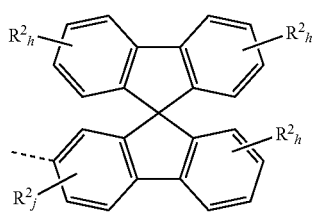
Formula (R¹-39)
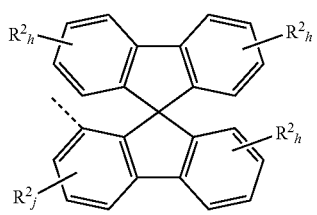
Formula (R¹-40)
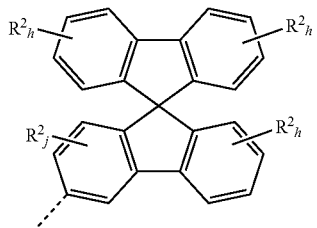
Formula (R¹-41)
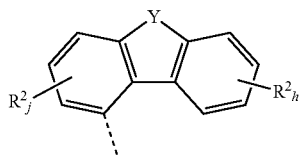
Formula (R¹-42)
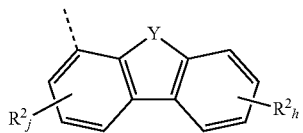
Formula (R¹-43)
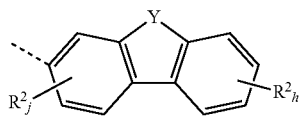
Formula (R¹-44)
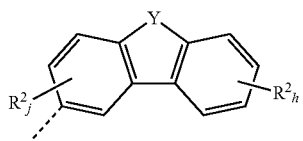
Formula (R¹-45)
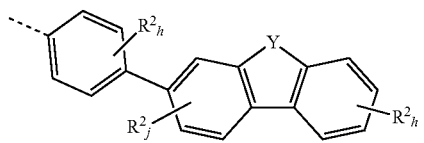
Formula (R¹-46)
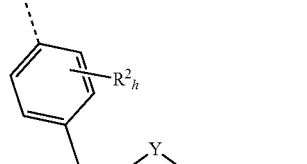
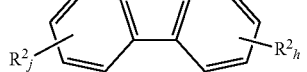
Formula (R¹-47)
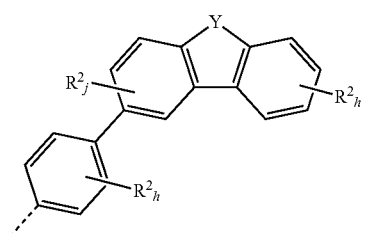
Formula (R¹-48)
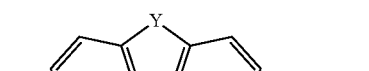
Formula (R¹-49)
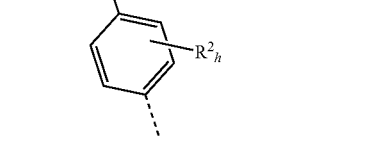
Formula (R¹-50)
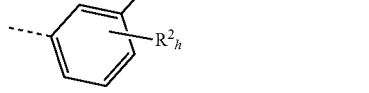
Formula (R¹-51)
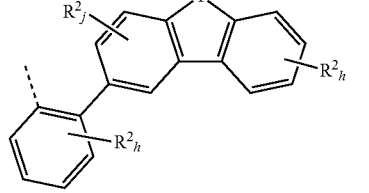
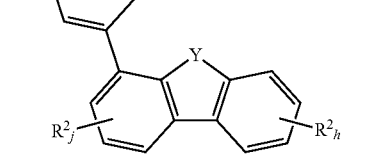
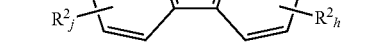

Formula (R¹-52)

Formula (R¹-53)

Formula (R¹-54)

Formula (R¹-55)

Formula (R¹-56)

Formula (R¹-57)

Formula (R¹-58)

Formula (R¹-59)

Formula (R¹-60)

Formula (R¹-61)

Formula (R¹-62)

Formula (R¹-63)

Formula (R¹-64)

Formula (R¹-65)

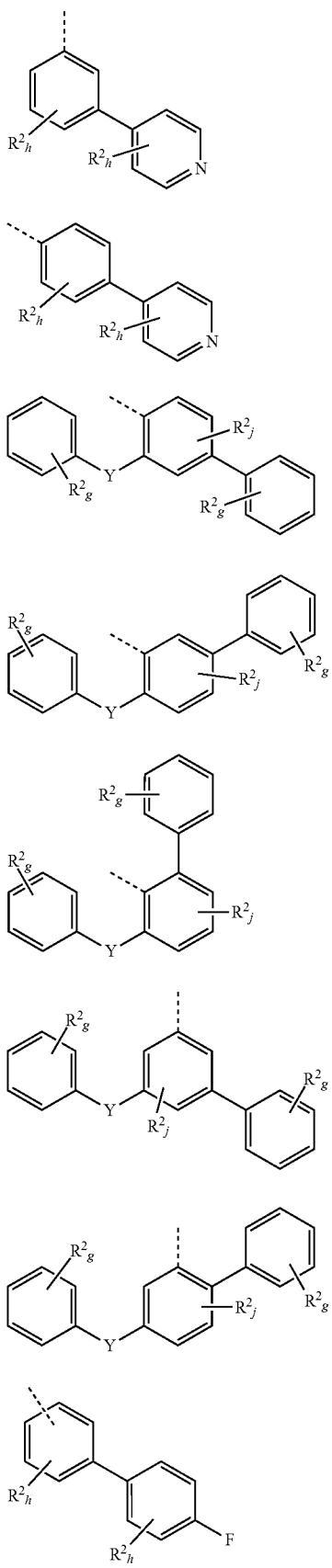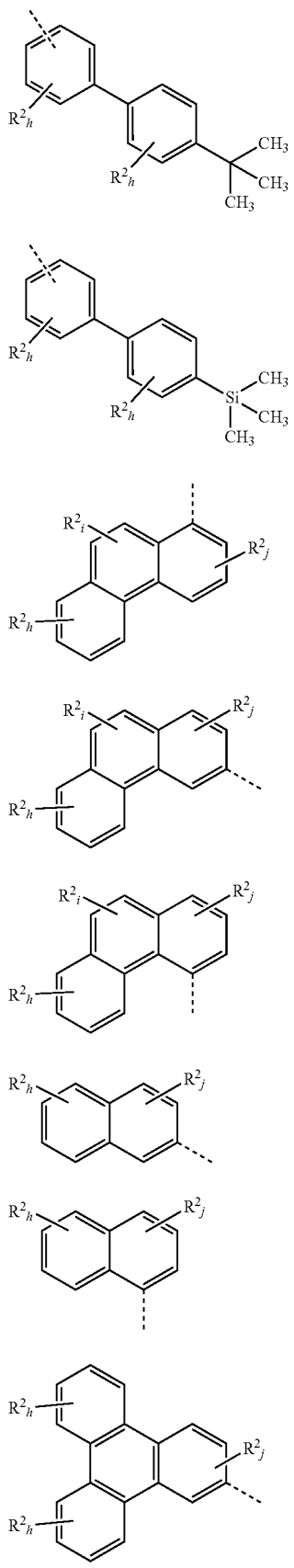

-continued

Formula (R¹-82)
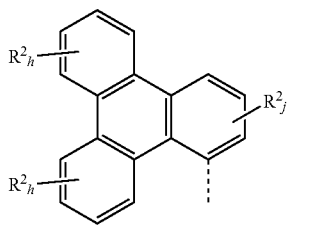

Formula (R¹-83)
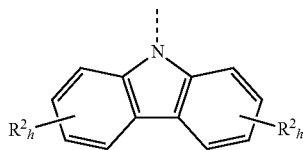

Formula (R¹-84)
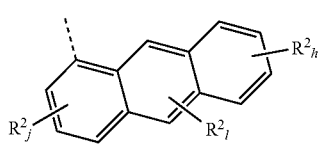

Formula (R¹-85)
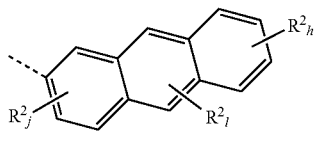

Formula (R¹-86)
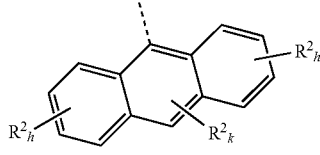

Formula (R¹-87)
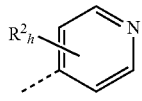

Formula (R¹-88)
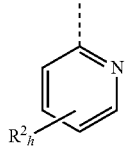

Formula (R¹-89)
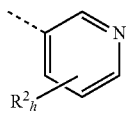

Formula (R¹-90)
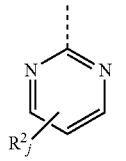

Formula (R¹-91)
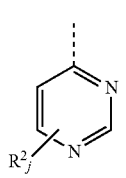

-continued

Formula (R¹-92)
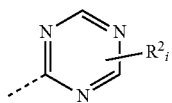

Formula (R¹-93)
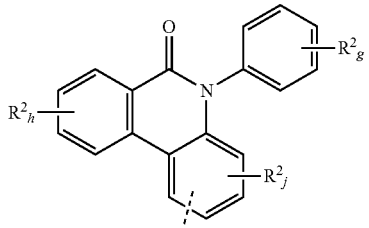

Formula (R¹-94)
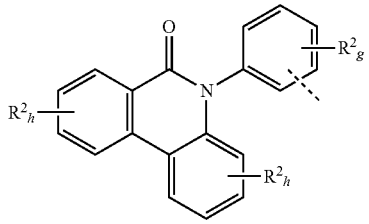

Formula (R¹-95)
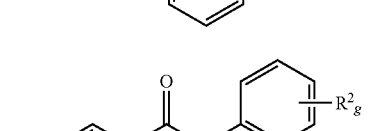

where the symbols used are as follows:
Y is O, S or NR²;
i at each instance is independently 0, 1 or 2;
j independently at each instance is 0, 1, 2 or 3;
h independently at each instance is 0, 1, 2, 3 or 4;
g independently at each instance is 0, 1, 2, 3, 4 or 5;
the dotted bond marks the position of attachment; and
R² has the definition given in claim 1.

7. A compound as claimed in claim 1, characterized in that the R¹ radical comprises a group, selected from the group consisting of the formulae (H-1') to (H-3')

Formula (H-1')
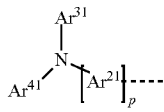

Formula (H-2')
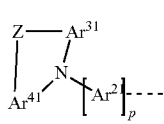

Formula (H-3')
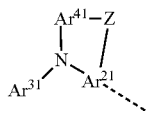

where the dotted bond marks the attachment position and
Ar$^{21}$, Ar$^{31}$, Ar$^{41}$ are each independently an aryl group having 6 to 40 carbon atoms or a heteroaryl group having 3 to 40 carbon atoms, each of which may be substituted by one or more R$^2$ radicals;

p is 0 or 1 and

Z is a bond, C(R$^2$)$_2$, C=O, N—Ar$^1$, O or S, where the R$^2$ radical has the definition given in claim 1 and Ar$^1$ represents an aromatic or heteroaromatic ring system which has 5 to 40 aromatic ring atoms and may be substituted in each case by one or more R$^2$ radicals, an aryloxy group which has 5 to 40 aromatic ring atoms and may be substituted by one or more R$^2$ radicals, or an aralkyl group which has 5 to 40 aromatic ring atoms and may be substituted in each case by one or more R$^2$ radicals; where it is optionally possible for two or more, R$^2$ substituents to form a mono- or polycyclic, aliphatic, heteroaliphatic, aromatic or heteroaromatic ring system which may be substituted by one or more R$^3$ radicals.

8. A compound as claimed in claim 1, characterized in that, in the structure of the formula (I) or (II),
not more than 2 of the symbols X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$, X$^{15}$, X$^{16}$ are not CH or CD or, in the structures of the formula (II), not more than 4 of the symbols X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$, X$^{15}$, X$^{16}$ X$^{17}$, X$^{18}$, X$^{19}$, X$^{20}$, X$^{21}$, X$^{22}$, X$^{23}$, X$^{24}$ are not CH or CD.

9. A compound as claimed in claim 1, characterized in that the R$^1$ radicals that are not H or D.

10. An oligomer, polymer or dendrimer containing one or more compounds as claimed in claim 1, wherein, rather than a hydrogen atom or a substituent, there are one or more bonds of the compounds to the polymer, oligomer or dendrimer.

11. A composition comprising at least one compound as claimed in claim 1 and at least one further compound selected from the group consisting of fluorescent emitters, phosphorescent emitters, host materials, matrix materials, electron transport materials, electron injection materials, hole conductor materials, hole injection materials, electron blocker materials and hole blocker materials.

12. A formulation comprising at least one compound as claimed in claim 1 and at least one solvent.

13. An electronic device comprising at least one compound as claimed in claim 1, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells and organic laser diodes.

14. A compound as claimed in claim 1, characterized in that the Ar radical is selected from the structures of the formula (H-1) and the Ar$^3$ and Ar$^4$ radicals are selected from groups of the formulae (R$^1$-1) to (R$^1$-95),

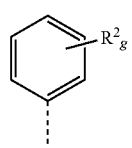

Formula (R$^1$-1)

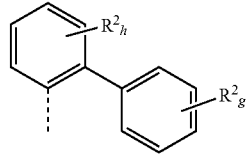

Formula (R$^1$-2)

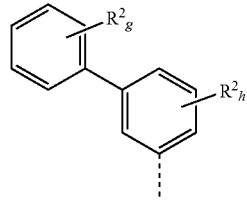

Formula (R$^1$-3)

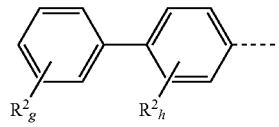

Formula (R$^1$-4)

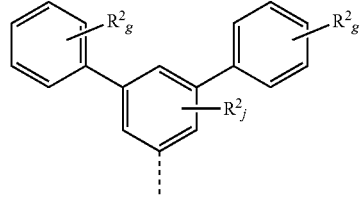

Formula (R$^1$-5)

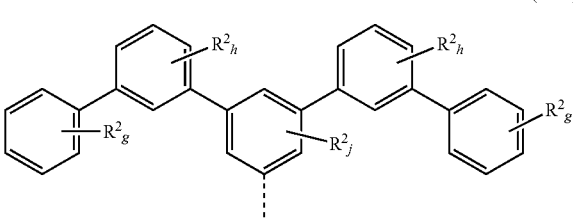

Formula (R$^1$-6)

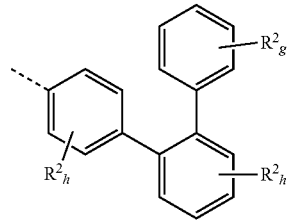

Formula (R$^1$-7)

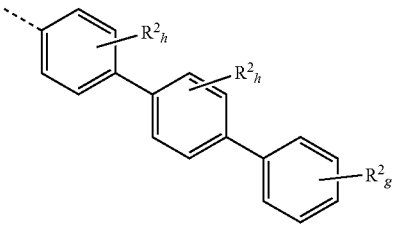

Formula (R$^1$-8)

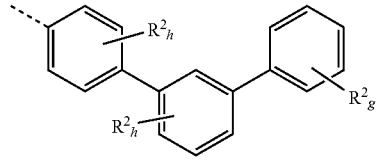

Formula (R$^1$-9)

-continued
Formula (R¹-10)
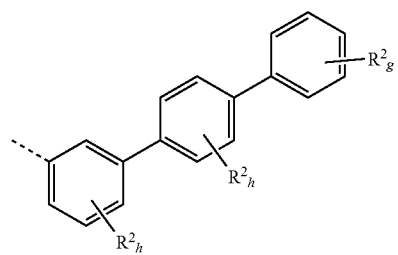
Formula (R¹-11)
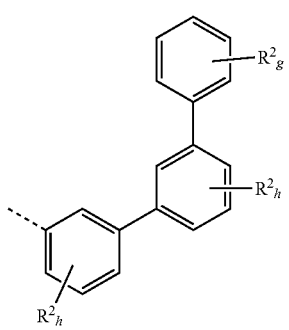
Formula (R¹-12)
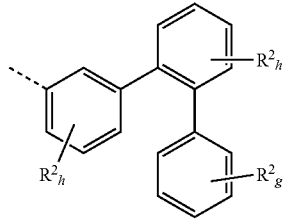
Formula (R¹-13)
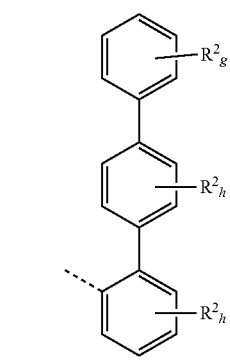
Formula (R¹-14)
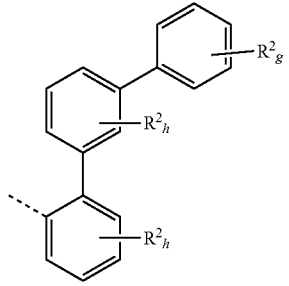
-continued
Formula (R¹-15)
Formula (R¹-16)
Formula (R¹-17)
Formula (R¹-18)
Formula (R¹-19)

Formula (R¹-20)
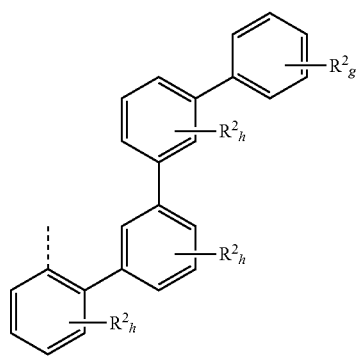
Formula (R¹-21)
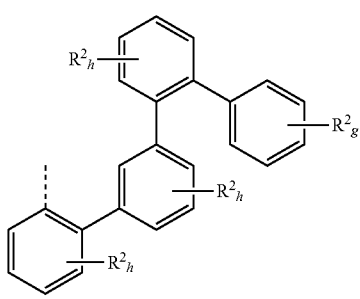
Formula (R¹-22)
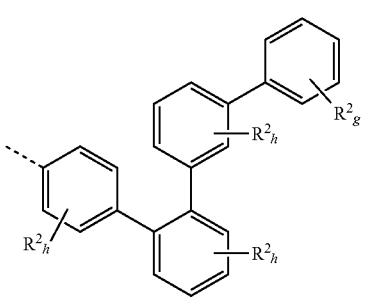
Formula (R¹-23)
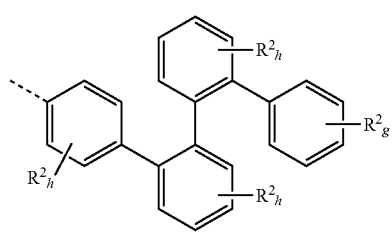
Formula (R¹-24)
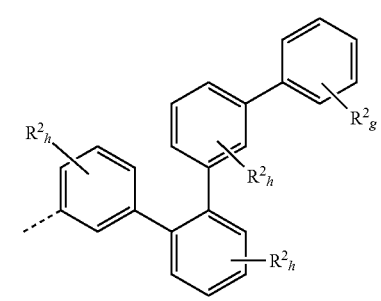
Formula (R¹-25)
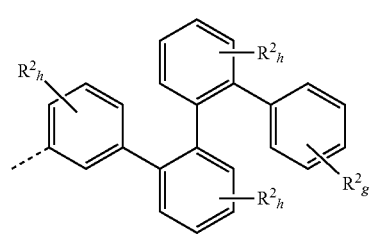
Formula (R¹-26)
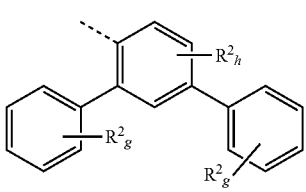
Formula (R¹-27)
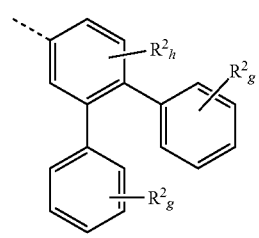
Formula (R¹-28)
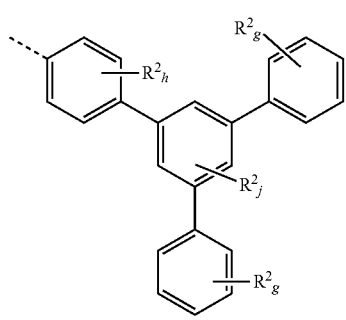
Formula (R¹-29)
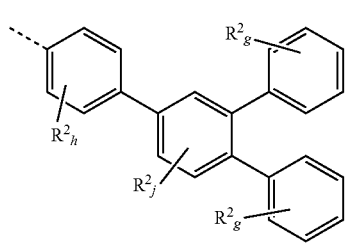
Formula (R¹-30)
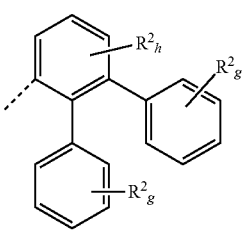

-continued
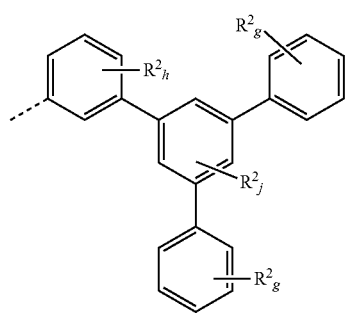
Formula (R¹-31)
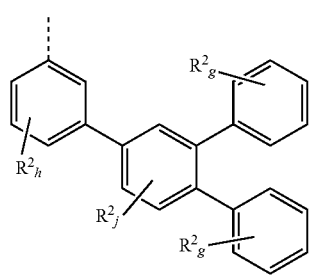
Formula (R¹-32)
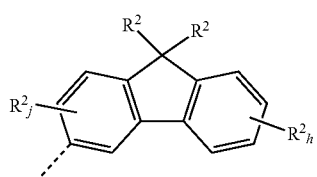
Formula (R¹-33)
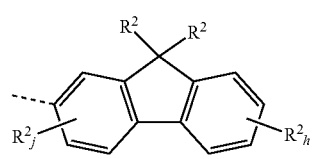
Formula (R¹-34)
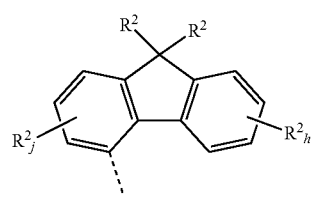
Formula (R¹-35)
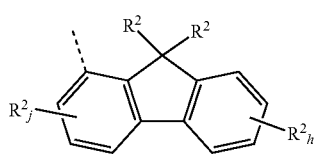
Formula (R¹-36)
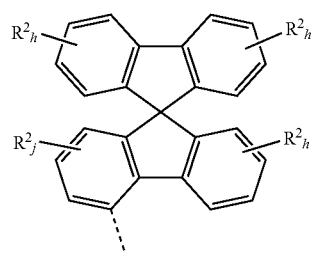
Formula (R¹-37)
-continued
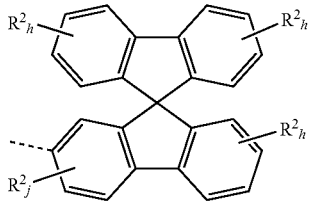
Formula (R¹-38)
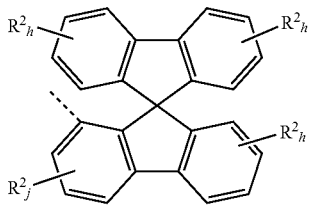
Formula (R¹-39)
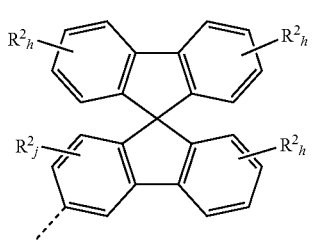
Formula (R¹-40)
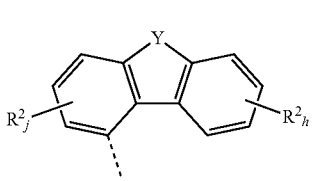
Formula (R¹-41)
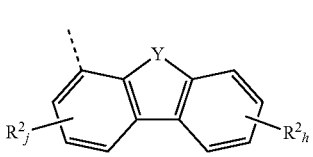
Formula (R¹-42)
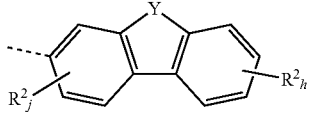
Formula (R¹-43)
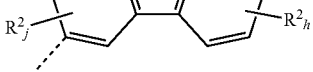
Formula (R¹-44)
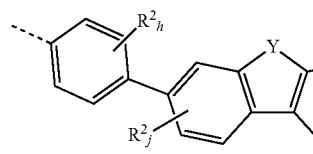
Formula (R¹-45)

Formula (R¹-46)
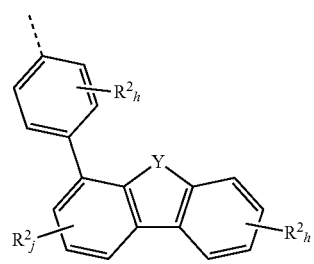
Formula (R¹-47)
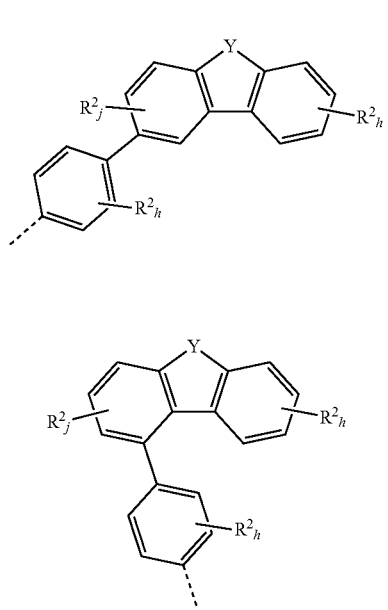
Formula (R¹-48)
Formula (R¹-49)
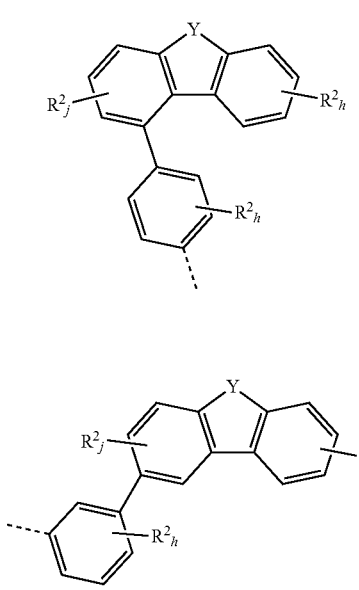
Formula (R¹-50)
Formula (R¹-51)
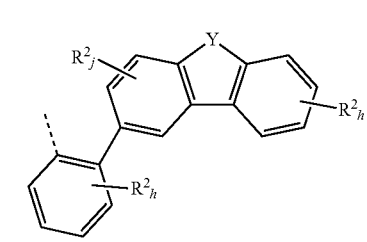
Formula (R¹-52)
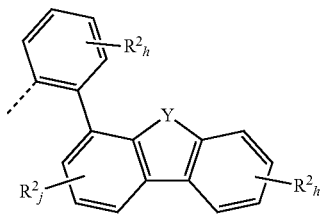
Formula (R¹-53)
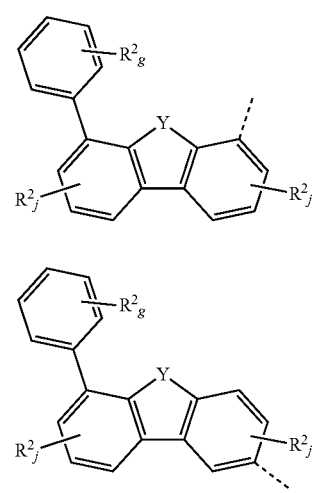
Formula (R¹-54)
Formula (R¹-55)
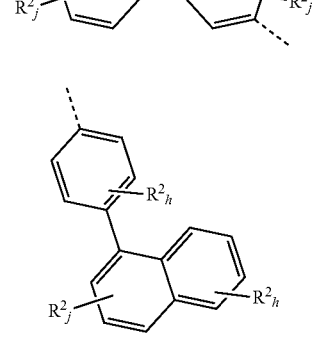
Formula (R¹-56)
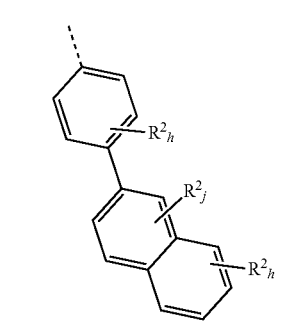
Formula (R¹-57)
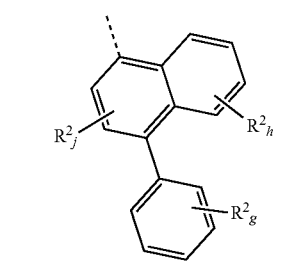

-continued
Formula (R¹-58)
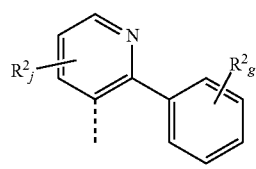
Formula (R¹-59)
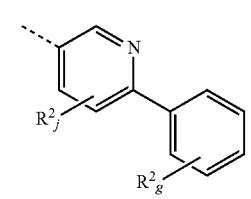
Formula (R¹-60)
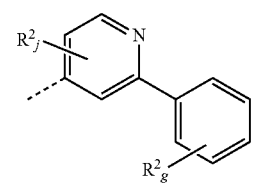
Formula (R¹-61)
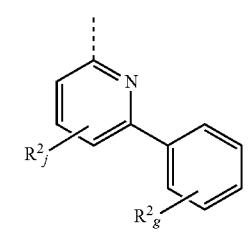
Formula (R¹-62)
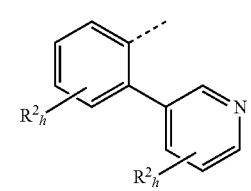
Formula (R¹-63)
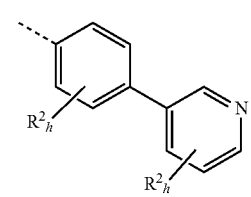
Formula (R¹-64)
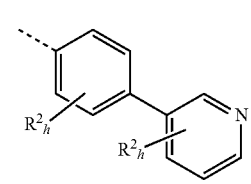
Formula (R¹-65)
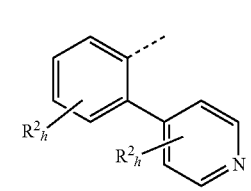
-continued
Formula (R¹-66)
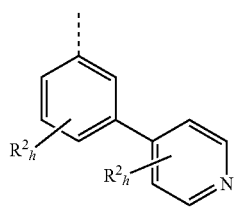
Formula (R¹-67)
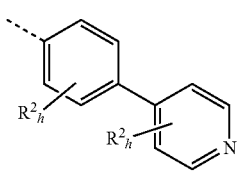
Formula (R¹-68)
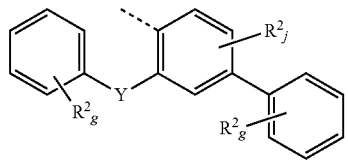
Formula (R¹-69)
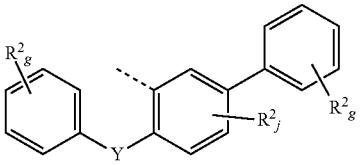
Formula (R¹-70)
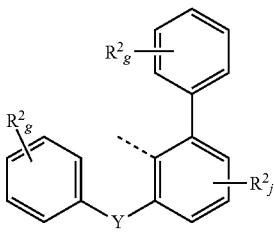
Formula (R¹-71)
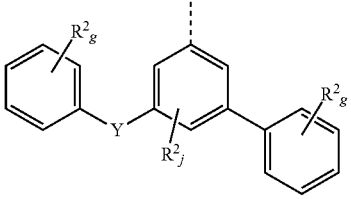
Formula (R¹-72)
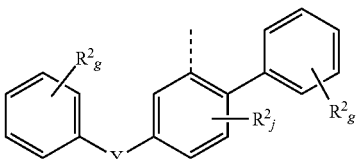
Formula (R¹-73)
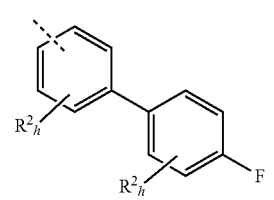

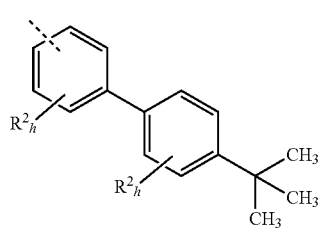 Formula (R¹-74)
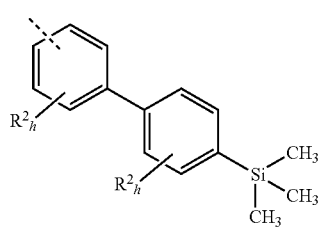 Formula (R¹-75)
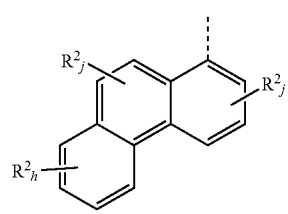 Formula (R¹-76)
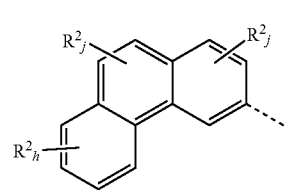 Formula (R¹-77)
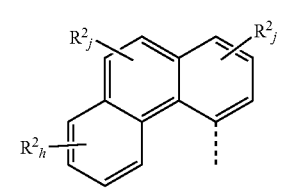 Formula (R¹-78)
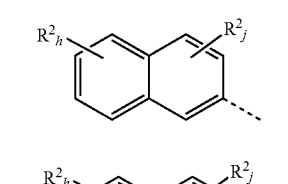 Formula (R¹-79)
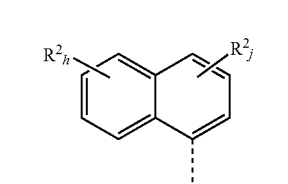 Formula (R¹-80)
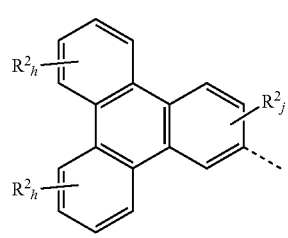 Formula (R¹-81)
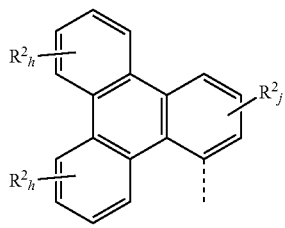 Formula (R¹-82)
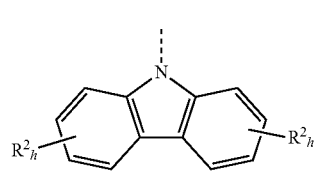 Formula (R¹-83)
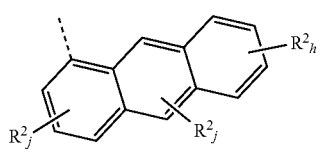 Formula (R¹-84)
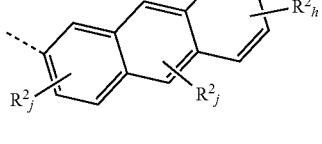 Formula (R¹-85)
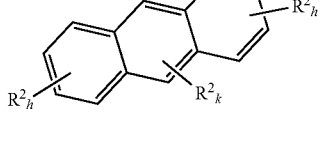 Formula (R¹-86)
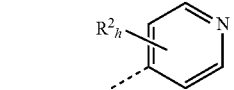 Formula (R¹-87)
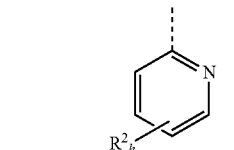 Formula (R¹-88)
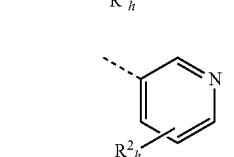 Formula (R¹-89)
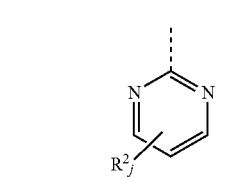 Formula (R¹-90)

-continued

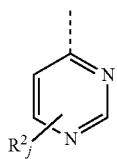
Formula (R¹-91)

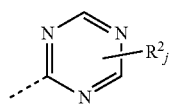
Formula (R¹-92)

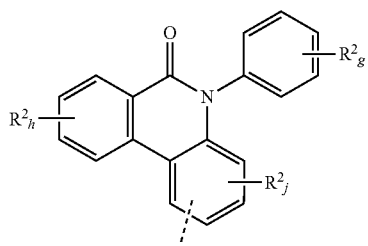
Formula (R¹-93)

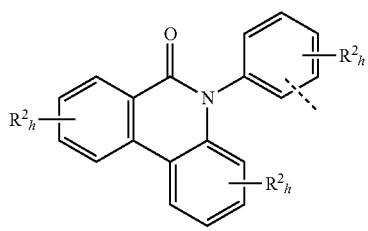
Formula (R¹-94)

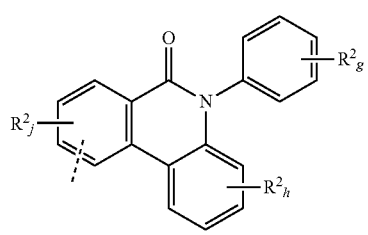
Formula (R¹-95)

where the symbols used are as follows:
Y is O, S or NR²;
i at each instance is independently 0, 1 or 2;
j independently at each instance is 0, 1, 2 or 3;
h independently at each instance is 0, 1, 2, 3 or 4;
g independently at each instance is 0, 1, 2, 3, 4 or 5;
the dotted bond marks the position of attachment; and
R² has the definition given in claim 1 and
the Ar² radical is selected from the groups of the formulae (L¹-1) to (L¹-108)

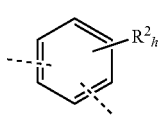
Formula (L¹-1)

-continued

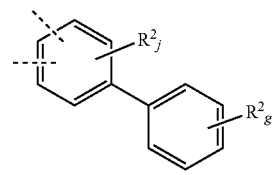
Formula (L¹-2)

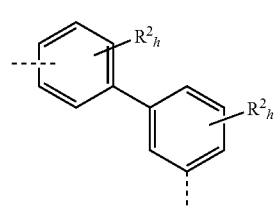
Formula (L¹-3)

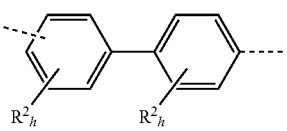
Formula (L¹-4)

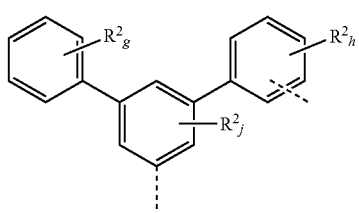
Formula (L¹-5)

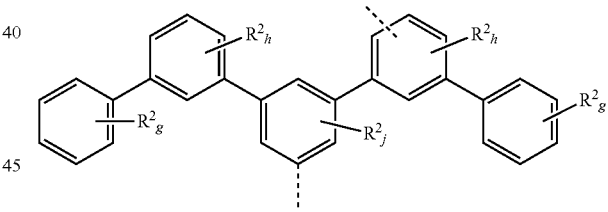
Formula (L¹-6)

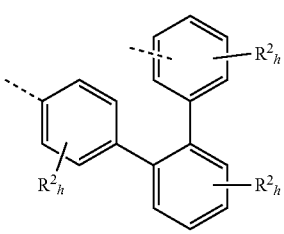
Formula (L¹-7)

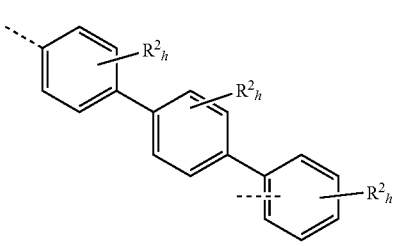
Formula (L¹-8)

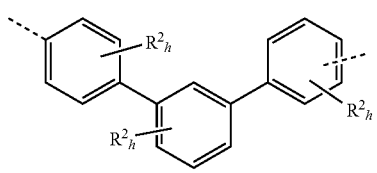
Formula (L¹-9)
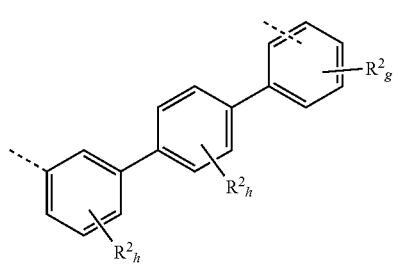
Formula (L¹-10)
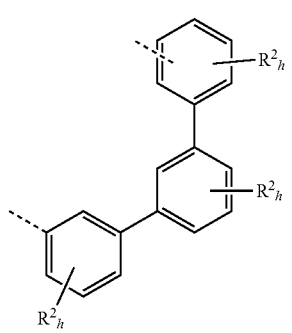
Formula (L¹-11)
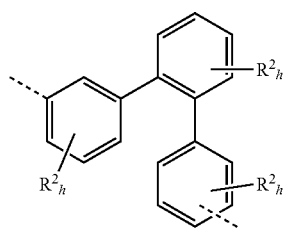
Formula (R¹-12)
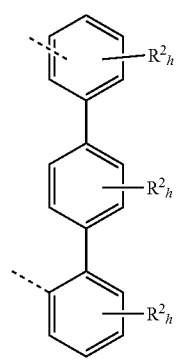
Formula (L¹-13)
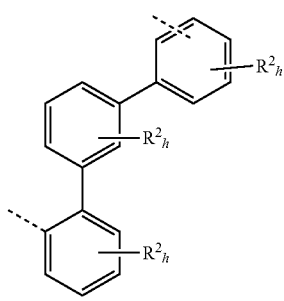
Formula (L¹-14)
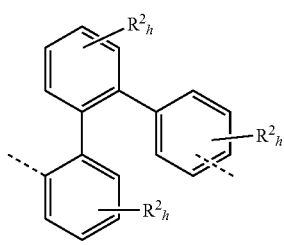
Formula (L¹-15)
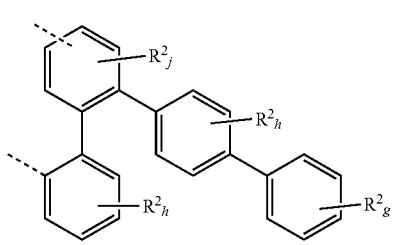
Formula (L¹-16)
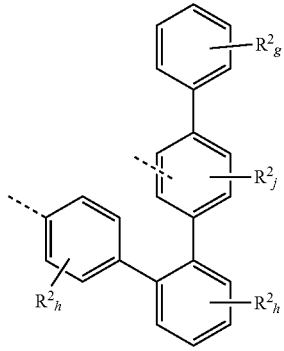
Formula (L¹-17)
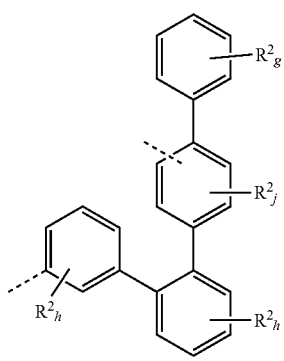
Formula (L¹-18)

Formula (L¹-19)
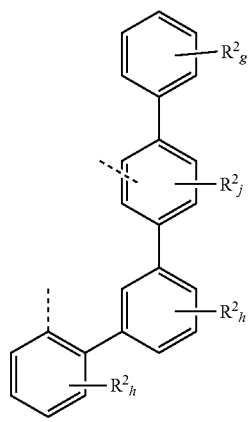
Formula (L¹-20)
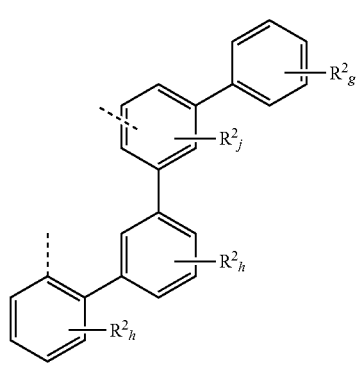
Formula (L¹-21)
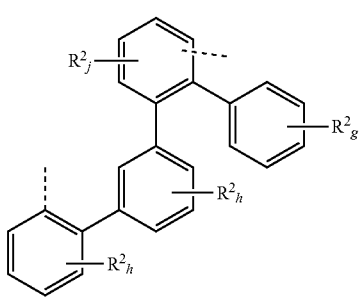
Formula (L¹-22)
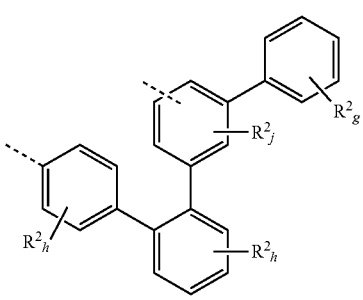
Formula (L¹-23)
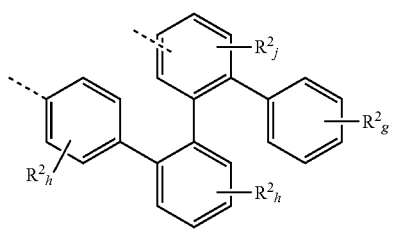
Formula (L¹-24)
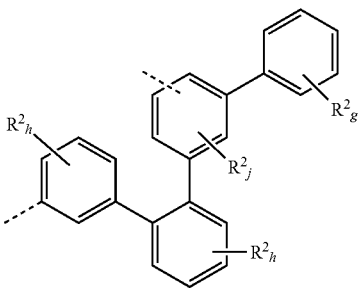
Formula (L¹-25)
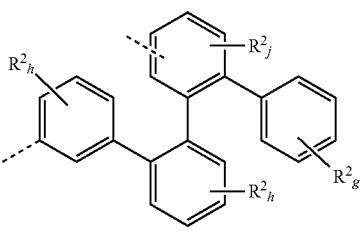
Formula (L¹-26)
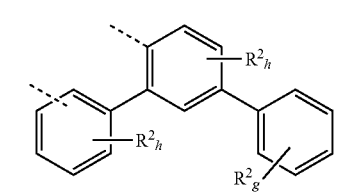
Formula (L¹-27)
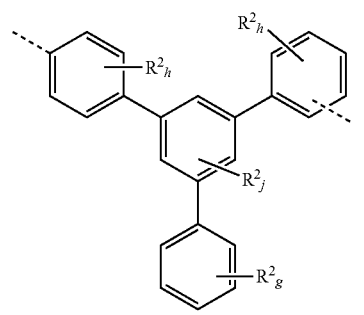
Formula (L¹-28)
Formula (L¹-29)
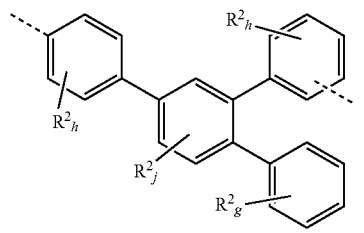

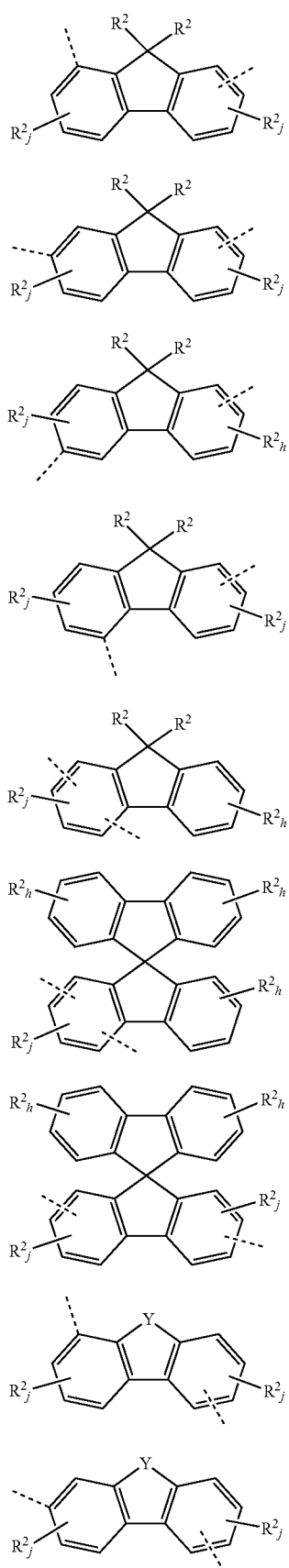
Formula (L¹-30)
Formula (L¹-31)
Formula (L¹-32)
Formula (L¹-33)
Formula (L¹-34)
Formula (L¹-35)
Formula (L¹-36)
Formula (L¹-37)
Formula (L¹-38)
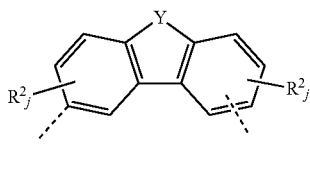
Formula (L¹-39)
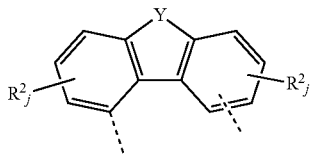
Formula (L¹-40)
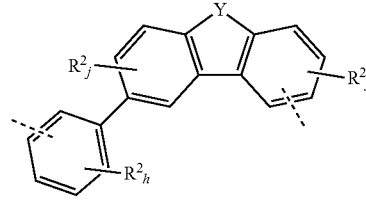
Formula (L¹-41)
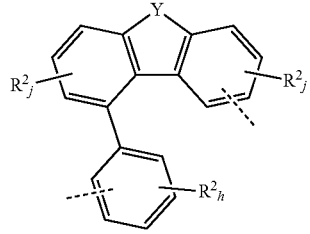
Formula (L¹-42)
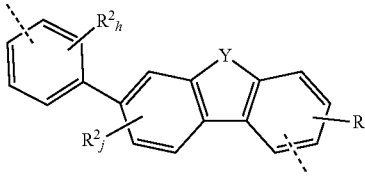
Formula (L¹-43)
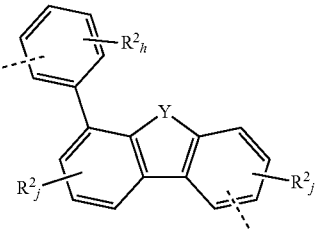
Formula (L¹-44)
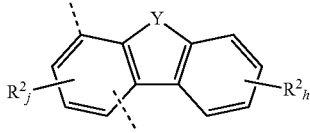
Formula (L¹-45)
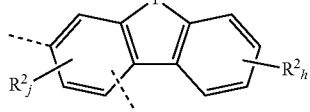
Formula (L¹-46)

Formula (L¹-47)

Formula (L¹-48)

Formula (L¹-49)

Formula (L¹-50)

Formula (L¹-51)

Formula (L¹-52)

Formula (L¹-53)

Formula (L¹-54)

Formula (L¹-55)

Formula (L¹-56)

Formula (L¹-57)

Formula (L¹-58)

Formula (L¹-59)

Formula (L¹-60)

Formula (L¹-61)

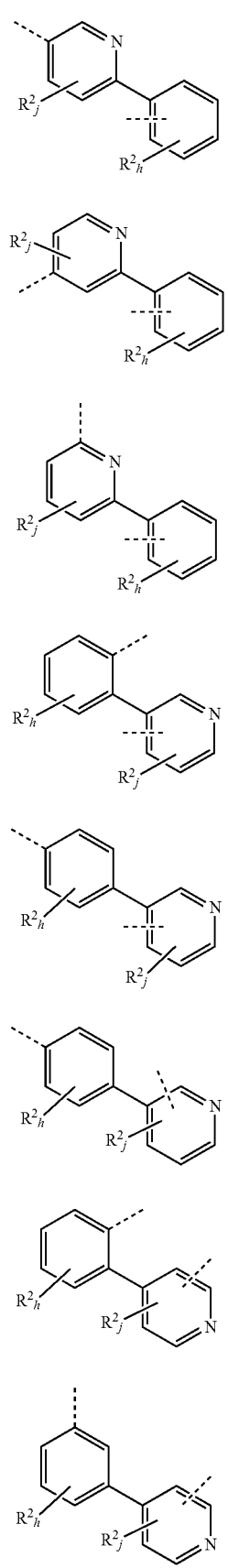
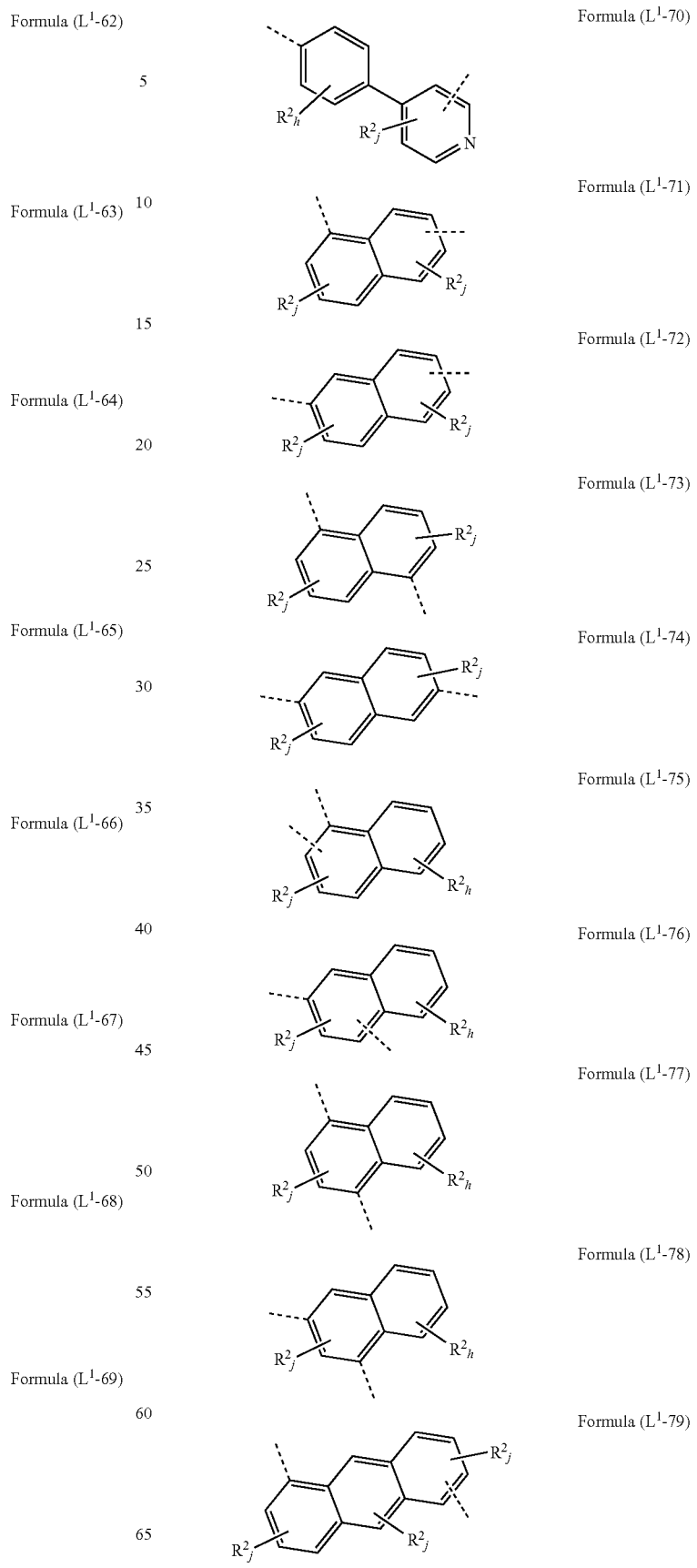

Formula (L¹-80)
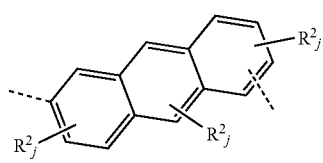
Formula (L¹-81)
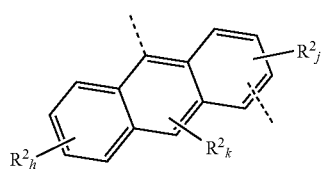
Formula (L¹-82)
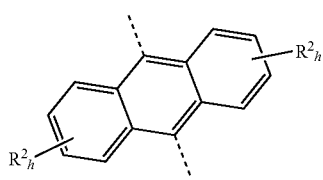
Formula (L¹-83)
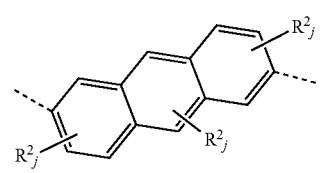
Formula (L¹-84)
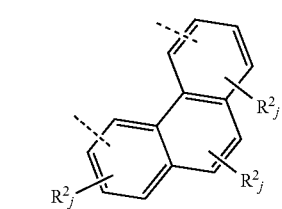
Formula (L¹-85)
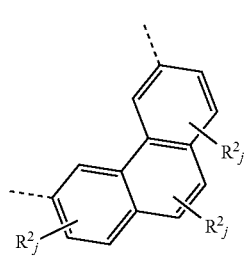
Formula (L¹-86)
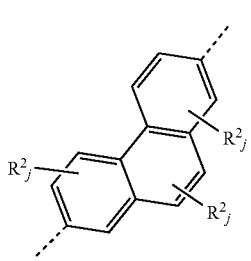
Formula (L¹-87)
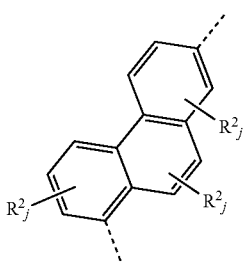
Formula (L¹-88)
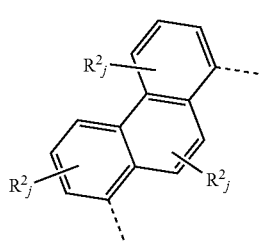
Formula (L¹-89)
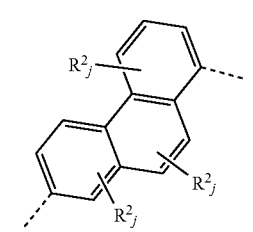
Formula (L¹-90)
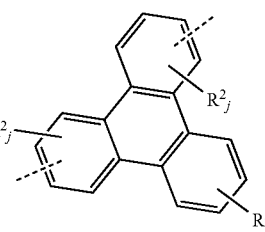
Formula (L¹-91)
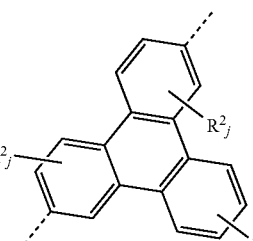
Formula (L¹-92)
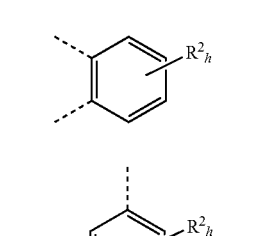
Formula (L¹-93)
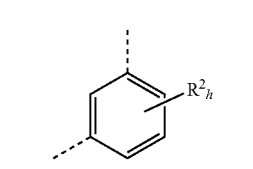

-continued

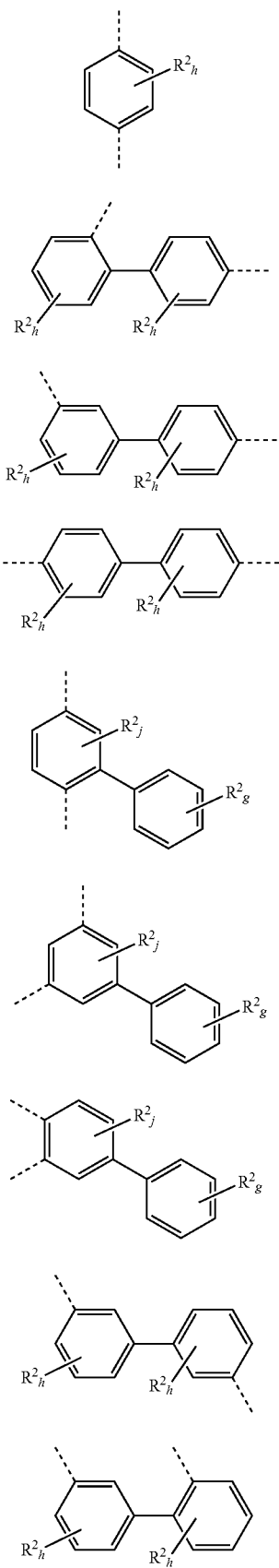

Formula (L¹-94)

Formula (L¹-95)

Formula (L¹-96)

Formula (L¹-97)

Formula (L¹-98)

Formula (L¹-99)

Formula (L¹-100)

Formula (L¹-101)

Formula (L¹-102)

-continued

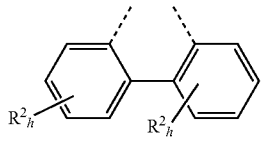
Formula (L¹-103)

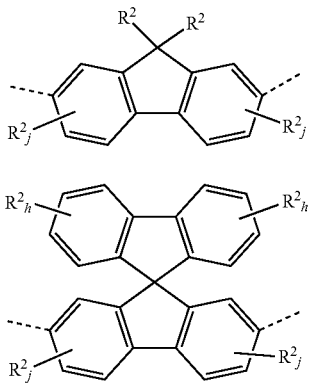
Formula (L¹-104)

Formula (L¹-105)

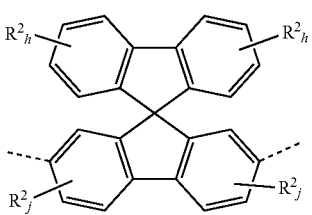
Formula (L¹-106)

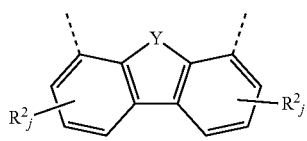
Formula (L¹-107)

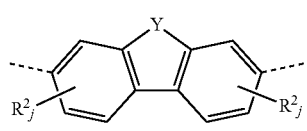
Formula (L¹-108)

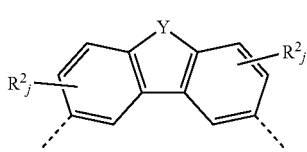

where the dotted bonds in each case mark the attachment positions, the index k is 0 or 1, the index l is 0, 1 or 2, the index j at each instance is independently 0, 1, 2 or 3; the index h at each instance is independently 0, 1, 2, 3 or 4, the index g is 0, 1, 2, 3, 4 or 5; the symbol Y is O, S or NR²; and the symbol R² has the definition given in claim 1.

15. A compound as claimed in claim 7, characterized in that, the Ar² group is a group selected from the formulae (L¹-1) to (L¹-108)

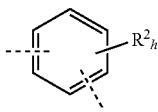
Formula (L¹-1)

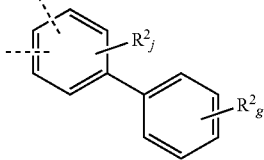
Formula (L¹-2)

Formula (L¹-3)
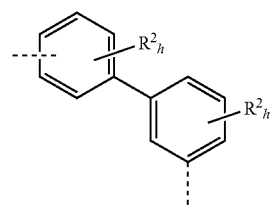
Formula (L¹-4)
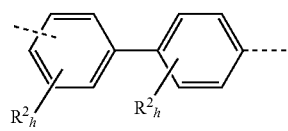
Formula (L¹-5)
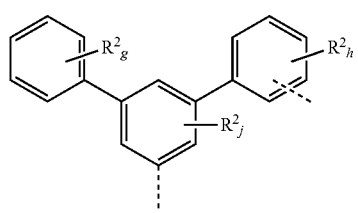
Formula (L¹-6)
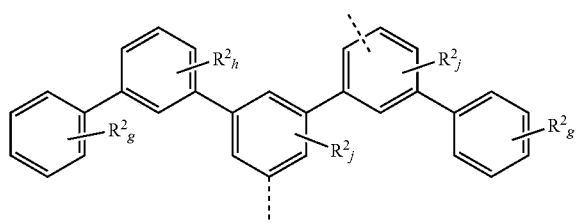
Formula (L¹-7)
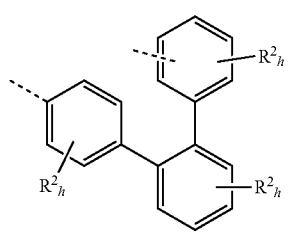
Formula (L¹-8)
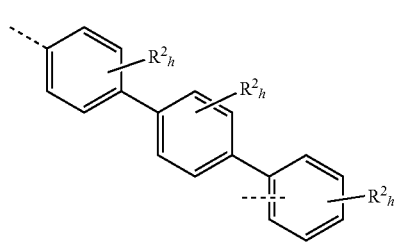
Formula (L¹-9)
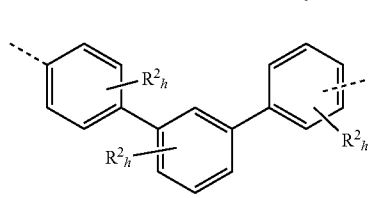
Formula (L¹-10)
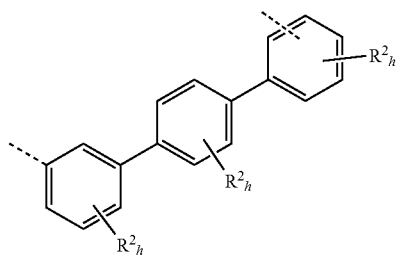
Formula (L¹-11)
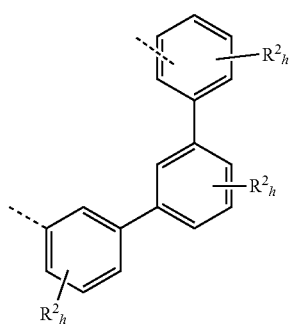
Formula (L¹-12)
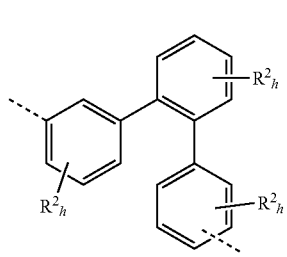
Formula (L¹-13)
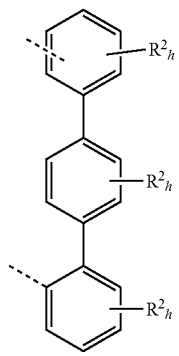
Formula (L¹-14)
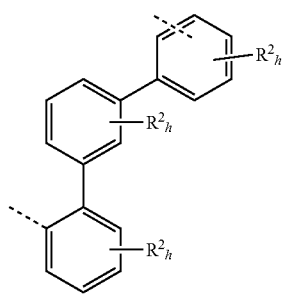

-continued
Formula (L¹-15)
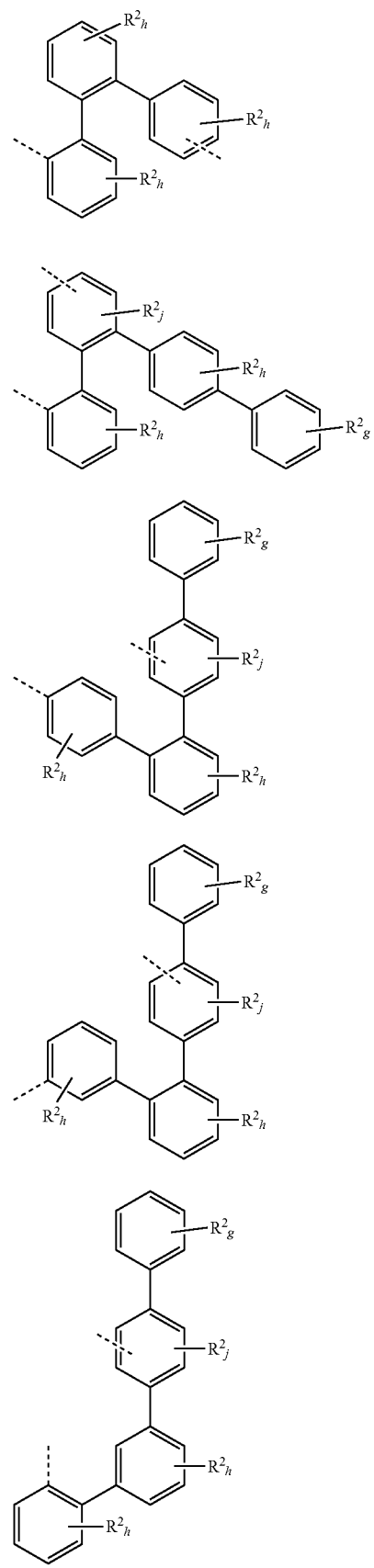
Formula (L¹-16)
Formula (L¹-17)
Formula (L¹-18)
Formula (L¹-19)
-continued
Formula (L¹-20)
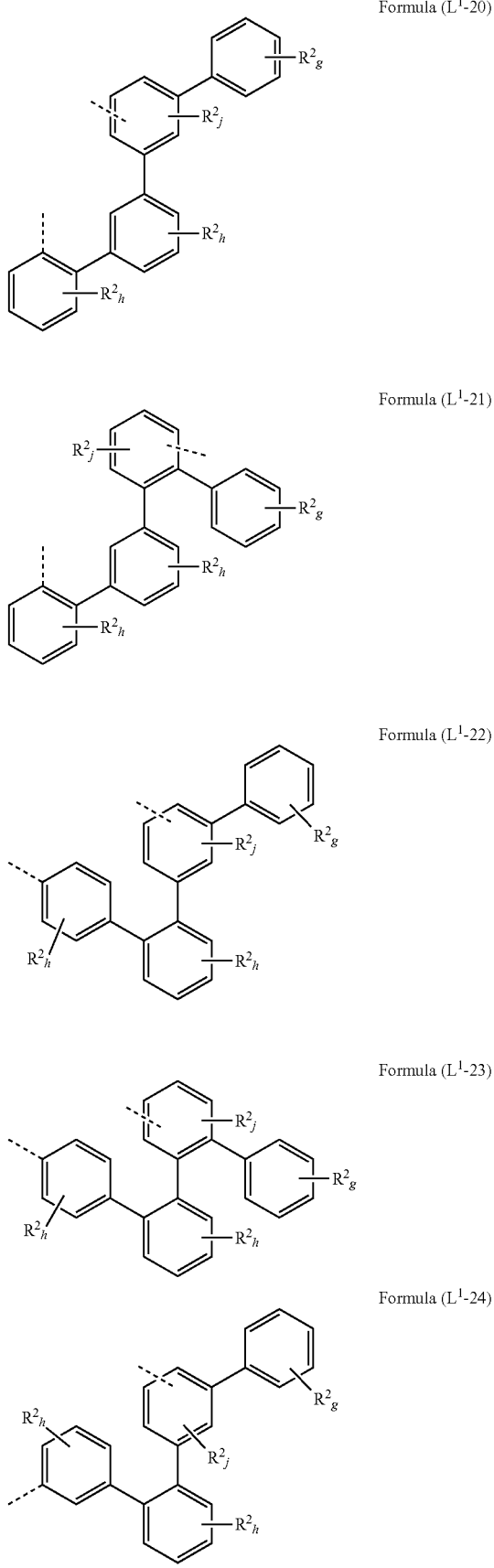
Formula (L¹-21)
Formula (L¹-22)
Formula (L¹-23)
Formula (L¹-24)

Formula (L¹-25)
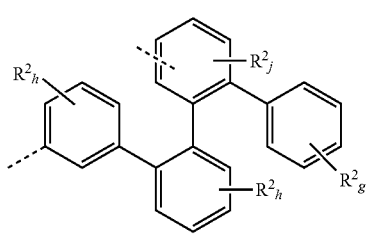
Formula (L¹-26)
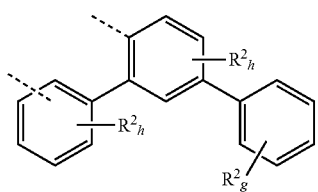
Formula (L¹-27)
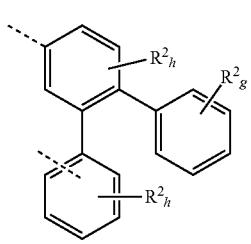
Formula (L¹-28)
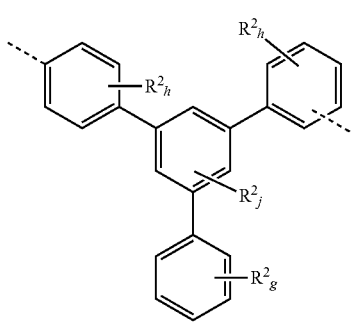
Formula (L¹-29)
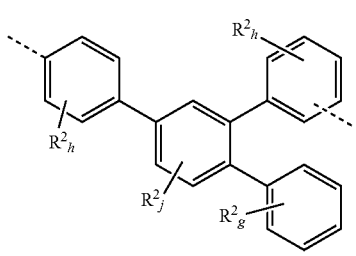
Formula (L¹-30)
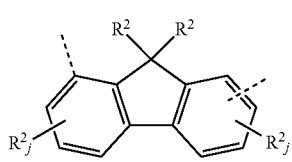
Formula (L¹-31)
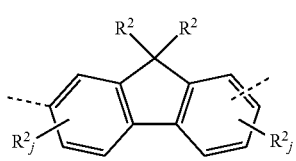
Formula (L¹-32)
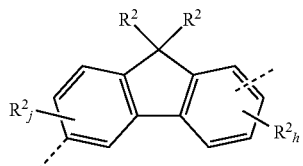
Formula (L¹-33)
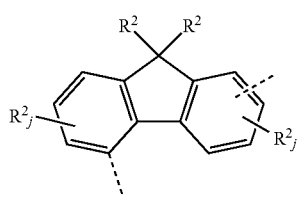
Formula (L¹-34)
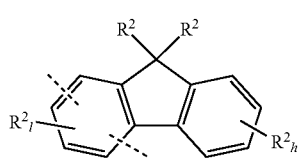
Formula (L¹-35)
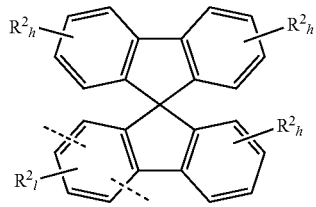
Formula (L¹-36)
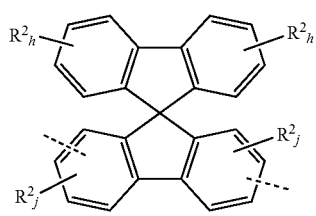
Formula (L¹-37)
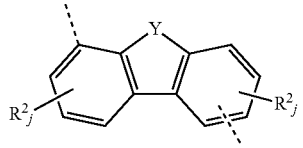
Formula (L¹-38)
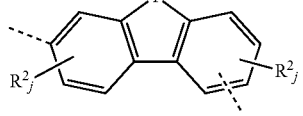
Formula (L¹-39)
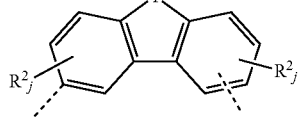
Formula (L¹-40)
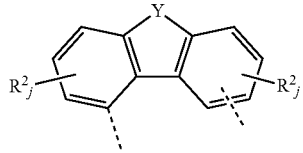

Formula (L¹-41)
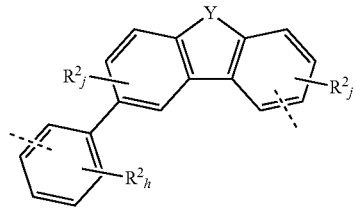
Formula (L¹-42)
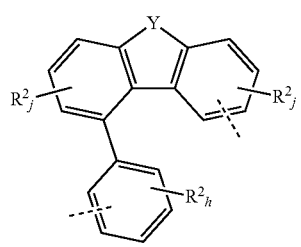
Formula (L¹-43)
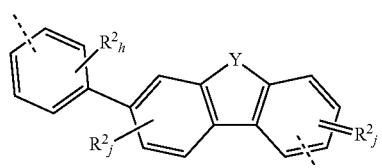
Formula (L¹-44)
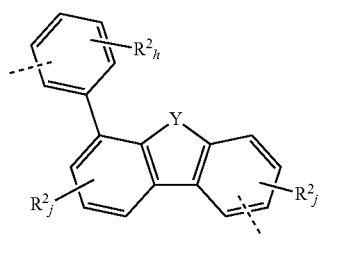
Formula (L¹-45)
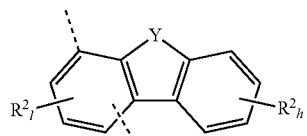
Formula (L¹-46)
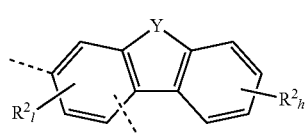
Formula (L¹-47)
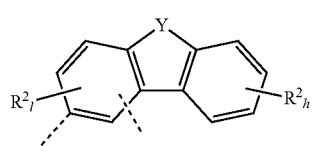
Formula (L¹-48)
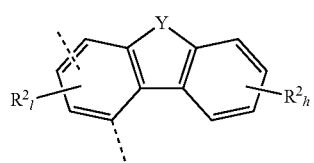
Formula (L¹-49)
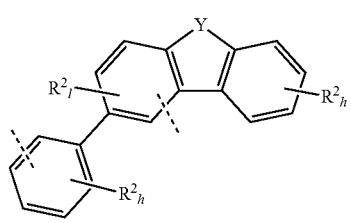
Formula (L¹-50)
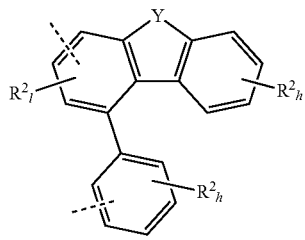
Formula (L¹-51)
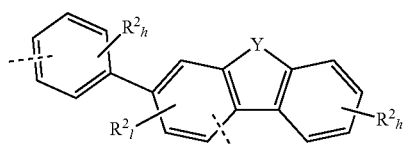
Formula (L¹-52)
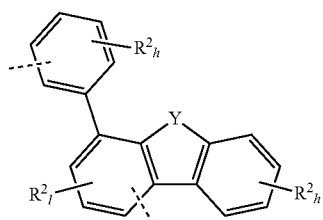
Formula (L¹-53)
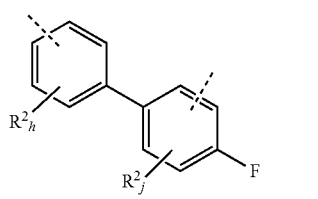
Formula (L¹-54)
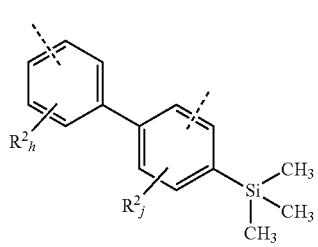
Formula (L¹-55)
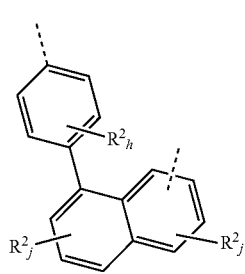

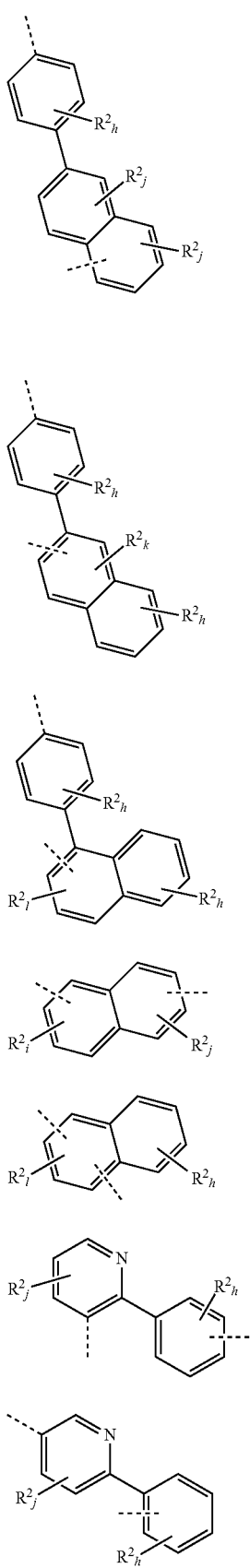
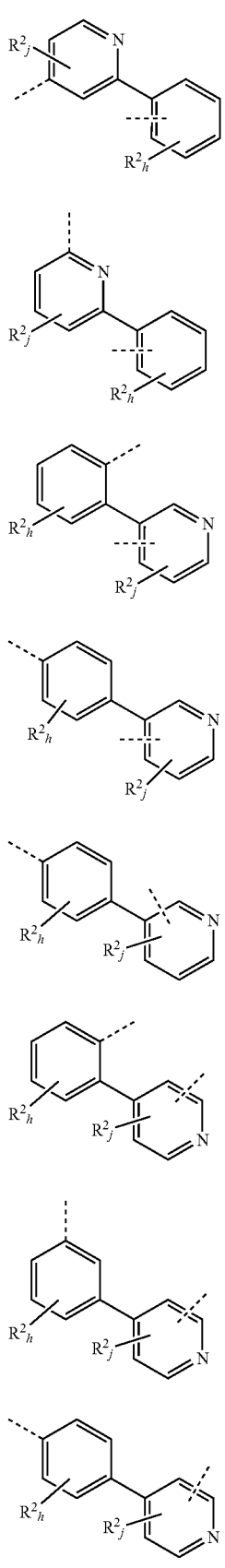

Formula (L¹-71)
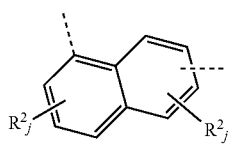
Formula (L¹-72)
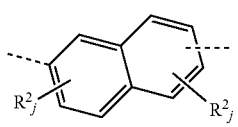
Formula (L¹-73)
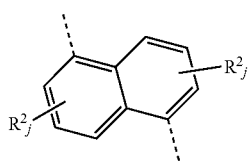
Formula (L¹-74)
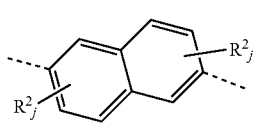
Formula (L¹-75)
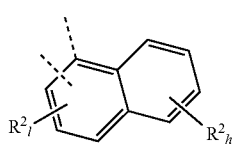
Formula (L¹-76)
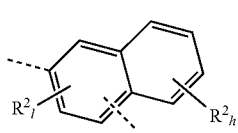
Formula (L¹-77)
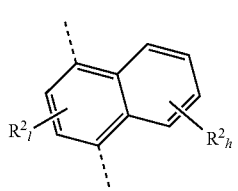
Formula (L¹-78)
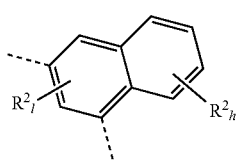
Formula (L¹-79)
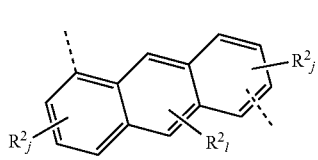
Formula (L¹-80)
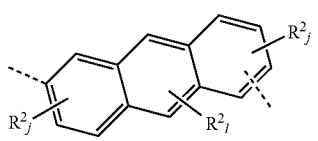
Formula (L¹-81)
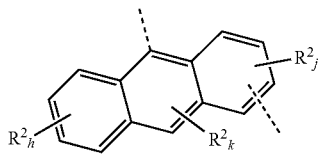
Formula (L¹-82)
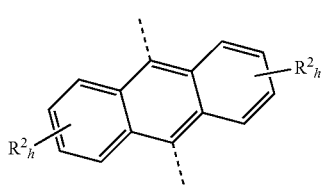
Formula (L¹-83)
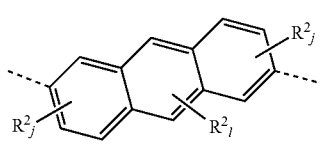
Formula (L¹-84)
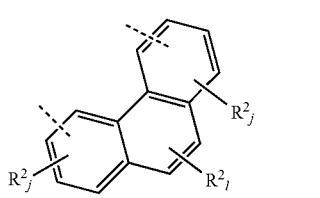
Formula (L¹-85)
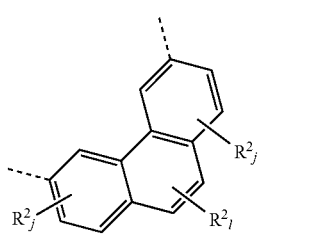
Formula (L¹-86)
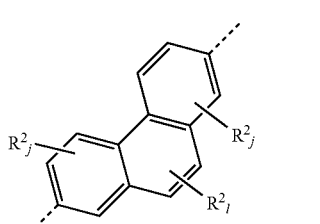
Formula (L¹-87)
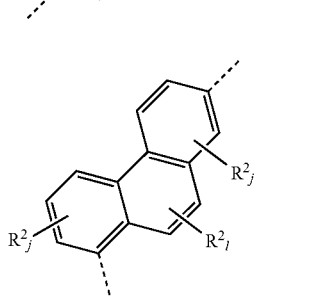

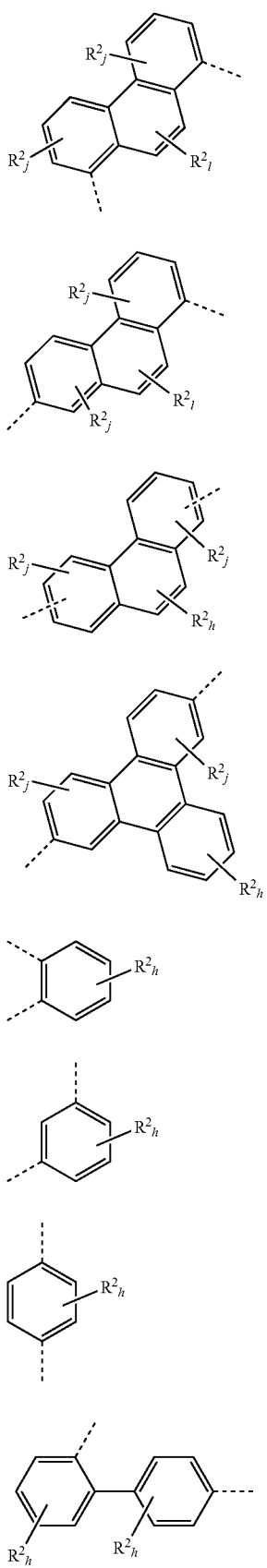
Formula (L¹-88)
Formula (L¹-89)
Formula (L¹-90)
Formula (L¹-91)
Formula (L¹-92)
Formula (L¹-93)
Formula (L¹-94)
Formula (L¹-95)
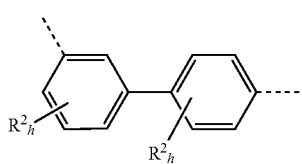
Formula (L¹-96)
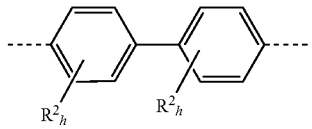
Formula (L¹-97)
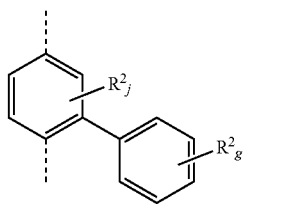
Formula (L¹-98)
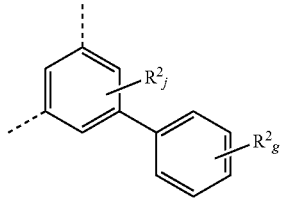
Formula (L¹-99)
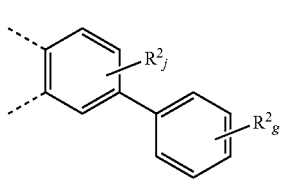
Formula (L¹-100)
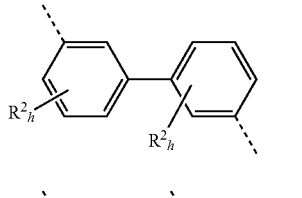
Formula (L¹-101)
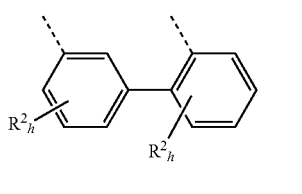
Formula (L¹-102)
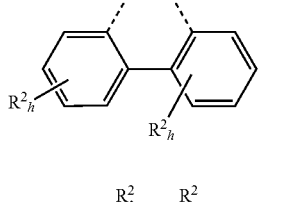
Formula (L¹-103)
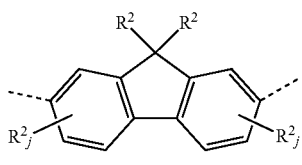
Formula (L¹-104)
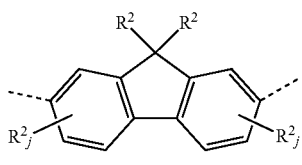

Formula (L¹-105)

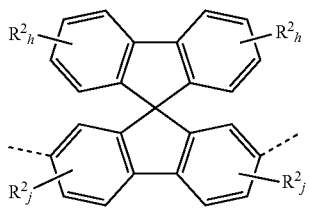

Formula (L¹-106)

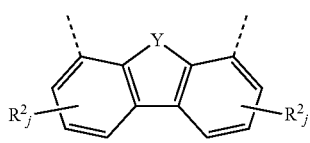

Formula (L¹-107)

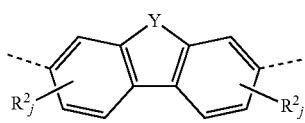

Formula (L¹-108)

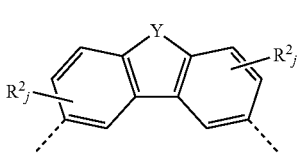

where the dotted bonds in each case mark the attachment positions, the index k is 0 or 1, the index l is 0, 1 or 2, the index j at each instance is independently 0, 1, 2 or 3; the index h at each instance is independently 0, 1, 2, 3 or 4, the index g is 0, 1, 2, 3, 4 or 5; the symbol Y is O, S or $NR^2$; and the symbol $R^2$ has the definition given in claim 1.

16. A compound as claimed in claim 1, characterized in that

Z is a bond, $C(R^2)_2$, C=O, N—$Ar^1$, O or S, where the $R^2$ radical has the definition given in claim 1 and $Ar^1$ represents an aromatic or heteroaromatic ring system which has 5 to 40 aromatic ring atoms and may be substituted in each case by one or more $R^2$ radicals, an aryloxy group which has 5 to 40 aromatic ring atoms and may be substituted by one or more $R^2$ radicals, or an aralkyl group which has 5 to 40 aromatic ring atoms and may be substituted in each case by one or more $R^2$ radicals; where it is optionally possible for two or more, adjacent $R^2$ substituents to form a mono- or polycyclic, aliphatic, heteroaliphatic, aromatic or heteroaromatic ring system which may be substituted by one or more $R^3$ radicals.

* * * * *